(12) United States Patent
Hopkins et al.

(10) Patent No.: US 12,240,838 B2
(45) Date of Patent: Mar. 4, 2025

(54) INHIBITING AGENTS FOR BRUTON'S TYROSINE KINASE

(71) Applicant: BIOGEN MA INC., Cambridge, MA (US)

(72) Inventors: Brian T. Hopkins, Cambridge, MA (US); Bin Ma, Cambridge, MA (US); Robin Prince, Cambridge, MA (US); Isaac Marx, Cambridge, MA (US); Jürgen Schulz, Cambridge, MA (US); Marta Nevalainen, Cambridge, MA (US)

(73) Assignee: BIOGEN MA INC., Cambridge, MA (US)

( * ) Notice: Subject to any disclaimer, the term of this patent is extended or adjusted under 35 U.S.C. 154(b) by 763 days.

(21) Appl. No.: 17/610,963

(22) PCT Filed: May 15, 2020

(86) PCT No.: PCT/US2020/033051
§ 371 (c)(1),
(2) Date: Nov. 12, 2021

(87) PCT Pub. No.: WO2020/232330
PCT Pub. Date: Nov. 19, 2020

(65) Prior Publication Data
US 2022/0259194 A1    Aug. 18, 2022

Related U.S. Application Data

(60) Provisional application No. 62/847,985, filed on May 15, 2019.

(51) Int. Cl.
| | | |
|---|---|---|
| *C07D 413/12* | (2006.01) | |
| *C07D 401/12* | (2006.01) | |
| *C07D 413/14* | (2006.01) | |
| *C07D 417/12* | (2006.01) | |

(52) U.S. Cl.
CPC ......... *C07D 413/12* (2013.01); *C07D 401/12* (2013.01); *C07D 413/14* (2013.01); *C07D 417/12* (2013.01)

(58) Field of Classification Search
CPC .................................................. C07D 413/12
See application file for complete search history.

(56) References Cited

U.S. PATENT DOCUMENTS 10,227,341 B2    3/2019    Hopkins et al.

FOREIGN PATENT DOCUMENTS

| WO | 2015/089337 A1 | 6/2015 |
| WO | 2017/106556 A1 | 6/2017 |

OTHER PUBLICATIONS

International Search Report and Written Opinion for Application No. PCT/US2020/033051, dated Jul. 16, 2020, 10 pages.

*Primary Examiner* — Golam M Shameem
(74) *Attorney, Agent, or Firm* — McCarter & English, LLP; Xin Zhang

(57) ABSTRACT

Provided are compounds of Formula (I), or pharmaceutically acceptable salts thereof, and methods for their use and production.

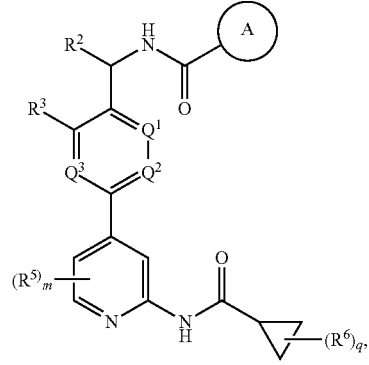

21 Claims, No Drawings

INHIBITING AGENTS FOR BRUTON'S TYROSINE KINASE

RELATED APPLICATIONS

This application is a 35 U.S.C. § 371 national stage filing of International Application No. PCT/US2020/033051, filed on May 15, 2020, which in turn claims the benefit of the filing date, under 35 U.S.C. § 119(e), of U.S. Provisional Application No. 62/847,985, filed on May 15, 2019. The entire contents of each of the foregoing applications are incorporated herein by reference.

TECHNICAL FIELD

Provided are certain agents that inhibit Bruton's tyrosine kinase (Btk), and methods of making and using such agents.

BACKGROUND

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk.

SUMMARY

A first embodiment of the invention is a compound of Formula (I):

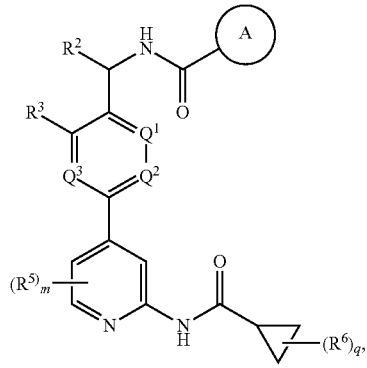

or a pharmaceutically acceptable salt, wherein:

Ring A is selected from aryl and 5- to 6-membered heteroaryl, wherein said aryl and 5- to 6-membered heteroaryl are optionally substituted with one or more $R^1$;

m is an integer selected from 0, 1, 2, and 3;

q is an integer selected from 0, 1, and 2;

$Q^1$, $Q^2$, and $Q^3$ are each selected from C—$R^4$ and N, wherein at most one of $Q^1$, $Q^2$, and $Q^3$ is N;

$R^1$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^{1a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^2$ is selected from H and $C_{1-6}$alkyl;

$R^3$ is selected from $C_{1-6}$alkyl, $C_{2-6}$alkenyl, $C_{2-6}$alkynyl, 4- to 6-membered monocyclic carbocyclyl, and 4- to 6-membered monocyclic heterocyclyl, halo —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$ wherein said $C_{1-6}$alkyl, $C_{2-6}$alkenyl, $_{2-6}$alkynyl, 4- to 6-membered monocyclic carbocyclyl, and 4- to 6-membered monocyclic heterocyclyl are optionally substituted with one or more $R^{30}$.

$R^{3a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{30}$;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$.

$R^4$ in each occurrence is independently selected from H, $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{4a}$, —C(O)$_2R^{4a}$, —C(O)N($R^{4a}$)$_2$, —N($R^{4a}$)$_2$, —N($R^{4a}$)C(O)$R^{4a}$, —N($R^{4a}$)C(O)$_2R^{4a}$, —N($R^{4a}$)C(O)N($R^{4a}$)$_2$, —N($R^{4a}$)S(O)$_2R^{4a}$, —O$R^{4a}$, —OC(O)$R^{4a}$, —OC(O)N($R^{4a}$)$_2$, —S$R^{4a}$, —S(O)$R^{4a}$, —S(O)$_2R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^{4a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^5$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{5a}$, —C(O)$_2R^{5a}$, —C(O)N($R^{5a}$)$_2$, —N($R^{5a}$)$_2$, —N($R^{5a}$)C(O)$R^{5a}$, —N($R^{5a}$)C(O)$_2R^{5a}$, —N($R^{5a}$)C(O)N($R^{5a}$)$_2$, —N($R^{5a}$)S(O)$_2R^{5a}$, —O$R^{1a}$, —OC(O)$R^{5a}$, —OC(O)N($R^{5a}$)$_2$, —S$R^{5a}$, —S(O)$R^{5a}$, —S(O)$_2R^{5a}$, —S(O)N($R^{5a}$)$_2$, and —S(O)$_2$N($R^{5a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$.

$R^{5a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$;

$R^6$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{6a}$, —C(O)$_2R^{6a}$, —C(O)N($R^{6a}$)$_2$, —N($R^{6a}$)$_2$, —N($R^{6a}$)C(O)$R^{6a}$, —N($R^{6a}$)C(O)$_2R^{6a}$, —N($R^{6a}$)C(O)N($R^{6a}$)$_2$, —N($R^{6a}$)S(O)$_2R^{6a}$, —O$R^{6a}$, —OC(O)$R^{6a}$, —OC(O)N($R^{6a}$)$_2$, —S$R_{6a}$, —S(O)$R^{6a}$, —S(O)$_2R^{6a}$, —S(O)N($R^{6a}$)$_2$, and —S(O)$_2$N($R^{6a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{60}$;

or two $R^6$ substituents, together with their intervening atoms, form a 3- to 5-membered carbocyclic or a 3- to 5-membered heterocyclic ring, wherein said 3- to 5-membered carbocyclic and 3- to 5-membered heterocyclic ring are optionally substituted with one or more $R^{60}$;

$R^{6a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{60}$;

$R^{10}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{20}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, —S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally substituted with one or more $R^{25}$;

$R^{20a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{25}$;

$R^{25}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{25a}$, —C(O)$_2R^{25a}$, —C(O)N($R^{25a}$)$_2$, —N($R^{25a}$)$_2$, —N($R^{25a}$)C(O)$R^{25a}$, —N($R^{25a}$)C(O)$_2R^{25a}$, —N($R^{25a}$)C(O)N($R^{25a}$)$_2$, —N($R^{25a}$)S(O)$_2R^{25a}$, —O$R^{25a}$, —OC(O)$R^{25a}$, —OC(O)N($R^{25}$)$_2$, —S$R^{25a}$, —S(O)$R^{25a}$, —S(O)$_2R^{25a}$, —S(O)N($R^{25a}$)$_2$, and —S(O)$_2$N($R^{25a}$)$_2$;

$R^{25a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{30}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{30a}$, —C(O)$_2R^{30a}$, —C(O)N($R^{30a}$)$_2$, —N($R^{30a}$)$_2$, —N($R^{30a}$)C(O)$R^{30a}$, —N($R^{30a}$)C(O)$_2R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{40}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)R$^{40a}$, —C(O)$_2$R$^{40a}$, —C(O)N(R$^{40a}$)$_2$, —N(R$^{40a}$)$_2$, —N(R$^{40a}$)C(O)R$^{40a}$, —N(R$^{40a}$)C(O)$_2$R$^{40a}$, —N(R$^{40a}$)C(O)N(R$^{40a}$)$_2$, —N(R$^{40a}$)S(O)$_2$R$^{40a}$, —OR$^{40a}$, —OC(O)R$^{40a}$, —OC(O)N(R$^{40a}$)$_2$, —SR$^{40a}$, —S(O)R$^{40a}$, —S(O)$_2$R$^{40a}$, —S(O)N(R$^{40a}$)$_2$, and —S(O)$_2$N(R$^{40a}$)$_2$;

$R^{40a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{50}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)R$^{50a}$, —C(O)$_2$R$^{50a}$, —C(O)N(R$^{50a}$)$_2$, —N(R$^{50a}$)$_2$, —N(R$^{50a}$)C(O)R$^{50a}$, —N(R$^{50a}$)C(O)$_2$R$^{50a}$, —N(R$^{50a}$)C(O)N(R$^{50a}$)$_2$, —N(R$^{50a}$)S(O)$_2$R$^{50a}$, —OR$^{50a}$, —OC(O)R$^{50a}$, —OC(O)N(R sa)$_2$, —SR$^{50a}$, —S(O)R$^{50a}$, —S(O)$_2$R$^{50a}$, —S(O)N(R$^{50a}$)$_2$, and —S(O)$_2$N(R$^{50a}$)$_2$;

$R^{50a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{60}$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)R$^{60a}$, —C(O)$_2$R$^{60a}$, —C(O)N(R$^{60a}$)$_2$, —N(R$^{60a}$)$_2$, —N(R$^{60a}$)C(O)R$^{60a}$, —N(R$^{60a}$)C(O)$_2$R$^{60a}$, —N(R$^{60a}$)C(O)N(R$^{60a}$)$_2$, —N(R$^{60a}$)S(O)$_2$R$^{60a}$, —OR$^{60a}$, —OC(O)R$^{60a}$, —OC(O)N(R$^{60a}$)$_2$, —SR$^{60a}$, —S(O)R$^{60a}$, —S(O)$_2$R$^{60a}$, —S(O)N(R$^{60a}$)$_2$, and —S(O)$_2$N(R$^{60a}$)$_2$; and $R^{60a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl.

The present invention also provides a pharmaceutical composition comprising at least one compound described herein, or a pharmaceutically acceptable salt thereof, and at least one pharmaceutically acceptable excipient.

In one embodiment, the invention is a method of treating a disorder responsive to inhibition of Btk in a subject comprising administering to said subject an effective amount of at least one compound described herein, or a pharmaceutically acceptable salt thereof.

The present invention also includes the use of at least one compound described herein, or a pharmaceutically acceptable salt thereof, for the manufacture of a medicament for the treatment of a disorder responsive to inhibition of Btk. Also provided is a compound described herein, or a pharmaceutically acceptable salt thereof for use as a medicament. In another embodiment, the present invention provides a compound described herein, or a pharmaceutically acceptable salt thereof for use in treating a disorder responsive to inhibition of Btk.

Other features or advantages will be apparent from the following detailed description of several embodiments, and also from the appended claims.

DETAILED DESCRIPTION

The compounds or pharmaceutically acceptable salts thereof as described herein, can have activity as Btk modulators. In particular, compounds or pharmaceutically acceptable salts thereof as described herein, can be Btk inhibitors.

In a second embodiment of the present invention, the compound is represented by formula (I), or a pharmaceutically acceptable salt thereof, wherein $Q^1$, $Q^2$, and $Q^3$ are each independently C—R$^4$ and the definitions for the other variables are as defined in the first embodiment.

In a third embodiment of the present invention, the compound is represented by formula (I), or a pharmaceutically acceptable salt thereof, wherein $Q^1$ is CH; and the definitions for the variables are as defined in the first or second embodiment.

In a fourth embodiment of the present invention, the compound is represented by formula (II) or (III):

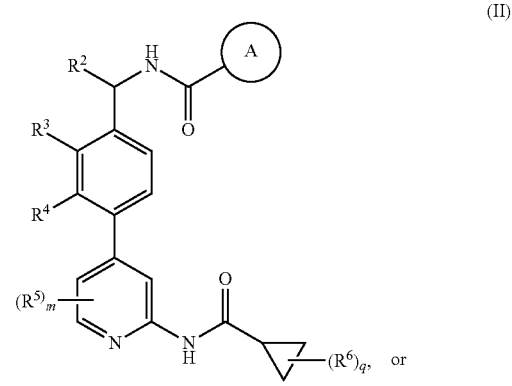

(II)

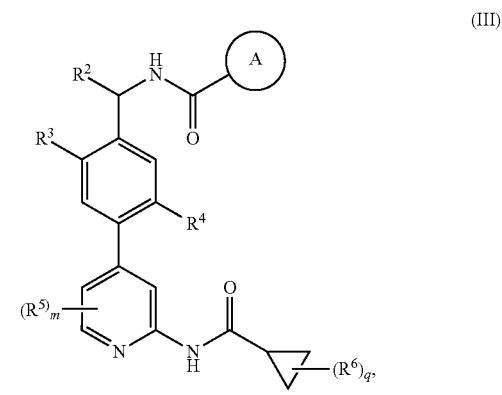

(III)

or a pharmaceutically acceptable salt thereof, wherein the definitions for the variables are as defined in the first, second or third embodiment.

In a fifth embodiment of the present invention, the compound is represented by formula (I), (II) or (III), or a pharmaceutically acceptable salt thereof, wherein m is 0 or 1; and the definitions for the other variables are as defined in the first, second, third, or fourth embodiment.

In a sixth embodiment of the present invention, the compound is represented by formula (IV) or (V):

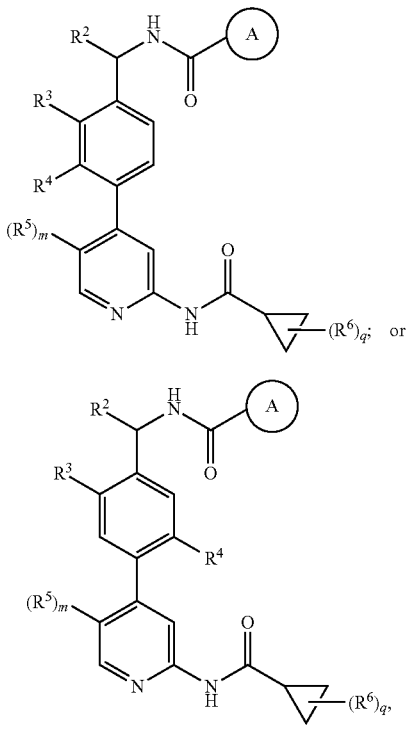

or a pharmaceutically acceptable salt thereof, wherein m is 0 or 1; and the definitions for the other variables are as defined in the first embodiment.

In a seventh embodiment of the present invention, the compound is represented by formula (I), (II), (III), (IV) or (V) or a pharmaceutically acceptable salt thereof, wherein:
$R^3$ is $C_{1-6}$alkyl, $C_{3-5}$cycloalkyl, halo, or —OR 3, wherein said $C_{1-6}$alkyl or $C_{3-5}$cycloalkyl is optionally substituted with one to three $R^{30}$ independently selected from $C_{1-3}$alkyl and halo;
$R^{3a}$ is $C_{1-6}$alkyl optionally substituted with one to three halo;
and the definitions for the other variables are as defined in the first, second, third, fourth, fifth or sixth embodiment. In a specific embodiment, $R^3$ is $C_{1-4}$alkyl, cyclopropyl, cyclobutyl, cyclopentyl, —F, —Cl, or —OR$^{3a}$, wherein said $C_{1-4}$alkyl is optionally substituted with one to three fluoro; and $R^{3a}$ is $C_{1-4}$alkyl optionally substituted with one to three fluoro. In another specific embodiment, $R^3$ is —CH$_3$, —CH$_2$CH$_3$, —CH(CH$_3$)$_2$, —C(CH$_3$)$_3$, —CHF$_2$, —CF$_3$, cyclopropyl, cyclobutyl, —F, —Cl, —OCF$_3$, or —OCH$_3$.

In an eighth embodiment of the present invention, the compound is represented by formula (I), (II), (III), (IV) or (V) or a pharmaceutically acceptable salt thereof, wherein $R^2$ is H or methyl; and the definitions for the variables are as defined in the first, second, third, fourth, fifth, sixth or seventh embodiment. In a more specific embodiment, $R^2$ is H.

In a ninth embodiment of the present invention, the compound is represented by formula (I), (II), (III), (IV) or (V) or a pharmaceutically acceptable salt thereof, wherein $R^2$ and $R^3$ together with their intervening atoms, form a seven-membered carbocyclic or heterocyclic ring, wherein said seven-membered heterocyclic ring has one heteroatom selected from N and O; and said seven-membered carbocyclic or heterocyclic ring is optionally substituted with one or two $R^{20}$; and the definitions for the other variables are as defined in the first, second, third, fourth, fifth, or sixth embodiment.

In a tenth embodiment of the present invention, the compounds is represented by formula (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'):

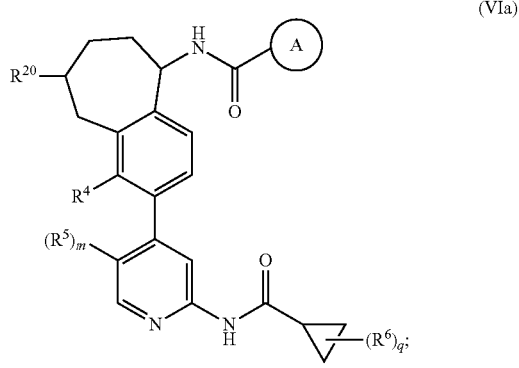

(VIa)

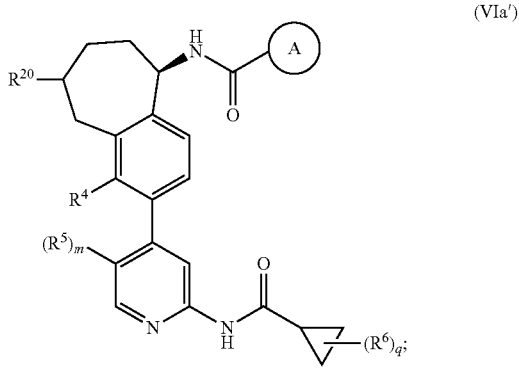

(VIa')

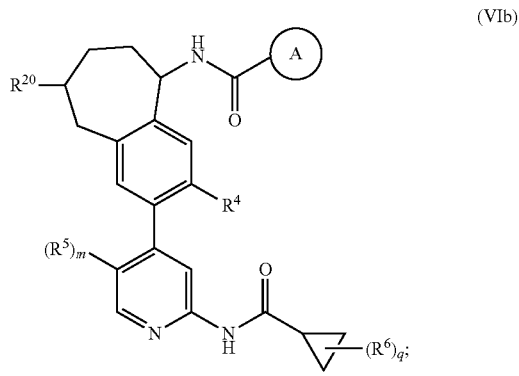

(VIb)

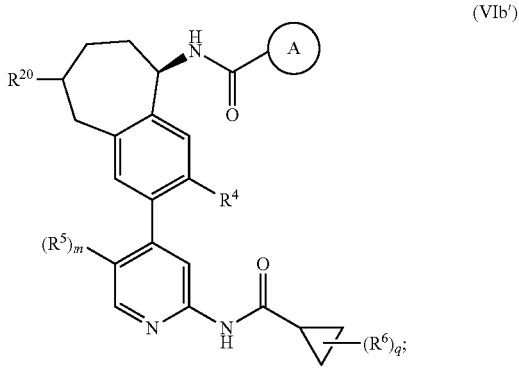

(VIb')

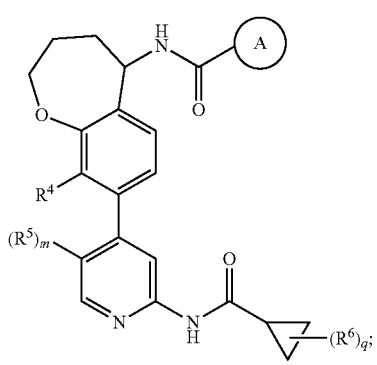
(VIIa)
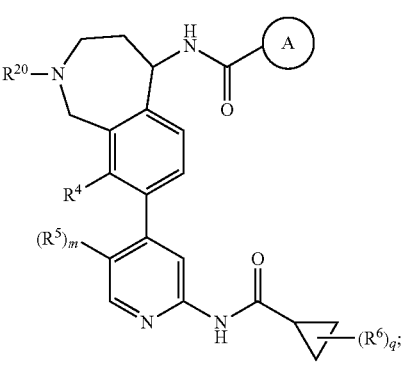
(VIIIa)
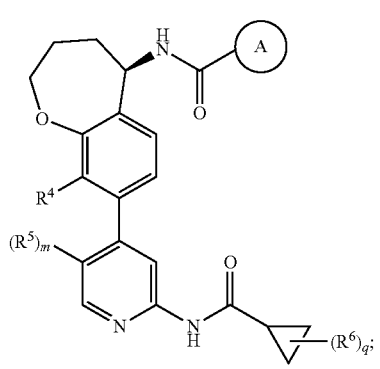
(VIIa')
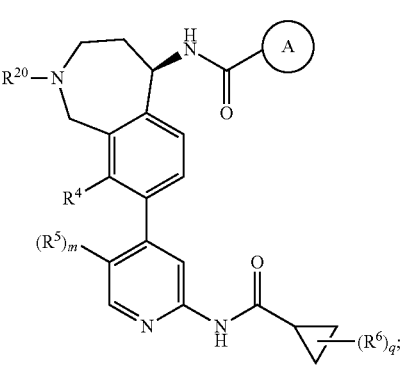
(VIIIa')
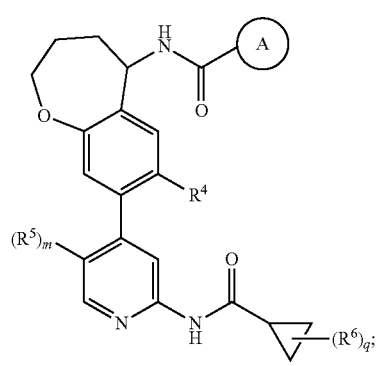
(VIIb)
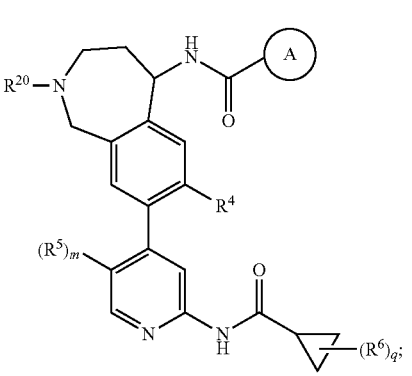
(VIIIb)
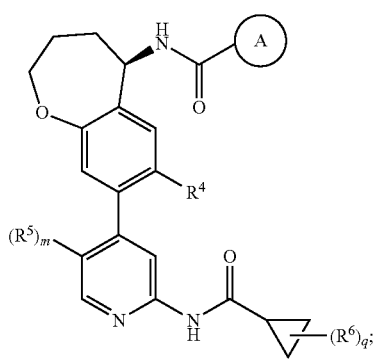
(VIIb')
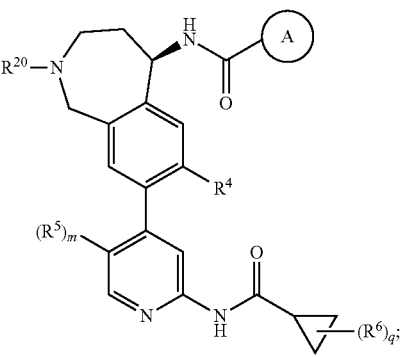
(VIIIb')

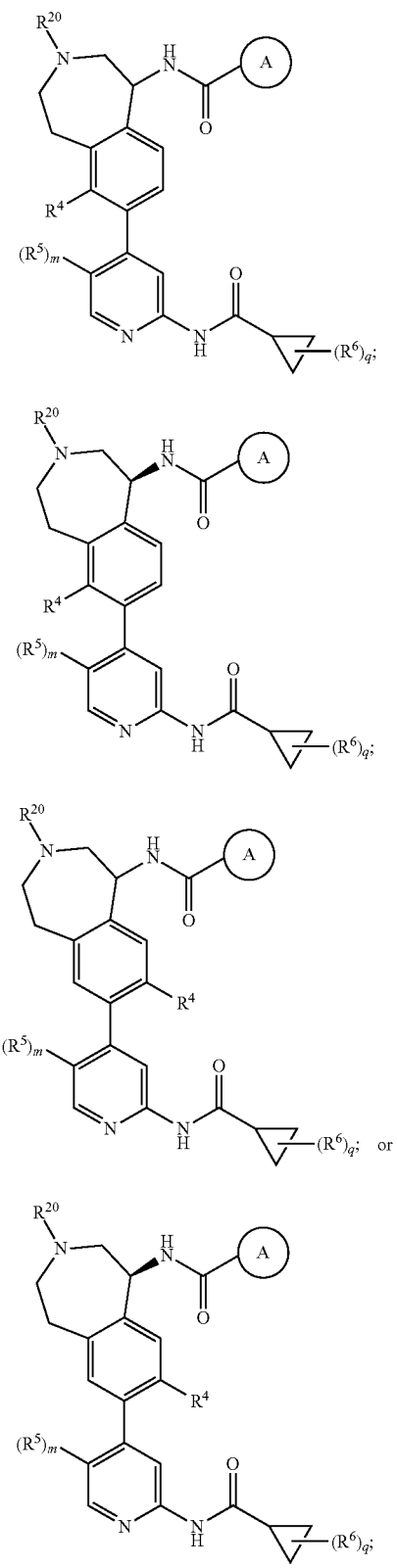

or a pharmaceutically acceptable salt thereof, wherein definitions for the variables are as defined in the first, second, third, fourth, fifth, or sixth embodiment.

In a eleventh embodiment of the present invention, the compound is represented by formula (VIa), (VIa'), (VIb) or (VIb'), or a pharmaceutically acceptable salt thereof, wherein:

$R^{20}$ is selected from H, $C_{1-6}$alkyl, $C_{3-6}$cycloalkyl, saturated 4- to 6-membered monocyclic heterocyclyl, halo, —$OR^{20a}$, —$OC(O)R^{20a}$, —$OC(O)N(R^{20a})_2$, and —$SR^{20a}$, wherein said $C_{1-6}$alkyl, $C_{3-6}$cycloalkyl, and saturated 4- to 6-membered monocyclic heterocyclyl are optionally substituted with one to three $R^{25}$;

$R^{20}$, in each occurrence is independently H or $C_{1-6}$alkyl, wherein said $C_{1-6}$alkyl in each occurrence is optionally and independently substituted with one $R^{25}$; and $R^{25}$ in each occurrence is independently selected from $C_{1-6}$alkyl or halo; and the definitions for the other variables are as defined in the first, second, third, fourth, fifth or sixth embodiment. In a specific embodiment, $R^{20}$ is H.

In a twelfth embodiment of the present invention, the compound is represented by formula (VIIIa), (VIIIa'), (VIIIb), (VIIIb'), (IXa), (IXa'), (IXb) or (IXb'), or a pharmaceutically acceptable salt thereof, wherein:

$R^{20}$ is selected from H, $C_{1-6}$alkyl, $C_{3-6}$cycloalkyl, saturated 4- to 6-membered monocyclic heterocyclyl, —$C(O)R^{20a}$, —$C(O)_2R^{20a}$, and —$S(O)_2R^{20a}$, wherein said $C_{1-6}$alkyl, $C_{3-6}$cycloalkyl, and saturated 4- to 6-membered monocyclic heterocyclyl are optionally substituted with one to three $R^{25}$;

$R^{20a}$ in each occurrence is independently selected from H, $C_{1-6}$alkyl, $C_{4-6}$cycloalkyl, and saturated 4- to 6-membered monocyclic heterocyclyl, wherein said $C_{1-6}$alkyl, $C_{4-6}$cycloalkyl, and saturated 4- to 6-membered monocyclic heterocyclyl in each occurrence are optionally and independently substituted with one or more $R^{25}$.

$R^{25}$ in each occurrence is independently selected from $C_{1-6}$alkyl, $C_{3-6}$cycloalkyl, saturated 4- to 6-membered monocyclic heterocyclyl, halo, —CN, —$N(R^{25a})_2$, and —$OR^{25a}$; and $R^{25a}$ in each occurrence is independently H or $C_{1-6}$alkyl; and the definitions for the other variables are as defined in the first, second, third, fourth, fifth or sixth embodiment. In a specific embodiment, $R^{20}$ is $C_{1-6}$alkyl optionally substituted with one to three fluoro. In another specific embodiment, $R^{20}$ is —$CH_2CF_3$.

In a thirteenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein Ring A is a 5-membered N-containing heteroaryl having 1 or 2 additional heteroatoms independently selected from O, N and S, wherein ring A is optionally substituted with one or two independently selected $R^1$; and the definitions for the other variables are as defined in the first, second, third, fourth, fifth, sixth, seventh, eighth, ninth, tenth, eleventh or twelfth embodiment or any specific embodiments described therein.

In a fourteenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein Ring A is selected from the group consisting of pyrazole, imidazole, oxazole, isoxazole, thiazole, isothiazole, 1,2,3-oxadiazole, 1,3,4-oxadiazole, 1,2,4-oxadizole, 1,2,3-thiadiazole, 1,3,4-thiadiazole, 1,2,4-thiadiazole, 1,2,3-triazole, and 1,2,4-triazole, each of which is optionally substituted with one or two independently selected R¹; and the definitions for the other variables are as defined in the first, second, third, fourth, fifth, sixth, seventh, eighth, ninth, tenth, eleventh or twelfth embodiment or any specific embodiments described therein.

In a fifteenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein Ring A is represented by the following formula:

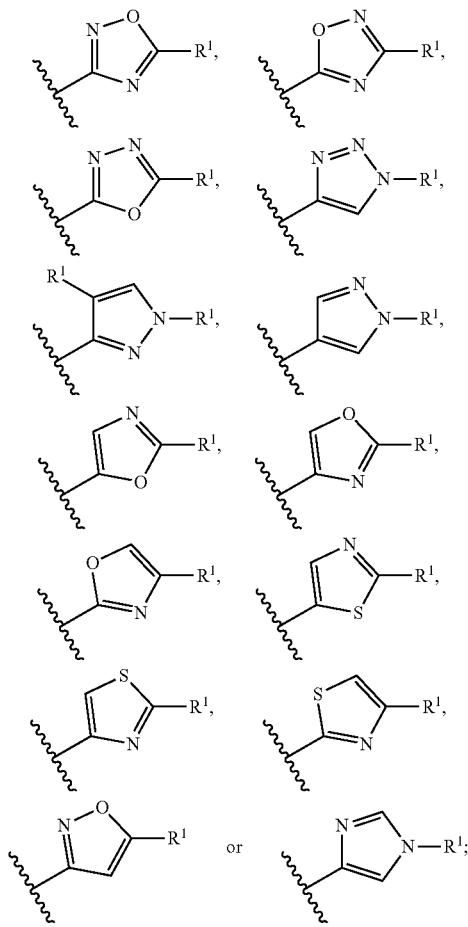

and the definitions for the other variables are as defined in the first, second, third, fourth, fifth, sixth, seventh, eighth, ninth, tenth, eleventh or twelfth embodiment or any specific embodiments described therein.

In a sixteenth embodiment, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein:
  R¹ in each occurrence is independently halo, $C_{1-6}$alkyl or $C_{3-5}$cycloalkyl; wherein said $C_{1-6}$alkyl and $C_{3-5}$cycloalkyl are optionally substituted with one to three independently selected $R^{10}$.
  $R^{10}$ in each occurrence is independently selected from halo, —OH, and $C_{1-6}$alkyl; and the definitions for the other variables are as defined in the first, second, third, fourth, fifth, sixth, seventh, eighth, ninth, tenth, eleventh, twelfth, thirteenth, fourteenth or fifteenth embodiment or any specific embodiments described therein.

In a seventeenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein R¹ in each occurrence is independently halo, $C_{1-4}$alkyl, cyclopropyl, cyclobutyl or cyclopentyl, wherein said $C_{1-4}$alkyl, cyclopropyl, cyclobutyl or cyclopentyl is optionally substituted with one to three $R^{10}$ independently selected from methyl, fluoro and —OH; and the definitions for the other variables are as defined in the sixteenth embodiment.

In a specific embodiment, R¹ in each occurrence is independently —F, —C(CH₃)₃, —C(CH₂OH)(CH₃)₂, —C(CH₂F)(CH₃)₂, or

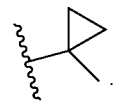

In an eighteenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein R⁴ is H, halo or $C_{1-3}$alkyl; and the definitions for the other variables are as defined in the first, second, third, fourth, fifth, sixth, seventh, eighth, ninth, tenth, eleventh, twelfth, thirteenth, fourteenth, fifteenth, sixteenth or seventeenth embodiment or any specific embodiments described therein. In a specific embodiment, R⁴ is H, —F, —Cl, or —CH₃.

In a nineteenth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein m is 0; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth or eighteenth embodiment or any specific embodiments described therein.

In a twentieth embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein m is 1; R⁵ is halo or $C_{1-3}$alkyl optionally substituted with one to three fluoro; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth or eighteenth embodiment or any specific embodiments described therein. In a specific embodiment, R⁵ is —F, —Cl, or —CF₃.

In a twenty-first embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein q is 0; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth or twentieth embodiment or any specific embodiments described therein.

In a twenty-second embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein $R^6$ in each occurrence is independently selected from halo, —CN, and $C_{1-6}$alkyl optionally substituted with one to three halo; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth or twentieth embodiment or any specific embodiments described therein. In a specific embodiment, $R^6$ in each occurrence is independently —$CH_3$, —$CF_3$, —F, or —CN.

In a twenty-third embodiment of the present invention, the compound is represented by formula (I), (II), (III), (IV), (V), (VIa), (VIa'), (VIb), (VIb'), (VIIa), (VIIa'), (VIIb), (VIIb'), (VIIIa), (VIIIa'), (VIIIb), (VIIIb'), (IXa), (IXa'), (IXb) or (IXb'), or a pharmaceutically acceptable salt thereof, wherein q is 2; and two $R^6$ substituents, together with their intervening atoms, form a three- to five-membered cycloalkyl or a four- to five-membered saturated heterocyclic ring; and the definitions for the other variables are as defined in the first, second, third, fourth, fifth, sixth, seventh, eighth, ninth, tenth, eleventh, twelfth, thirteenth, fourteenth, fifteenth, sixteenth, seventeenth, eighteenth, nineteenth or twentieth embodiment or any specific embodiments described therein. In a specific embodiment, two $R^6$ substituents, together with their intervening atoms, form cyclopropyl, cyclobutyl, cyclopentyl, azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, or oxathiolanyl. In another specific embodiment, two $R^6$ substituents, together with their intervening atoms, form cyclopropyl, cyclobutyl, cyclopentyl, or tetrahydrofuranyl.

In a twenty-fourth embodiment of the present invention, the compound is represented by formula (IV) or (V):

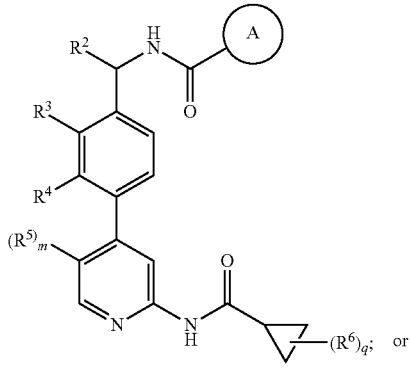

(IV)

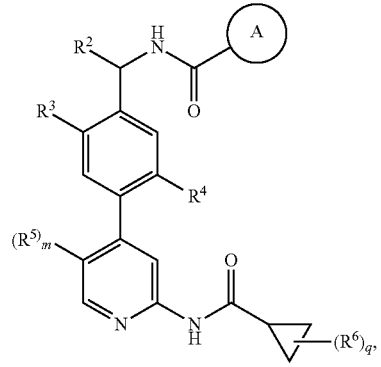

(V)

or a pharmaceutically acceptable salt thereof, wherein:
Ring A is oxadiazole optionally substituted with one or two independently selected $R^1$;
$R^1$ in each occurrence is independently halo or $C_{1-6}$alkyl;
$R^2$ is H or $C_{1-3}$alkyl;
$R^3$ is halo or $C_{1-3}$alkyl; or $R^2$ and $R^3$, together with their intervening atoms, form a seven-membered carbocyclic or heterocyclic ring, wherein said seven-membered heterocyclic ring has one heteroatom selected from N and O; and said seven-membered carbocyclic or heterocyclic ring is optionally substituted with one $R^{20}$;
$R^{20}$ is $C_{1-6}$alkyl optionally substituted with one to three fluoro;
$R^4$ is H or halo;
$R^5$ is halo;
$R^6$ is halo or $C_{1-3}$alkyl;
m is 0 or 1; and
q is 0 or 1.

In a twenty-fifth embodiment, the compound is represented by formula (IV) or (V), or a pharmaceutically acceptable salt thereof, wherein Ring A is represented by the following formula:

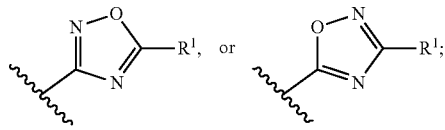

and the definitions for the other variables are as defined in the twenty-fourth embodiment.

In a twenty-sixth embodiment, the compound is represented by formula (IV) or (V), or a pharmaceutically acceptable salt thereof, wherein $R^1$ is —$C(CH_3)_3$; and the definitions for the other variables are as defined in a twenty-fourth or twenty-fifth embodiment.

In a twenty-seventh embodiment, the compound is represented by formula (IV) or (V), or a pharmaceutically acceptable salt thereof, wherein q is 0; or q is 1, $R^6$ is —F or —$CH_3$; and the definitions for the other variables are as defined in the twenty-fourth, twenty-fifth or twenty-sixth embodiment.

In a twenty-eighth embodiment, the compound is represented by formula (IV) or (V), or a pharmaceutically acceptable salt thereof, wherein m is 0; or m is 1; $R^5$ is —F or —Cl; and the definitions for the other variables are as defined in the twenty-fourth, twenty-fifth, twenty-sixth or twenty-seventh embodiment.

In a twenty-ninth embodiment, the compound is represented by formula (IV) or (V), or a pharmaceutically acceptable salt thereof, wherein $R^2$ is H or —$CH_3$; $R^3$ is —Cl, —$CH_3$, or —$CF_3$; and definitions for the other variables are as defined in the twenty-fourth, twenty-fifth, twenty sixth, twenty-seventh or twenty-eighth embodiment.

In a thirtieth embodiment, the compound is represented by formula (IV) or (V), or a pharmaceutically acceptable salt thereof, wherein $R^4$ is H or —F; and the definitions for the other variables are as defined in the twenty-fourth, twenty-fifth, twenty sixth, twenty-seventh, twenty-eighth or twenty-ninth embodiment.

In a thirty-first embodiment, the compound is represented by formula (VIc), (VIc'), (VIIIc) or (VIIIc'):

(VIc)

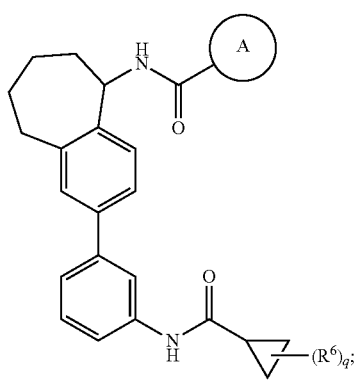

(VIc')

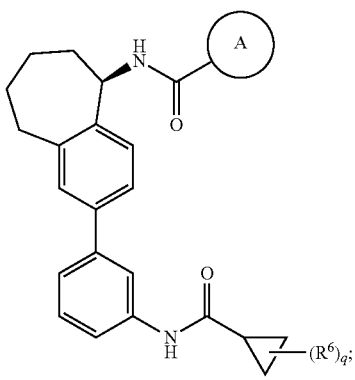

(VIIIc)

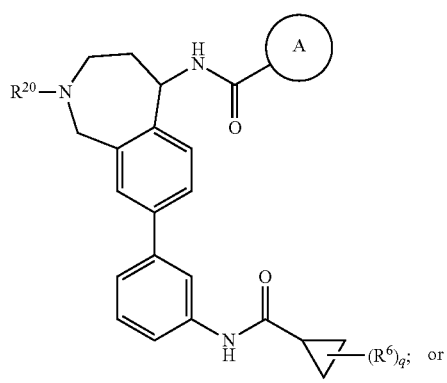

(VIIIc')

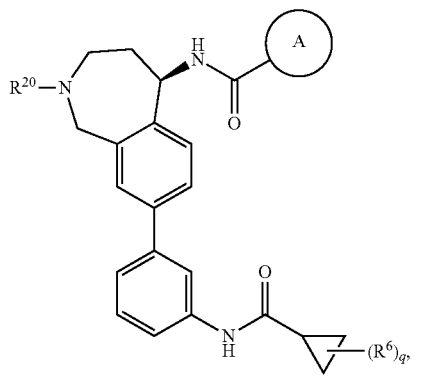

or a pharmaceutically acceptable salt thereof, wherein the definitions for the variables are as defined in the twenty-fourth, twenty-fifth, twenty-sixth or twenty seventh embodiment. In a specific embodiment, $R^{20}$ is $C_{1-6}$alkyl or saturated 4- to 6-membered monocyclic heterocyclyl, wherein said $C_{1-6}$alkyl and saturated 4- to 6-membered monocyclic heterocyclyl are optionally substituted with one to three $R^{25}$; and $R^{25}$ in each occurrence is independently halo. $R^{20}$ is $C_{1-6}$alkyl or saturated 4- to 6-membered monocyclic heterocyclyl selected from azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, and dioxinyl, wherein aid $C_{1-6}$alkyl is optionally substituted with one to three halo. In another specific embodiment, $R^{20}$ is —$CH_2CF_3$.

In a thirty-second embodiment, the compound of the present invention is selected from:

3-(tert-butyl)-N-(4-(2-(cyclopropanecarboxamido)pyridin-4-yl)-2-methylbenzyl)-1,2,4-oxadiazole-5-carboxamide hydrochloride;

5-(tert-butyl)-N-(4-(2-(cyclopropanecarboxamido)pyridin-4-yl)-2-methylbenzyl)-1,2,4-oxadiazole-3-carboxamide hydrochloride;

5-(tert-butyl)-N-(4-(2-(2-fluorocyclopropane-1-carboxamido)pyridin-4-yl)-2-methylbenzyl)-1,2,4-oxadiazole-3-carboxamide;

5-(tert-butyl)-N-(4-(2-((1S,2S)-2-fluorocyclopropane-1-carboxamido)pyridin-4-yl)-2-methylbenzyl)-1,2,4-oxadiazole-3-carboxamide;

5-(tert-butyl)-N-(4-(2-((1R,2R)-2-fluorocyclopropane-1-carboxamido)pyridin-4-yl)-2-methylbenzyl)-1,2,4-oxadiazole-3-carboxamide;

5-(tert-butyl)-N-(4-(2-((1S,2R)-2-fluorocyclopropane-1-carboxamido)pyridin-4-yl)-2-methylbenzyl)-1,2,4-oxadiazole-3-carboxamide;

5-(tert-butyl)-N-(4-(2-((1R,2S)-2-fluorocyclopropane-1-carboxamido)pyridin-4-yl)-2-methylbenzyl)-1,2,4-oxadiazole-3-carboxamide;

5-(tert-butyl)-N-(2-methyl-4-(2-(2-methylcyclopropane-1-carboxamido)pyridin-4-yl)benzyl)-1,2,4-oxadiazole-3-carboxamide;

5-(tert-butyl)-N-(2-methyl-4-(2-((1S,2S)-2-methylcyclopropane-1-carboxamido)pyridin-4-yl)benzyl)-1,2,4-oxadiazole-3-carboxamide;

5-(tert-butyl)-N-(2-methyl-4-(2-((1S,2R)-2-methylcyclopropane-1-carboxamido)pyridin-4-yl)benzyl)-1,2,4-oxadiazole-3-carboxamide;

5-(tert-butyl)-N-(2-methyl-4-(2-(((1R,2S)-2-methylcyclopropane-1-carboxamido)pyridin-4-yl)benzyl)-1,2,4-oxadiazole-3-carboxamide;
5-(tert-butyl)-N-(2-methyl-4-(2-(((1R,2R)-2-methylcyclopropane-1-carboxamido)pyridin-4-yl)benzyl)-1,2,4-oxadiazole-3-carboxamide;
5-(tert-butyl)-N-(4-(5-chloro-2-(cyclopropanecarboxamido)pyridin-4-yl)-2-methylbenzyl)-1,2,4-oxadiazole-3-carboxamide;
5-(tert-butyl)-N-(2-chloro-4-(2-(cyclopropanecarboxamido)pyridin-4-yl)benzyl)-1,2,4-oxadiazole-3-carboxamide;
3-(tert-butyl)-N-(2-chloro-4-(2-(cyclopropanecarboxamido)pyridin-4-yl)benzyl)-1,2,4-oxadiazole-5-carboxamide;
5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide;
(R)-5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide;
(S)-5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide;
5-(tert-butyl)-N-(4-(2-(cyclopropanecarboxamido)pyridin-4-yl)-3-fluoro-2-methylbenzyl)-1,2,4-oxadiazole-3-carboxamide;
3-(tert-butyl)-N-(4-(2-(cyclopropanecarboxamido)pyridin-4-yl)-5-fluoro-2-methylbenzyl)-1,2,4-oxadiazole-5-carboxamide;
5-(tert-butyl)-N-(4-(2-(cyclopropanecarboxamido)pyridin-4-yl)-5-fluoro-2-methylbenzyl)-1,2,4-oxadiazole-3-carboxamide;
5-(tert-butyl)-N-(2-chloro-4-(2-(cyclopropanecarboxamido)pyridin-4-yl)-3-fluorobenzyl)-1,2,4-oxadiazole-3-carboxamide;
3-(tert-butyl)-N-(2-chloro-4-(2-(cyclopropanecarboxamido)pyridin-4-yl)-3-fluorobenzyl)-1,2,4-oxadiazole-5-carboxamide;
5-(tert-butyl)-N-(4-(2-(cyclopropanecarboxamido)pyridin-4-yl)-2-(trifluoromethyl)benzyl)-1,2,4-oxadiazole-3-carboxamide;
3-(tert-butyl)-N-(4-(2-(cyclopropanecarboxamido)pyridin-4-yl)-2-(trifluoromethyl)benzyl)-1,2,4-oxadiazole-5-carboxamide;
3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide;
(R)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide;
(S)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide;
5-(tert-butyl)-N-(1-(4-(2-(cyclopropanecarboxamido)pyridin-4-yl)-2-methylphenyl)ethyl)-1,2,4-oxadiazole-3-carboxamide;
(R)-5-(tert-butyl)-N-(1-(4-(2-(cyclopropanecarboxamido)pyridin-4-yl)-2-methylphenyl)ethyl)-1,2,4-oxadiazole-3-carboxamide;
(S)-5-(tert-butyl)-N-(1-(4-(2-(cyclopropanecarboxamido)pyridin-4-yl)-2-methylphenyl)ethyl)-1,2,4-oxadiazole-3-carboxamide;
5-(tert-butyl)-N-(4-(2-(cyclopropanecarboxamido)-5-fluoropyridin-4-yl)-2-methylbenzyl)-1,2,4-oxadiazole-3-carboxamide;
5-(tert-butyl)-N-(1-(2-chloro-4-(2-(cyclopropanecarboxamido)pyridin-4-yl)phenyl)ethyl)-1,2,4-oxadiazole-3-carboxamide;
(R)-5-(tert-butyl)-N-(1-(2-chloro-4-(2-(cyclopropanecarboxamido)pyridin-4-yl)phenyl)ethyl)-1,2,4-oxadiazole-3-carboxamide;
(S)-5-(tert-butyl)-N-(1-(2-chloro-4-(2-(cyclopropanecarboxamido)pyridin-4-yl)phenyl)ethyl)-1,2,4-oxadiazole-3-carboxamide;
5-(tert-butyl)-N-(1-(2-chloro-4-(2-(cyclopropanecarboxamido)-5-fluoropyridin-4-yl)phenyl)ethyl)-1,2,4-oxadiazole-3-carboxamide;
(R)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide;
(S)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide;
N-(4-(2-(3-oxabicyclo[3.1.0]hexane-6-carboxamido)pyridin-4-yl)-2-methylbenzyl)-5-(tert-butyl)-1,2,4-oxadiazole-3-carboxamide;
5-(tert-butyl)-N-(2-(2-(cyclopropanecarboxamido)pyridin-4-yl)-3-fluoro-6,7,8,9-tetrahydro-5H-benzo[7]annulen-5-yl)-1,2,4-oxadiazole-3-carboxamide;
(R)-5-(tert-butyl)-N-(2-(2-(cyclopropanecarboxamido)pyridin-4-yl)-3-fluoro-6,7,8,9-tetrahydro-5H-benzo[7]annulen-5-yl)-1,2,4-oxadiazole-3-carboxamide;
(S)-5-(tert-butyl)-N-(2-(2-(cyclopropanecarboxamido)pyridin-4-yl)-3-fluoro-6,7,8,9-tetrahydro-5H-benzo[7]annulen-5-yl)-1,2,4-oxadiazole-3-carboxamide;
5-(tert-butyl)-N-(2-methyl-4-(2-(2-(trifluoromethyl)cyclopropane-1-carboxamido)pyridin-4-yl)benzyl)-1,2,4-oxadiazole-3-carboxamide
5-(tert-butyl)-N-(2-methyl-4-(2-(((1R,2R)-2-(trifluoromethyl)cyclopropane-1-carboxamido)pyridin-4-yl)benzyl)-1,2,4-oxadiazole-3-carboxamide;
5-(tert-butyl)-N-(2-methyl-4-(2-(((1R,2S)-2-(trifluoromethyl)cyclopropane-1-carboxamido)pyridin-4-yl)benzyl)-1,2,4-oxadiazole-3-carboxamide;
5-(tert-butyl)-N-(2-methyl-4-(2-(((1S,2R)-2-(trifluoromethyl)cyclopropane-1-carboxamido)pyridin-4-yl)benzyl)-1,2,4-oxadiazole-3-carboxamide;
5-(tert-butyl)-N-(2-methyl-4-(2-(((1S,2S)-2-(trifluoromethyl)cyclopropane-1-carboxamido)pyridin-4-yl)benzyl)-1,2,4-oxadiazole-3-carboxamide;
5-(tert-butyl)-N-(4-(2-(cyclopropanecarboxamido)-5-(trifluoromethyl)pyridin-4-yl)-2-methylbenzyl)-1,2,4-oxadiazole-3-carboxamide;
3-(tert-butyl)-N-(4-(2-(cyclopropanecarboxamido)pyridin-4-yl)-2-(difluoromethyl)-3-fluorobenzyl)-1,2,4-oxadiazole-5-carboxamide;
1-(tert-butyl)-N-(4-(2-(cyclopropanecarboxamido)pyridin-4-yl)-2-methylbenzyl)-4-fluoro-1H-pyrazole-3-carboxamide;
1-(tert-butyl)-N-(4-(2-(cyclopropanecarboxamido)pyridin-4-yl)-2-cyclopropyl-3-fluorobenzyl)-4-fluoro-1H-pyrazole-3-carboxamide;
2-(tert-butyl)-N-(4-(2-(cyclopropanecarboxamido)pyridin-4-yl)-2-cyclopropyl-3-fluorobenzyl)oxazole-5-carboxamide;
1-(tert-butyl)-N-(4-(2-(cyclopropanecarboxamido)pyridin-4-yl)-3-fluoro-2-methylbenzyl)-4-fluoro-1H-pyrazole-3-carboxamide;
2-(tert-butyl)-N-(4-(2-(cyclopropanecarboxamido)pyridin-4-yl)-3-fluoro-2-methylbenzyl)oxazole-5-carboxamide;
5-(tert-butyl)-N-(4-(2-(cyclopropanecarboxamido)pyridin-4-yl)-2-cyclopropyl-3-fluorobenzyl)-1,2,4-oxadiazole-3-carboxamide;

3-(tert-butyl)-N-(4-(2-(cyclopropanecarboxamido)pyridin-4-yl)-2-cyclopropyl-3-fluorobenzyl)-1,2,4-oxadiazole-5-carboxamide;

N-(4-(2-(cyclopropanecarboxamido)pyridin-4-yl)-2-methylbenzyl)-5-(1-hydroxy-2-methylpropan-2-yl)-1,2,4-oxadiazole-3-carboxamide;

5-(tert-butyl)-N-(2-methyl-4-(2-(spiro[2.3]hexane-1-carboxamido)pyridin-4-yl)benzyl)-1,2,4-oxadiazole-3-carboxamide;

5-(tert-butyl)-N-(4-(2-((1R,2S)-2-fluorocyclopropane-1-carboxamido)pyridin-4-yl)-2-methylbenzyl)-1,2,4-oxadiazole-3-carboxamide;

5-(tert-butyl)-N-(4-(2-((1S,2R)-2-fluorocyclopropane-1-carboxamido)pyridin-4-yl)-2-methylbenzyl)-1,2,4-oxadiazole-3-carboxamide;

N-(4-(2-(cyclopropanecarboxamido)pyridin-4-yl)-2-methylbenzyl)-3-(1-fluoro-2-methylpropan-2-yl)-1,2,4-oxadiazole-5-carboxamide;

5-(tert-butyl)-N-(2-(2-(cyclopropanecarboxamido)pyridin-4-yl)-1-fluoro-6,7,8,9-tetrahydro-5H-benzo[7]annulen-5-yl)-1,2,4-oxadiazole-3-carboxamide;

(R)-5-(tert-butyl)-N-(2-(2-(cyclopropanecarboxamido)pyridin-4-yl)-1-fluoro-6,7,8,9-tetrahydro-5H-benzo[7]annulen-5-yl)-1,2,4-oxadiazole-3-carboxamide;

(S)-5-(tert-butyl)-N-(2-(2-(cyclopropanecarboxamido)pyridin-4-yl)-1-fluoro-6,7,8,9-tetrahydro-5H-benzo[7]annulen-5-yl)-1,2,4-oxadiazole-3-carboxamide;

N-(4-(2-(cyclopropanecarboxamido)pyridin-4-yl)-2-methylbenzyl)-5-(1-fluoro-2-methylpropan-2-yl)-1,2,4-oxadiazole-3-carboxamide;

3-(tert-butyl)-N-(2-(2-(spiro[2.3]hexane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—(R)-2-(2-((R)-spiro[2.3]hexane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((S)-spiro[2.3]hexane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((R)-spiro[2.3]hexane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((S)-spiro[2.3]hexane-1-carboxamido)pyridin-4-yl)-6,7,8,9-tetrahydro-5H-benzo[7]annulen-5-yl)-1,2,4-oxadiazole-5-carboxamide;

3-(tert-butyl)-N-(2-(2-(spiro[2.2]pentane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((R)-spiro[2.2]pentane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((S)-spiro[2.2]pentane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((R)-spiro[2.2]pentane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((S)-spiro[2.2]pentane-1-carboxamido)pyridin-4-yl)-6,7,8,9-tetrahydro-5H-benzo[7]annulen-5-yl)-1,2,4-oxadiazole-5-carboxamide;

5-(tert-butyl)-N-(4-(2-(cyclopropanecarboxamido)-3-fluoropyridin-4-yl)-2-methylbenzyl)-1,2,4-oxadiazole-3-carboxamide;

3-(tert-butyl)-N—((R)-2-(2-((R)-2,2-dimethylcyclopropane-1-carboxamido)pyridin-4-yl)-6,7,8,9-tetrahydro-5H-benzo[7]annulen-5-yl)-1,2,4-oxadiazole-5-carboxamide;

N-(2-(2-(3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1R,5S,6s)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1R,5S,6r)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1R,5R)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1S,5S)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1S,5R,6r)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((R)-2-(2-((1S,5R,6s)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((S)-2-(2-((1R,5S,6s)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((S)-2-(2-((1R,5S,6r)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((S)-2-(2-((1R,5R)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide N—((S)-2-(2-((1S,5S)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((S)-2-(2-((1S,5R,6r)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N—((S)-2-(2-((1S,5R,6s)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide;

N-(4-(2-(cyclopropanecarboxamido)pyridin-4-yl)-2-methylbenzyl)-5-(1-methylcyclopropyl)-1,2,4-oxadiazole-3-carboxamide;

5-(tert-butyl)-N-(4-(2-(2,2-dimethylcyclopropane-1-carboxamido)pyridin-4-yl)-2-methylbenzyl)-1,2,4-oxadiazole-3-carboxamide;

5-(tert-butyl)-N-(4-(2-(2,2-difluorocyclopropane-1-carboxamido)pyridin-4-yl)-2-methylbenzyl)-1,2,4-oxadiazole-3-carboxamide;

3-(tert-butyl)-N-(2-(2-(2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N-(2-(2-(2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N-(2-(2-(2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2R)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1R,2S)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2R)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((R)-2-(2-((1S,2S)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2R)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1R,2S)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2R)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N—((S)-2-(2-((1S,2S)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide;

5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;

(S)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;

(R)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;

3-(tert-butyl)-N-(8-(2-(cyclopropanecarboxamido)pyridin-4-yl)-2,3,4,5-tetrahydrobenzo[b]oxepin-5-yl)-1,2,4-oxadiazole-5-carboxamide;

3-(tert-butyl)-N-(8-(2-(cyclopropanecarboxamido)pyridin-4-yl)-2,3,4,5-tetrahydrobenzo[b]oxepin-5-yl)-1,2,4-oxadiazole-5-carboxamide;

(R)-3-(tert-butyl)-N-(8-(2-(cyclopropanecarboxamido)pyridin-4-yl)-2,3,4,5-tetrahydrobenzo[b]oxepin-5-yl)-1,2,4-oxadiazole-5-carboxamide;

(S)-3-(tert-butyl)-N-(8-(2-(cyclopropanecarboxamido)pyridin-4-yl)-2,3,4,5-tetrahydrobenzo[b]oxepin-5-yl)-1,2,4-oxadiazole-5-carboxamide;

5-(tert-butyl)-N-(4-(2-(cyclopropanecarboxamido)pyridin-4-yl)-2-isopropylbenzyl)-1,2,4-oxadiazole-3-carboxamide;

5-(tert-butyl)-N-(4-(2-(cyclopropanecarboxamido)-5-fluoropyridin-4-yl)-3-fluoro-2-methylbenzyl)-1,2,4-oxadiazole-3-carboxamide;

3-(tert-butyl)-N-(2-(2-(2,2-difluorocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N-((5R)-2-(2-(2,2-difluorocyclopropane-1-carboxamido)pyridin-4-yl)-6,7,8,9-tetrahydro-5H-benzo[7]annulen-5-yl)-1,2,4-oxadiazole-5-carboxamide;

3-(tert-butyl)-N-((5S)-2-(2-(2,2-difluorocyclopropane-1-carboxamido)pyridin-4-yl)-6,7,8,9-tetrahydro-5H-benzo[7]annulen-5-yl)-1,2,4-oxadiazole-5-carboxamide;

N-(2-chloro-4-(2-(cyclopropanecarboxamido)pyridin-4-yl)-3-fluorobenzyl)-5-(1-methylcyclopropyl)-1,2,4-oxadiazole-3-carboxamide;

N-(2-chloro-4-(2-(cyclopropanecarboxamido)pyridin-4-yl)benzyl)-5-(1-methylcyclopropyl)-1,2,4-oxadiazole-3-carboxamide;

5-(tert-butyl)-N-(4-(2-(cyclopropanecarboxamido)pyridin-4-yl)-3,5-difluoro-2-methylbenzyl)-1,2,4-oxadiazole-3-carboxamide;
5-(tert-butyl)-N-(4-(2-(cyclopropanecarboxamido)pyridin-4-yl)-5-fluoro-2-(trifluoromethyl)benzyl)-1,2,4-oxadiazole-3-carboxamide;
2-(tert-butyl)-N-(2-chloro-4-(2-(cyclopropanecarboxamido)pyridin-4-yl)benzyl)oxazole-4-carboxamide;
2-(tert-butyl)-N-(4-(2-(cyclopropanecarboxamido)pyridin-4-yl)-2-methylbenzyl)oxazole-4-carboxamide;
5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;
(R)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;
(S)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide;
3-(tert-butyl)-N-(1-(4-(2-(cyclopropanecarboxamido)pyridin-4-yl)-3-fluoro-2-methylphenyl)ethyl)-1,2,4-oxadiazole-5-carboxamide;
(R)-3-(tert-butyl)-N-(1-(4-(2-(cyclopropanecarboxamido)pyridin-4-yl)-3-fluoro-2-methylphenyl)ethyl)-1,2,4-oxadiazole-5-carboxamide;
(S)-3-(tert-butyl)-N-(1-(4-(2-(cyclopropanecarboxamido)pyridin-4-yl)-3-fluoro-2-methylphenyl)ethyl)-1,2,4-oxadiazole-5-carboxamide;
5-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-3-carboxamide;
(R)-5-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-3-carboxamide;
(S)-5-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-3-carboxamide;
2-(tert-butyl)-N-(2-(2-(cyclopropanecarboxamido)pyridin-4-yl)-6,7,8,9-tetrahydro-5H-benzo[7]annulen-5-yl)oxazole-4-carboxamide;
(R)-2-(tert-butyl)-N-(2-(2-(cyclopropanecarboxamido)pyridin-4-yl)-6,7,8,9-tetrahydro-5H-benzo[7]annulen-5-yl)oxazole-4-carboxamide;
(S)-2-(tert-butyl)-N-(2-(2-(cyclopropanecarboxamido)pyridin-4-yl)-6,7,8,9-tetrahydro-5H-benzo[7]annulen-5-yl)oxazole-4-carboxamide;
3-(tert-butyl)-N-(4-(2-(cyclopropanecarboxamido)pyridin-4-yl)-3-fluoro-2-(trifluoromethyl)benzyl)-1,2,4-oxadiazole-5-carboxamide;
3-(tert-butyl)-N-(1-(2-chloro-4-(2-(cyclopropanecarboxamido)pyridin-4-yl)-5-fluorophenyl)ethyl)-1,2,4-oxadiazole-5-carboxamide;
(R)-3-(tert-butyl)-N-(1-(2-chloro-4-(2-(cyclopropanecarboxamido)pyridin-4-yl)-5-fluorophenyl)ethyl)-1,2,4-oxadiazole-5-carboxamide;
(S)-3-(tert-butyl)-N-(1-(2-chloro-4-(2-(cyclopropanecarboxamido)pyridin-4-yl)-5-fluorophenyl)ethyl)-1,2,4-oxadiazole-5-carboxamide;
5-(tert-butyl)-N-(1-(4-(2-(cyclopropanecarboxamido)pyridin-4-yl)-3-fluoro-2-methylphenyl)ethyl)-1,2,4-oxadiazole-3-carboxamide;
(R)-5-(tert-butyl)-N-(1-(4-(2-(cyclopropanecarboxamido)pyridin-4-yl)-3-fluoro-2-methylphenyl)ethyl)-1,2,4-oxadiazole-3-carboxamide;
(S)-5-(tert-butyl)-N-(1-(4-(2-(cyclopropanecarboxamido)pyridin-4-yl)-3-fluoro-2-methylphenyl)ethyl)-1,2,4-oxadiazole-3-carboxamide;
5-(tert-butyl)-N-(2-(tert-butyl)-4-(2-(cyclopropanecarboxamido)pyridin-4-yl)benzyl)-1,2,4-oxadiazole-3-carboxamide;
5-(tert-butyl)-N-(4-(2-(cyclopropanecarboxamido)pyridin-4-yl)-2-ethylbenzyl)-1,2,4-oxadiazole-3-carboxamide;
5-(tert-butyl)-N-(1-(2-chloro-4-(2-(cyclopropanecarboxamido)pyridin-4-yl)-3-fluorophenyl)ethyl)-1,2,4-oxadiazole-3-carboxamide;
(R)-5-(tert-butyl)-N-(1-(2-chloro-4-(2-(cyclopropanecarboxamido)pyridin-4-yl)-3-fluorophenyl)ethyl)-1,2,4-oxadiazole-3-carboxamide;
(S)-5-(tert-butyl)-N-(1-(2-chloro-4-(2-(cyclopropanecarboxamido)pyridin-4-yl)-3-fluorophenyl)ethyl)-1,2,4-oxadiazole-3-carboxamide;
3-(tert-butyl)-N-(1-(2-chloro-4-(2-(cyclopropanecarboxamido)pyridin-4-yl)-3-fluorophenyl)ethyl)-1,2,4-oxadiazole-5-carboxamide;
(R)-3-(tert-butyl)-N-(1-(2-chloro-4-(2-(cyclopropanecarboxamido)pyridin-4-yl)-3-fluorophenyl)ethyl)-1,2,4-oxadiazole-5-carboxamide;
(S)-3-(tert-butyl)-N-(1-(2-chloro-4-(2-(cyclopropanecarboxamido)pyridin-4-yl)-3-fluorophenyl)ethyl)-1,2,4-oxadiazole-5-carboxamide;
5-(tert-butyl)-N-(1-(2-chloro-4-(2-(cyclopropanecarboxamido)pyridin-4-yl)-5-fluorophenyl)ethyl)-1,2,4-oxadiazole-3-carboxamide;
(R)-5-(tert-butyl)-N-(1-(2-chloro-4-(2-(cyclopropanecarboxamido)pyridin-4-yl)-5-fluorophenyl)ethyl)-1,2,4-oxadiazole-3-carboxamide;
(S)-5-(tert-butyl)-N-(1-(2-chloro-4-(2-(cyclopropanecarboxamido)pyridin-4-yl)-5-fluorophenyl)ethyl)-1,2,4-oxadiazole-3-carboxamide;
5-(tert-butyl)-N-(4-(2-(cyclopropanecarboxamido)pyridin-4-yl)-2-cyclopropylbenzyl)-1,2,4-oxadiazole-3-carboxamide;
5-(tert-butyl)-N-(1-(4-(2-(cyclopropanecarboxamido)pyridin-4-yl)-2-(trifluoromethyl)phenyl)ethyl)-1,2,4-oxadiazole-3-carboxamide;
(R)-5-(tert-butyl)-N-(1-(4-(2-(cyclopropanecarboxamido)pyridin-4-yl)-2-(trifluoromethyl)phenyl)ethyl)-1,2,4-oxadiazole-3-carboxamide;
(S)-5-(tert-butyl)-N-(1-(4-(2-(cyclopropanecarboxamido)pyridin-4-yl)-2-(trifluoromethyl)phenyl)ethyl)-1,2,4-oxadiazole-3-carboxamide;
3-(tert-butyl)-N-(1-(4-(2-(cyclopropanecarboxamido)pyridin-4-yl)-2-(trifluoromethyl)phenyl)ethyl)-1,2,4-oxadiazole-5-carboxamide;
(R)-3-(tert-butyl)-N-(1-(4-(2-(cyclopropanecarboxamido)pyridin-4-yl)-2-(trifluoromethyl)phenyl)ethyl)-1,2,4-oxadiazole-5-carboxamide;
(S)-3-(tert-butyl)-N-(1-(4-(2-(cyclopropanecarboxamido)pyridin-4-yl)-2-(trifluoromethyl)phenyl)ethyl)-1,2,4-oxadiazole-5-carboxamide;
3-(tert-butyl)-N-(4-(2-(cyclopropanecarboxamido)pyridin-4-yl)-2-(trifluoromethoxy)benzyl)-1,2,4-oxadiazole-5-carboxamide;
2-(tert-butyl)-N-(4-(2-(cyclopropanecarboxamido)pyridin-4-yl)-2-methylbenzyl)thiazole-5-carboxamide;
5-(tert-butyl)-N-(4-(2-(1-fluorocyclopropane-1-carboxamido)pyridin-4-yl)-2-methylbenzyl)-1,2,4-oxadiazole-3-carboxamide;
5-(tert-butyl)-N-(1-(4-(2-(cyclopropanecarboxamido)pyridin-4-yl)-2-(trifluoromethoxy)phenyl)ethyl)-1,2,4-oxadiazole-3-carboxamide;
(R)-5-(tert-butyl)-N-(1-(4-(2-(cyclopropanecarboxamido)pyridin-4-yl)-2-(trifluoromethoxy)phenyl)ethyl)-1,2,4-oxadiazole-3-carboxamide;

(S)-5-(tert-butyl)-N-(1-(4-(2-(cyclopropanecarboxamido)pyridin-4-yl)-2-(trifluoromethoxy)phenyl)ethyl)-1,2,4-oxadiazole-3-carboxamide;
5-(tert-butyl)-N-(3-chloro-4-(2-(cyclopropanecarboxamido)pyridin-4-yl)-2-methylbenzyl)-1,2,4-oxadiazole-3-carboxamide;
5-(tert-butyl)-N-(1-(4-(2-(cyclopropanecarboxamido)pyridin-4-yl)-5-fluoro-2-methylphenyl)ethyl)-1,2,4-oxadiazole-3-carboxamide;
(R)-5-(tert-butyl)-N-(1-(4-(2-(cyclopropanecarboxamido)pyridin-4-yl)-5-fluoro-2-methylphenyl)ethyl)-1,2,4-oxadiazole-3-carboxamide;
(S)-5-(tert-butyl)-N-(1-(4-(2-(cyclopropanecarboxamido)pyridin-4-yl)-5-fluoro-2-methylphenyl)ethyl)-1,2,4-oxadiazole-3-carboxamide;
5-(tert-butyl)-N-(4-(2-(cyclopropanecarboxamido)pyridin-4-yl)-3-fluoro-2-(trifluoromethyl)benzyl)-1,2,4-oxadiazole-3-carboxamide;
5-(tert-butyl)-N-(4-(2-(cyclopropanecarboxamido)pyridin-4-yl)-2-methoxybenzyl)-1,2,4-oxadiazole-3-carboxamide;
5-(tert-butyl)-N-(2-cyclobutyl-4-(2-(cyclopropanecarboxamido)pyridin-4-yl)benzyl)-1,2,4-oxadiazole-3-carboxamide;
1-(tert-butyl)-N-(4-(2-(cyclopropanecarboxamido)pyridin-4-yl)-2-methylbenzyl)-1H-1,2,3-triazole-4-carboxamide;
5-(tert-butyl)-N-(4-(2-(cyclopropanecarboxamido)pyridin-4-yl)-2-methylbenzyl)-1,3,4-oxadiazole-2-carboxamide;
3-(tert-butyl)-N-(1-(2-chloro-4-(2-(cyclopropanecarboxamido)pyridin-4-yl)phenyl)ethyl)-1,2,4-oxadiazole-5-carboxamide;
(R)-3-(tert-butyl)-N-(1-(2-chloro-4-(2-(cyclopropanecarboxamido)pyridin-4-yl)phenyl)ethyl)-1,2,4-oxadiazole-5-carboxamide;
(S)-3-(tert-butyl)-N-(1-(2-chloro-4-(2-(cyclopropanecarboxamido)pyridin-4-yl)phenyl)ethyl)-1,2,4-oxadiazole-5-carboxamide;
3-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-5-carboxamide;
(R)-3-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-5-carboxamide;
(S)-3-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-5-carboxamide;
3-(tert-butyl)-N-(1-(4-(2-(cyclopropanecarboxamido)pyridin-4-yl)-2-methylphenyl)ethyl)-1,2,4-oxadiazole-5-carboxamide;
(R)-3-(tert-butyl)-N-(1-(4-(2-(cyclopropanecarboxamido)pyridin-4-yl)-2-methylphenyl)ethyl)-1,2,4-oxadiazole-5-carboxamide;
(S)-3-(tert-butyl)-N-(1-(4-(2-(cyclopropanecarboxamido)pyridin-4-yl)-2-methylphenyl)ethyl)-1,2,4-oxadiazole-5-carboxamide;
3-(tert-butyl)-N-(4-(2-(cyclopropanecarboxamido)pyridin-4-yl)-3-fluoro-2-methylbenzyl)-1,2,4-oxadiazole-5-carboxamide;
1-(tert-butyl)-N-(4-(2-(cyclopropanecarboxamido)pyridin-4-yl)-2-methylbenzyl)-1H-imidazole-4-carboxamide;
1-(tert-butyl)-N-(4-(2-(cyclopropanecarboxamido)pyridin-4-yl)-2-methylbenzyl)-1H-pyrazole-4-carboxamide;
4-(tert-butyl)-N-(4-(2-(cyclopropanecarboxamido)pyridin-4-yl)-2-methylbenzyl)oxazole-2-carboxamide;
5-(tert-butyl)-N-(4-(2-(cyclopropanecarboxamido)pyridin-4-yl)-2-methylbenzyl)oxazole-2-carboxamide;
1-(tert-butyl)-N-(4-(2-(cyclopropanecarboxamido)pyridin-4-yl)-2-methylbenzyl)-1H-pyrazole-3-carboxamide;
3-(tert-butyl)-N-(4-(2-(cyclopropanecarboxamido)pyridin-4-yl)-2-fluoro-3-methylbenzyl)-1,2,4-oxadiazole-5-carboxamide;
5-(tert-butyl)-N-(4-(2-(cyclopropanecarboxamido)pyridin-4-yl)-2-fluoro-3-methylbenzyl)-1,2,4-oxadiazole-3-carboxamide;
5-(tert-butyl)-N-(4-(2-(cyclopropanecarboxamido)pyridin-4-yl)-2-fluoro-5-methylbenzyl)-1,2,4-oxadiazole-3-carboxamide;
5-(tert-butyl)-N-(4-(2-(cyclopropanecarboxamido)-5-fluoropyridin-4-yl)-5-fluoro-2-methylbenzyl)-1,2,4-oxadiazole-3-carboxamide;
5-(tert-butyl)-N-(2-chloro-4-(2-(cyclopropanecarboxamido)pyridin-4-yl)-5-fluorobenzyl)-1,2,4-oxadiazole-3-carboxamide;
5-(tert-butyl)-N-(4-(2-(cyclopropanecarboxamido)pyridin-4-yl)-2-methylbenzyl)isoxazole-3-carboxamide;
5-(tert-butyl)-N-(4-(2-(cyclopropanecarboxamido)-5-fluoropyridin-4-yl)-2-methylbenzyl)-1,2,4-oxadiazole-3-carboxamide; and
5-(tert-butyl)-N-(4-(2-(cyclopropanecarboxamido)pyridin-4-yl)-2-(trifluoromethoxy)benzyl)-1,2,4-oxadiazole-3-carboxamide,
or a pharmaceutically acceptable salt thereof.

In a specific embodiment, the compound of the present invention is selected from:

3-(tert-butyl)-N-(4-(2-(cyclopropanecarboxamido)pyridin-4-yl)-2-methylbenzyl)-1,2,4-oxadiazole-5-carboxamide hydrochloride;
5-(tert-butyl)-N-(4-(2-(cyclopropanecarboxamido)pyridin-4-yl)-2-methylbenzyl)-1,2,4-oxadiazole-3-carboxamide hydrochloride;
5-(tert-butyl)-N-(4-(2-((1S,2S)-2-fluorocyclopropane-1-carboxamido)pyridin-4-yl)-2-methylbenzyl)-1,2,4-oxadiazole-3-carboxamide;
5-(tert-butyl)-N-(4-(2-((1R,2R)-2-fluorocyclopropane-1-carboxamido)pyridin-4-yl)-2-methylbenzyl)-1,2,4-oxadiazole-3-carboxamide;
5-(tert-butyl)-N-(2-methyl-4-(2-((1S,2S)-2-methylcyclopropane-1-carboxamido)pyridin-4-yl)benzyl)-1,2,4-oxadiazole-3-carboxamide;
5-(tert-butyl)-N-(2-methyl-4-(2-((1R,2R)-2-methylcyclopropane-1-carboxamido)pyridin-4-yl)benzyl)-1,2,4-oxadiazole-3-carboxamide;
5-(tert-butyl)-N-(4-(5-chloro-2-cyclopropanecarboxamido)pyridin-4-yl)-2-methylbenzyl)-1,2,4-oxadiazole-3-carboxamide;
5-(tert-butyl)-N-(2-chloro-4-(2-(cyclopropanecarboxamido)pyridin-4-yl)benzyl)-1,2,4-oxadiazole-3-carboxamide;
3-(tert-butyl)-N-(2-chloro-4-(2-(cyclopropanecarboxamido)pyridin-4-yl)benzyl)-1,2,4-oxadiazole-5-carboxamide;
(R)-5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide;
5-(tert-butyl)-N-(4-(2-(cyclopropanecarboxamido)pyridin-4-yl)-3-fluoro-2-methylbenzyl)-1,2,4-oxadiazole-3-carboxamide;
3-(tert-butyl)-N-(4-(2-(cyclopropanecarboxamido)pyridin-4-yl)-5-fluoro-2-methylbenzyl)-1,2,4-oxadiazole-5-carboxamide;
5-(tert-butyl)-N-(4-(2-(cyclopropanecarboxamido)pyridin-4-yl)-5-fluoro-2-methylbenzyl)-1,2,4-oxadiazole-3-carboxamide;

5-(tert-butyl)-N-(2-chloro-4-(2-(cyclopropanecarboxamido) pyridin-4-yl)-3-fluorobenzyl)-1,2,4-oxadiazole-3-carboxamide;

3-(tert-butyl)-N-(2-chloro-4-(2-(cyclopropanecarboxamido) pyridin-4-yl)-3-fluorobenzyl)-1,2,4-oxadiazole-5-carboxamide;

5-(tert-butyl)-N-(4-(2-(cyclopropanecarboxamido)pyridin-4-yl)-2-(trifluoromethyl)benzyl)-1,2,4-oxadiazole-3-carboxamide;

3-(tert-butyl)-N-(4-(2-(cyclopropanecarboxamido)pyridin-4-yl)-2-(trifluoromethyl)benzyl)-1,2,4-oxadiazole-5-carboxamide;

(R)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide;

(R)-5-(tert-butyl)-N-(1-(4-(2-(cyclopropanecarboxamido) pyridin-4-yl)-2-methylphenyl)ethyl)-1,2,4-oxadiazole-3-carboxamide;

5-(tert-butyl)-N-(4-(2-(cyclopropanecarboxamido)-5-fluoropyridin-4-yl)-2-methylbenzyl)-1,2,4-oxadiazole-3-carboxamide;

(R)-5-(tert-butyl)-N-(1-(2-chloro-4-(2-(cyclopropanecarboxamido)pyridin-4-yl)phenyl)ethyl)-1,2,4-oxadiazole-3-carboxamide; and (R)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide, or a pharmaceutically acceptable salt thereof.

As used herein, the term "alkyl" refers to a fully saturated branched or unbranched hydrocarbon moiety. Preferably the alkyl comprises 1 to 6 carbon atoms, or 1 to 4 carbon atoms.

In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, or n-hexyl.

"Alkenyl" refers to an unsaturated hydrocarbon group which may be linear or branched and has at least one carbon-carbon double bond. Alkenyl groups with 2-6 carbon atoms can be preferred. The alkenyl group may contain 1, 2 or 3 carbon-carbon double bonds, or more.

Examples of alkenyl groups include ethenyl, n-propenyl, iso-propenyl, n-but-2-enyl, n-hex-3-enyl and the like.

"Alkynyl" refers to an unsaturated hydrocarbon group which may be linear or branched and has at least one carbon-carbon triple bond. Alkynyl groups with 2-6 carbon atoms can be preferred. The alkynyl group may contain 1, 2 or 3 carbon-carbon triple bonds, or more. Examples of alkynyl groups include ethynyl, n-propynyl, n-but-2-ynyl, n-hex-3-ynyl and the like.

The number of carbon atoms in a group is specified herein by the prefix "$C_{x-xx}$", wherein x and xx are integers. For example, "$C_{1-4}$alkyl" is an alkyl group which has from 1 to 4 carbon atoms.

"Halogen" or "halo" may be fluoro, chloro, bromo or iodo.

As used herein, the term "heterocyclyl" refers to a saturated or unsaturated, monocyclic or bicyclic (e.g., fused, bridged or spiro ring systems) ring system which has from 3- to 11-ring members, or in particular 3- to 8-ring members, 3- to 7-ring members, 3- to 6-ring members, 4- to 6-ring members, 5- to 7-ring members, or 4- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings.

As used herein, the term "heteroaryl" refers to an aromatic 5- or 6-membered monocyclic ring system, having 1 to 4 heteroatoms independently selected from O, S and N, and wherein N can be oxidized (e.g., N(O)) or quaternized, and S can be optionally oxidized to sulfoxide and sulfone. Examples of heteroaryls include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl. In one embodiment, the heteroaryl is an aromatic 5-membered monocyclic ring system. Examples of 5-membered heteroaryl include, but are not limited to, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, and tetrazolyl. As used herein, a "5-membered N-containing heteroaryl" is a 5-membered heteroaryl having at least one nitrogen ring atom.

In one embodiment, a heterocyclyl is a 3- to 7-membered saturated monocyclic or a 3- to 6-membered saturated monocyclic or a 5- to 7-membered saturated monocyclic ring or a 4- to 6-membered saturated monocyclic ring. In one embodiment, a heterocyclyl is a 4- to 6-membered monocyclic ring. In another embodiment, a heterocyclyl is a 11-membered bicyclic ring. In yet another embodiment, a heterocyclyl is a 4- to 7-membered monocyclic non-aromatic ring. In another embodiment, a heterocyclyl is 6- to 8-membered spiro or bridged bicyclic ring. The heterocyclyl group can be attached at a heteroatom or a carbon atom. Examples of heterocyclyls include, but are not limited to, aziridinyl, oxiranyl, thiiranyl, oxaziridinyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like.

The term "fused ring system", as used herein, is a ring system that has two rings each of which are independently selected from a carbocyclyl or a heterocyclyl, wherein the two ring structures share two adjacent ring atoms. A fused ring system may have from 9 to 12 ring members.

The term "bridged ring system", as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6 to 8 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 8 ring members.

In one embodiment, a heterocyclyl is a 4- to 6-membered monocyclic heterocyclyl. Examples of 4- to 6-membered monocyclic heterocyclic ring systems include, but are not limited to azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, dihydrofuranyl, imidazolinyl, dihydropyranyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, and tetrazinyl.

In another embodiment, a heterocyclyl is a saturated 4- to 6-membered monocyclic heterocyclyl. Examples of saturated 4- to 6-membered monocyclic heterocyclic ring systems include, but are not limited to azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, and dithiinyl. In another embodiment, a saturated 4- to 6-membered monocyclic heterocyclyl is oxetanyl, tetrahydrofuranyl, or tetrahydropyranyl.

In another embodiment, a heterocyclyl is a saturated 4- to 5-membered monocyclic heterocyclyl. Examples of saturated 4- to 5-membered monocyclic heterocyclic ring systems include, but are not limited to azetidinyl, oxetanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, and oxathiolanyl.

As used herein, the term "carbocyclyl" refers to saturated or unsaturated monocyclic or bicyclic hydrocarbon groups of 3-12, 3-7, 3-5, 3-6, 4-6, or 5-7 carbon atoms. The term "carbocyclyl" encompasses cycloalkyl groups and aromatic groups. The term "cycloalkyl" refers to completely saturated monocyclic or bicyclic or spiro hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopentenyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1] heptyl, spiro[2.2]pentanyl, and spiro[3.3]heptanyl. In one embodiment, the carbocyclyl is a 4- to 6-membered monocyclic carbocyclyl. In another embodiment, the carbocyclyl is a $C_{3-5}$cycloalkyl, such as cyclopropyl, cyclobutyl, or cyclopentyl. In one embodiment, the carbocyclyl is a $C_{4-6}$ cycloalkyl, such as, cyclobutyl, cyclopentyl or cyclohexyl.

In cases where a compound provided herein is sufficiently basic or acidic to form stable nontoxic acid or base salts, preparation and administration of the compounds as pharmaceutically acceptable salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocycloalkyl amines, diheterocycloalkyl amines, triheterocycloalkyl amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocycloalkyl and the like. Also included are amines where the two or three substituents, together with the amino nitrogen, form a heterocycloalkyl or heteroaryl group. Non-limiting examples of amines can include, isopropylamine, trimethyl amine, diethyl amine, tri(iso-propyl) amine, tri(n-propyl) amine, ethanolamine, 2-dimethylaminoethanol, trimethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

The compounds or pharmaceutically acceptable salts thereof as described herein, can contain one or more asymmetric centers in the molecule. In accordance with the present disclosure any structure that does not designate the stereochemistry is to be understood as embracing all the various stereoisomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase).

When a particular stereoisomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired stereoisomer relative to the combined weight of all stereoisomers.

When a particular enantiomer of a compound is depicted by name or structure, the stereochemical purity of the compounds is at least 20%, 30%, 40%, 50%, 60%, 70%, 80%, 90%, 95%, 97%, 99%, 99.5% or 99.9%. "Stereochemical purity" means the weight percent of the desired enantiomer relative to the combined weight of all stereoisomers.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 20%, 30%, 40%, 50%, 60%, 70%, 80%, 90%, 95%, 97%, 99%, 99.5% or 99.9%. The stereoisomeric purity the weight percent of the desired stereoisomers encompassed by the name or structure relative to the combined weight of all of the stereoisomers.

When a disclosed compound is named or depicted by structure without indicating the stereochemistry, and the compound has one chiral center, it is to be understood that the name or structure encompasses one enantiomer of compound in pure or substantially pure form, as well as mixtures thereof (such as a racemic mixture of the compound and mixtures enriched in one enantiomer relative to its corresponding optical isomer).

When a disclosed compound is named or depicted by structure without indicating the stereochemistry and, e.g., the compound has at least two chiral centers, it is to be understood that the name or structure encompasses one stereoisomer in pure or substantially pure form, as well as mixtures thereof (such as mixtures of stereoisomers, and mixtures of stereoisomers in which one or more stereoisomers is enriched relative to the other stereoisomer(s)).

The disclosed compounds may exist in tautomeric forms and mixtures and separate individual tautomers are contemplated. In addition, some compounds may exhibit polymorphism.

In one embodiment, the compounds of the invention or a pharmaceutically acceptable salt thereof include deuterium.

Another embodiment is a pharmaceutical composition comprising at least one compound described herein, or a pharmaceutically acceptable salt thereof, and at least one pharmaceutically acceptable carrier.

The compounds, or pharmaceutically acceptable salts thereof described herein may be used to decrease the activity of Btk, or to otherwise affect the properties and/or behavior of Btk, e.g., stability, phosphorylation, kinase activity, interactions with other proteins, etc.

In some embodiments, the present invention provides methods of decreasing Btk enzymatic activity. In some embodiments, such methods include contacting a Btk with an effective amount of a Btk inhibitor. Therefore, the present invention further provides methods of inhibiting Btk enzymatic activity by contacting a Btk with a Btk inhibitor of the present invention.

One embodiment of the invention includes a method of treating a disorder responsive to inhibition of Btk in a subject comprising administering to said subject an effective amount of at least one compound described herein, or a pharmaceutically acceptable salt thereof.

In one embodiment, the present invention provides methods of treating autoimmune disorders, inflammatory disorders, and cancers in a subject in need thereof comprising administering to said subject an effective amount of at least one compound described herein, or a pharmaceutically acceptable salt thereof.

The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barre syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjogren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In some embodiments, the present invention provides a method of treating rheumatoid arthritis or lupus. In some embodiments, the present invention provides a method of treating multiple sclerosis.

The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

As used herein, the term "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or "treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; or delaying, inhibiting or decreasing the likelihood of the progression of the disease, disorder or syndrome.

The effective dose of a compound provided herein, or a pharmaceutically acceptable salt thereof, administered to a subject can be 10 µg-500 mg.

Administering a compound described herein, or a pharmaceutically acceptable salt thereof, to a mammal comprises any suitable delivery method. Administering a compound described herein, or a pharmaceutically acceptable salt thereof, to a mammal includes administering a compound described herein, or a pharmaceutically acceptable salt thereof, topically, enterally, parenterally, transdermally, transmucosally, via inhalation, intracisternally, epidurally, intravaginally, intravenously, intramuscularly, subcutaneously, intradermally or intravitreally to the mammal. Administering a compound described herein, or a pharmaceutically acceptable salt thereof, to a mammal also includes administering topically, enterally, parenterally, transdermally, transmucosally, via inhalation, intracisternally, epidurally, intravaginally, intravenously, intramuscularly, subcutaneously, intradermally or intravitreally to a mammal a compound that metabolizes within or on a surface of the body of the mammal to a compound described herein, or a pharmaceutically acceptable salt thereof.

Thus, a compound or pharmaceutically acceptable salt thereof as described herein, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound or pharmaceutically acceptable salt thereof as described herein may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent.

The active compound may also be administered intravenously or intraperitoneally by infusion or injection. Solutions of the active compound or its salts can be prepared in water, optionally mixed with a nontoxic surfactant.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions. In all cases, the ultimate dosage form should be sterile, fluid and stable under the conditions of manufacture and storage.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

Exemplary solid carriers can include finely divided solids such as talc, clay, microcrystalline cellulose, silica, alumina and the like. Useful liquid carriers include water, alcohols or glycols or water-alcohol/glycol blends, in which the compounds or pharmaceutically acceptable salts thereof as described herein can be dissolved or dispersed at effective levels, optionally with the aid of non-toxic surfactants.

Useful dosages of a compound or pharmaceutically acceptable salt thereof as described herein can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

The amount of a compound or pharmaceutically acceptable salt thereof as described herein, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The a compound or pharmaceutically acceptable salt thereof as described herein can be conveniently administered in unit dosage form; for example, containing 0.01 to 10 mg, or 0.05 to 1 mg, of active ingredient per unit dosage form. In some embodiments, a dose of 5 mg/kg or less can be suitable.

The desired dose may conveniently be presented in a single dose or as divided doses administered at appropriate intervals.

The disclosed method can include a kit comprising a compound or pharmaceutically acceptable salt thereof as described herein and instructional material which can describe administering a compound or pharmaceutically acceptable salt thereof as described herein or a composition comprising a compound or pharmaceutically acceptable salt thereof as described herein to a cell or a subject. This should be construed to include other embodiments of kits that are known to those skilled in the art, such as a kit comprising a (such as sterile) solvent for dissolving or suspending a compound or pharmaceutically acceptable salt thereof as described herein or composition prior to administering a compound or pharmaceutically acceptable salt thereof as described herein or composition to a cell or a subject. In some embodiments, the subject can be a human.

EXEMPLIFICATIONS

LCMS methods: Samples were analyzed on a Waters Acquity UPLC BEH C18 1.7 μM 2.1×50 mm, part number 186002350 machine, MS mode: MS:ESI+ scan range 100-1000 daltons. PDA detection 210-400 nm. The method utilized was 95% $H_2O$/5% $CH_3CN$ (initial conditions) linear gradient to 5% $H_2O$/95% $CH_3CN$ at 1 min, HOLD 5% $H_2O$/95% $CH_3CN$ to 1.3 min at 0.7 ml/min in 0.1% trifluoroacetic acid (0.1% v/v) and the injection volume was 0.5 μL.

Example 1: 3-(tert-butyl)-N-(4-(2-(cyclopropanecarboxamido)pyridin-4-yl)-2-methylbenzyl)-1,2,4-oxadiazole-5-carboxamide hydrochloride (Compound 1)

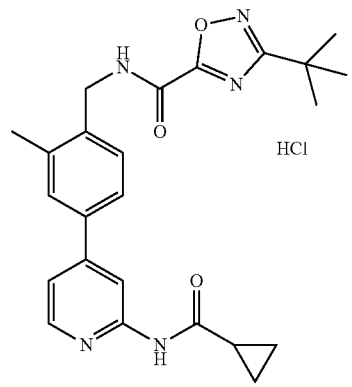

1. Synthesis of (4-bromo-2-methylphenyl)methanamine

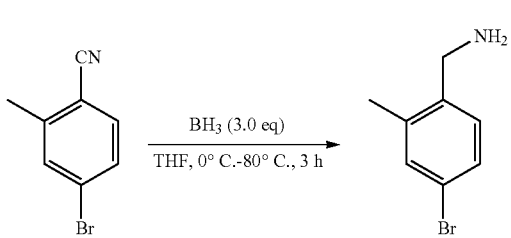

To a solution of 4-bromo-2-methylbenzonitrile (3 g, 15 mmol) in THF (20 mL) was added BH$_3$·THF (1 M, 45 mL, 45 mmol) at 0° C. The solution was stirred for 1 h and heated to 80° C. for 2 h. The mixture was quenched with H$_2$O (50 mL) and extracted with EtOAc (50 mL×3). The organic layer was concentrated in vacuo to afford a residue which was suspended in a saturated HCl/EtOAc solution and filtered. The filter cake was washed with diethyl ether (20 mL×3) and dried under vacuum to afford (4-bromo-2-methylphenyl)methanamine hydrochloride as white solid (2.1 g, yield: 69%). ESI-MS (M+H)$^+$: 200.1.

2. Synthesis of tert-butyl 4-bromo-2-methylbenzylcarbamate

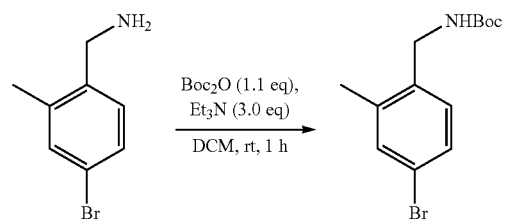

To a solution of (4-bromo-2-methylphenyl)methanamine (1.2 g, 6 mmol) in DCM (30 mL) were added Et$_3$N (1.82 g, 18 mmol) and Boc$_2$O (1.43 g, 6.6 mmol). The mixture was stirred at rt for 1 h, diluted with water (50 mL), and extracted with DCM (50 mL×2). The organic phase was washed with brine (50 mL), dried (Na$_2$SO$_4$), filtered, and concentrated in vacuo to afford tert-butyl (4-bromo-2-methylbenzyl)carbamate as a white solid (1.7 g, yield: 95%), which was carried forward without further purification. ESI-MS (M+H)$^+$: 300.1.

3. Synthesis of tert-butyl 2-methyl-4-(4,4,5,5-tetramethyl-1,3,2-dioxaborolan-2-yl)benzylcarbamate

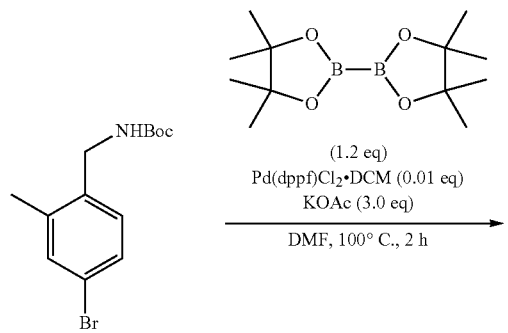

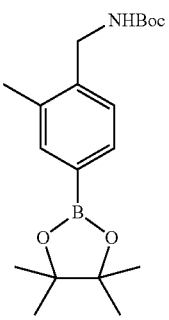

To a solution of tert-butyl (4-bromo-2-methylbenzyl)carbamate (1.5 g, 5.0 mmol) in DMF (6 mL) were added bis(pinacolato)diboron (1.52 g, 6.0 mmol), KOAc (1.75 g, 18 mmol) and Pd(dppf)Cl$_2$·DCM (407 mg, 0.5 mmol) under nitrogen. The mixture was stirred at 100° C. for 2 h, cooled to rt, diluted with water (50 mL), and extracted with EtOAc (100 mL×3). The combined organic layer was washed with brine, dried (Na$_2$SO$_4$), concentrated in vacuo, and purified by silica-gel column chromatography (petroleum ether/EtOAc, 10:1) to give tert-butyl (2-methyl-4-(4,4,5,5-tetramethyl-1,3,2-dioxaborolan-2-yl)benzyl)carbamate as white solid (1.2 g, yield: 69%). ESI-MS (M+H)$^+$: 348.2. $^1$H NMR (400 MHz, CDCl$_3$) δ: 7.61-7.59 (m, 2H), 7.26 (s, 1H), 4.68 (br s, 1H), 4.33 (d, J=5.6 Hz, 2H), 2.32 (s, 3H), 1.45 (s, 9H), 1.34 (s, 12H).

4. Synthesis of N-(4-bromo-2-pyridyl)cyclopropanecarboxamide

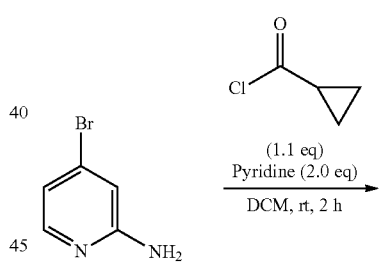

Pyridine (914 mg, 12 mmol, 933 μL) was added to a solution of 4-bromopyridin-2-amine (1.00 g, 6 mmol) in DCM (19 mL) and the reaction mixture was stirred at rt for 5 min. Cyclopropanecarbonyl chloride (725 mg, 7 mmol, 631 μL) was added and the solution was stirred for 2 h. The reaction mixture was concentrated and purified by silica-gel column chromatography (EtOAc/heptanes, grading from 0% to 50%) to give N-(4-bromo-2-pyridyl)cyclopropanecarboxamide as a white solid (1.39 g, yield: 100%). ESI-MS (M+H)$^+$: 243.0.

5. Synthesis of tert-butyl N-[[4-[2-(cyclopropanecarbonylamino)-4-pyridyl]-2-methyl-phenyl]methyl]carbamate

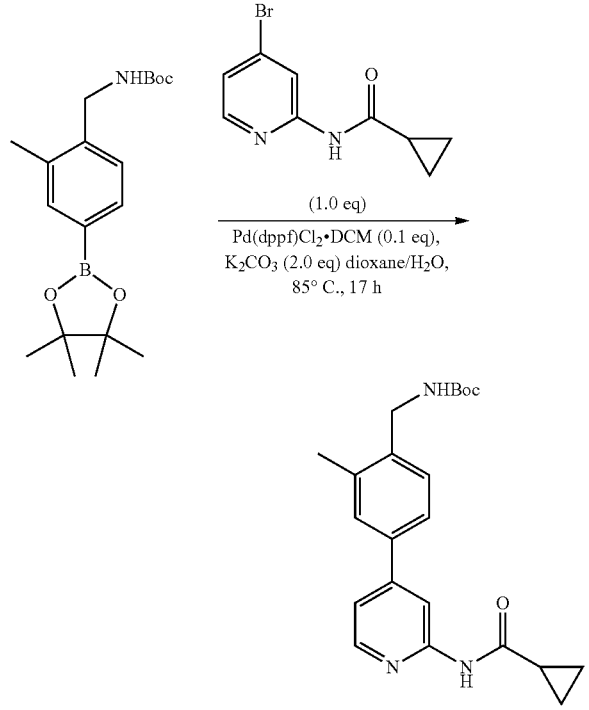

To a solution of tert-butyl N-[[2-methyl-4-(4,4,5,5-tetramethyl-1,3,2-dioxaborolan-2-yl)phenyl]methyl]carbamate (3.00 g, 8.6 mmol) in 1,4-dioxane/H$_2$O (v/v=20/1, 210 mL) were added N-(4-bromo-2-pyridyl)cyclopropanecarboxamide (2.1 g, 8.6 mmol), Pd(dppf)Cl$_2$·DCM (353 mg, 432 μmol) and K$_2$CO$_3$ (2.4 g, 17.3 mmol). The mixture was heated to 85° C. and was stirred at that temperature for 17 h. The mixture was concentrated to give crude material, which was purified by silica-gel column chromatography (petroleum ether/EtOAc, grading from 10:1 to 2:1) to give tert-butyl N-[[4-[2-(cyclopropanecarbonylamino)-4-pyridyl]-2-methyl-phenyl]methyl]carbamate as a white solid (3.1 g, yield: 94%). ESI-MS (M+H)$^+$: 382.4.

6. Synthesis of N-[4-[4-(aminomethyl)-3-methyl-phenyl]-2-pyridyl]cyclopropanecarboxamide hydrochloride

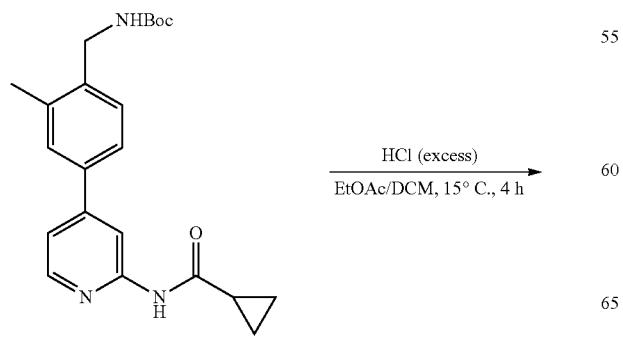

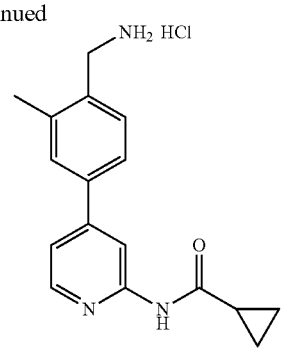

To a solution of tert-butyl N-[[4-[2-(cyclopropanecarbonylamino)-4-pyridyl]-2-methyl-phenyl]methyl]carbamate (3.1 g, 8.1 mmol) in DCM (150 mL) was added a solution of HCl in EtOAc (4.0 M, 60 mL). The mixture was stirred at 15° C. for 4 h. The reaction mixture was concentrated to give crude N-[4-[4-(aminomethyl)-3-methyl-phenyl]-2-pyridyl]cyclopropane-carboxamide hydrochloride (2.5 g, yield: 97%), which was carried forward without further purification. ESI-MS (M+H)$^+$: 282.0.

7. Synthesis of 3-(tert-butyl)-N-(4-(2-(cyclopropanecarboxamido)pyridin-4-yl)-2-methylbenzyl)-1,2,4-oxadiazole-5-carboxamide hydrochloride (Compound 1)

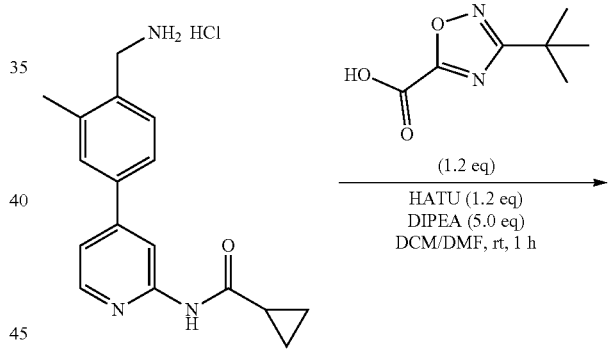

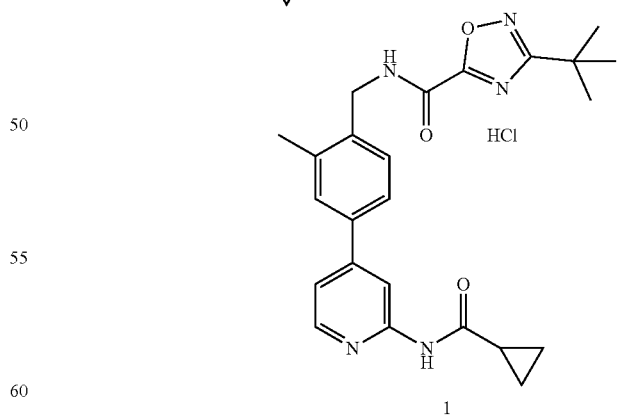

To a solution of N-(4-(4-(aminomethyl)-3-methylphenyl)pyridin-2-yl)cyclopropanecarboxamide hydrochloride (120 mg, 377 μmol) in a mixture of DCM/DMF (v/v=25/1, 52 mL) were added 3-(tert-butyl)-1,2,4-oxadiazole-5-carboxylic acid (77 mg, 453 μmol), HATU (172 mg, 453 μmol) and DIPEA (244 mg, 1.89 mmol). The reaction mixture was stirred at rt for 1 h. The mixture was poured into H$_2$O (100 mL) and was extracted with DCM (50 mL×2). The combined organic layers were concentrated to give crude material, which was purified by prep-HPLC (CH$_3$CN/H$_2$O with 0.05% HCl/H$_2$O as mobile phase) to give 3-(tert-butyl)-N-(4-(2-(cyclopropanecarboxamido)pyridin-4-yl)-2-methylbenzyl)-1,2,4-oxadiazole-5-carboxamide hydrochloride as a white solid (59 mg, yield: 36%). ESI-MS (M+H)$^+$: 434.2. $^1$H NMR (400 MHz, CD$_3$OD) δ: 8.31 (d, J=6.4 Hz, 1H), 7.79 (s, 1H), 7.77-7.74 (m, 1H), 7.70-7.64 (m, 2H), 7.52 (d, J=8.0 Hz, 1H), 4.65 (s, 2H), 2.50 (s, 3H), 1.97-1.91 (m, 1H), 1.41 (s, 9H), 1.16-1.12 (m, 2H), 1.10-1.05 (m, 2H).

Example 2: 5-(tert-butyl)-N-(4-(2-(cyclopropanecarboxamido)pyridin-4-yl)-2-methylbenzyl)-1,2,4-oxadiazole-3-carboxamide hydrochloride (Compound 2)

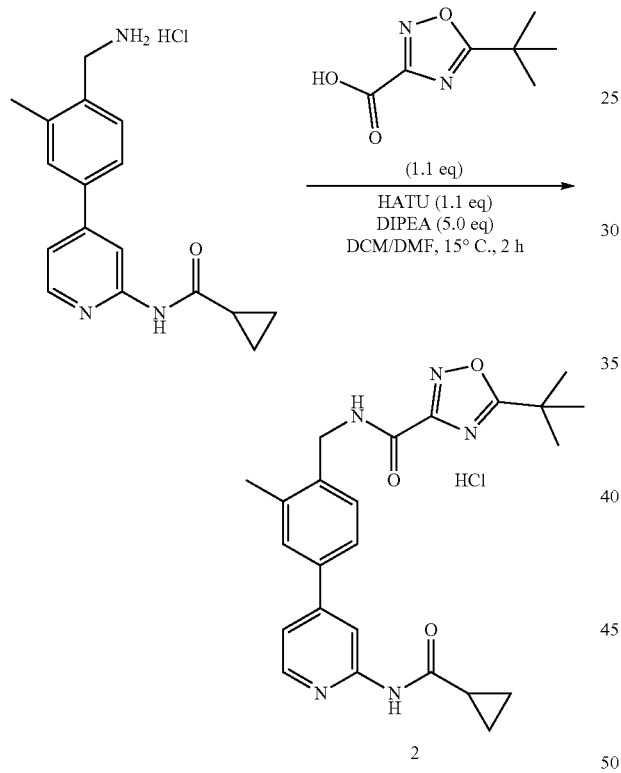

To a solution of N-[4-[4-(aminomethyl)-3-methyl-phenyl]-2-pyridyl]cyclopropane-carboxamide hydrochloride (1.30 g, 4.09 mmol) in a mixture of DCM/DMF (v/v=30/1, 310 mL) were added 5-tert-butyl-1,2,4-oxadiazole-3-carboxylic acid (766 mg, 4.50 mmol), HATU (1.72 g, 4.50 mmol) and DIPEA (2.64 g, 20.5 mmol, 3.57 mL). The reaction mixture was stirred at 15° C. for 2 h. The reaction mixture was poured into H$_2$O (400 mL) and extracted with DCM (150 mL×3). The combined organic layers were concentrated to give crude material, which was purified by silica-gel column chromatography (petroleum ether/EtOAc, grading from 4:1 to 1:1) to give crude product (3.1 g, crude). The material was then purified by prep-HPLC (CH$_3$CN/H$_2$O with 0.05% HCl/H$_2$O as mobile phase) to give 5-tert-butyl-N-[[4-[2-(cyclopropanecarbonyl-amino)-4-pyridyl]-2-methyl-phenyl]methyl]-1,2,4-oxadiazole-3-carboxamide hydrochloride as a white solid (1.30 g, yield: 67%). ESI-MS (M+H)$^+$: 434.1. $^1$H NMR (400 MHz, CD$_3$OD-d$_4$) δ: 8.32 (d, J=6.4 Hz, 1H), 7.87 (dd, J$_1$=6.8 Hz, J$_2$=1.6 Hz, 1H), 7.74-7.63 (m, 2H), 7.66 (d, J=1.2 Hz, 1H), 7.53 (d, J=8.0 Hz, 1H), 4.66 (s, 2H), 2.51 (s, 3H), 1.98-1.91 (m, 1H), 1.48 (s, 9H), 1.20-1.16 (m, 2H), 1.14-1.10 (m, 2H).

Examples 3 and 4: 5-(tert-butyl)-N-(4-(2-((1S,2S)-2-fluorocyclopropane-1-carboxamido)pyridin-4-yl)-2-methylbenzyl)-1,2,4-oxadiazole-3-carboxamide (Compound 3) and 5-(tert-butyl)-N-(4-(2-((1R,2R)-2-fluorocyclopropane-1-carboxamido)pyridin-4-yl)-2-methylbenzyl)-1,2,4-oxadiazole-3-carboxamide (Compound 4)

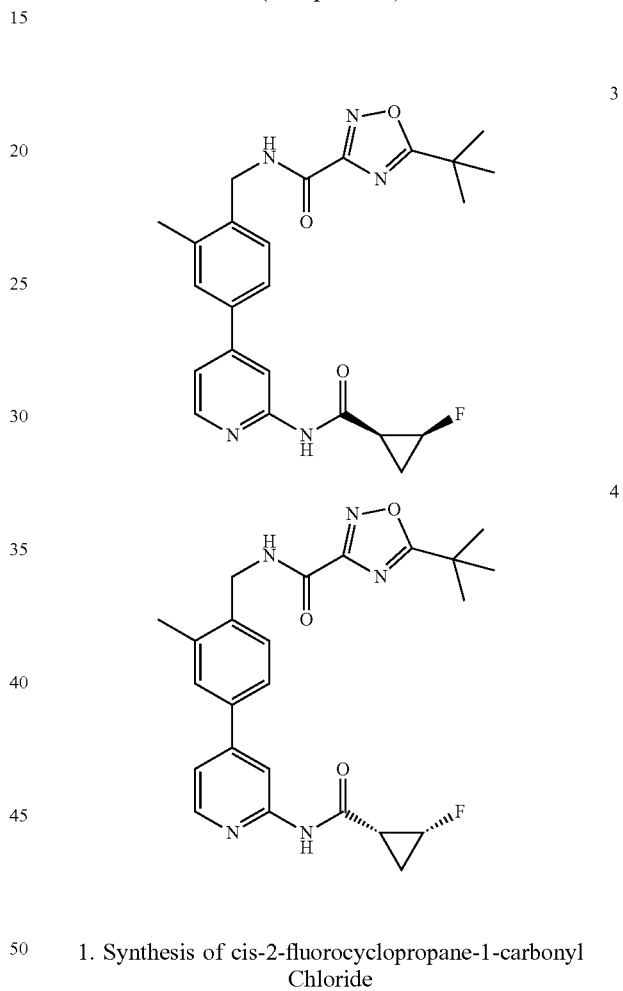

1. Synthesis of cis-2-fluorocyclopropane-1-carbonyl Chloride

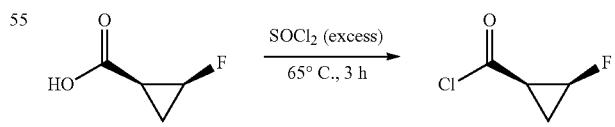

cis-2-Fluorocyclopropane-1-carboxylic acid (200 mg, 1.92 mmol) was added into SOCl$_2$ (3 mL) precooled to 8° C. The reaction mixture was then heated to 65° C. and stirred at that temperature for 3 h. The reaction mixture was cooled to rt and concentrated to give crude cis-2-fluorocyclopropane-1-carbonyl chloride as a colorless oil (220 mg, crude) which was carried forward without further purification.

2. Synthesis of cis-N-(4-bromopyridin-2-yl)-2-fluorocyclopropane-1-carboxamide

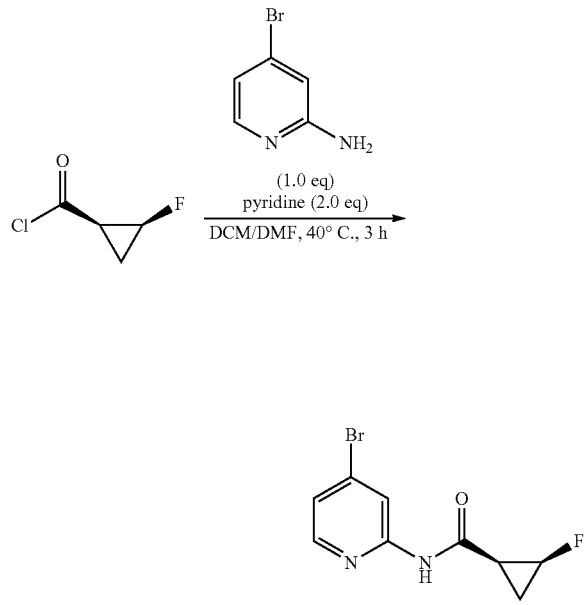 [SMILES: Nc1cc(Br)ccn1 ; O=C(Cl)[C@@H]1C[C@@H]1F ; O=C(Nc1cc(Br)ccn1)[C@@H]1C[C@@H]1F]

To a solution of 4-bromopyridin-2-amine (430 mg, 2.5 mol) and pyridine (395 mg, 5 mmol) in a mixture of DMF (1 mL) and DCM (20 mL) in an ice-water cooling bath at 8° C. was added crude cis-2-fluorocyclopropane-1-carbonyl chloride (220 mg, crude). The reaction mixture was then heated to 40° C. and stirred at that temperature for 3 h. The reaction mixture was concentrated in vacuo to give crude product, which was purified by prep-HPLC ($CH_3CN/H_2O$ with 0.05% $NH_4OH/H_2O$ as mobile phase) to give cis-N-(4-bromopyridin-2-yl)-2-fluorocyclopropane-1-carboxamide as a white solid (145 mg, yield: 29% over two steps). $^1H$ NMR: (400 MHz, $CDCl_3$) δ: 8.50 (s, 1H), 8.21 (br s, 1H), 8.08 (d, J=6.0 Hz, 1H), 7.21 (d, J=4.0 Hz, 1H), 1.97-1.89 (m, 1H), 1.83-1.79 (m, 1H), 1.28-1.23 (m, 2H).

3. Synthesis of tert-butyl (4-(2-((cis-2-fluorocyclopropane-1-carboxamido)pyridin-4-yl)-2-methylbenzyl)carbamate

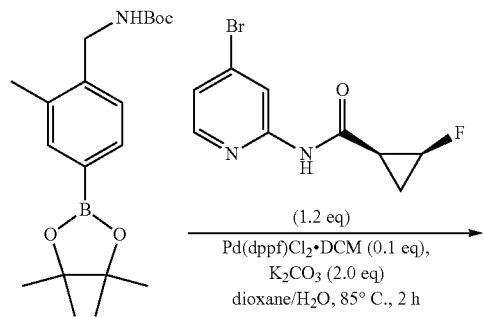

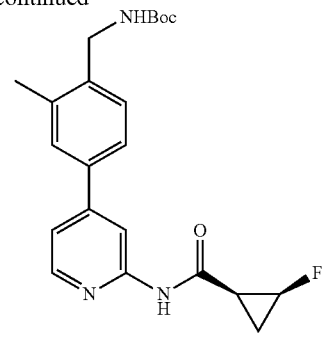

Synthesis of tert-butyl (4-(2-((cis-2-fluorocyclopropane-1-carboxamido)pyridin-4-yl)-2-methylbenzyl)carbamate was similar to that of tert-butyl N-[[4-[2-(cyclopropanecarbonylamino)-4-pyridyl]-2-methyl-phenyl]methyl]carbamate in Example 1, Step 5. The crude material was purified by silica-gel column chromatography (petroleum ether/EtOAc, grading from 4:1 to 1:3) to give tert-butyl (4-(2-(cis-2-fluorocyclopropane-1-carboxamido)pyridin-4-yl)-2-methylbenzyl)carbamate as a light gray solid (145 mg, yield: 65%). $^1H$ NMR (400 MHz, $CDCl_3$) δ: 8.51 (s, 1H), 8.33-8.27 (m, 2H), 7.49 (s, 2H), 7.33 (s, 1H), 7.31 (s, 1H), 4.75 (br s, 1H), 4.35 (d, J=5.2 Hz, 2H), 2.38 (s, 3H), 1.93-1.85 (m, 2H), 1.25-1.23 (m, 10H).

4. Synthesis of cis-N-(4-(4-(aminomethyl)-3-methylphenyl)pyridin-2-yl)-2-fluorocyclopropane-1-carboxamide hydrochloride

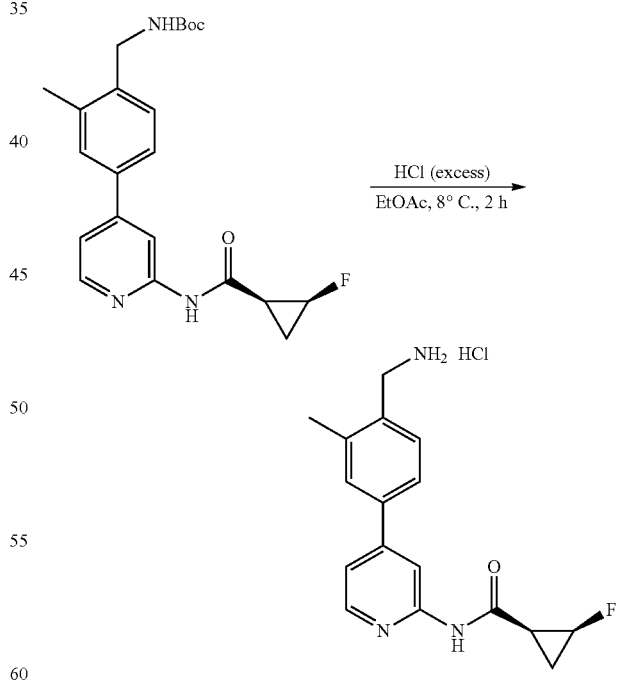

tert-Butyl (4-(2-(cis-2-fluorocyclopropane-1-carboxamido)pyridin-4-yl)-2-methylbenzyl)carbamate (145 mg, 0.36 mmol) was added to a solution of HCl in EtOAc (2 M, 8 mL) at 8° C. The reaction mixture was stirred at 8° C. for 2 h. The reaction mixture was concentrated in vacuo to give cis-N-(4-(4-(aminomethyl)-3-methylphenyl)pyridin-2-yl)-

2-fluorocyclopropane-1-carboxamide hydrochloride as a gray solid (110 mg, yield: 91%). ESI-MS (M+H)+: 300.0.

5. Synthesis of 5-(tert-butyl)-N-(4-(cis-2-fluorocyclopropane-1-carboxamido)pyridin-4-yl)-2-methylbenzyl)-1,2,4-oxadiazole-3-carboxamide

6. Chiral Separation of 5-(tert-butyl)-N-(4-(2-((1S,2S)-2-fluorocyclopropane-1-carboxamido)pyridin-4-yl)-2-methylbenzyl)-1,2,4-oxadiazole-3-carboxamide (3) and 5-(tert-butyl)-N-(4-(2-((1R,2R)-2-fluorocyclopropane-1-carboxamido)pyridin-4-yl)-2-methylbenzyl)-1,2,4-oxadiazole-3-carboxamide (4)

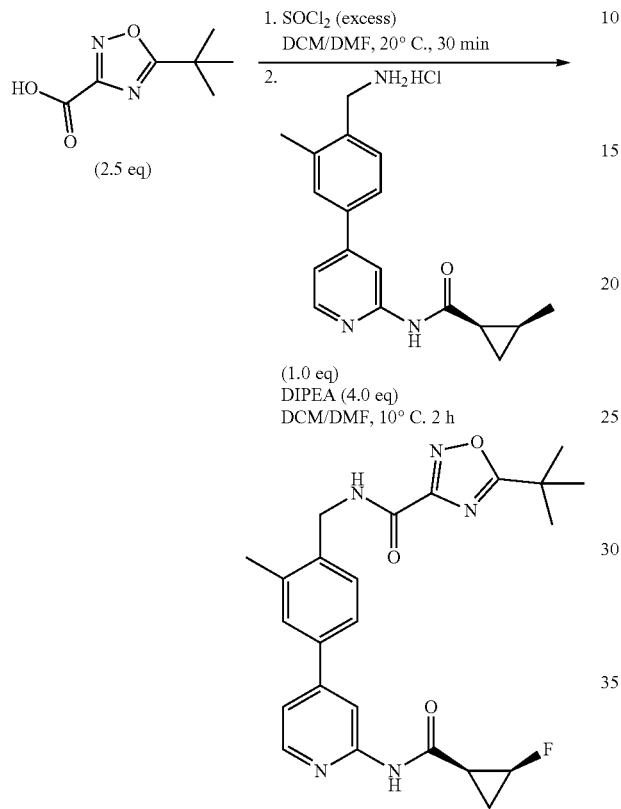

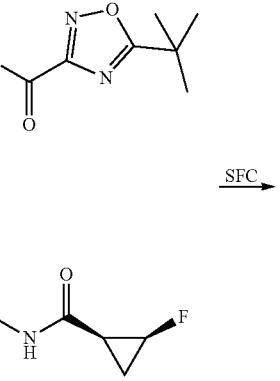

To a solution of 5-tert-butyl-1,2,4-oxadiazole-3-carboxylic acid (200 mg, 0.85 mmol) in a mixture of DCM (35 mL) and DMF (500 μL) was added SOCl₂ (450 mg, 3.78 mmol, 276 μL) at 20° C. The reaction mixture was stirred at 20° C. for 30 min and then was concentrated in vacuo to give crude 5-tert-butyl-1,2,4-oxadiazole-3-carbonyl chloride. The crude material was dissolved in DCM (20 mL) and added to a solution of cis-N-(4-(4-(aminomethyl)-3-methylphenyl)pyridin-2-yl)-2-fluorocyclopropane-1-carboxamide hydrochloride (110 mg, 0.33 mmol) and DIPEA (169 mg, 1.308 mmol) in a mixture of DCM (30 mL) and DMF (2 mL) at 10° C. The reaction mixture was stirred at 10° C. for 2 h. The reaction mixture was concentrated in vacuo and purified by prep-HPLC (CH₃CN/H₂O with 10 mM NH₄OH/H₂O as mobile phase) to give 5-(tert-butyl)-N-(4-(cis-2-fluorocyclopropane-1-carboxamido)pyridin-4-yl)-2-methylbenzyl)-1,2,4-oxadiazole-3-carboxamide as a white solid (40 mg, yield: 27%) $^1$H NMR (400 MHz, CD₃OD) δ: 8.37 (s, 1H), 8.30 (d, J=5.2 Hz, 1H), 7.57-7.51 (m, 2H), 7.41 (d, J=8.4 Hz, 1H), 7.36 (dd, J₁=5.2 Hz, J₁=1.6 Hz, 1H), 4.97-4.77 (m, 1H), 4.63 (s, 2H), 2.45 (s, 3H), 2.12-2.10 (m, 1H), 1.84-1.76 (m, 1H), 1.47 (s, 9H), 1.23-1.19 (m, 1H).

5-(tert-Butyl)-N-(4-(cis-2-fluorocyclopropane-1-carboxamido)pyridin-4-yl)-2-methylbenzyl)-1,2,4-oxadiazole-3-carboxamide (40.3 mg, 0.089 mmol, 1 eq.) was purified by SFC (Mobile phase: Supercritical CO₂/EtOH (0.05% Et₂NH); Column: Chiralcel OD-3 150×4.6 mm I.D., 3 μm; Detection wavelength: 220 nm) to give (arbitrarily assigned) 5-(tert-butyl)-N-(4-(2-((1S,2S)-2-fluorocyclopropane-1-carboxamido)pyridin-4-yl)-2-methylbenzyl)-1,2,4-oxadiazole-3-carboxamide as a white solid (R$_t$=0.691 min, 15 mg, yield: 37%) and 5-(tert-butyl)-N-(4-(2-((1R,2R)-2-fluorocyclopropane-1-carboxamido)pyridin-4-yl)-2-methylbenzyl)-1,2,4-oxadiazole-3-carboxamide as a white solid (R$_t$=1.109 min, 13 mg, yield: 32%).

(1S,2S): ESI-MS (M+Na)$^+$: 474.1. $^1$H NMR (400 MHz, CD$_3$OD) δ: 8.38 (s, 1H), 8.30 (d, J=5.2 Hz, 1H), 7.57-7.53 (m, 2H), 7.42 (d, J=7.6 Hz, 1H), 7.37 (dd, J$_1$=5.2 Hz, J$_1$=1.6 Hz, 1H), 4.97-4.77 (m, 1H), 4.64 (s, 2H), 2.46 (s, 3H), 2.14-2.12 (m, 1H), 1.83-1.76 (m, 1H), 1.48 (s, 9H), 1.23-1.19 (m, 1H).

(1R,2R): ESI-MS (M+Na)$^+$: 474.1. $^1$H NMR (400 MHz, CD$_3$OD) δ: 8.38 (s, 1H), 8.30 (d, J=5.2 Hz, 1H), 7.57-7.53 (m, 2H), 7.42 (d, J=7.6 Hz, 1H), 7.37 (dd, J$_1$=5.2 Hz, J$_1$=1.6 Hz, 1H), 4.97-4.77 (m, 1H), 4.64 (s, 2H), 2.46 (s, 3H), 2.14-2.12 (m, 1H), 1.83-1.76 (m, 1H), 1.48 (s, 9H), 1.23-1.19 (m, 1H).

Example 5: 5-(tert-butyl)-N-(2-methyl-4-(2-((1S,2S)-2-methylcyclopropane-1-carboxamido)pyridin-4-yl)benzyl)-1,2,4-oxadiazole-3-carboxamide (Compound 5)

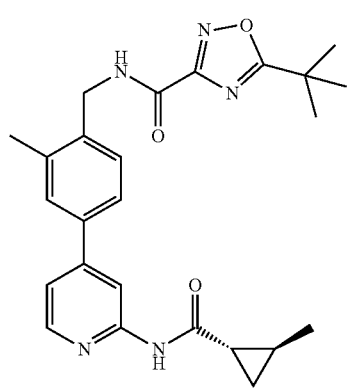

1. Synthesis of (1S,2S)—N-(4-bromo-2-pyridyl)-2-methyl-cyclopropanecarboxamide

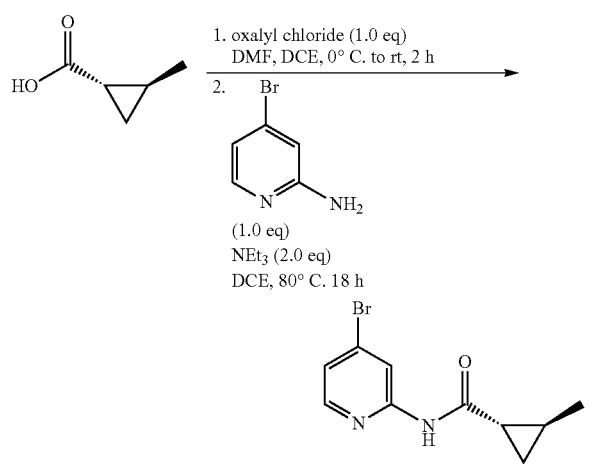

Oxalyl chloride (1.01 g, 7.98 mmol, 675 μL) was slowly added to a suspension of (1S,2S)-2-methylcyclopropanecarboxylic acid (799 mg, 7.98 mmol, 799 μL) in DCE (13 mL) at 0° C., followed by two drops of DMF. The mixture was stirred for 2 h as it warmed to rt. Then, 4-bromopyridin-2-amine (1.15 g, 6.65 mmol) and Et$_3$N (2.02 g, 20 mmol, 2.77 mL) were added. The reaction mixture was heated to 80° C. and stirred at that temperature for 18 h. The reaction mixture was cooled to rt, diluted with water (30 mL) and extracted with DCM (50 mL×2). The combined organic extracts were washed with brine (75 mL), dried (Na$_2$SO$_4$), filtered, and concentrated. The crude material was purified by silica-gel column chromatography (EtOAc/heptanes, grading from 0% to 50%) to give (1S,2S)—N-(4-bromo-2-pyridyl)-2-methyl-cyclopropanecarboxamide as a light-yellow oil (645 mg, yield: 38%) ESI-MS (M+H)$^+$: 257.0.

2. Synthesis of tert-butyl N-[[2-methyl-4-[2-[[(1S,2S)-2-methylcyclopropanecarbonyl]amino]-4-pyridyl]phenyl]methyl]carbamate

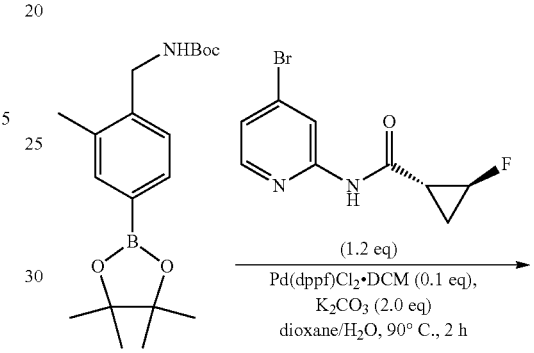

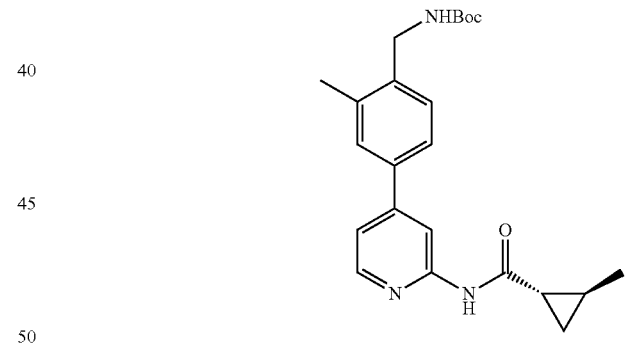

Synthesis of tert-butyl N-[[2-methyl-4-[2-[[(1S,2S)-2-methylcyclopropanecarbonyl]amino]-4-pyridyl]phenyl]methyl]carbamate was similar to that of tert-butyl N-[[4-[2-(cyclopropanecarbonylamino)-4-pyridyl]-2-methyl-phenyl]methyl]carbamate in Example 1, Step 5. The crude material was purified by silica-gel column chromatography ([3:1 EtOAc:EtOH]/heptanes, grading from 0% to 75%) to give tert-butyl N-[[2-methyl-4-[2-[[(1S,2S)-2-methylcyclopropanecarbonyl]amino]-4-pyridyl]phenyl]methyl]carbamate as a light yellow solid (198 mg, yield: 87%). ESI-MS (M+H)$^+$: 396.3.

3. Synthesis of (1S,2S)—N-[4-[4-(aminomethyl)-3-methyl-phenyl]-2-pyridyl]-2-methyl-cyclopropanecarboxamide Hydrochloride

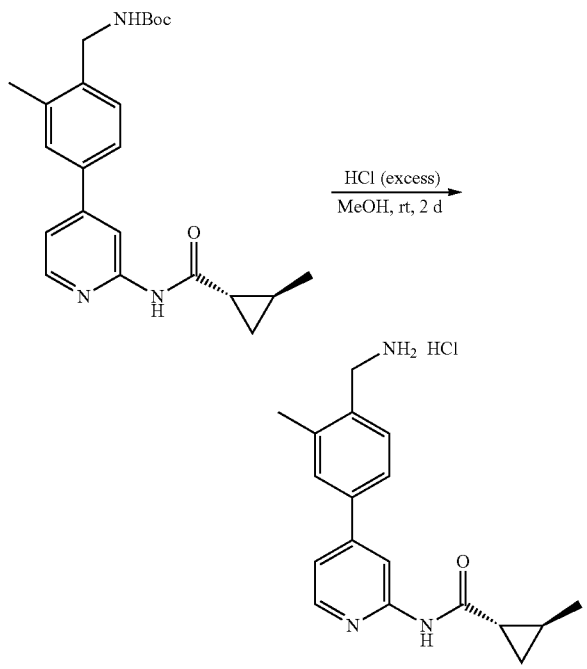

tert-Butyl N-[[2-methyl-4-[2-[[(1S,2S)-2-methylcyclopropanecarbonyl]amino]-4-pyridyl]phenyl]methyl]carbamate (198 mg, 501 μmol) was dissolved in MeOH (1.74 mL) and placed in an ice-water cooling bath. An HCl solution (1.25 M in MeOH, 4.01 mL) was added dropwise over 2 minutes. After stirring for 5 min at 0° C., the ice-water cooling bath was removed and the reaction mixture was warmed to rt and stirred for 48 h at that temperature. The reaction was concentrated in vacuo to afford (1S,2S)—N-[4-[4-(aminomethyl)-3-methyl-phenyl]-2-pyridyl]-2-methyl-cyclopropanecarboxamide hydrochloride as a yellow solid (168 mg, yield: 91%) which was carried forward without further purification. ESI-MS (M+H)$^+$: 296.2.

4. Synthesis of 5-(tert-butyl)-N-(2-methyl-4-(2-((1S,2S)-2-methylcyclopropane-1-carboxamido)pyridin-4-yl)benzyl)-1,2,4-oxadiazole-3-carboxamide (Compound 5)

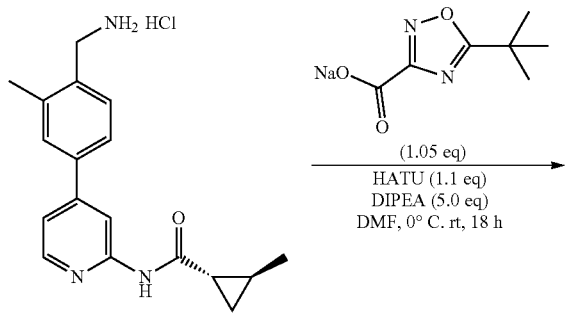

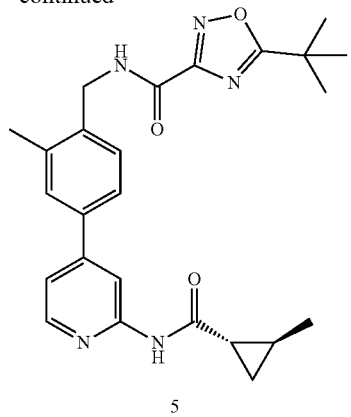

5

To a solution of (1S,2S)—N-[4-[4-(aminomethyl)-3-methyl-phenyl]-2-pyridyl]-2-methyl-cyclopropanecarboxamide hydrochloride (75 mg, 254 μmol) and sodium 5-tert-butyl-1,2,4-oxadiazole-3-carboxylate (51 mg, 267 μmol) in DMF (1.69 mL) was added by DIPEA (164 mg, 1.27 mmol, 222 μL). The reaction mixture was cooled to 0° C. and HATU (116 mg, 305 μmol) was added in a single portion. The reaction mixture was allowed to warm to rt and continued to stir at that temperature for 18 h. The reaction mixture was diluted with EtOAc (20 mL) and was washed sequentially with H$_2$O (20 mL×2) and brine (50 mL). The organic phase was then dried (Na$_2$SO$_4$), filtered, and concentrated. The crude material was purified by silica-gel column chromatography ([3:1 EtOAc:EtOH]/heptanes, grading from 0% to 100%) to give 5-(tert-butyl)-N-(2-methyl-4-(2-((1S,2S)-2-methylcyclopropane-1-carboxamido)pyridin-4-yl)benzyl)-1,2,4-oxadiazole-3-carboxamide as an off-white solid (25 mg, yield: 22%). ESI-MS (M+H)$^+$: 448.3. $^1$H NMR (500 MHz, DMSO-d$_6$) δ: 10.78 (s, 1H), 9.45 (t, J=5.80 Hz, 1H), 8.41-8.28 (m, 2H), 7.56-7.46 (m, 2H), 7.42-7.31 (m, 2H), 4.49 (d, J=5.5 Hz, 2H), 2.40 (s, 3H), 1.79 (dt, J$_1$=8.1 Hz, J$_2$=4.2 Hz, 1H), 1.43 (s, 9H), 1.32-1.21 (m, 2H), 1.09 (d, J=6.1 Hz, 3H), 1.06-1.00 (m, 1H), 0.70-0.64 (m, 1H).

Example 6: 5-(tert-butyl)-N-(2-methyl-4-(2-((1R,2R)-2-methylcyclopropane-1-carboxamido)pyridin-4-yl)benzyl)-1,2,4-oxadiazole-3-carboxamide (Compound 6)

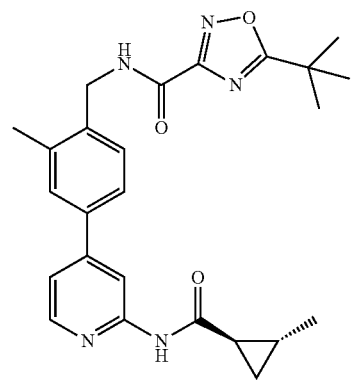

6

1. Synthesis of (1R,2R)—N-(4-bromo-2-pyridyl)-2-methyl-cyclopropanecarboxamide

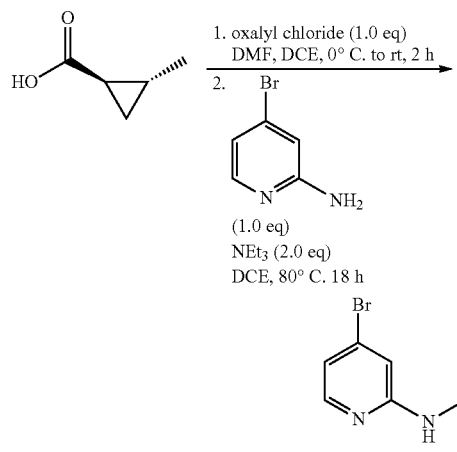

Synthesis of (1R,2R)—N-(4-bromo-2-pyridyl)-2-methyl-cyclopropanecarboxamide was similar to that of (1S,2S)—N-(4-bromo-2-pyridyl)-2-methyl-cyclopropanecarboxamide in Example 5, Step 1. The crude material was purified by silica-gel column chromatography (EtOAc/heptanes, grading from 0% to 50%) to give (1R,2R)—N-(4-bromo-2-pyridyl)-2-methyl-cyclopropanecarboxamide as a light-yellow oil (73 mg, yield: 34%) ESI-MS (M+H)$^+$: 257.0.

2. Synthesis of tert-butyl N-[[2-methyl-4-[2-[[(1R,2R)-2-methylcyclopropanecarbonyl]amino]-4-pyridyl]phenyl]methyl]carbamate

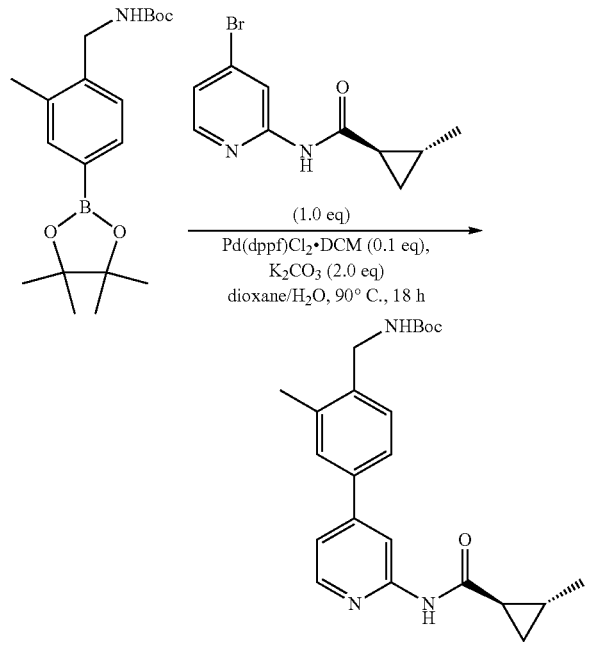

Synthesis of tert-butyl N-[[2-methyl-4-[2-[[(1R,2R)-2-methylcyclopropanecarbonyl]amino]-4-pyridyl]phenyl]methyl]carbamate was similar to that of tert-butyl N-[[2-methyl-4-[2-[[(1S,2S)-2-methylcyclopropanecarbonyl]amino]-4-pyridyl]phenyl]methyl]carbamate in Example 5, Step 2. The crude material was purified by silica-gel column chromatography (EtOAc/heptanes, grading from 0% to 50%) to give tert-butyl N-[[2-methyl-4-[2-[[(1R,2R)-2-methylcyclopropanecarbonyl]amino]-4-pyridyl]phenyl]methyl]carbamate as a light yellow solid (100 mg, yield: 88%). ESI-MS (M+H)$^+$: 396.2.

3. Synthesis of (1R,2R)—N-[4-[4-(aminomethyl)-3-methyl-phenyl]-2-pyridyl]-2-methyl-cyclopropanecarboxamide Hydrochloride

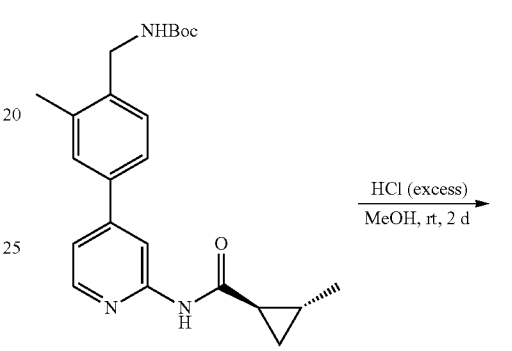

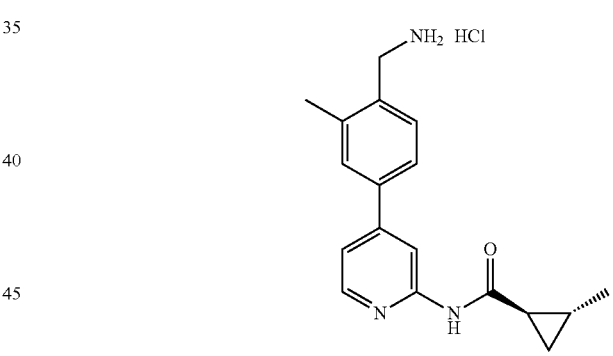

Synthesis of (1R,2R)—N-[4-[4-(aminomethyl)-3-methyl-phenyl]-2-pyridyl]-2-methyl-cyclopropanecarboxamide hydrochloride was similar to that of (1S,2S)—N-[4-[4-(aminomethyl)-3-methyl-phenyl]-2-pyridyl]-2-methyl-cyclopropanecarboxamide hydrochloride in Example 5, Step 3. The reaction mixture was concentrated in vacuo to afford (1R,2R)—N-[4-[4-(aminomethyl)-3-methyl-phenyl]-2-pyridyl]-2-methyl-cyclopropanecarboxamide hydrochloride as a white solid (80 mg, yield: 95%), which was carried forward without further purification. ESI-MS (M+H)$^+$: 296.1.

4. Synthesis of 5-(tert-butyl)-N-(2-methyl-4-(2-((1R,2R)-2-methylcyclopropane-1-carboxamido)pyridin-4-yl)benzyl)-1,2,4-oxadiazole-3-carboxamide (Compound 6)

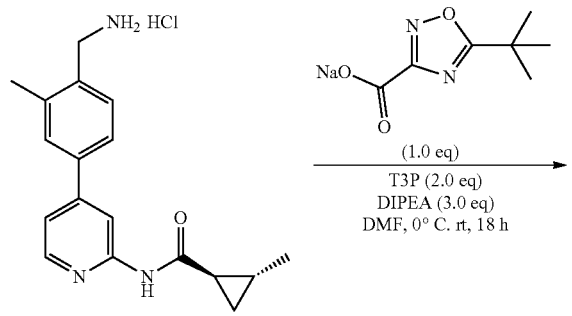

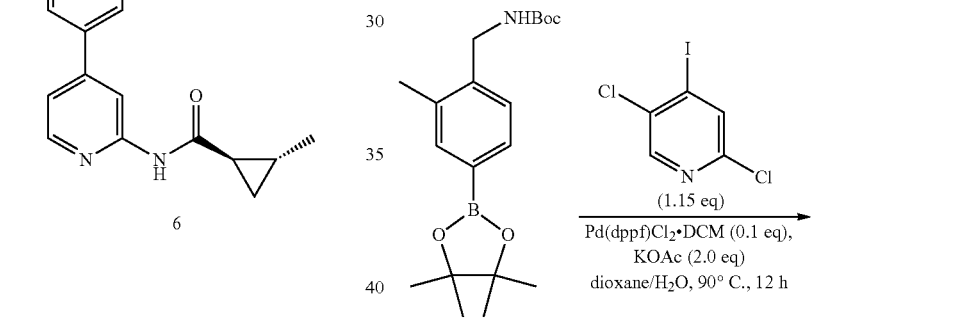

To a solution of (1R,2R)—N-[4-[4-(aminomethyl)-3-methyl-phenyl]-2-pyridyl]-2-methyl-cyclopropanecarboxamide hydrochloride (40 mg, 121 μmol) and sodium 5-tert-butyl-1,2,4-oxadiazole-3-carboxylate (23 mg, 121 μmol) in DMF (1.21 mL) was added DIPEA (47 mg, 362 μmol, 63 μL). The reaction mixture was cooled to 0° C., then T3P (153 mg, 241 μmol, 163 μL, 50% purity) was added in a single portion. The reaction mixture was allowed to warm to rt and was stirred at that temperature for 18 h. The reaction mixture was diluted with EtOAc (20 mL) and was washed sequentially with $H_2O$ (20 mL×2) and brine (50 mL). The organic phase was then dried ($Na_2SO_4$), filtered, and concentrated. The crude material was purified by silica-gel column chromatography ([3:1 EtOAc:EtOH]/heptanes, grading from 0% to 100%) to give 5-(tert-butyl)-N-(2-methyl-4-(2-((1R,2R)-2-methylcyclopropane-1-carboxamido)pyridin-4-yl)benzyl)-1,2,4-oxadiazole-3-carboxamide as an off-white solid (32 mg, yield: 59%). ESI-MS (M+H)⁺: 448.2. ¹H NMR (500 MHz, DMSO-$d_6$) δ: 10.78 (s, 1H), 9.45 (t, J=5.8 Hz, 1H), 8.38-8.31 (m, 2H), 7.55-7.47 (m, 2H), 7.41-7.32 (m, 2H), 4.49 (d, J=6.1 Hz, 2H), 2.40 (s, 3H), 1.79 (dt, $J_1$=8.1 Hz, $J_2$=4.2 Hz, 1H), 1.43 (s, 9H), 1.31-1.22 (m, 1H), 1.09 (d, J=5.5 Hz, 3H), 1.06-1.01 (m, 1H), 0.71-0.62 (m, 1H).

Example 7: 5-(tert-butyl)-N-(4-(5-chloro-2-(cyclopropanecarboxamido)pyridin-4-yl)-2-methylbenzyl)-1,2,4-oxadiazole-3-carboxamide (Compound 7)

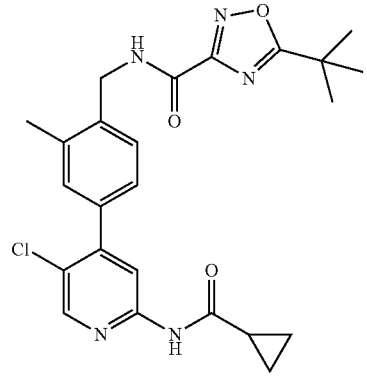

1. Synthesis of tert-butyl (4-(2,5-dichloropyridin-4-yl)-2-methylbenzyl)carbamate

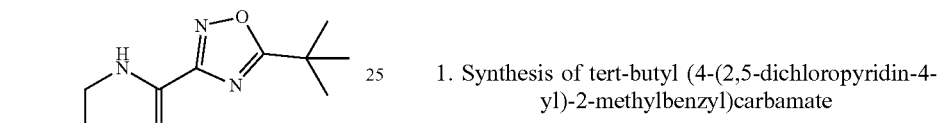

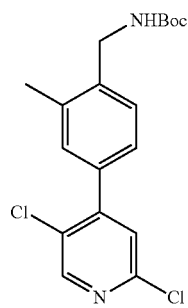

A solution of tert-butyl (2-methyl-4-(4,4,5,5-tetramethyl-1,3,2-dioxaborolan-2-yl)benzyl)carbamate (400 mg, 1.15 mmol), 2,5-dichloro-4-iodopyridine (316 mg, 1.15 mmol), KOAc (226 mg, 2.30 mmol) and Pd(dppf)Cl₂·DCM (50 mg, 0.12 mmol) in 1,4-dioxane/H₂O (5:1, 12 mL) was stirred at 90° C. under N₂ for 12 h. The reaction mixture was cooled to rt and filtered. The filtrate was dissolved in EtOAc (50 mL) and washed with water (10 mL×3). The organic phase was dried (Na₂SO₄), filtered, and concentrated in vacuo. The residue was purified by silica-gel column chromatography (petroleum ether/EtOAc, 10:1) to give tert-butyl (4-(2,5-dichloropyridin-4-yl)-2-methylbenzyl)carbamate as a colorless oil (350 mg, yield: 83%) ESI-MS (M+H)⁺: 367.0.

2. Synthesis of tert-butyl (4-(5-chloro-2-(cyclopropanecarboxamido)pyridin-4-yl)-2-methylbenzyl)carbamate

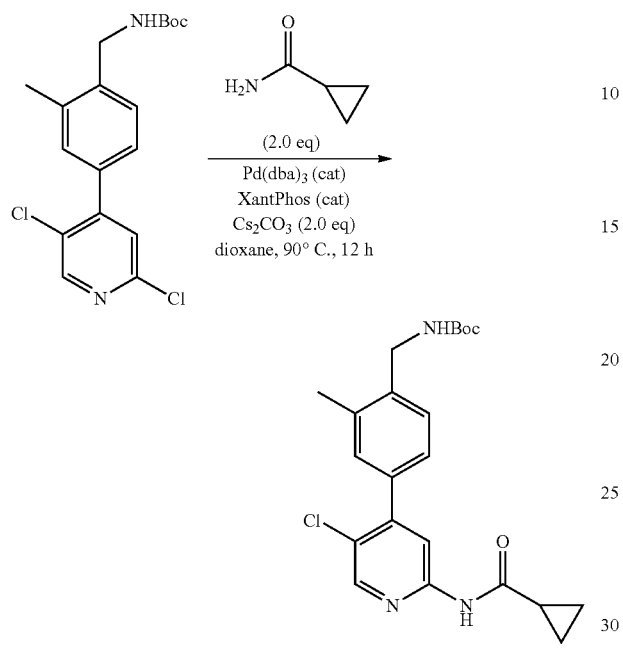

A solution of tert-butyl (4-(2,5-dichloropyridin-4-yl)-2-methylbenzyl)carbamate (350 mg, 953 μmol), cyclopropanecarboxamide (162 mg, 1.91 mmol), Pd$_2$(dba)$_3$ (50 mg, cat), Xantphos (30 mg, cat) and Cs$_2$CO$_3$ (621 mg, 1.91 mmol) in 1,4-dioxane (10 mL) was stirred at 90° C. under N$_2$ for 12 h. The reaction mixture was cooled to rt and filtered. The filtrate was concentrated in vacuo and the residue was purified by silica-gel column chromatography (petroleum ether/EtOAc, grading from 10:1 to 5:1) to give tert-butyl (4-(5-chloro-2-(cyclopropanecarboxamido)pyridin-4-yl)-2-methylbenzyl)carbamate as a colorless oil (300 mg, yield: 76%). ESI-MS (M+H)$^+$: 416.1.

3. Synthesis of N-(4-(4-(aminomethyl)-3-methylphenyl)-5-chloropyridin-2-yl)cyclopropanecarboxamide Hydrochloride

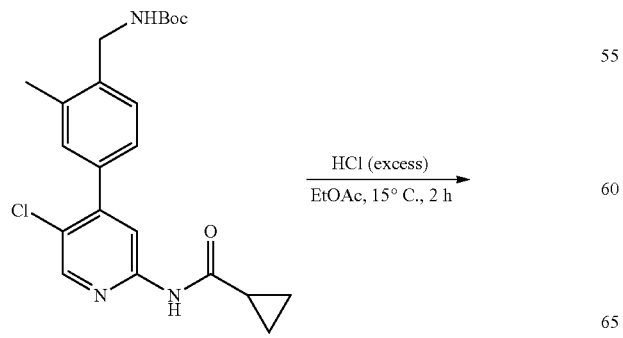

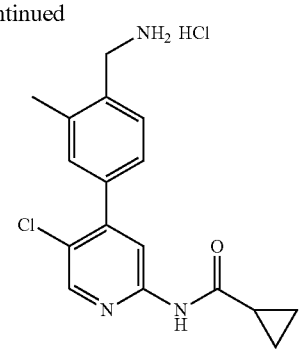

A solution of tert-butyl (4-(5-chloro-2-(cyclopropanecarboxamido)pyridin-4-yl)-2-methylbenzyl)carbamate (300 mg, 721 μmol) in an HCl/EtOAc solution (4 M, 10 mL) was stirred at 15° C. for 2 h. The reaction mixture was concentrated in vacuo to give crude N-(4-(4-(aminomethyl)-3-methylphenyl)-5-chloropyridin-2-yl)cyclopropanecarboxamide hydrochloride as a white solid (254 mg, yield: 100%), which was carried forward without further purification. ESI-MS (M+H)$^+$: 315.9.

4. Synthesis of 5-(tert-butyl)-N-(4-(5-chloro-2-(cyclopropanecarboxamido)pyridin-4-yl)-2-methylbenzyl)-1,2,4-oxadiazole-3-carboxamide (Compound 7)

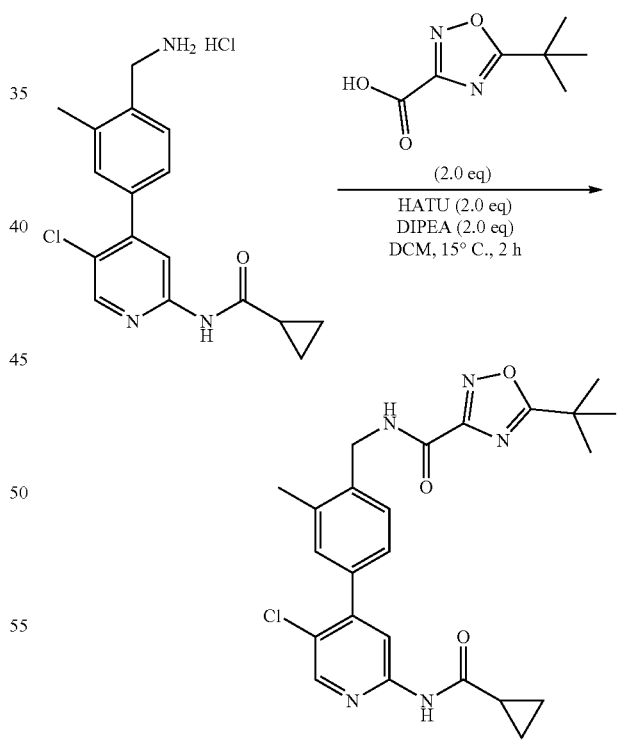

A mixture of N-(4-(4-(aminomethyl)-3-methylphenyl)-5-chloropyridin-2-yl)cyclopropanecarboxamide hydrochloride (250 mg, 0.71 mmol), 5-(tert-butyl)-1,2,4-oxadiazole-3-carboxylic acid (242 mg, 1.42 mmol), HATU (424 mg, 1.42 mmol) and DIPEA (183 mg, 1.42 mmol) in DCM (10 mL) was stirred at 15° C. for 2 h. The reaction mixture was diluted with additional DCM (50 mL) and washed with H₂O (10 mL×3). The combined organic extracts were dried (Na₂SO₄), filtered, and concentrated in vacuo. The crude material was purified by prep-HPLC (CH₃CN/H₂O with 10 mM NH₄OH/H₂O as mobile phase) to give 5-(tert-butyl)-N-(4-(5-chloro-2-(cyclopropanecarboxamido)pyridin-4-yl)-2-methylbenzyl)-1,2,4-oxadiazole-3-carboxamide as a white solid (100 mg, yield: 30%). ESI-MS (M+Na)⁺: 490.1. ¹H NMR (400 MHz, CDCl₃) δ: 8.36 (s, 1H), 8.15 (s, 1H), 7.44-7.42 (m, 1H), 7.35-7.29 (m, 2H), 4.67 (s, 2H), 2.46 (s, 3H), 1.92-1.89 (m, 1H), 1.51 (s, 9H), 1.00-0.98 (m, 2H), 0.93-0.91 (m, 2H).

Example 8: 5-(tert-butyl)-N-(2-chloro-4-(2-(cyclopropanecarboxamido)pyridin-4-yl)benzyl)-1,2,4-oxadiazole-3-carboxamide (Compound 8)

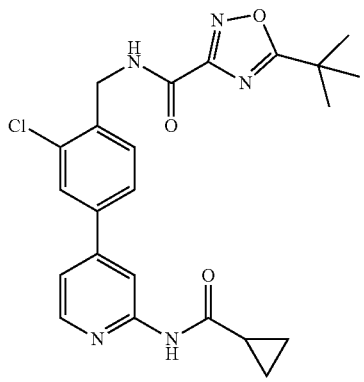

1. Synthesis of (4-bromo-2-chlorophenyl)methanamine

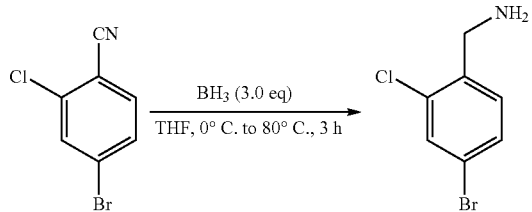 [SMILES: N#Cc1ccc(Br)cc1Cl ; NCc1ccc(Br)cc1Cl]

To a solution of 4-bromo-2-chlorobenzonitrile (3.2 g, 15 mmol) in THF (20 mL) at 0° C. was added BH₃·THF (45 mL, 45 mmol). The solution was stirred at 0° C. for 1 h and then was heated to 80° C. for 2 h. The mixture was quenched with H₂O and extracted with EtOAc (50 mL×3). The organic layer was collected and concentrated in vacuo. The residue was stirred with a saturated HCl/EtOAc solution and filtered. The filter cake was rinsed with ether (20 mL×3) and dried under vacuum to afford (4-bromo-2-chlorophenyl) methanamine as a white solid (2.3 g, yield: 70%). ESI-MS (M+H)⁺: 220.1.

2. Synthesis of tert-butyl (4-bromo-2-chlorobenzyl)carbamate

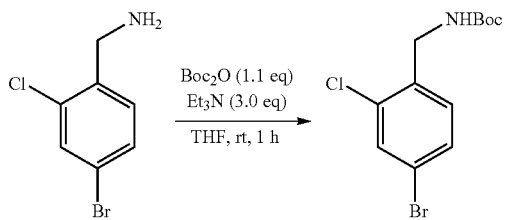 [SMILES: NCc1ccc(Br)cc1Cl ; CC(C)(C)OC(=O)NCc1ccc(Br)cc1Cl]

To a solution of (4-bromo-2-chlorophenyl)methanamine (1.3 g, 6 mmol) in DCM (30 mL) was added Et₃N (1.82 g, 18 mmol) and Boc₂O (1.43 g, 6.6 mmol). The mixture was stirred at rt for 1 h. After diluting with water (50 mL), the mixture was extracted with DCM (50 mL×2). The combined organic extracts were washed with brine (50 mL), dried (Na₂SO₄), filtered, and concentrated to give crude tert-butyl (4-bromo-2-chlorobenzyl)carbamate as a white solid (1.5 g, yield: 80%), which was used directly in the next step without further purification. ESI-MS (M+H)+: 320.1.

3. Synthesis of tert-butyl (2-chloro-4-(4,4,5,5-tetramethyl-1,3,2-dioxaborolan-2-yl)benzyl)carbamate

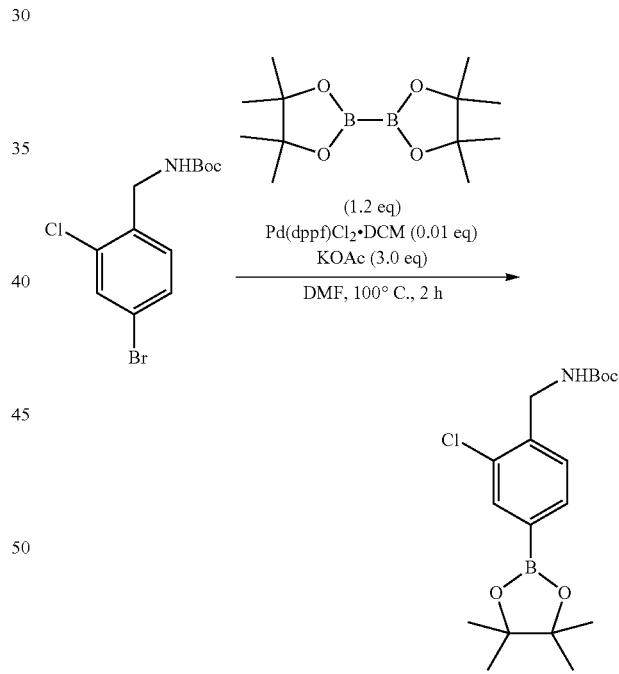

To a solution of tert-butyl (4-bromo-2-chlorobenzyl)carbamate (1.6 g, 5.0 mmol) in dry DMF (6 mL) were added bis(pinacolato)diboron (1.52 g, 6.0 mmol), KOAc (1.75 g, 18 mmol) and Pd(dppf)Cl₂·DCM (407 mg, 0.5 mmol) under N₂. The mixture was stirred at 100° C. for 2 h. After cooling to rt, the mixture was diluted with water (50 mL) and extracted with EtOAc (100 mL×3). The combined organic extracts were washed with brine (200 mL), dried, concentrated, and purified by silica-gel column chromatography (petroleum ether/EtOAc, 10:1) to give tert-butyl (2-chloro-4-(4,4,5,5-tetramethyl-1,3,2-dioxaborolan-2-yl)benzyl)carbamate as a white solid (1.1 g, yield: 60%). ESI-MS (2M+Na)⁺: 757.2. ¹H NMR (400 MHz, CDCl₃) δ: 7.78 (s, 1H), 7.65 (d, J=7.6 Hz, 1H), 7.37 (d, J=7.6 Hz, 1H), 5.01 (br s, 1H), 4.41 (d, J=6.4 Hz, 2H), 1.44 (s, 9H), 1.35 (s, 12H).

4. Synthesis of tert-butyl (2-chloro-4-(2-(cyclopropanecarboxamido)pyridin-4-yl)benzyl)carbamate

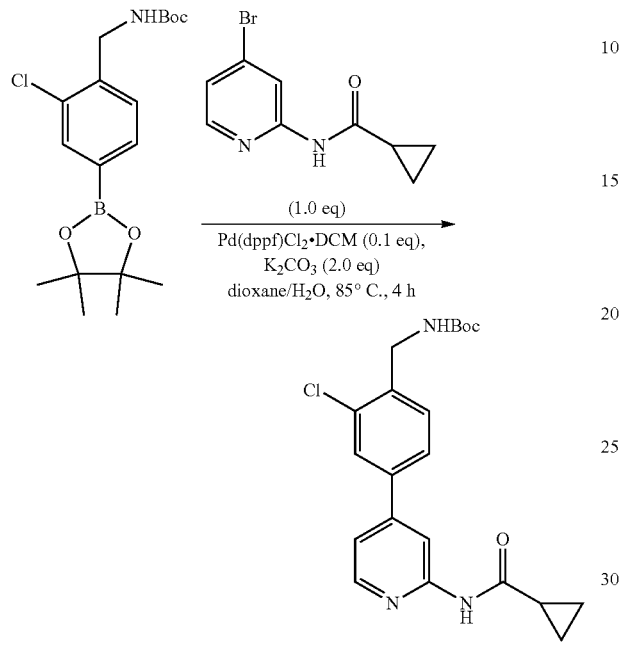

Synthesis of tert-butyl (2-chloro-4-(2-(cyclopropanecarboxamido)pyridin-4-yl)benzyl)carbamate was similar to that of tert-butyl N-[[4-[2-(cyclopropanecarbonylamino)-4-pyridyl]-2-methyl-phenyl]methyl]carbamate in Example 1, Step 5. The crude material was purified by silica-gel column chromatography (petroleum ether/EtOAc, grading from 3:1 to 1:1) to give tert-butyl (2-chloro-4-(2-(cyclopropanecarboxamido)pyridin-4-yl)benzyl)carbamate as a yellow oil (300 mg, yield: 91%). ESI-MS (M+H)⁺: 402.1. ¹H NMR (400 MHz, CD₃OD) δ: 8.37-8.35 (m, 2H), 7.75 (d, J=1.6 Hz, 1H), 7.66 (d, J=8.0 Hz, 1H), 7.49 (d, J=8.0 Hz, 1H), 7.37 (dd, J₁=5.2, Hz, J₂=1.2 Hz, 1H), 4.39 (d, J=4.4 Hz, 2H), 1.96-1.87 (m, 1H), 1.49 (s, 9H), 1.06-0.99 (m, 2H), 0.97-0.91 (m, 2H).

5. Synthesis of N-(4-(4-(aminomethyl)-3-chlorophenyl)pyridin-2-yl)cyclopropanecarboxamide Hydrochloride

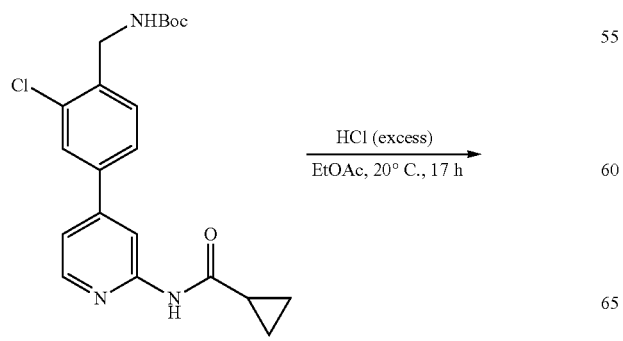

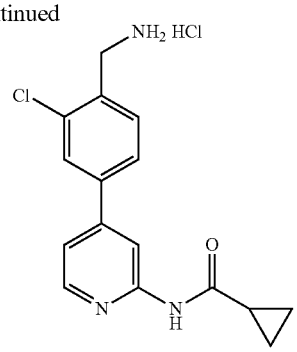

To a solution of tert-butyl (2-chloro-4-(2-(cyclopropanecarboxamido)pyridin-4-yl)benzyl)carbamate (300 mg, 0.75 mmol) in EtOAc (1 mL) was added an HCV/EtOAc solution (1 M, 10 mL) at 20° C. The reaction mixture continued to stir at that temperature for 17 h. The reaction mixture was filtered and the filter cake was dried to give N-(4-(4-(aminomethyl)-3-chlorophenyl)pyridin-2-yl)cyclopropanecarboxamide hydrochloride as a yellow solid (200 mg, yield: 79%), which was carried forward without further purification. ESI-MS (M+H)⁺: 301.9.

6. Synthesis of 5-(tert-butyl)-N-(2-chloro-4-(2-(cyclopropanecarboxamido)pyridin-4-yl)benzyl)-1,2,4-oxadiazole-3-carboxamide (Compound 8)

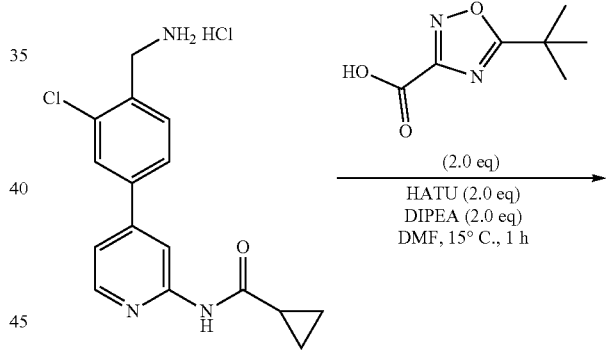

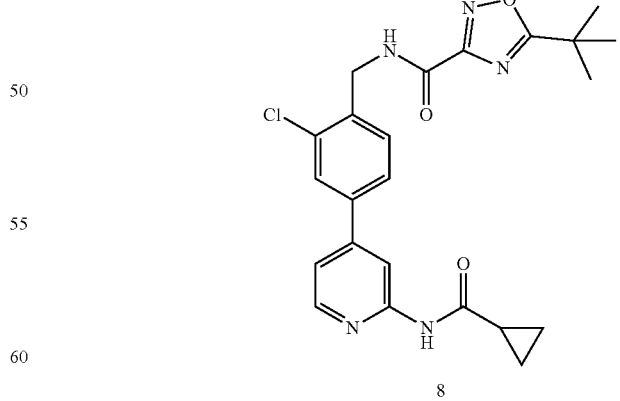

To a solution of N-(4-(4-(aminomethyl)-3-chlorophenyl)pyridin-2-yl)cyclopropanecarboxamide hydrochloride (150 mg, 0.44 mmol) in DMF (5 mL) at 15° C. was added DIPEA (115 mg, 0.89 mmol), 5-(tert-butyl)-1,2,4-oxadiazole-3-carboxylic acid (151 mg, 0.89 mmol), and HATU (338 mg, 0.89 mmol). The reaction mixture was stirred at that temperature for 1 h. The mixture was filtered and the filtrate was concentrated. The crude material was purified by prep-HPLC (CH$_3$CN/H$_2$O with 10 mM NH$_4$OH/H$_2$O as mobile phase) to give 5-(tert-butyl)-N-(2-chloro-4-(2-(cyclopropanecarboxamido)pyridin-4-yl)benzyl)-1,2,4-oxadiazole-3-carboxamide as a white solid (125 mg, yield: 63%) as white solid. ESI-MS (M+H)$^+$: 454.0. $^1$H NMR (400 MHz, DMSO-d$_6$) δ: 10.92 (s, 1H), 9.54 (t, J=5.6 Hz, 1H), 8.37-8.36 (m, 2H), 7.76 (d, J=1.6 Hz, 1H), 7.66 (dd, J$_1$=8.0 Hz, J$_2$=1.6 Hz, 1H), 7.46 (d, J=8.0 Hz, 1H), 7.41 (dd, J$_1$=4.8 Hz, J$_2$=1.2 Hz, 1H), 4.56 (d, J=6.0 Hz, 2H), 2.05-1.99 (m, 1H), 1.42 (s, 9H), 0.82-0.78 (m, 4H).

Example 9: 3-(tert-butyl)-N-(2-chloro-4-(2-(cyclopropanecarboxamido)pyridin-4-yl)benzyl)-1,2,4-oxadiazole-5-carboxamide (Compound 9)

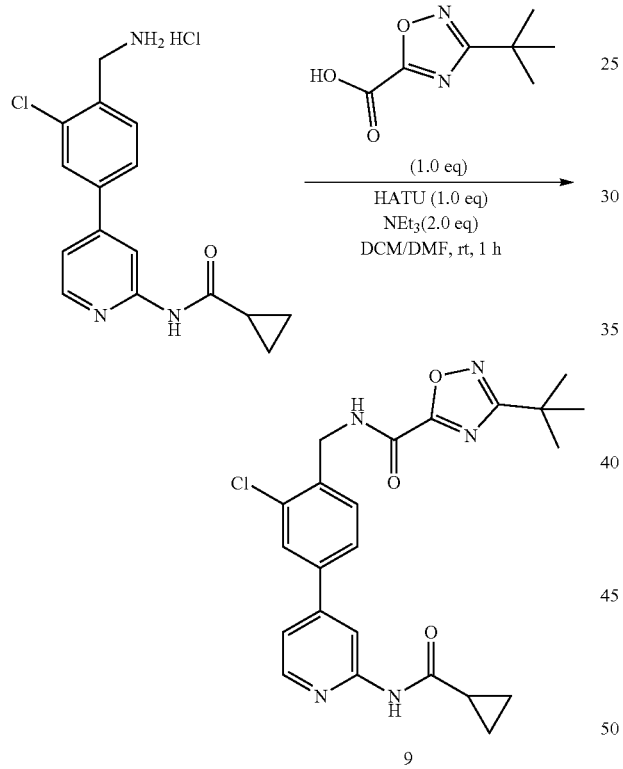

To a solution of N-(4-(4-(aminomethyl)-3-chlorophenyl)pyridin-2-yl)cyclopropanecarboxamide hydrochloride (80 mg, 0.24 mmol) in DMF (1 mL) and DCM (20 mL) was added Et$_3$N (49 mg, 0.48 mmol), 3-(tert-butyl)-1,2,4-oxadiazole-5-carboxylic acid (40 mg, 0.24 mmol), and HATU (90 mg, 0.24 mmol). The reaction mixture was stirred at rt for 1 h. The reaction mixture was washed with H$_2$O (15 mL), and the organic phase was dried (Na$_2$SO$_4$), filtered, and concentrated in vacuo. The residue was purified by prep-HPLC (CH$_3$CN/H$_2$O with 0.05% HCl/H$_2$O as mobile phase) to give 3-(tert-butyl)-N-(2-chloro-4-(2-(cyclopropanecarboxamido)pyridin-4-yl)benzyl)-1,2,4-oxadiazole-5-carboxamide as an off-white solid (44 mg, yield: 41%). ESI-MS (M+Na)$^+$: 476.1. $^1$H NMR: (400 MHz, CD$_3$OD) δ: 8.35 (s, 1H), 7.99 (s, 1H), 7.88 (s, 1H), 7.74-7.71 (m, 1H), 7.61-7.59 (s, 2H), 4.73 (s, 2H), 1.92 (br s, 1H), 1.41 (s, 9H), 1.10-1.01 (m, 4H).

Example 10: (R)-5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide (Compound 10)

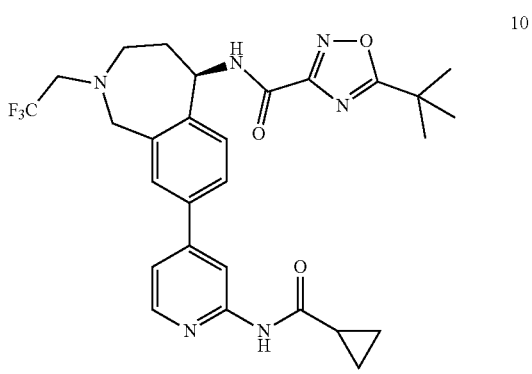 [SMILES: CC(C)(C)c1nc(C(=O)N[C@@H]2CCN(CC(F)(F)F)Cc3cc(-c4ccnc(NC(=O)C5CC5)c4)ccc32)no1]

1. Synthesis of 3-(3-bromo-benzylamino)-propionic Acid Ethyl Ester

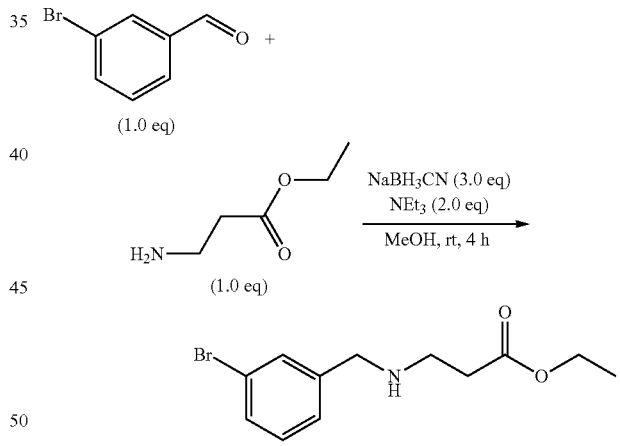

To a solution of ethyl 3-aminopropanoate (46.0 g, 0.3 mol) and 3-bromobenzaldehyde (55.5 g, 0.3 mol) in MeOH (1.2 L) were added Et$_3$N (60.7 g, 0.6 mol) and NaCNBH$_3$ (56.5 g, 0.9 mol) portion-wise. The resulting mixture was stirred at rt for 4 h. The reaction mixture was concentrated in vacuo and the residue was diluted with water (600 mL). The mixture was extracted with EtOAc (500 mL×3). The combined organic layer was washed with brine (100 mL), dried (Na$_2$SO$_4$), filtered, and concentrated in vacuo to give 3-(3-bromo-benzylamino)-propionic acid ethyl ester as a light yellow oil (46.5 g, yield: 54%). $^1$H NMR (300 MHz, DMSO-d$_6$,): δ 7.52 (s, 1H), 7.40 (d, J=7.5 Hz, 1H), 7.31-7.25 (m, 2H), 4.04 (q, J=7.2 Hz, 2H), 3.67 (s, 2H), 2.69 (t, J=7.2 Hz, 2H), 2.42 (t, J=6.9 Hz, 2H), 1.17 (t, J=6.9 Hz, 3H).

2. Synthesis of 3-[(3-bromo-benzyl)-(toluene-4-sulfonyl)-amino]-propionic Acid Ethyl Ester

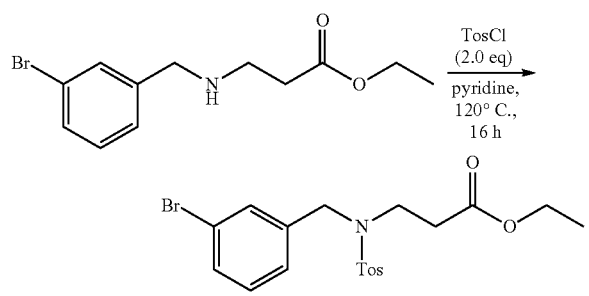

To a solution of 3-(3-bromo-benzylamino)-propionic acid ethyl ester (45.6 g, 0.16 mol) in pyridine (500 mL) was added TosCl (61.0 g, 0.32 mol) at rt. The reaction mixture was stirred at 120° C. for 16 h. The solvent was removed in vacuo to give the crude product. The crude product was purified by silica-gel column chromatography (petroleum ether/EtOAc, grading from 10:1 to 5:1) to afford 3-[(3-bromo-benzyl)-(toluene-4-sulfonyl)-amino]-propionic acid ethyl ester as a light-yellow oil (61 g, yield: 88%). $^1$H NMR (300 MHz, DMSO-d$_6$): δ 7.74 (d, J=8.4 Hz, 2H), 7.49-7.41 (m, 4H), 7.31 (d, J=5.1 Hz, 2H), 4.33 (s, 2H), 3.93 (q, J=7.2 Hz, 2H), 3.32 (t, J=7.2 Hz, 2H), 2.41 (s, 3H), 2.36 (t, J=6.9 Hz, 2H), 1.10 (t, J=6.9 Hz, 3H).

3. Synthesis of 3-[(3-bromo-benzyl)-(toluene-4-sulfonyl)-amino]-propionic Acid

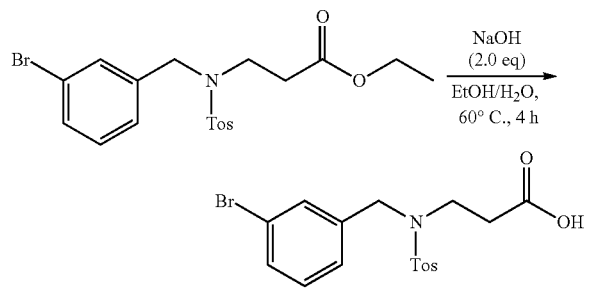

To a solution of 3-[(3-bromo-benzyl)-(toluene-4-sulfonyl)-amino]-propionic acid ethyl ester (60.0 g, 0.14 mol) in a mixed solvent of EtOH (600 mL) and H$_2$O (60 mL) was added NaOH (11.2 g, 0.28 mol) portion-wise. The reaction solution was then heated to 60° C. and was stirred at that temperature for 4 h. The reaction solution was cooled to 0° C. and acidified to pH=5 with concentrated HCl. The solvent was concentrated in vacuo to give a residue which was extracted with EtOAc (150 mL×3). The combined organic extracts were dried (Na$_2$SO$_4$), filtered, and concentrated in vacuo to give 3-[(3-bromo-benzyl)-(toluene-4-sulfonyl)-amino]-propionic acid as a white solid (45.2 g, yield: 79%). $^1$H NMR (300 MHz, DMSO-d$_6$): δ 12.28 (br, 1H), 7.74 (d, J=8.1 Hz, 2H), 7.49-7.41 (m, 4H), 7.32 (d, J=5.1 Hz, 2H), 4.33 (s, 2H), 3.29 (t, J=6.9 Hz, 2H), 2.41 (s, 3H), 2.27 (t, J=7.5 Hz, 2H).

4. Synthesis of 3-[(3-bromo-benzyl)-(toluene-4-sulfonyl)-amino]-propionyl Chloride

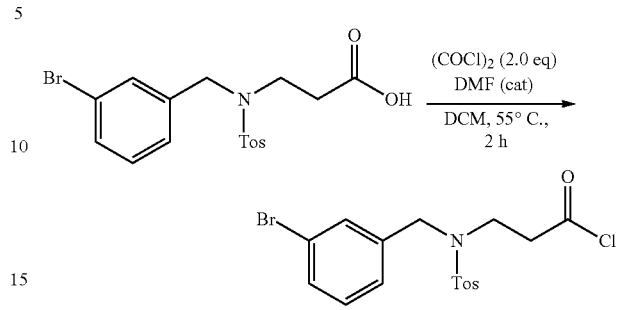

To a solution of 3-[(3-bromo-benzyl)-(toluene-4-sulfonyl)-amino]-propionic acid (45.2 g, 0.11 mol) in DCM (1000 mL) were added DMF (1 mL) dropwise and oxalyl chloride (27.9 g, 0.22 mol) portion-wise. The reaction solution was heated to 55° C. and stirred at that temperature for 2 h. The mixture was concentrated in vacuo to give the crude 3-[(3-bromo-benzyl)-(toluene-4-sulfonyl)-amino]-propionyl chloride as a black oil (47.2 g, yield: 99%), which was used in the next step without further purification.

5. Synthesis of 8-bromo-2-(toluene-4-sulfonyl)-1,2,3,4-tetrahydro-benzo[c]azepin-5-one

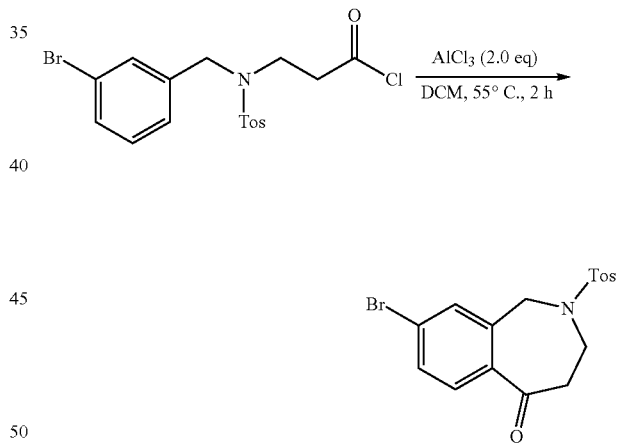

To a solution of 3-[(3-bromo-benzyl)-(toluene-4-sulfonyl)-amino]-propionyl chloride (47.0 g, 0.11 mol) in anhydrous DCM (1200 mL) was added AlCl$_3$ (29.3 g, 0.22 mol) portion-wise at rt. The reaction mixture was heated to 55° C. and stirred at that temperature for 2 h. The reaction mixture was poured into ice water (1.2 L) and extracted with DCM (500 mL). The organic layer was concentrated in vacuo to give the crude product. The crude product was purified by silica-gel column chromatography (petroleum ether/EtOAc, grading from 5:1 to 2:1) to afford 8-bromo-2-(toluene-4-sulfonyl)-1,2,3,4-tetrahydro-benzo[c]azepin-5-one as a white solid (35 g, yield: 81%). $^1$H NMR (300 MHz, DMSO-d$_6$): δ 7.65 (d, J=8.4 Hz, 3H), 7.60-7.51 (m, 2H), 7.36 (d, J=8.1 Hz, 2H), 4.68 (s, 2H), 3.42 (t, J=9.2 Hz, 2H), 2.96 (t, J=6.3 Hz, 2H), 2.37 (s, 3H).

6. Synthesis of [8-bromo-2-(toluene-4-sulfonyl)-2,3,4,5-tetrahydro-1H-benzo[c]azepin-5-yl]-carbamic Acid Tert-Butyl Ester

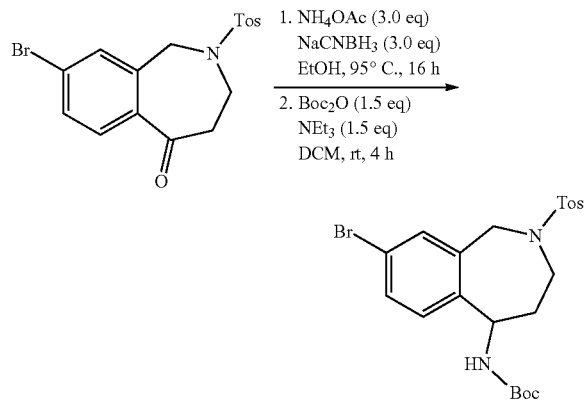

To a solution of 8-bromo-2-(toluene-4-sulfonyl)-1,2,3,4-tetrahydro-benzo[c]azepin-5-one (32.0 g, 0.08 mol) in EtOH (600 mL) were added NH₄OAc (18.5 g, 0.24 mol) and NaCNBH₃ (14.9 g, 0.24 mol) portion-wise at rt. Then the reaction mixture was heated to 95° C. and stirred at that temperature for 16 h. The mixture was poured into ice water (500 mL) and then EtOH was removed in vacuo. The residue was extracted with DCM (500 mL×3). The combined extracts were concentrated. The residue was redissolved in DCM (300 mL) and Et₃N (12.2 g, 0.12 mol) and Boc₂O (34.6 g, 0.12 mol) were added at rt. The mixture was stirred at rt for 4 h and then concentrated in vacuo to give the crude product. The crude product was purified by silica-gel column chromatography (peteroleum ether/EtOAc, grading from 8:1 to 2:1) to afford [8-bromo-2-(toluene-4-sulfonyl)-2,3,4,5-tetrahydro-1H-benzo[c]azepin-5-yl]-carbamic acid tert-butyl ester as a white solid (16.7 g, yield: 42%). $^1$H NMR (300 MHz, DMSO-d₆): δ 7.62-7.51 (m, 2H), 7.47 (d, J=9.9 Hz, 1H), 7.41-7.34 (m, 3H), 7.10 (d, J=8.4 Hz, 1H), 4.81-4.74 (m, 1H), 4.53 (d, J=15.0 Hz, 1H), 4.28 (d, J=15.3 Hz, 1H), 3.64-3.57 (m, 1H), 3.41-3.30 (m, 1H), 2.35 (s, 3H), 1.85-1.77 (m, 1H), 1.69-1.63 (m, 1H), 1.36 (s, 9H).

7. Synthesis of 8-bromo-2-(toluene-4-sulfonyl)-2,3,4,5-tetrahydro-1H-benzo[c]azepin-5-ylamine

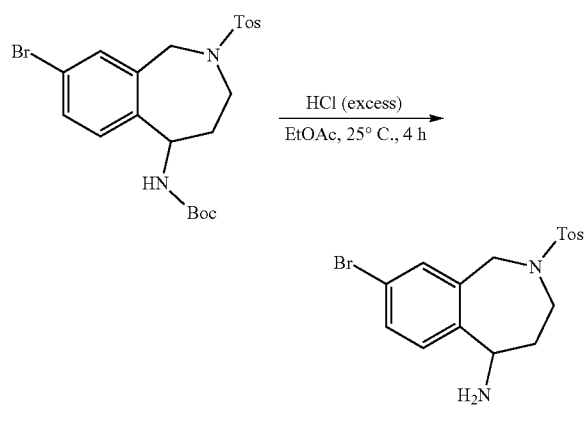

A solution of [8-bromo-2-(toluene-4-sulfonyl)-2,3,4,5-tetrahydro-1H-benzo[c]azepin-5-yl]-carbamic acid tert-butyl ester (14.8 g, 0.03 mol) in an HCl/EtOAc solution (150 mL) was stirred at 25° C. for 4 h. The resulting solid was filtered and washed with MeOH and Et₂O to give the product 8-bromo-2-(toluene-4-sulfonyl)-2,3,4,5-tetrahydro-1H-benzo[c]azepin-5-ylamine as a white solid (10.5 g, yield: 89%). ESI-MS (M+H)⁺: 395.0/397.0. $^1$H NMR (300 MHz, DMSO-d₆): δ 8.79 (br s, 3H), 7.64-7.58 (m, 3H), 7.53 (s, 1H), 7.36 (d, J=8.4 Hz, 2H), 7.15 (d, J=8.4 Hz, 1H), 4.71-4.61 (m, 2H), 4.31 (d, J=15.3 Hz, 1H), 3.82 (d, J=18.3 Hz, 1H), 2.38 (s, 3H), 2.14-2.07 (m, 1H), 1.77-1.71 (m, 1H).

8. Synthesis of 8-bromo-2,3,4,5-tetrahydro-1H-benzo[c]azepin-5-amine

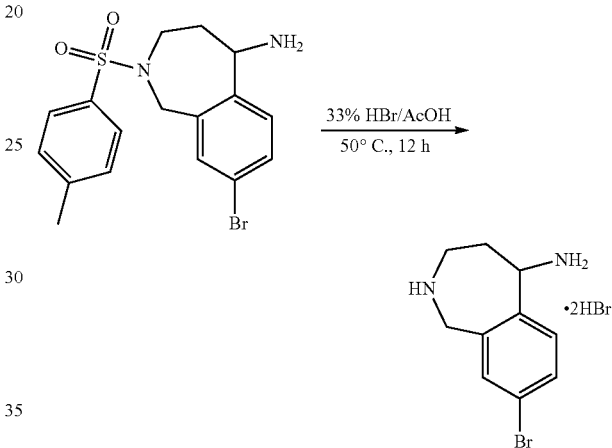

A solution of 8-bromo-2-(toluene-4-sulfonyl)-2,3,4,5-tetrahydro-1H-benzo[c]azepin-5-ylamine (2.00 g, 5.06 mmol) in HBr (33% solution in acetic acid, 20 mL) was heated at 50° C. and stirred at that temperature for 12 h. After cooling to rt, the mixture was diluted EtOAc (50 mL). The white solid was collected by filtration and dried in vacuo to afford crude product 8-bromo-2,3,4,5-tetrahydro-1H-benzo[c]azepin-5-amine (1.66 g, yield: 82%), which was used directly in the next step. ESI-MS (M+H)⁺: 241.1. $^1$H NMR (400 MHz, CD₃OD) δ: 7.72-7.55 (m, 2H), 7.18 (d, J=8.4 Hz, 1H), 4.99-4.98 (m, 1H), 4.51 (d, J=14.4 Hz, 1H), 4.39 (d, J=14.4 Hz, 1H), 3.62-3.49 (m, 2H), 2.38-2.24 (m, 1H), 2.16-2.00 (m, 1H).

9. Synthesis of tert-butyl 5-amino-8-bromo-4,5-dihydro-1H-benzo[c]azepine-2(3H)-carboxylate

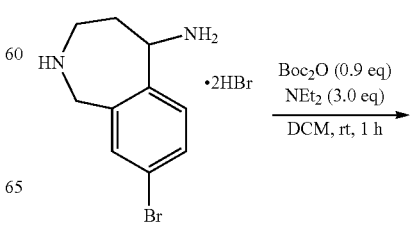

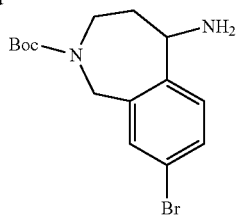

To a solution of 8-bromo-2,3,4,5-tetrahydro-1H-benzo[c]azepin-5-amine (640 mg, 1.6 mmol) and Et₃N (490 mg, 4.8 mmol) in DCM (20 mL) was added Boc₂O (314 mg, 1.4 mmol). The mixture was stirred at rt for 1 h. After diluting with DCM (100 mL), the mixture was washed with brine (20 mL×2). The organic phase was concentrated in vacuo and the residue was purified by prep-HPLC (CH₃CN/H₂O with 0.05% NH₄OH/H₂O as mobile phase) to give tert-butyl 5-amino-8-bromo-4,5-dihydro-1H-benzo[c]azepine-2(3H)-carboxylate as a colorless oil (364 mg, yield: 67%). ESI-MS (M+H)⁺: 341.1.

10. Synthesis of tert-butyl (5R)-8-bromo-5-(((4-oxidodinaphtho[2,1-d:1',2'-f][1,3,2]dioxaphosphepin-4-yl)oxy)amino)-1,3,4,5-tetrahydro-2H-benzo[c]azepine-2-carboxylate

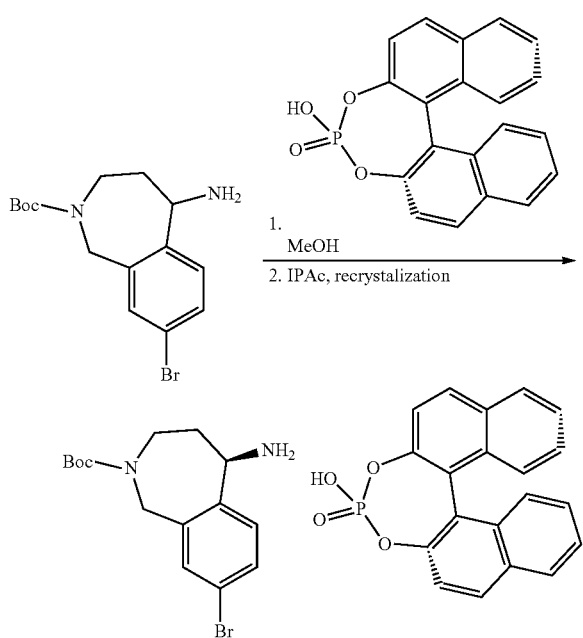

To tert-butyl 5-amino-8-bromo-4,5-dihydro-1H-benzo[c]azepine-2(3H)-carboxylate (23.5 g, 69.1 mmol) was added MeOH (141 mL, 6 vol) and (S)-(−)-1,1'-binaphthyl-2,2'-diyl hydrogenphosphate (24.0 g, 69.1 mmol). The mixture was stirred at 25° C. for 30 min and formed a yellow paste slurry. The slurry was then heated to reflux (~70° C.) and stirred at that temperature until the solids dissolved, giving a yellow solution. The mixture was then concentrated to dryness on rotary evaporator to give racemic product (50.4 g). IPAc (100 mL, 2 vol) was added and the mixture was heated to 70° C. for 3 h and then cooled to rt. Additional IPAc (100 mL, 2 vol) was added and the mixture was continued to stir at 25° C. for 16 h. The slurry was filtered by centrifuge and the cake was washed three times, each with 7 vol IPAc. The wet cake was briefly dried to afford product as a white solid with 91.3% ee. IPAc (350 mL, 7 vol) was added and the mixture was heated to 70° C. for 3 h, then cooled to 25° C. and stirred for an additional 16 h. The thick slurry was filtered by centrifuge and the cake was washed with IPAc three times, each with 10 vol (500 mL). The cake was then dried at 80° C. for 36 h under vacuum to afford tert-butyl (5R)-8-bromo-5-(((4-oxidodinaphtho[2,1-d:1',2'-f][1,3,2]dioxaphosphepin-4-yl)oxy)amino)-1,3,4,5-tetrahydro-2H-benzo[c]azepine-2-carboxylate as a white solid (40.5 g, 97.2% ee, yield: 85%). ESI-MS (M+H)⁺: 340.9.

11. Synthesis of tert-butyl (5R)-5-amino-8-bromo-1,3,4,5-tetrahydro-2-benzazepine-2-carboxylate

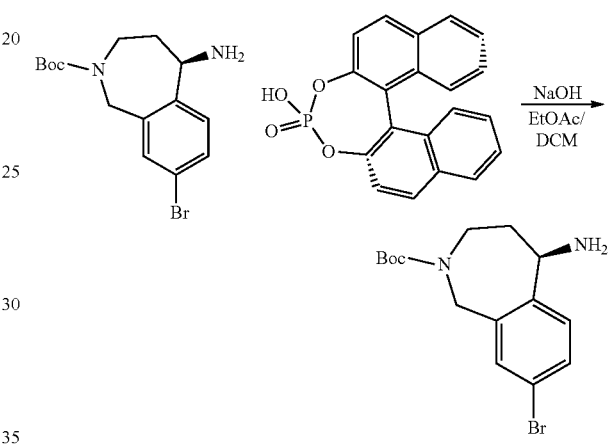

tert-Butyl (5R)-8-bromo-5-(((4-oxidodinaphtho[2,1-d:1',2'-f][1,3,2]dioxaphosphepin-4-yl)oxy)amino)-1,3,4,5-tetrahydro-2H-benzo[c]azepine-2-carboxylate (40.5 g, 58.7 mmol) was suspended in EtOAc (500 mL) and an aqueous solution of NaOH (2N, 500 mL) was added. The biphasic suspension/mixture was transferred to a 2 L sep funnel and vigourously shaken. The previously insoluble salt dissolved into the biphasic mixture and a different white solid began to crash out of solution. The entire biphasic mixture was filtered to remove the white solid. The insoluble solid was rinsed with additional portions of EtOAc and 2M NaOH solutions. After this initial filtation, the phases were separated and the aqueous phase was extracted with additional portions of EtOAc (500 mL×2). The organic phases were combined and concentrated. The residue was dissolved in dichloromethane (500 mL) and transferred into a 2 L sep funnel. An aqueous NaOH solution (1M, 500 mL) was added and the layers were shaken vigourously. The entire biphasic suspension was filtered through a Celite® pad. After filtration, the layers were separated and the aqueous phase was extracted with additional portions of DCM (500 mL×2). The organic layers were combined, washed with brine (1000 mL), dried (Na₂SO₄), filtered, and concentrated in vacuo to afford tert-butyl (5R)-8-bromo-5-[(5-tert-butyl-1,2,4-oxadiazole-3-carbonyl)amino]-1,3,4,5-tetrahydro-2-benzazepine-2-carboxylate as a yellow oil (20.0 g, yield: 100%). ESI-MS (M+H)⁺: 340.9. ¹H NMR (400 MHz, CD₃OD) δ: 7.44-7.31 (m, 3H), 4.33-4.23 (m, 2H), 4.01 (br dd, J₁=9.3 Hz, J₂=3.3 Hz, 1H), 3.96-3.86 (m, 1H), 3.62-3.40 (m, 1H), 2.00-1.86 (m, 1H), 1.75-1.60 (m, 1H), 1.41-1.36 (m, 9H).

12. Synthesis of tert-butyl (5R)-8-bromo-5-[(5-tert-butyl-1,2,4-oxadiazole-3-carbonyl)amino]-1,3,4,5-tetrahydro-2-benzazepine-2-carboxylate

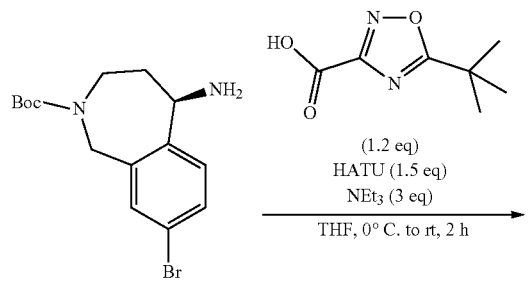

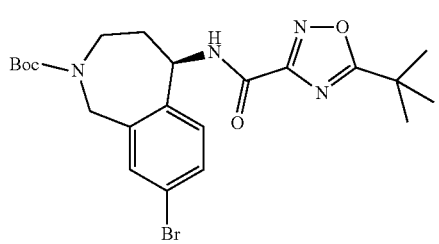

To a solution of 5-tert-butyl-1,2,4-oxadiazole-3-carboxylic acid (2.99 g, 17.6 mmol) in THF (60 mL) in an ice water cooling bath was added Et₃N (4.45 g, 44.0 mmol, 6.09 mL) and HATU (8.64 g, 22.0 mmol). The reaction mixture was stirred at 0° C. for 10 min before tert-butyl (5R)-5-amino-8-bromo-1,3,4,5-tetrahydro-2-benzazepine-2-carboxylate (5.00 g, 14.7 mmol) was added. The reaction mixture was warmed to 23° C. and stirred at rt for 2 h. Water (100 mL) was added to quench the reaction. EtOAc (100 mL) was added and the layers were separated. The aqueous phase was extracted with EtOAc (100 mL×2). The organic phases were combined, washed with brine (150 mL), dried (Na₂SO₄), filtered, and concentrated. The crude material purified by silica-gel column chromatography (EtOAc/heptanes, grading from 5% to 100%) to afford tert-butyl (5R)-8-bromo-5-[(5-tert-butyl-1,2,4-oxadiazole-3-carbonyl)amino]-1,3,4,5-tetrahydro-2-benzazepine-2-carboxylate as a white foam (6.84 g, yield: 95%). ESI-MS (M-t-Bu)⁺: 439.1.

13. Synthesis of N-[(5R)-8-bromo-2,3,4,5-tetrahydro-1H-2-benzazepin-5-yl]-5-tert-butyl-1,2,4-oxadiazole-3-carboxamide Hydrochloride

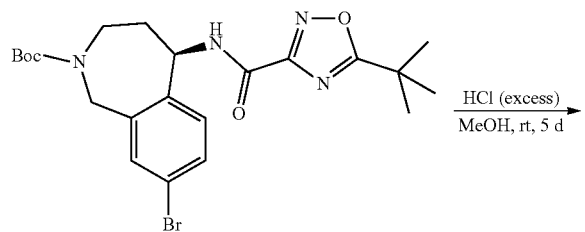

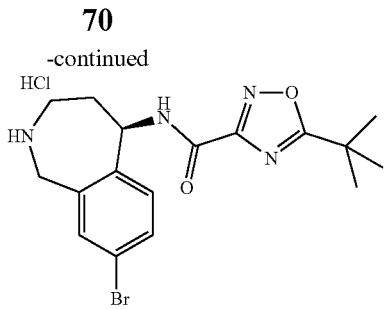

To a solution of tert-butyl (5R)-8-bromo-5-[(5-tert-butyl-1,2,4-oxadiazole-3-carbonyl)amino]-1,3,4,5-tetrahydro-2-benzazepine-2-carboxylate (1.50 g, 3.04 mmol) in MeOH (12 mL) was added HCl (1.25 M in MeOH, 12 mL). The reaction mixture was stirred for five days at ambient temperature. The reaction mixture was concentrated in vacuo to afford crude N-[(5R)-8-bromo-2,3,4,5-tetrahydro-1H-2-benzazepin-5-yl]-5-tert-butyl-1,2,4-oxadiazole-3-carboxamide hydrochloride as a white solid (1.29 g, yield: 99%), which was carried forward without further purification. ESI-MS (M+H)⁺: 395.1.

14. Synthesis of N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide

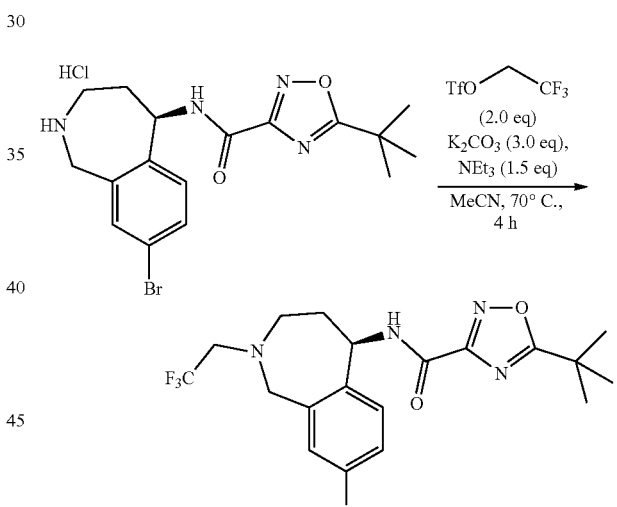

To a mixture of N-[(5R)-8-bromo-2,3,4,5-tetrahydro-1H-2-benzazepin-5-yl]-5-tert-butyl-1,2,4-oxadiazole-3-carboxamide hydrochloride (602 mg, 1.4 mmol) in acetonitrile (7 mL) was added K₂CO₃ (580 mg, 4.2 mmol), followed by 2,2,2-trifluoroethyl trifluoromethanesulfonate (650 mg, 2.8 mmol, 404 µL) and Et₃N (213 mg, 2.1 mmol, 291 µL). The mixture was heated to 70° C. and stirred at that temperature for 4 h. The mixture was diluted with DCM (20 mL) and filtered. The filter residue was washed with DCM (50 mL) and the combined filtrates were concentrated in vacuo. The crude material was purified by silica-gel column chromatography (EtOAc/heptanes, grading from 0% to 100%) to afford N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide as am off-white solid (571 mg, yield: 86%). ESI-MS (M+H)⁺: 477.0.

15. Synthesis of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide

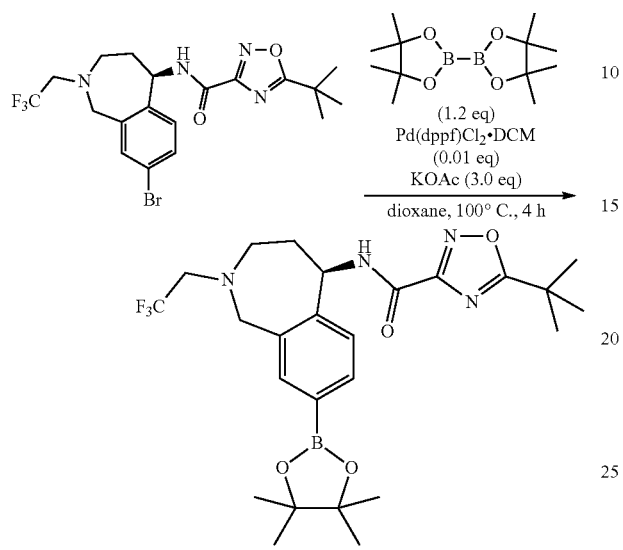

A solution of N-[(5R)-8-bromo-2-(2,2,2-trifluoroethyl)-1,3,4,5-tetrahydro-2-benzazepin-5-yl]-5-tert-butyl-1,2,4-oxadiazole-3-carboxamide (570 mg, 1.2 mmol), KOAc (353 mg, 3.6 mmol), Pd(dppf)Cl$_2$·DCM (98 mg, 0.12 mmol), and bis(pinacolato)diboron (339 mg, 1.32 mmol) in 1,4-dioxane (12 mL) was heated to 100° C. and stirred at that temperature for 4 h. The reaction mixture was cooled to rt, diluted with EtOAc (50 mL), and filtered through a pad of Celite®. The solids were washed with EtOAc (100 mL), and the filtrates were combined and concentrated in vacuo. The crude material was purified by silica-gel column chromatography (EtOAc/heptanes, 0% to 100%) to afford 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide as an off-white solid (381 mg, yield: 61%). ESI-MS (M+H)$^+$: 523.3.

16. Synthesis of N-(4-iodopyridin-2-yl)cyclopropanecarboxamide

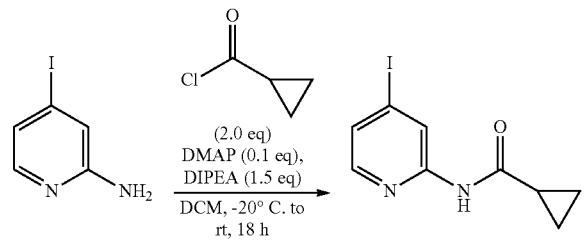 [SMILES: Nc1cc(I)ccn1 ; O=C(Cl)C1CC1 ; O=C(Nc1cc(I)ccn1)C1CC1]

A mixture of 4-iodopyridin-2-amine (2.21 g, 10 mmol, 1.21 mL), DMAP (123 mg, 1 mmol), and DIPEA (1.95 g, 15 mmol, 2.63 mL) in DCM (40 mL) was cooled to −20° C. Cyclopropanecarbonyl chloride (2.10 g, 20 mmol, 1.83 mL) was added dropwise with stirring. The mixture was allowed to warm to rt and continued to stir at rt for 18 h. The reaction was quenched with H$_2$O (40 mL) and the layers were separated. The aqueous phase was back-extracted with DCM (50 mL) and the combined DCM phases were dried (MgSO$_4$) and filtered. The filtrate was concentrated in vacuo and the residue was purified by silica-gel column chromatography (EtOAc/heptanes, grading from 0% to 50%) to afford N-(4-iodopyridin-2-yl)cyclopropanecarboxamide as a white solid (2.2 g, yield: 95%). ESI-MS (M+H)$^+$: 289.0. $^1$H NMR (400 MHz, CD$_3$OD) δ: 8.57-8.54 (m, 1H), 7.97 (d, J=5.3 Hz, 1H), 7.46 (dd, J$_1$=5.3 Hz, J$_2$=1.5 Hz, 1H), 1.90-1.82 (m, 1H), 1.01-0.94 (m, 2H), 0.92-0.86 (m, 2H).

17. Synthesis of (R)-5-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-3-carboxamide (Compound 10)

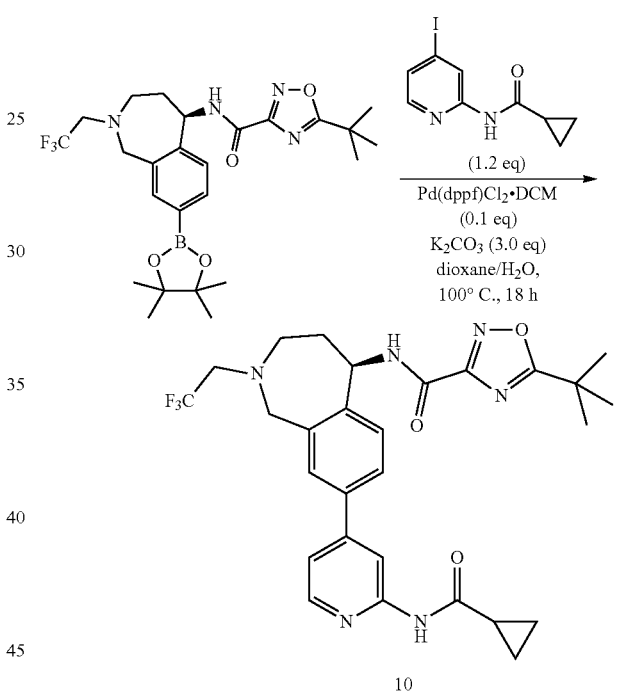

A mixture of 5-tert-butyl-N-[(5R)-8-(4,4,5,5-tetramethyl-1,3,2-dioxaborolan-2-yl)-2-(2,2,2-trifluoroethyl)-1,3,4,5-tetrahydro-2-benzazepin-5-yl]-1,2,4-oxadiazole-3-carboxamide (114 mg, 218 μmol), N-(4-iodo-2-pyridyl)cyclopropanecarboxamide (75 mg, 262 μmol), K$_2$CO$_3$ (90 mg, 655 μmol), and Pd(dppf)Cl$_2$·DCM (8.9 mg, 11 μmol) was dissolved in 1,4-dioxane (1.75 mL) and H$_2$O (438 μL). The reaction mixture was heated to 100° C. and stirred at that temperature for 18 h. The reaction was diluted with H$_2$O (10 mL) and extracted EtOAc (10 mL×2). The combined organic extracts were washed with brine (20 mL), dried (Na$_2$SO$_4$), filtered, and concentrated. The crude material was purified by silica-gel column chromatography ([3:1 EtOAc:EtOH]/heptanes, grading from 0% to 100%) to give 5-tert-butyl-N-[(5R)-8-[2-(cyclopropanecarbonylamino)-4-pyridyl]-2-(2,2,2-trifluoroethyl)-1,3,4,5-tetrahydro-2-benzazepin-5-yl]-1,2,4-oxadiazole-3-carboxamide as a white solid (64 mg, yield: 53%). ESI-MS (M+H)$^+$: 557.2. $^1$H NMR (500 MHz, DMSO-d$_6$) δ:10.89 (s, 1H), 9.56 (br d, J=7.9 Hz, 1H), 8.39 (s, 1H), 8.37 (d, J=5.5 Hz, 1H), 7.61 (dd, J$_1$=7.9 Hz, J$_2$=1.8 Hz, 1H), 7.54 (d, J=1.8 Hz, 1H), 7.41 (dd, J$_1$=5.5 Hz, J$_2$=1.8 Hz, 1H), 7.35 (d, J=7.9 Hz, 1H), 5.42 (br t, J=9.5 Hz, 1H), 4.26 (br d, J=15.3 Hz, 1H), 4.03-3.96 (m, 1H), 3.34-3.26 (m, 1H), 3.22-3.04 (m, 3H), 2.12-2.00 (m, 2H), 1.79 (br d, J=14.7 Hz, 1H), 1.45 (s, 9H), 0.87-0.78 (m, 4H).

Example 11: 5-(tert-butyl)-N-(4-(2-(cyclopropanecarboxamido)pyridin-4-yl)-3-fluoro-2-methylbenzyl)-1,2,4-oxadiazole-3-carboxamide (Compound 11)

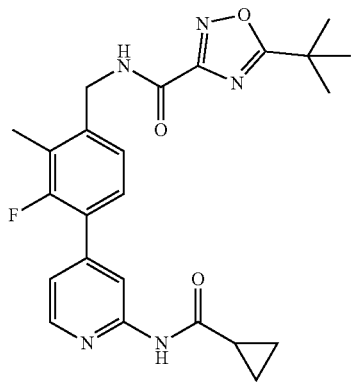

1. Synthesis of 4-bromo-2-fluoro-3-methylaniline

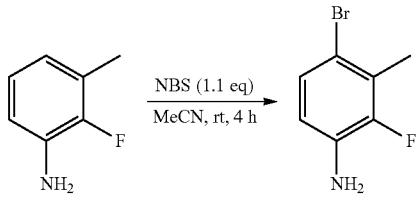

To a solution of 2-fluoro-3-methylaniline (25.0 g, 200 mmol) in MeCN (200 mL) was added dropwise a solution of NBS (39.1 g, 220 mmol) in MeCN (100 mL) at 25° C. The reaction mixture was stirred at 25° C. for 4 h. The reaction mixture was concentrated and purified by silica-gel column chromatography (petroleum ether/EtOAc, 50:1) to give 4-bromo-2-fluoro-3-methylaniline as a brown oil (30 g, yield: 74%). $^1$H NMR: (400 MHz, DMSO-d$_6$) δ: 7.02 (dd, J$_1$=8.8 Hz, J$_2$=1.6 Hz, 1H), 6.55 (t, J=8.8 Hz, 1H), 5.21 (s, 2H), 2.16 (d, J=2.4 Hz, 3H).

2. Synthesis of N-(4-bromo-2-fluoro-3-methylphenyl)acetamide

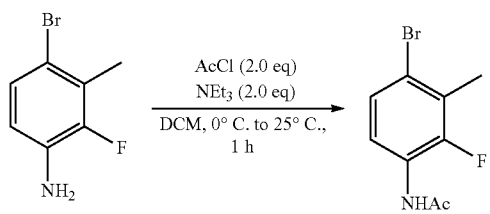

To a solution of 4-bromo-2-fluoro-3-methylaniline (30 g, 147 mmol) and Et$_3$N (29.8 g, 294 mmol) in DCM (300 mL) was added dropwise AcCl (23.1 g, 294 mmol) at 0° C. The mixture was then stirred at 25° C. for 1 h. The reaction mixture was poured into H$_2$O (300 mL) and extracted with DCM (200 mL×2). The combined organic layers were washed with brine (400 mL), dried (Na$_2$SO$_4$), filtered, and concentrated to give N-(4-bromo-2-fluoro-3-methylphenyl) acetamide as a brown solid (34.0 g, yield: 94%). $^1$H NMR: (400 MHz, DMSO-d$_6$) δ: 9.74 (s, 1H), 7.71 (t, J=8.4 Hz, 1H), 7.36 (d, J=8.8 Hz, 1H), 2.25 (d, J=2.4 Hz, 3H), 2.06 (s, 3H).

3. Synthesis of N-(4-cyano-2-fluoro-3-methylphenyl)acetamide

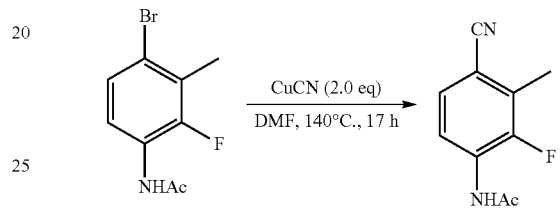

A mixture of N-(4-bromo-2-fluoro-3-methylphenyl)acetamide (32 g, 0.13 mol) and Cu(I)CN (23.3 g, 0.26 mol) in DMF (300 mL) was prepared under N$_2$ and heated at 140° C. for 17 h. The reaction mixture was poured into H$_2$O (500 mL) and extracted with EtOAc (300 mL×3). The combined organic extracts were washed with brine (500 mL), dried (Na$_2$SO$_4$), filtered, and concentrated to give crude material. The crude material was triturated with a petroleum ether/EtOAc solution (50:1, 300 mL), filtered, and concentrated to give N-(4-cyano-2-fluoro-3-methylphenyl)acetamide as a yellow solid (25.0 g, yield: 94%). $^1$H NMR: (400 MHz, DMSO-d$_6$) δ: 10.04 (s, 1H), 8.08 (s, 1H), 7.54 (d, J=8.4 Hz, 1H), 2.36 (s, 3H), 2.11 (s, 3H).

4. Synthesis of 4-amino-3-fluoro-2-methylbenzonitrile

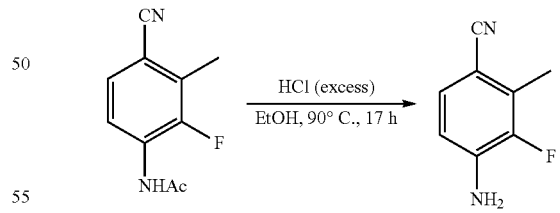

To a solution of N-(4-cyano-2-fluoro-3-methylphenyl)acetamide (25.0 g, 130 mmol) in EtOH (200 mL) was added concentrated HCl solution (12 N, 100 mL). The mixture was heated at 90° C. for 17 h. The mixture was concentrated under vacuum. The resulting white solid was dissolved in EtOAc (200 mL) and the pH of the solution was adjusted to pH=7 with saturated aqueous Na$_2$CO$_3$ solution (100 mL). The layers were separated and the organic phase was dried (Na$_2$SO$_4$), filtered, and concentrated under vacuum to give 4-amino-3-fluoro-2-methylbenzonitrile as a brown solid (19.0 g, yield: 97%). ¹H NMR: (400 MHz, DMSO-d₆) δ: 7.20 (d, J=8.4 Hz, 1H), 6.61 (t, J=8.4 Hz, 1H), 6.13 (s, 2H), 2.24 (d, J=2.4 Hz, 3H).

5. Synthesis of 4-bromo-3-fluoro-2-methylbenzonitrile

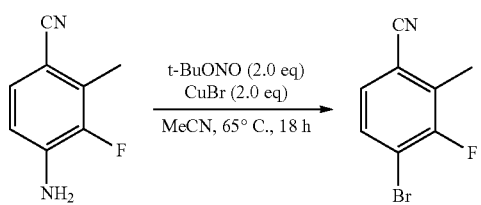

To a suspension of Cu(I)Br (32.5 g, 226 mmol) in MeCN (300 mL) was added tert-butyl nitrite (23.4 g, 226 mmol) at rt. Then, a solution of 4-amino-3-fluoro-2-methylbenzonitrile (17 g, 113 mmol) in MeCN (50 mL) was added dropwise at 65° C. over 1 h. The mixture was stirred at 65° C. for 17 h, cooled to rt, and concentrated to give crude material. The crude material was purified by silica-gel column chromatography (petroleum ether/EtOAc, 15:1) to give 4-bromo-3-fluoro-2-methylbenzonitrile as a yellow oil (14.5 g, yield: 60%). ¹H NMR: (400 MHz, DMSO-d₆) δ: 7.74 (t, J=7.6 Hz, 1H), 7.59 (dd, J₁=8.4 Hz, J₂=0.8 Hz, 1H), 2.41 (d, J=2.4 Hz, 3H).

6. Synthesis of (4-bromo-3-fluoro-2-methylphenyl)methanamine

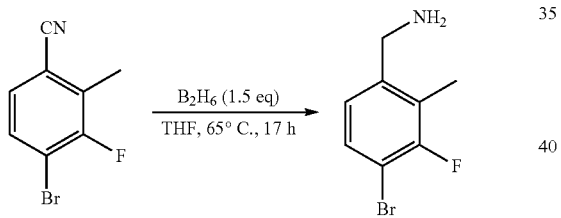

To a solution of 4-bromo-3-fluoro-2-methylbenzonitrile (15.0 g, 70 mmol) in THF (150 mL) was added B₂H₆ (10.5 mL, 105 mmol, 10 M in Me₂S) at 25° C. slowly. The reaction mixture was heated at 65° C. for 17 h. The mixture was quenched with MeOH (10 mL) and concentrated under vacuum to give crude (4-bromo-3-fluoro-2-methylphenyl)methanamine (15 g, crude), which was used for the next step directly without further purification.

7. Synthesis of tert-butyl (4-bromo-3-fluoro-2-methylbenzyl)carbamate

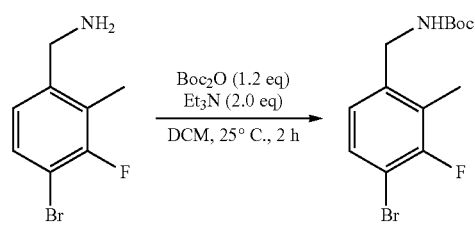 [SMILES: Cc1c(CN)ccc(Br)c1F ; Cc1c(CNC(=O)OC(C)(C)C)ccc(Br)c1F]

To a solution of (4-bromo-3-fluoro-2-methylphenyl)methanamine (14 g, 64 mmol) in DCM (100 mL) was added Et₃N (13 g, 128 mmol) and Boc₂O (16.8 g, 77 mmol) at 25° C. The mixture was stirred at 25° C. for 2 h. The mixture was concentrated under vacuum and was purified by silica-gel column chromatography (petroleum ether/EtOAc, 50:1) to give tert-butyl (4-bromo-3-fluoro-2-methylbenzyl)carbamate as a white solid (12.0 g, yield: 59%). ¹H NMR: (400 MHz, DMSO-d₆) δ: 7.47 (t, J=7.6 Hz, 1H), 7.37 (t, J=5.2 Hz, 1H), 6.96 (d, J=8.0 Hz, 1H), 4.07 (d, J=6.0 Hz, 2H), 2.19 (d, J=2.0 Hz, 3H), 1.37 (s, 9H).

8. Synthesis of tert-butyl (3-fluoro-2-methyl-4-(4,4,5,5-tetramethyl-1,3,2-dioxaborolan-2-yl)benzyl)carbamate

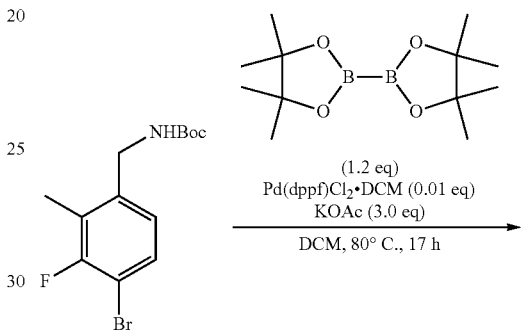

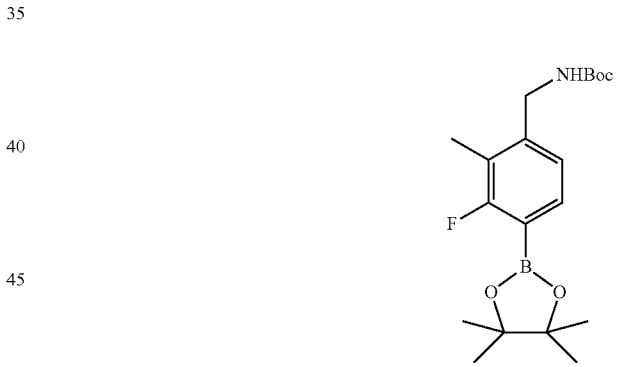

To a solution of tert-butyl (4-bromo-3-fluoro-2-methylbenzyl)carbamate (10 g, 31.4 mmol) in 1,4-dioxane (150 mL) was added bis(pinacolato)diboron (9.6 g, 37.7 mmol) and KOAc (6.2 g, 62.9 mmol). Then Pd(dppf)Cl₂·DCM (2.1 g, 2.5 mmol) was added under N₂ atmosphere. The reaction mixture was stirred at 80° C. for 17 h under N₂. The reaction mixture was concentrated under vacuum and purified by silica-gel column chromatography (petroleum ether/EtOAc, 20:1) to give tert-butyl (3-fluoro-2-methyl-4-(4,4,5,5-tetramethyl-1,3,2-dioxaborolan-2-yl)benzyl)carbamate as a yellow solid (13.0 g, impure) which was used without additional purification. ESI-MS (M-t-Bu)⁺: 310.1.

9. Synthesis of tert-butyl (4-(2-(cyclopropanecarboxamido)pyridin-4-yl)-3-fluoro-2-methylbenzyl)carbamate

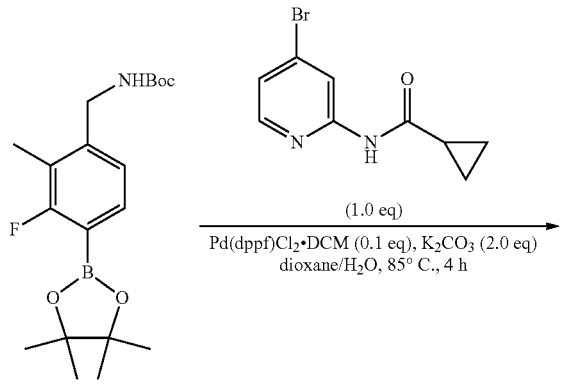

To a solution of tert-butyl (3-fluoro-2-methyl-4-(4,4,5,5-tetramethyl-1,3,2-dioxaborolan-2-yl)benzyl)carbamate (400 mg, 1.10 mmol) in a mixture of 1,4-dioxane/H₂O (v/v=3/1, 8 mL) was added N-(4-bromopyridin-2-yl)cyclopropanecarboxamide (264 mg, 1.10 mmol) and K₂CO₃ (303 mg, 2.20 mmol). Then Pd(dppf)Cl₂·DCM (90 mg, 0.11 mmol) was added under an N₂ atmosphere. The mixture was heated to 85° C. and stirred at that temperature for 4 h under N₂. The mixture was concentrated under vacuum to give crude material. The crude material was purified by silica-gel column chromatography (petroleum ether/EtOAc, grading from 3:1 to 1:1) to give tert-butyl (4-(2-(cyclopropanecarboxamido)pyridin-4-yl)-3-fluoro-2-methylbenzyl)carbamate as a yellow oil (350 mg, yield: 80%). ESI-MS (M+H)⁺: 400.2. ¹H NMR: (400 MHz, CD₃OD) δ: 8.33 (d, J=4.8 Hz, 1H), 8.29 (s, 1H), 7.36 (t, J=8.4 Hz, 1H), 7.29 (d, J=4.8 Hz, 1H), 7.20 (d, J=7.6 Hz, 1H), 4.31 (d, J=4.0 Hz, 2H), 2.30 (d, J=2.0 Hz, 3H), 1.96-1.88 (m, 1H), 1.49 (s, 9H), 1.03-0.99 (m, 2H), 0.94-0.90 (m, 2H).

10. Synthesis of N-(4-(4-(aminomethyl)-2-fluoro-3-methylphenyl)pyridin-2-yl)cyclopropanecarboxamide hydrochloride

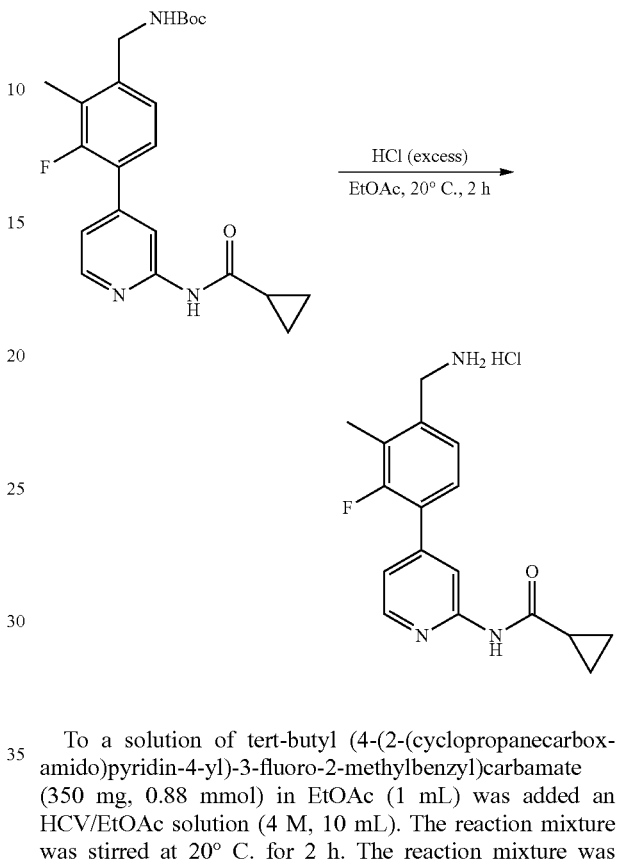

To a solution of tert-butyl (4-(2-(cyclopropanecarboxamido)pyridin-4-yl)-3-fluoro-2-methylbenzyl)carbamate (350 mg, 0.88 mmol) in EtOAc (1 mL) was added an HCV/EtOAc solution (4 M, 10 mL). The reaction mixture was stirred at 20° C. for 2 h. The reaction mixture was filtered and the filter cake was dried to give N-(4-(4-(aminomethyl)-2-fluoro-3-methylphenyl)pyridin-2-yl)cyclopropanecarboxamide hydrochloride as a yellow solid (200 mg, yield: 68%), which was carried forward without further purification. ESI-MS (M+H)⁺: 300.1.

11. Synthesis of 5-(tert-butyl)-N-(4-(2-(cyclopropanecarboxamido)pyridin-4-yl)-3-fluoro-2-methylbenzyl)-1,2,4-oxadiazole-3-carboxamide (Compound 11)

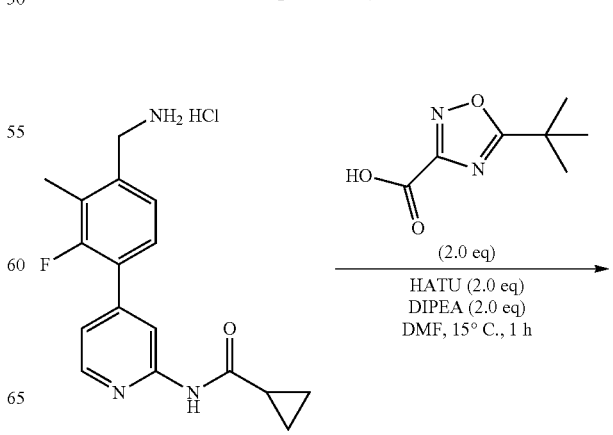

-continued

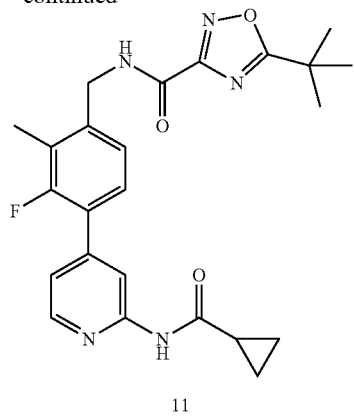

11

To a solution of N-(4-(4-(aminomethyl)-2-fluoro-3-methylphenyl)pyridin-2-yl)cyclopropanecarboxamide hydrochloride (150 mg, 0.45 mmol) in DMF (5 mL) was added DIPEA (116 mg, 0.90 mmol), 5-(tert-butyl)-1,2,4-oxadiazole-3-carboxylic acid (152 mg, 0.90 mmol), and HATU (342 mg, 0.90 mmol). The reaction mixture was stirred at 15° C. for 1 h. The reaction mixture was filtered and the filtrate was purified by prep-HPLC (CH$_3$CN/H$_2$O with 0.05% NH$_4$OH/H$_2$O as mobile phase) to give impure product (130 mg), which was re-purified by prep-HPLC (CH$_3$CN/H$_2$O with 0.05% HCl/H$_2$O as mobile phase) to give 5-(tert-butyl)-N-(4-(2-(cyclopropanecarboxamido)pyridin-4-yl)-3-fluoro-2-methylbenzyl)-1,2,4-oxadiazole-3-carboxamide as a white solid (117 mg, yield: 58%). ESI-MS (M+H)$^+$: 452.1. $^1$H NMR: (400 MHz, CD$_3$OD) δ: 8.38 (d, J=4.8 Hz, 1H), 7.80 (d, J=6.0 Hz, 1H), 7.72 (s, 1H), 7.58 (t, J=7.6 Hz, 1H), 7.38 (d, J=8.0 Hz, 1H), 4.70 (s, 2H), 2.42 (d, J=2.0 Hz, 3H), 1.98 (m, 1H), 1.51 (s, 9H), 1.22-1.14 (m, 4H).

Example 12: 3-(tert-butyl)-N-(4-(2-(cyclopropanecarboxamido)pyridin-4-yl)-5-fluoro-2-methylbenzyl)-1,2,4-oxadiazole-5-carboxamide (Compound 12)

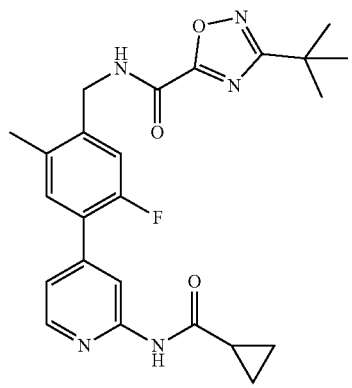

12

1. Synthesis of tert-butyl (4-bromo-5-fluoro-2-methylbenzyl)carbamate

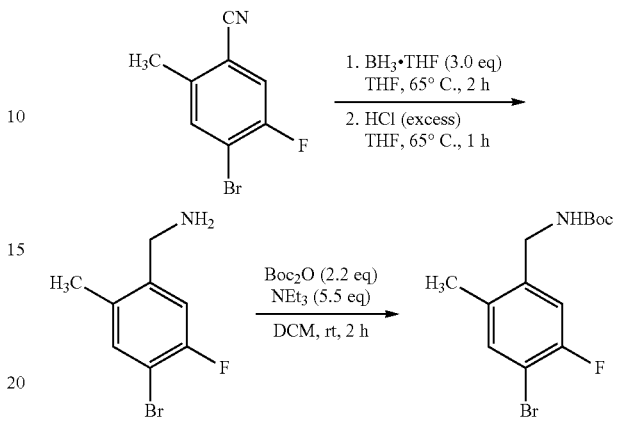

To a solution of 4-bromo-5-fluoro-2-methylbenzonitrile (15.4 g, 72.0 mmol) in THF (185 mL), was added BH$_3$·THF (1.0 M in THF, 223 mL, 223 mmol) and the mixture was heated under reflux for 2 h. The reaction was cooled down to rt and an HCl solution (1 M, 45 mL) was added dropwise to the solution (CAUTION: REACTION VERY EXOTHERMIC!) and the mixture was again heated to refluxed for 1 h. Then, it was cooled down to rt and the solvent was removed under reduced pressure. The residue was dissolved in DCM (690 mL) and Et$_3$N (57 mL, 409 mmol) and Boc$_2$O (35 mL, 152 mmol) were added. The mixture was left to stir at rt for 2 h. Then, H$_2$O (500 mL) was added and the layers were separated. The aqueous layer was extracted with DCM (500 mL×2) and the combined organic layers were dried (Na$_2$SO$_4$), filtered, and concentrated in vacuo. the solvent removed under reduced pressure. The crude material was purified by silica-gel column chromatography (EtOAc/heptanes, grading from 0% to 20%) to give tert-butyl (4-bromo-5-fluoro-2-methylbenzyl)carbamate as a white solid (17.2 g, yield:75%). ESI-MS (M-t-Bu)$^+$: 262.0.

2. Synthesis of tert-butyl (5-fluoro-2-methyl-4-(4,4,5,5-tetramethyl-1,3,2-dioxaborolan-2-yl)benzyl)carbamate

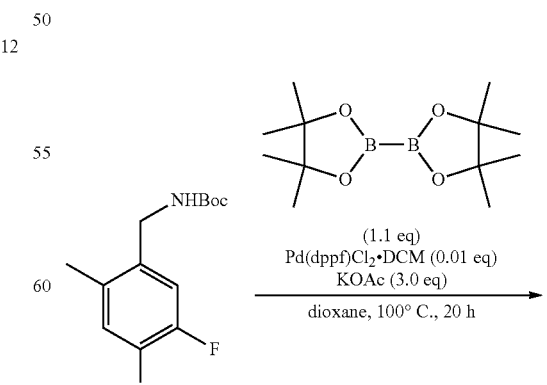

-continued

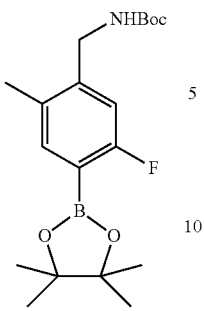

A solution of tert-butyl (4-bromo-5-fluoro-2-methylbenzyl)carbamate (2.45 g, 6.73 mmol) and bis(pinacolato)diboron (1.88 g, 7.40) in dry 1,4-dioxane (58 mL) was degassed with N₂ for 10 min. Then, KOAc (1.98 g, 20.2 mmol) and Pd(dppf)Cl₂·DCM (0.49 g, 0.67 mmol) were added and the solution was degassed with N₂ for 10 min. The reaction mixture was heated to 100° C. and stirred at that temperature for 20 h. The reaction mixture was cooled to rt and filtered through a pad of Celite®. The solvent was removed under reduced pressure and the residue was diluted with EtOAc (100 mL). Water (100 mL) was added and the layers were separated. The aqueous layer was extracted with EtOAc (100 mL×2). The combined organic extracts were dried (Na2SO4), filtered, and concentrated in vacuo. The crude material was purified by silica-gel column chromatography (EtOAc/heptanes, grading from 0% to 10%) to give impure product as a light-yellow oil. This impure oil was triturated with pentane to give tert-butyl (5-fluoro-2-methyl-4-(4,4,5,5-tetramethyl-1,3,2-dioxaborolan-2-yl)benzyl)carbamate as a white solid (1.89 g, yield: 77%). ESI-MS (M-t-Bu)⁺: 310.2.

3. Synthesis of tert-butyl (4-(2-(cyclopropanecarboxamido)pyridin-4-yl)-5-fluoro-2-methylbenzyl)carbamate

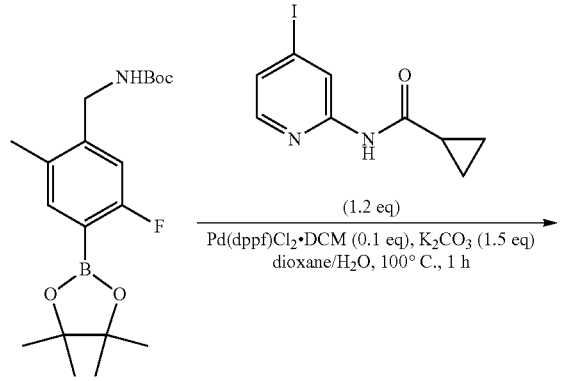

-continued

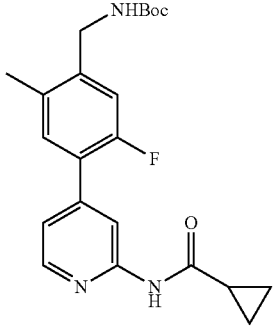

To a solution of tert-butyl (5-fluoro-2-methyl-4-(4,4,5,5-tetramethyl-1,3,2-dioxaborolan-2-yl)benzyl)carbamate (150 mg, 0.41 mmol) in a mixture of 1,4-dioxane/H₂O (v/v=15/1, 6 mL) were added N-(4-iodopyridin-2-yl)cyclopropanecarboxamide (142 mg, 0.49 mmol) and K₂CO₃ (85 mg, 0.61 mmol). The reaction mixture was degassed with N₂ for 5 min before Pd(dppf)Cl₂·DCM (17 mg, 0.02 mmol) was added under an N₂ atmosphere. The mixture was heated to 100° C. and stirred at that temperature for 1 h under N₂. The reaction mixture was cooled to rt and EtOAc (50 mL) was added. The organic phase was washed with H₂O (50 mL×2), dried (Na₂SO₄), filtered and concentrated in vacuo. The crude material was purified by silica-gel column chromatography ([3:1 EtOAc:EtOH]/heptanes, grading from 5% to 100%) to give tert-butyl (4-(2-(cyclopropanecarboxamido)pyridin-4-yl)-5-fluoro-2-methylbenzyl)carbamate as an off-white solid (140 mg, yield: 85%). ESI-MS (M+H)⁺: 400.3.

4. Synthesis of N-(4-(4-(aminomethyl)-2-fluoro-5-methylphenyl)pyridin-2-yl)cyclopropanecarboxamide Hydrochloride

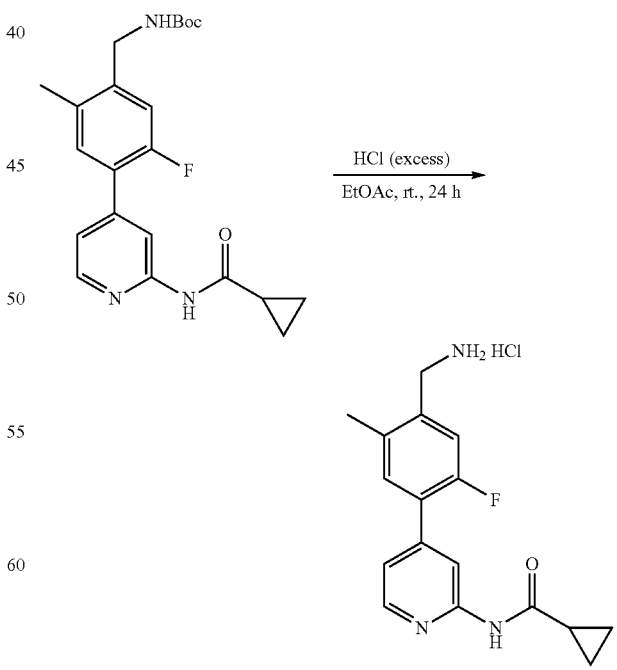

To a solution of tert-butyl (4-(2-(cyclopropanecarboxamido)pyridin-4-yl)-5-fluoro-2-methylbenzyl)carbamate (140 mg, 0.35 mmol) in EtOAc (3 mL) was added a solution of HCl/EtOAc (1.25 M, 1.54 mL). The reaction mixture was stirred at rt for 24 h. The reaction mixture was concentrated in vacuo to give N-(4-(4-(aminomethyl)-2-fluoro-5-methylphenyl)pyridin-2-yl)cyclopropanecarboxamide hydrochloride as a yellow solid (105 mg, crude), which was carried forward without further purification. ESI-MS (M+H)+: 300.1.

5. Synthesis of 3-(tert-butyl)-N-(4-(2-(cyclopropanecarboxamido)pyridin-4-yl)-5-fluoro-2-methylbenzyl)-1,2,4-oxadiazole-5-carboxamide (Compound 12)

ecarboxamido)pyridin-4-yl)-5-fluoro-2-methylbenzyl)-1,2,4-oxadiazole-5-carboxamide as a white solid (31 mg, yield: 32%). ESI-MS (M+H)+: 452.2. ¹H NMR (400 MHz, CD₃OD) δ: 8.34 (d, J=6.0 Hz, 1H), 7.94-7.89 (m, 1H), 7.59 (d, J=6.0 Hz, 1H), 7.51 (d, J=7.5 Hz, 1H), 7.26 (d, J=12.0 Hz, 1H), 4.62 (s, 2H), 2.44 (s, 3H), 1.91 (s, 1H), 1.46-1.39 (m, 9H), 1.14-1.08 (m, 2H), 1.04 (dt, J₁=8.0 Hz, J₂=3.2 Hz, 2H).

Example 13: 5-(tert-butyl)-N-(4-(2-(cyclopropanecarboxamido)pyridin-4-yl)-5-fluoro-2-methylbenzyl)-1,2,4-oxadiazole-3-carboxamide (Compound 13)

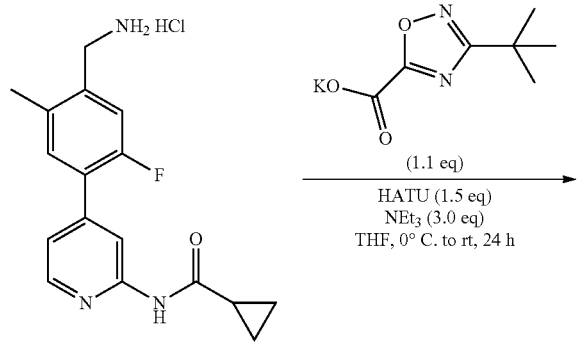
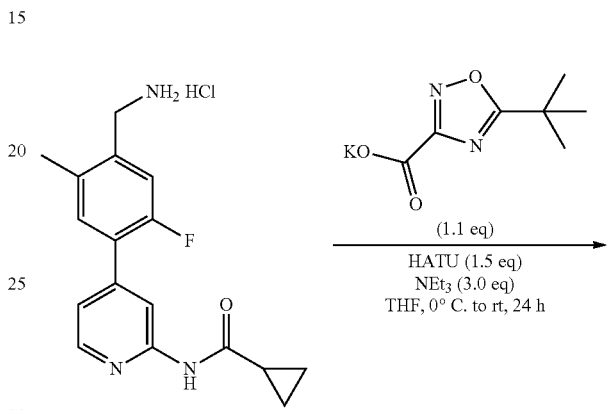

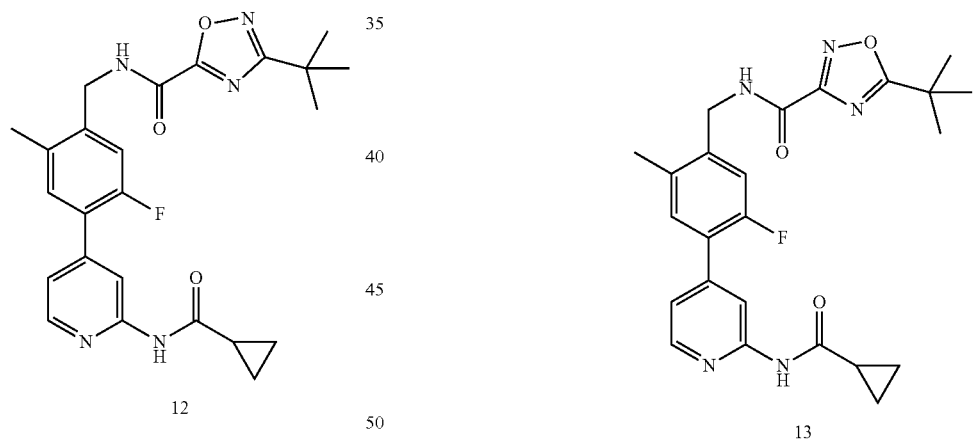

To a solution of potassium 3-(tert-butyl)-1,2,4-oxadiazole-5-carboxylate (40 mg, 0.19 mmol) in THF (1.7 mL) in an ice-water cooling bath were added Et₃N (53 mg, 0.53 mmol, 73 μL) and HATU (103 mg, 0.26 mmol). The reaction mixture was stirred at 0° C. for 10 min before N-(4-(4-(aminomethyl)-2-fluoro-5-methylphenyl)pyridin-2-yl)cyclopropanecarboxamide hydrochloride (52 mg, 0.17 mmol) was added. The reaction mixture was warmed to rt and continued to stir at that temperature for 24 h. Water (5 mL) was added, followed by EtOAc (5 mL) and the layers were separated. The aqueous phase was extracted with EtOAc (5 mL×2). The combined organic extracts were washed with brine (10 mL), dried (Na₂SO₄), filtered and concentrated in vacuo. The crude material was purified by prep-HPLC (CH₃CN/H₂O with 0.05% TFA/H₂O as mobile phase) to give the TFA salt of 3-(tert-butyl)-N-(4-(2-(cyclopropan- Synthesis of 5-(tert-butyl)-N-(4-(2-(cyclopropanecarboxamido)pyridin-4-yl)-5-fluoro-2-methylbenzyl)-1,2,4-oxadiazole-3-carboxamide was similar to that of 3-(tert-butyl)-N-(4-(2-(cyclopropanecarboxamido)pyridin-4-yl)-5-fluoro-2-methylbenzyl)-1,2,4-oxadiazole-5-carboxamide in Example 12, Step 5. The crude material was purified by prep-HPLC (CH₃CN/H₂O with 0.05% TFA/H₂O as mobile phase) to give the TFA salt of 5-(tert-butyl)-N-(4-(2-(cyclopropanecarboxamido)pyridin-4-yl)-5-fluoro-2-methylbenzyl)-1,2,4-oxadiazole-3-carboxamide as a white solid (47 mg, yield: 47%). ESI-MS (M+H)+: 452.2. ¹H NMR (400 MHz, CD₃OD) δ: 8.34 (d, J=5.8 Hz, 1H), 7.86 (s, 1H), 7.63 (dt, J₁=6.2 Hz, J₂=1.4 Hz, 1H), 7.52 (d, J=7.8 Hz, 1H), 7.24 (d, J=12.0 Hz, 1H), 4.63 (s, 2H), 2.45 (s, 3H), 2.02-1.82 (m, 1H), 1.49 (s, 9H), 1.17-1.10 (m, 2H), 1.08-1.01 (m, 2H).

Example 14: 5-(tert-butyl)-N-(2-chloro-4-(2-(cyclopropanecarboxamido)pyridin-4-yl)-3-fluorobenzyl)-1,2,4-oxadiazole-3-carboxamide (Compound 14)

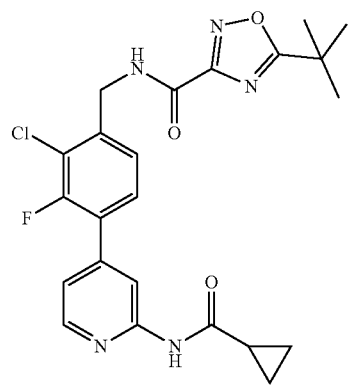

1. Synthesis of 4-bromo-3-chloro-2-fluoroaniline

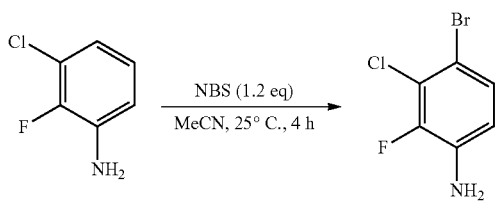 [SMILES: Nc1cccc(Cl)c1F ; Nc1ccc(Br)c(Cl)c1F]

To a mixture of 3-chloro-2-fluoroaniline (18.0 g, 124 mmol) in MeCN (100 mL) was added a solution of NBS (26.4 g, 148 mmol) in MeCN (100 mL) in a dropwise manner at 25° C. The mixture was stirred at 25° C. for 4 h. The reaction mixture was concentrated to give the crude product. The crude material was purified by silica-gel column chromatography (petroleum ether/EtOAc, 50:1) to give 4-bromo-3-chloro-2-fluoroaniline as a brown oil (18.0 g, yield: 65%). $^1$H NMR: (400 MHz, CD$_3$OD) δ: 7.13 (dd, J$_1$=8.8 Hz, J$_2$=2.0 Hz, 1H), 6.66 (t, J=8.4 Hz, 1H).

2. Synthesis of N-(4-bromo-3-chloro-2-fluorophenyl)acetamide

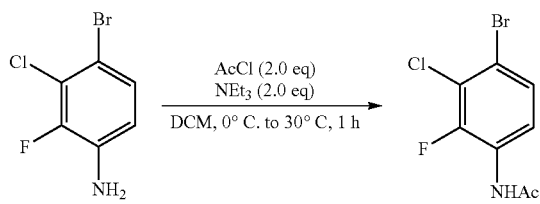

To a solution of 4-bromo-3-chloro-2-fluoroaniline (18.0 g, 80 mmol) in DCM (150 mL) in an ice-water cooling bath at 0° C. was added AcCl (12.6 g, 160 mmol) in a dropwise manner, followed by Et$_3$N (16.2 g, 160 mmol). The mixture was then stirred at 30° C. for 1 h. The reaction mixture was poured in H$_2$O (200 mL) and extracted with DCM (100 mL×2). The combined organic extracts were washed with brine (400 mL), dried (Na$_2$SO$_4$), filtered, and concentrated to give crude N-(4-bromo-3-chloro-2-fluorophenyl)acetamide (20.0 g, crude). The crude material was carried forward without further purification. $^1$H NMR: (400 MHz, CD$_3$OD) δ: 7.85 (t, J=8.8 Hz, 1H), 7.44 (d, J=10.0 Hz, 1H), 2.17 (s, 3H).

3. Synthesis of N-(3-chloro-4-cyano-2-fluorophenyl)acetamide

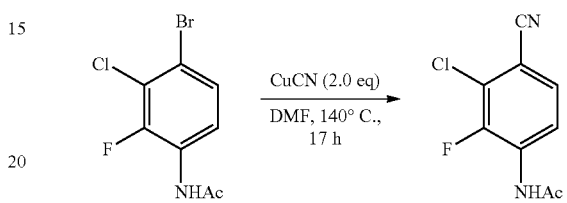

A solution of N-(4-bromo-3-chloro-2-fluorophenyl)acetamide (20.0 g, 75 mmol) and Cu(I)CN (13.4 g, 150 mmol) in DMF (200 mL) was heated to 140° C. and stirred at that temperature under N$_2$ for 17 h. The reaction mixture was poured in H$_2$O (500 mL) and extracted with EtOAc (200 mL×3). The combined organic extracts were washed with brine (500 mL), dried (Na$_2$SO$_4$), filtered, and concentrated to give crude N-(3-chloro-4-cyano-2-fluorophenyl)acetamide as a brown solid (14.0 g, yield: 88%). The crude material was carried forward without further purification. $^1$H NMR: (400 MHz, CD$_3$OD) δ: 8.30 (t, J=7.2 Hz, 1H), 7.57 (d, J=8.0 Hz, 1H), 2.19 (s, 3H).

4. Synthesis of 4-amino-2-chloro-3-fluorobenzonitrile

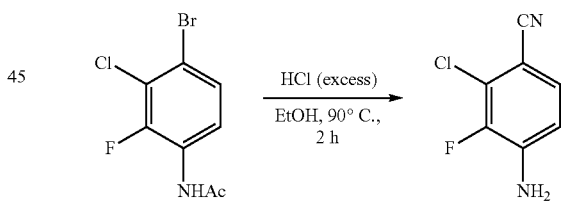

To a solution of N-(3-chloro-4-cyano-2-fluorophenyl)acetamide (8.0 g, 38 mmol) in EtOH (100 mL) was added concentrated HCl solution (12N, 50 mL). The mixture was heated at 90° C. for 2 h. The reaction mixture was concentrated under vacuum and the resulting white solid was dissolved in EtOAc (100 mL). The pH of the solution was adjusted to pH=7 with saturated aqueous Na$_2$CO$_3$ solution (100 mL) and the layers were separated. The organic phase was dried (Na$_2$SO$_4$), filtered, and concentrated. The crude material was purified by silica-gel column chromatography (petroleum ether/EtOAc, 2:1) to give 4-amino-2-chloro-3-fluorobenzonitrile as a yellow solid (5.0 g, yield: 78%). $^1$H NMR: (400 MHz, CDCl$_3$) δ: 7.23 (dd, J$_1$=8.8 Hz, J$_2$=1.6 Hz, 1H), 6.66 (t, J=8.4 Hz, 1H), 4.36 (s, 2H).

5. Synthesis of 2-chloro-3-fluoro-4-iodobenzonitrile

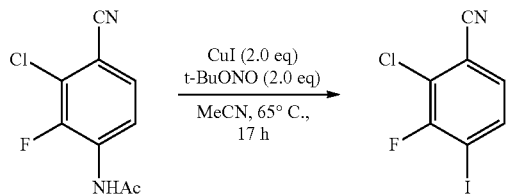 [SMILES: CC(=O)Nc1ccc(C#N)c(Cl)c1F ; N#Cc1ccc(I)c(F)c1Cl]

To a suspension of Cu(I)I (11.2 g, 59 mmol) in MeCN (50 mL) was added tert-butyl nitrite (6.0 g, 59 mmol) at rt. The reaction mixture was heated to 65° C. and a solution of 4-amino-2-chloro-3-fluorobenzonitrile (5.0 g, 29 mmol) in MeCN (50 mL) was added dropwise at 65° C. over 1 h. The mixture was stirred at 65° C. for 17 h and then was concentrated. The crude material was purified by silica-gel column chromatography (petroleum ether/EtOAc, 2:1) to give 2-chloro-3-fluoro-4-iodobenzonitrile as a yellow solid (6.0 g, yield: 73%). $^1$H NMR: (400 MHz, CDCl$_3$) δ: 7.78 (s, 1H), 7.20 (d, J=7.2 Hz, 1H).

6. Synthesis of (2-chloro-3-fluoro-4-iodophenyl)methanamine

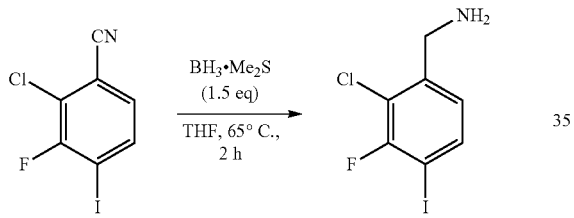

To a solution of 2-chloro-3-fluoro-4-iodobenzonitrile (6.0 g, 21 mmol) in THF (50 mL) was added BH$_3$·Me$_2$S (3.2 mL, 32 mmol, 10 M) at 30° C. The mixture was heated to 65° C. and stirred at that temperature for 2 h. MeOH (5 mL) was added and the reaction mixture was concentrated under vacuum. The crude material was purified by silica-gel column chromatography (petroleum ether/EtOAc, grading from 5:1 to 2:1) to give (2-chloro-3-fluoro-4-iodophenyl)methanamine as a yellow solid (3.5 g, yield: 58%). $^1$H NMR: (400 MHz, DMSO-d$_6$) δ: 7.79 (dd, J$_1$=8.4 Hz, J$_2$=6.4 Hz, 1H), 7.24 (d, J=8.0 Hz, 1H), 3.77 (s, 2H).

7. Synthesis of tert-butyl (2-chloro-3-fluoro-4-iodobenzyl)carbamate

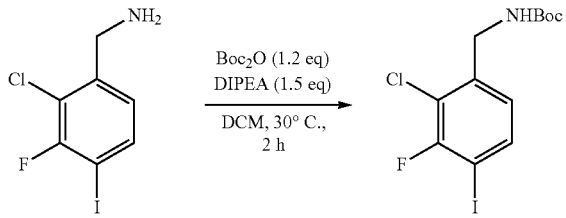 [SMILES: NCc1ccc(I)c(F)c1Cl ; CC(C)(C)OC(=O)NCc1ccc(I)c(F)c1Cl]

To a solution of (2-chloro-3-fluoro-4-iodophenyl)methanamine (3.5 g, 12 mmol) in DCM (50 mL) was added DIPEA (2.4 g, 18 mmol) and Boc$_2$O (3.2 g, 15 mmol). The mixture was heated at 30° C. for 2 h. The mixture was concentrated under vacuum and the crude material was purified by silica-gel column chromatography (petroleum ether/EtOAc, 10:1) to give tert-butyl (2-chloro-3-fluoro-4-iodobenzyl)carbamate as a yellow oil (4.5 g, yield: 95%). $^1$H NMR: (400 MHz, DMSO-d$_6$) δ: 7.77 (dd, J$_1$=8.0 Hz, J$_2$=6.4 Hz, 1H), 7.48 (t, J=4.8 Hz, 1H), 6.92 (d, J=8.4 Hz, 1H), 4.14 (d, J=6.0 Hz, 2H), 1.36 (s, 9H).

8. Synthesis of tert-butyl (2-chloro-3-fluoro-4-(4,4,5,5-tetramethyl-1,3,2-dioxaborolan-2-yl)benzyl)carbamate

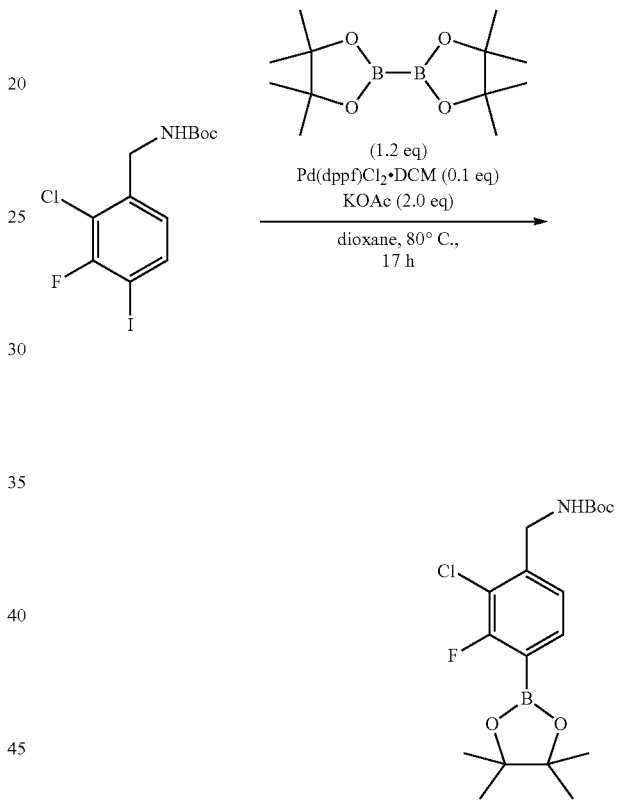

To a solution of tert-butyl (2-chloro-3-fluoro-4-iodobenzyl)carbamate (3.5 g, 9.1 mmol) in 1,4-dioxane (50 mL) under an N$_2$ atmosphere was added bis(pinacolato)diboron (2.8 g, 10.9 mmol), KOAc (1.8 g, 18.2 mmol), and Pd(dppf)Cl$_2$·DCM (734 mg, 0.9 mmol) sequentially. The mixture was heated to 80° C. and stirred at that temperature for 17 h under N$_2$. The mixture was poured into H$_2$O (100 mL) and extracted with DCM (50 mL×3). The combined organic extracts were washed with brine (100 mL), dried (Na$_2$SO$_4$), filtered, and concentrated under vacuum. The crude material, tert-butyl (2-chloro-3-fluoro-4-(4,4,5,5-tetramethyl-1,3,2-dioxaborolan-2-yl)benzyl)carbamate, was used for the next step without further purification. ESI-MS (M-t-Bu)$^+$: 329.9.

9. Synthesis of tert-butyl (2-chloro-4-(2-(cyclopropanecarboxamido)pyridin-4-yl)-3-fluorobenzyl)carbamate

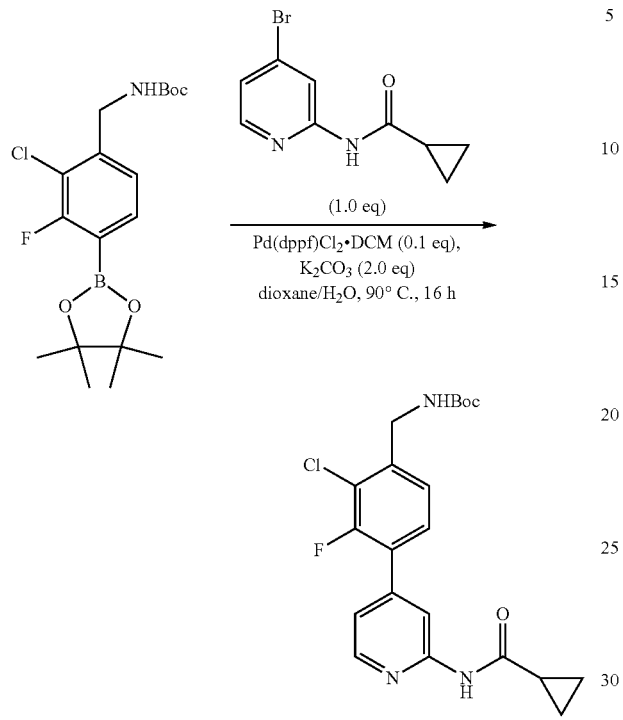

To a solution of tert-butyl (2-chloro-3-fluoro-4-(4,4,5,5-tetramethyl-1,3,2-dioxaborolan-2-yl)benzyl)carbamate (300 mg, 0.78 mmol) in a mixture of 1,4-dioxane/H₂O (v/v=10/1, 22 mL) was added N-(4-bromopyridin-2-yl)cyclopropanecarboxamide (187 mg, 0.78 mmol) and K₂CO₃ (215 mg, 1.56 mmol). Then Pd(dppf)Cl₂·DCM (32 mg, 0.04 mmol) was added under an N₂ atmosphere. The mixture was heated to 90° C. and stirred at that temperature for 16 h under N₂. The mixture was concentrated under vacuum to give crude material. The crude material was purified by silica-gel column chromatography (petroleum ether/EtOAc, grading from 10:1 to 1:1) to give tert-butyl (2-chloro-4-(2-(cyclopropanecarboxamido)pyridin-4-yl)-3-fluorobenzyl)carbamate as a yellow solid (280 mg, yield: 86%). ESI-MS (M+H)⁺: 420.1.

10. Synthesis of N-(4-(4-(aminomethyl)-3-chloro-2-fluorophenyl)pyridin-2-yl)cyclopropanecarboxamide hydrochloride

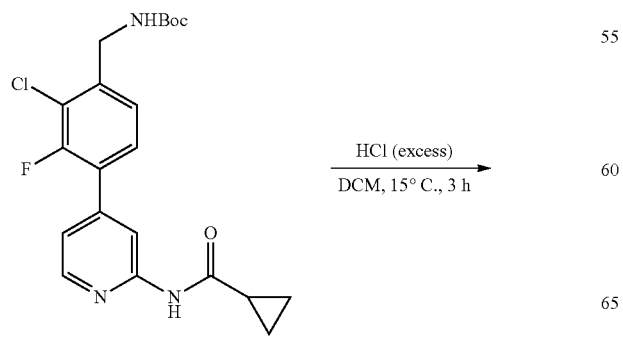

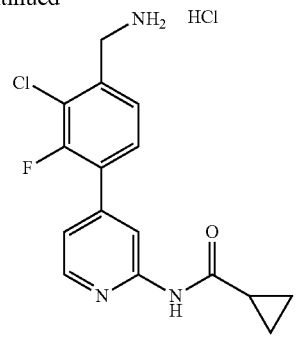

To a solution of tert-butyl (2-chloro-4-(2-(cyclopropanecarboxamido)pyridin-4-yl)-3-fluorobenzyl)carbamate (280 mg, 0.67 mmol) in DCM (10 mL) was added an HCV/EtOAc solution (1 M, 10 mL). The reaction mixture was stirred at 15° C. for 3 h. The reaction mixture was concentrated in vacuo to give N-(4-(4-(aminomethyl)-3-chloro-2-fluorophenyl)pyridin-2-yl)cyclopropanecarboxamide hydrochloride as a yellow solid (200 mg, crude), which was carried forward without further purification. ESI-MS (M+H)⁺: 320.1.

11. Synthesis of 5-(tert-butyl)-N-(2-chloro-4-(2-(cyclopropanecarboxamido)pyridin-4-yl)-3-fluorobenzyl)-1,2,4-oxadiazole-3-carboxamide (Compound 14)

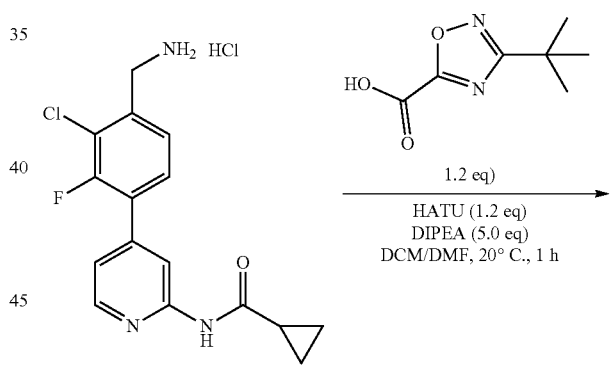

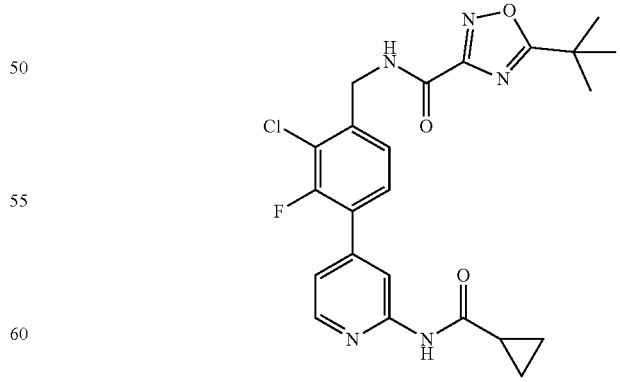

To a solution of N-(4-(4-(aminomethyl)-3-chloro-2-fluorophenyl)pyridin-2-yl)cyclopropanecarboxamide hydrochloride (180 mg, 0.56 mmol) in a mixture of DCM/DMF (v/v=50/1, 102 mL) was added 5-(tert-butyl)-1,2,4-oxadiazole-3-carboxylic acid (115 mg, 0.67 mmol), HATU (257 mg, 0.67 mmol), and DIPEA (364 mg, 2.8 mmol). The reaction mixture was stirred at 20° C. for 1 h. The reaction mixture was poured in H$_2$O (100 mL) and extracted with DCM (100 mL×2). The combined organic extracts were concentrated in vacuo. The crude material was purified by prep-HPLC (CH$_3$CN/H$_2$O with 0.05% HCl/H$_2$O as mobile phase) to give 5-(tert-butyl)-N-(2-chloro-4-(2-(cyclopropanecarboxamido)pyridin-4-yl)-3-fluorobenzyl)-1,2,4-oxadiazole-3-carboxamide as a white solid (153 mg, yield: 58%). ESI-MS (M+H)$^+$: 472.1. $^1$H NMR: (400 MHz, CD$_3$OD) δ: 8.39 (d, J=6.4 Hz, 1H), 7.77-7.70 (m, 2H), 7.68-7.63 (m, 1H), 7.48-7.44 (m, 1H), 4.76 (s, 2H), 1.98-1.90 (m, 1H), 1.49 (s, 9H), 1.19-1.14 (m, 2H), 1.12-1.07 (m, 2H).

Example 15: 3-(tert-butyl)-N-(2-chloro-4-(2-(cyclopropanecarboxamido)pyridin-4-yl)-3-fluorobenzyl)-1,2,4-oxadiazole-5-carboxamide (Compound 15)

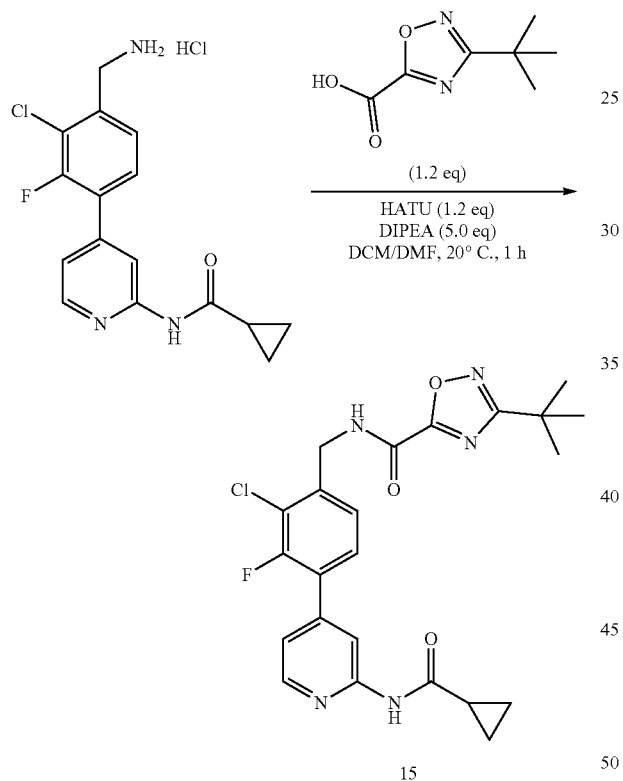

Synthesis of 3-(tert-butyl)-N-(2-chloro-4-(2-(cyclopropanecarboxamido)pyridin-4-yl)-3-fluorobenzyl)-1,2,4-oxadiazole-5-carboxamide was similar to that of 5-(tert-butyl)-N-(2-chloro-4-(2-(cyclopropanecarboxamido)pyridin-4-yl)-3-fluorobenzyl)-1,2,4-oxadiazole-3-carboxamide in Example 14, Step 11. The crude material was purified by prep-HPLC (CH$_3$CN/H$_2$O with 0.05% HCl/H$_2$O as mobile phase) to give 3-(tert-butyl)-N-(2-chloro-4-(2-(cyclopropanecarboxamido)pyridin-4-yl)-3-fluorobenzyl)-1,2,4-oxadiazole-5-carboxamide as a white solid (86 mg, yield: 44%). ESI-MS (M+H)$^+$: 472.1. $^1$H NMR: (400 MHz, DMSO-d$_6$) δ: 11.00 (s, 1H), 9.94 (t, J=6.0 Hz, 1H), 8.40 (d, J=5.2 Hz, 1H), 8.27 (s, 1H), 7.53 (t, J=8.0 Hz, 1H), 7.38 (d, J=8.0 Hz, 1H), 7.30-7.26 (m, 1H), 4.59 (d, J=6.0 Hz, 2H), 2.04-1.98 (m, 1H), 1.35 (s, 9H), 0.83-0.80 (m, 4H).

Example 16: 5-(tert-butyl)-N-(4-(2-(cyclopropanecarboxamido)pyridin-4-yl)-2-(trifluoromethyl)benzyl)-1,2,4-oxadiazole-3-carboxamide (Compound 16)

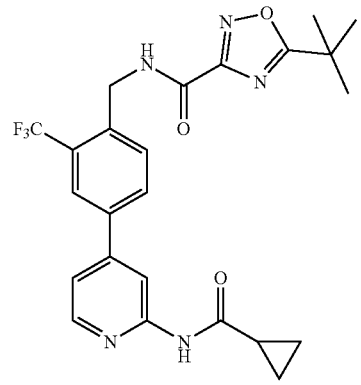

1. Synthesis of tert-butyl (4-(2-(cyclopropanecarboxamido)pyridin-4-yl)-2-(trifluoromethyl)benzyl)carbamate

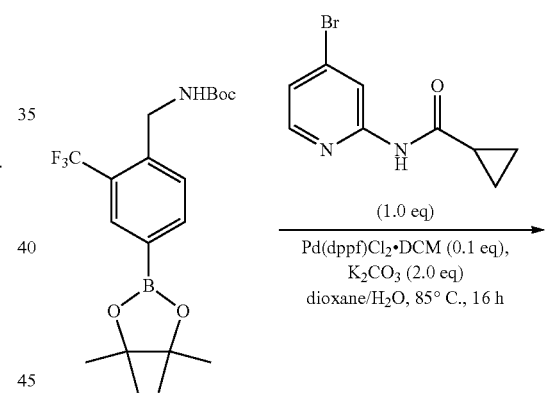

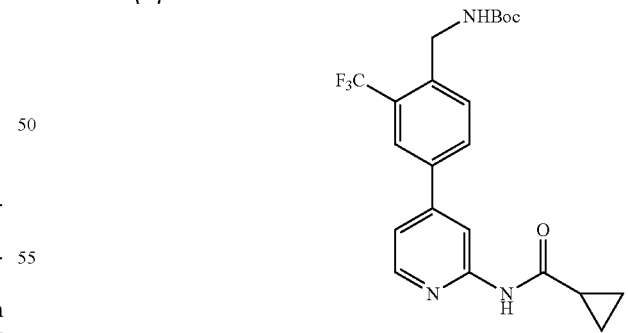

Synthesis of tert-butyl (4-(2-(cyclopropanecarboxamido)pyridin-4-yl)-2-(trifluoromethyl)benzyl)carbamate was similar to that of tert-butyl (4-(2-(cyclopropanecarboxamido)pyridin-4-yl)-3-fluoro-2-methylbenzyl)carbamate in Example 11, Step 9. tert-Butyl (4-(4,4,5,5-tetramethyl-1,3,2-dioxaborolan-2-yl)-2-(trifluoromethyl)benzyl)carbamate was prepared as described in WO 2015/089337. The crude material was purified by silica-gel column chromatography (petroleum ether/EtOAc, 2:1) to give tert-butyl (4-(2-(cyclopropanecarboxamido)pyridin-4-yl)-2-(trifluoromethyl)benzyl)carbamate as a white solid (380 mg, yield: 80%). ESI-MS (M+H)+: 436.1

2. Synthesis of N-(4-(4-(aminomethyl)-3-(trifluoromethyl)phenyl)pyridin-2-yl)cyclopropanecarboxamide Hydrochloride

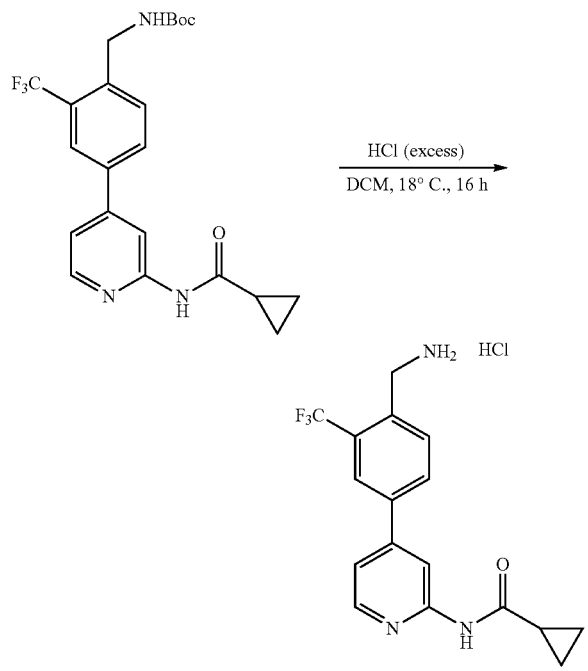

Synthesis of N-(4-(4-(aminomethyl)-3-(trifluoromethyl)phenyl)pyridin-2-yl)cyclopropanecarboxamide hydrochloride was similar to that of N-(4-(4-(aminomethyl)-2-fluoro-3-methylphenyl)pyridin-2-yl)cyclopropanecarboxamide hydrochloride in Example 11, Step 10. The reaction mixture was concentrated in vacuo to give N-(4-(4-(aminomethyl)-3-(trifluoromethyl)phenyl)pyridin-2-yl)cyclopropanecarboxamide hydrochloride as a white solid (280 mg, crude), which was carried forward without further purification. ESI-MS (M+H)+: 336.0.

3. Synthesis of 5-(tert-butyl)-N-(4-(2-(cyclopropanecarboxamido)pyridin-4-yl)-2-(trifluoromethyl)benzyl)-1,2,4-oxadiazole-3-carboxamide (16)

-continued

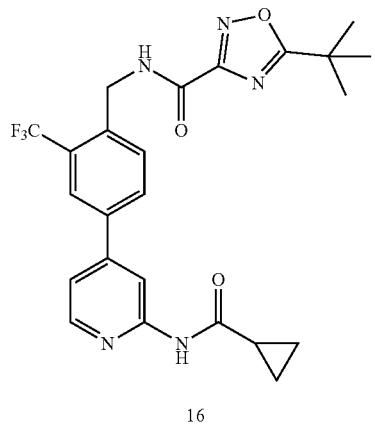

Synthesis of 5-(tert-butyl)-N-(4-(2-(cyclopropanecarboxamido)pyridin-4-yl)-2-(trifluoromethyl)benzyl)-1,2,4-oxadiazole-3-carboxamide was similar to that of 5-(tert-butyl)-N-(2-chloro-4-(2-(cyclopropanecarboxamido)pyridin-4-yl)-3-fluorobenzyl)-1,2,4-oxadiazole-3-carboxamide in Example 14, Step 11. The reaction mixture was concentrated in vacuo and the residue was purified by prep-HPLC (CH$_3$CN/H$_2$O with 0.05% HCl/H$_2$O as mobile phase) to give 5-(tert-butyl)-N-(4-(2-(cyclopropanecarboxamido)pyridin-4-yl)-2-(trifluoromethyl)benzyl)-1,2,4-oxadiazole-3-carboxamide as a white solid (104 mg, yield: 51%). ESI-MS (M+H)+: 488.1. $^1$H NMR: (400 MHz, CD$_3$OD) δ: 8.39-8.37 (m, 1H), 8.14 (s, 1H), 8.08-8.05 (m, 1H), 7.92 (s, 1H), 7.79-7.74 (m, 2H), 4.88 (s, 2H), 1.95-1.92 (m, 1H), 1.50 (s, 9H), 1.14-1.06 (m, 4H).

Example 17: 3-(tert-butyl)-N-(4-(2-(cyclopropanecarboxamido)pyridin-4-yl)-2-(trifluoromethyl)benzyl)-1,2,4-oxadiazole-5-carboxamide (Compound 17)

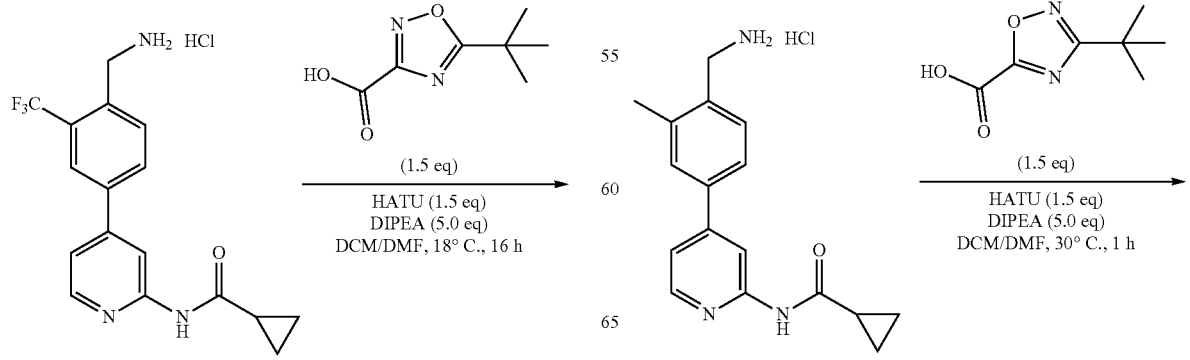

-continued

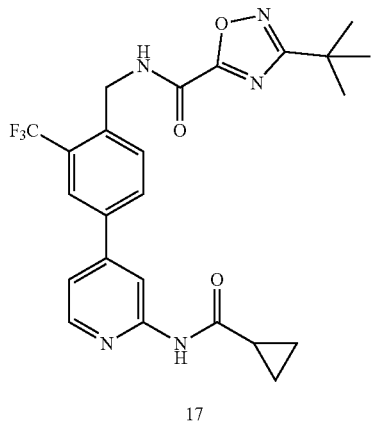

17

Synthesis of 3-(tert-butyl)-N-(4-(2-(cyclopropanecarboxamido)pyridin-4-yl)-2-(trifluoromethyl)benzyl)-1,2,4-oxadiazole-5-carboxamide was similar to that of 3-(tert-butyl)-N-(2-chloro-4-(2-(cyclopropanecarboxamido)pyridin-4-yl)-3-fluorobenzyl)-1,2,4-oxadiazole-5-carboxamide in Example 15. The reaction mixture was concentrated in vacuo and the crude material was purified by prep-HPLC (CH$_3$CN/H$_2$O with 0.05% HCl/H$_2$O as mobile phase) to give 3-(tert-butyl)-N-(4-(2-(cyclopropanecarboxamido)pyridin-4-yl)-2-(trifluoromethyl)benzyl)-1,2,4-oxadiazole-5-carboxamide as a white solid (88 mg, yield: 43%). ESI-MS (M+H)$^+$: 488.1. $^1$H NMR: (400 MHz, CD$_3$OD) δ: 8.39-8.37 (m, 1H), 8.13 (s, 1H), 8.07-8.05 (m, 1H), 7.98 (s, 1H), 7.80-7.78 (m, 1H), 7.72-7.70 (m, 1H), 4.86 (s, 2H), 1.95-1.92 (m, 1H), 1.43 (s, 9H), 1.13-1.04 (m, 4H).

Example 18: (R)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide (Compound 18)

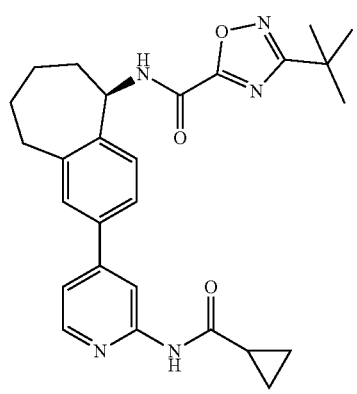

18

1. Synthesis of tert-butyl (R)-(2-(2-(cyclopropanecarboxamido)pyridin-4-yl)-6,7,8,9-tetrahydro-5H-benzo[7]annulen-5-yl)carbamate

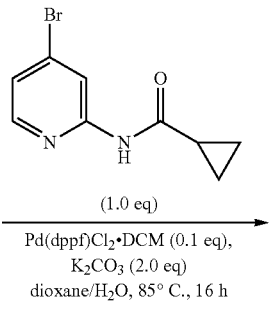

(1.0 eq)
Pd(dppf)Cl$_2$·DCM (0.1 eq),
K$_2$CO$_3$ (2.0 eq)
dioxane/H$_2$O, 85° C., 16 h

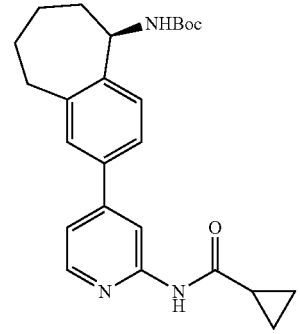

To a solution of tert-butyl (R)-(2-(4,4,5,5-tetramethyl-1,3,2-dioxaborolan-2-yl)-6,7,8,9-tetrahydro-5H-benzo[7]annulen-5-yl)carbamate (prepared as described in WO 2015/089327, 300 mg, 0.77 mmol) in 1,4-dioxane/H$_2$O (v/v=3/1, 12 mL) were added N-(4-bromopyridin-2-yl)cyclopropanecarboxamide (187 mg, 0.77 mmol) and K$_2$CO$_3$ (214 mg, 1.55 mmol). Then Pd(dppf)Cl$_2$·DCM (63 mg, 0.08 mmol) was added under an N$_2$ atmosphere. The mixture was heated to 85° C. and stirred at that temperature for 16 h under N$_2$. The reaction mixture was cooled to rt and concentrated under vacuum. The crude material was purified by silica-gel column chromatography (petroleum ether/EtOAc, 5:1) to give tert-butyl (R)-(2-(2-(cyclopropanecarboxamido)pyridin-4-yl)-6,7,8,9-tetrahydro-5H-benzo[7]annulen-5-yl)carbamate as a white solid (250 mg, yield: 77%). ESI-MS (M+H)$^+$: 422.2. $^1$H NMR (400 MHz, DMSO-d$_6$) δ: 10.85 (s, 1H), 8.36 (s, 1H), 8.31 (d, J=5.2 Hz, 1H), 7.54 (d, J=8.0 Hz, 1H), 7.48 (d, J=8.4 Hz, 1H), 7.43 (s, 1H), 7.36 (dd, J$_1$=5.2 Hz, J$_2$=1.2 Hz, 1H), 7.28 (d, J=8.0 Hz, 1H), 4.72 (t, J=8.8 Hz, 1H), 2.87-2.79 (m, 2H), 2.04-2.00 (m, 1H), 1.84-1.73 (m, 4H), 1.49-1.47 (m, 1H), 1.39 (s, 9H), 1.25-1.23 (m, 1H), 0.81-0.79 (m, 4H).

2. Synthesis of (R)—N-(4-(5-amino-6,7,8,9-tetrahydro-5H-benzo[7]annulen-2-yl)pyridin-2-yl)cyclopropanecarboxamide Hydrochloride

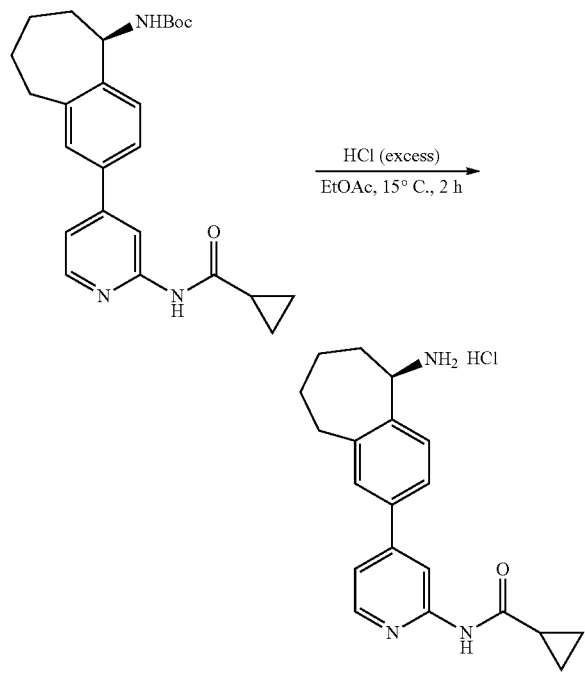

To a solution of tert-butyl (R)-(2-(2-(cyclopropanecarboxamido)pyridin-4-yl)-6,7,8,9-tetrahydro-5H-benzo[7]annulen-5-yl)carbamate (250 mg, 0.59 mmol) in EtOAc (2 mL) at 15° C. was added an HCV/EtOAc solution (4 M, 6 mL) and the resulting mixture was stirred at 15° C. for 2 h. The reaction mixture was filtered and the filter cake was dried to give (R)—N-(4-(5-amino-6,7,8,9-tetrahydro-5H-benzo[7]annulen-2-yl)pyridin-2-yl)cyclopropanecarboxamide hydrochloride as a white solid (180 mg, yield: 95%), which was carried forward without further purification. ESI-MS (M+H)+: 322.2.

3. Synthesis of (R)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide (Compound 18)

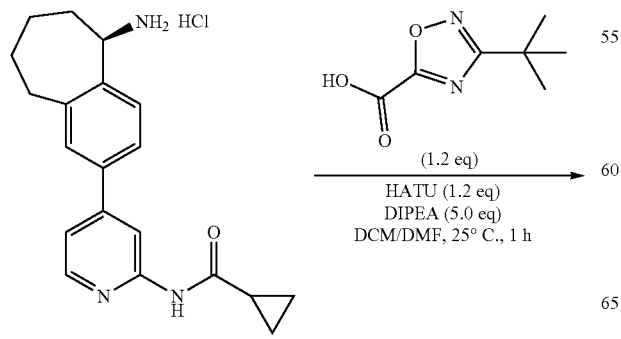

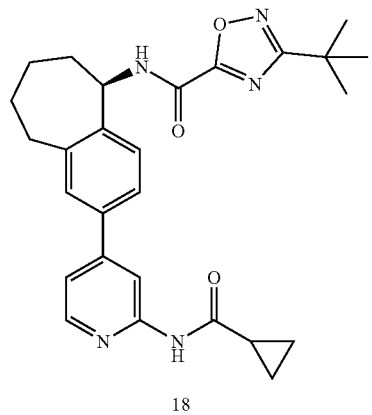

18

To a solution of (R)—N-(4-(5-amino-6,7,8,9-tetrahydro-5H-benzo[7]annulen-2-yl)pyridin-2-yl)cyclopropanecarboxamide hydrochloride (130 mg, 0.36 mmol) in DCM/DMF (v/v=25/1, 52 mL) were added 3-(tert-butyl)-1,2,4-oxadiazole-5-carboxylic acid (74 mg, 0.44 mmol), HATU (166 mg, 0.44 mmol) and DIPEA (235 mg, 1.82 mmol). The reaction mixture was stirred at 25° C. for 1 h, poured into H$_2$O (100 mL), and extracted with DCM (50 mL×2). The combined organic extracts were concentrated in vacuo. The crude material was purified by prep-HPLC (CH$_3$CN/H$_2$O with 0.05% HCl/H$_2$O as mobile phase) to give (R)-3-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-5-carboxamide as a white solid (84 mg, yield: 49%, ee=100%). ESI-MS (M+H)+: 474.0. $^1$H NMR: (400 MHz, CD$_3$OD) δ: 8.31 (d, J=6.4 Hz, 1H), 7.81-7.74 (m, 2H), 7.69-7.65 (m, 2H), 7.46-7.44 (m, 1H), 5.40 (d, J=9.6 Hz, 1H), 3.11-3.00 (m, 2H), 2.13-1.82 (m, 6H), 1.45 (s, 9H), 1.41-1.37 (m, 1H), 1.16-1.12 (m, 2H), 1.10-1.05 (m, 2H).

Example 19: (R)-5-(tert-butyl)-N-(1-(4-(2-(cyclopropanecarboxamido)pyridin-4-yl)-2-methylphenyl)ethyl)-1,2,4-oxadiazole-3-carboxamide (Compound 19)

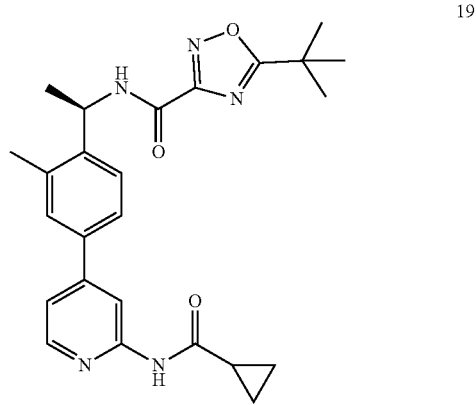 [SMILES: Cc1cc(-c2ccnc(NC(=O)C3CC3)c2)ccc1[C@@H](C)NC(=O)c1noc(C(C)(C)C)n1]

19

1. Synthesis of 1-(4-bromo-2-methylphenyl)ethan-1-one

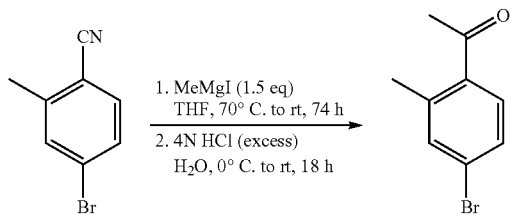

To a solution of 4-bromo-2-methyl-benzonitrile (4.0 g, 20.4 mmol) in THF (20 mL) was added dropwise iodo(methyl)magnesium (3 M, 10.2 mL) at rt. The reaction mixture was heated to reflux (~70° C.) for 2 h and then was cooled to rt and stirred for 72 h. The reaction mixture was placed in an ice-water cooling bath and saturated aqueous NH$_4$Cl solution (100 mL) was added, followed by EtOAc (100 mL). The layers were separated and the aqueous phase was extracted with EtOAc (100 mL). The combined organic extracts were concentrated in vacuo and the resulting residue was treated with an HCl solution (4 N, 20 mL) at 0° C. The mixture was then stirred at rt for 18 h. The reaction mixture was extracted with EtOAc (50 mL) and the organic layer was washed with H$_2$O (50 mL), dried (Na$_2$SO$_4$), and filtered. The filtrate was concentrated in vacuo to give 1-(4-bromo-2-methylphenyl)ethan-1-one as a pale orange oil (3.04 g, yield: 70%). ESI-MS (M+H)$^+$: 213.0. $^1$H NMR (500 MHz, CDCl$_3$) δ: 7.57 (d, J=7.9 Hz, 1H), 7.43-7.40 (m, 2H), 2.56 (s, 3H), 2.52 (s, 3H).

2. Synthesis of (R,E)-N-(1-(4-bromo-2-methylphenyl)ethylidene)-2-methylpropane-2-sulfinamide

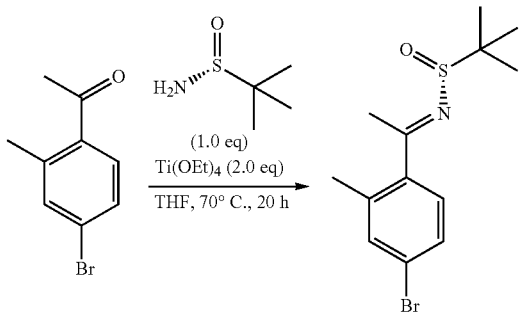

To a solution of 1-(4-bromo-2-methylphenyl)ethan-1-one (3.04 g, 14.3 mmol) in THF (48 mL) were added (R)-(+)-2-methyl-2-propanesulfinamide (1.73 g, 14.3 mmol) and Ti(IV)(OEt)$_4$ (6.51 g, 28.5 mmol, 5.97 mL). The reaction mixture was heated to 70° C. for 20 h. After cooling to rt, the mixture was quenched with brine (100 mL) and EtOAc (100 mL) was added, affording a biphasic solution with a thick white precipitate. The solution was filtered and the solids were washed with EtOAc (100 mL). The filtrate layers were separated and the organic layer was dried (Na$_2$SO$_4$), filtered and concentrated in vacuo. The crude material was purified by silica-gel column chromatography (EtOAc/heptanes, grading from 0% to 50%) to give (R,E)-N-(1-(4-bromo-2-methylphenyl)ethylidene)-2-methylpropane-2-sulfinamide as a yellow oil (2.96 g, yield: 66%). ESI-MS (M+H)$^+$: 318.0.

3. Synthesis of (R)—N—((R)-1-(4-bromo-2-methylphenyl)ethyl)-2-methylpropane-2-sulfinamide

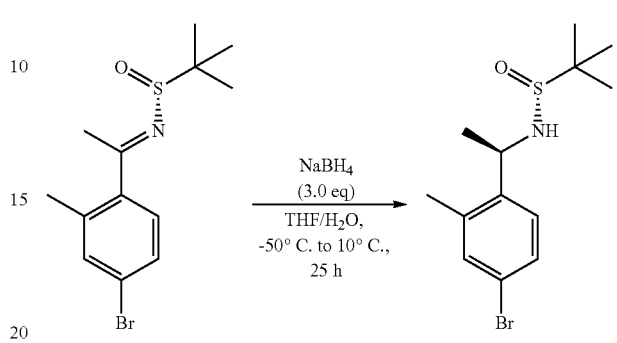

To a solution of (R,E)-N-(1-(4-bromo-2-methylphenyl)ethylidene)-2-methylpropane-2-sulfinamide (2.96 g, 9.4 mmol) in a mixture of THF/H$_2$O (98/2, 62.4 mL) cooled to −50° C. in a dry ice/acetonitrile cooling bath was added NaBH$_4$ (1.06 g, 28.1 mmol) slowly portion-wise. The mixture was stirred for 7 h at −50° C., then was stirred for 18 h as the internal temperature warmed to 10° C. The reaction was quenched with H$_2$O (20 mL) and diluted with EtOAc (100 mL). The layers were separated and the organic phase was dried (Na$_2$SO$_4$), filtered, and concentrated in vacuo. The crude material was purified by silica-gel column chromatography (EtOAc/heptanes, grading from 20% to 100%) to give (R)—N—((R)-1-(4-bromo-2-methylphenyl)ethyl)-2-methylpropane-2-sulfinamide as a colorless oil (1.6 g, yield: 55%). ESI-MS (M+H)$^+$: 320.1. $^1$H NMR (400 MHz, CDCl$_3$) δ: ppm 7.37-7.33 (m, 1H), 7.33-7.31 (m, 1H), 7.29-7.25 (m, 1H), 4.78-4.68 (m, 1H), 3.31 (br s, 1H), 2.36 (s, 3H), 1.47 (d, J=6.5 Hz, 3H), 1.24 (s, 9H).

4. Synthesis of (R)-1-(4-bromo-2-methylphenyl)ethan-1-amine Hydrochloride

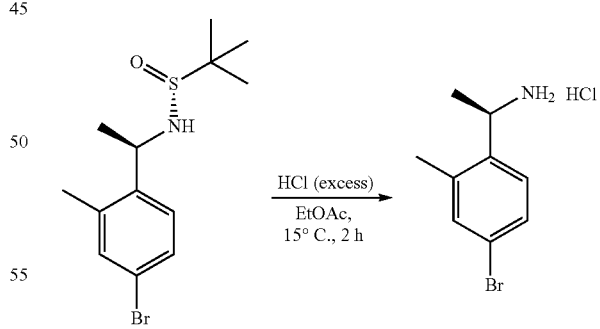

To a solution of (R)—N—((R)-1-(4-bromo-2-methylphenyl)ethyl)-2-methylpropane-2-sulfinamide (4.5 g, 14.1 mmol) in EtOAc (5 mL) at 15° C. was added an HC/EtOAc solution (4 M, 30 mL). The reaction mixture was stirred for 2 h and filtered. The filter cake was dried under vacuum to give (R)-1-(4-bromo-2-methylphenyl)ethan-1-amine hydrochloride as a white solid (3.3 g, yield: 93%), which was carried forward without further purification. ESI-MS (M-NH$_2$)$^+$: 198.9. $^1$H NMR (400 MHz, DMSO-d$_6$) δ: 8.54

(s, 1H), 7.53-7.50 (m, 2H), 7.47 (s, 1H), 4.47 (t, J=6.0 Hz, 1H), 2.33 (s, 3H), 1.43 (d, J=6.4 Hz, 3H).

5. Synthesis of tert-butyl (R)-(1-(4-bromo-2-methylphenyl)ethyl)carbamate

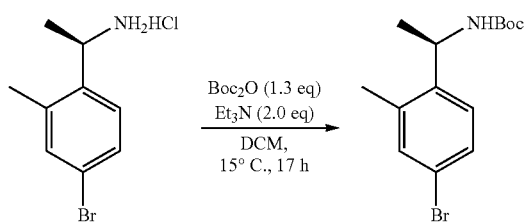

To a mixture of (R)-1-(4-bromo-2-methylphenyl)ethan-1-amine hydrochloride (3.3 g, 13.2 mmol) in DCM (40 mL) at 15° C. was added Et₃N (2.67 g, 26.3 mmol) and Boc₂O (3.7 g, 17.1 mmol). The mixture was stirred at 15° C. for 17 h, concentrated in vacuo, and purified by silica-gel column chromatography (petroleum ether/EtOAc, 20:1) to give tert-butyl (R)-(1-(4-bromo-2-methylphenyl)ethyl)carbamate as a white solid (3.8 g, yield: 92%)d. ESI-MS (M-Boc-NH₂)⁺: 198.8.

6. Synthesis of tert-butyl (R)-(1-(2-methyl-4-(4,4,5,5-tetramethyl-1,3,2-dioxaborolan-2-yl)phenyl)ethyl)carbamate

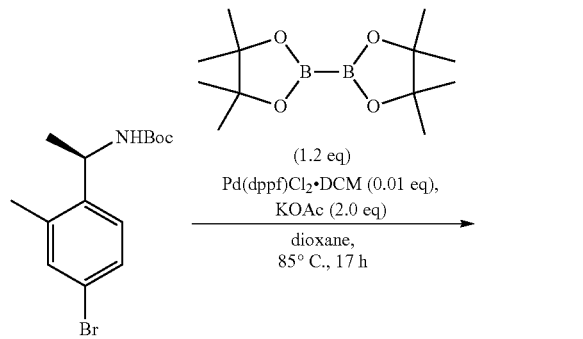

To a solution of tert-butyl (R)-(1-(4-bromo-2-methylphenyl)ethyl)carbamate (3.8 g, 12.1 mmol) in 1,4-dioxane (30 mL) under N₂ were added bis(pinacolato)diboron (3.69 g, 14.5 mmol), Pd(dppf)Cl₂·DCM (987 mg, 1.2 mmol) and KOAc (2.37 g, 24.2 mmol). The mixture was heated to 85° C. under N₂ and stirred at that temperature for 17 h, cooled to rt, and concentrated in vacuo. The crude material was purified by silica-gel column chromatography (petroleum ether/EtOAc, 20:1) to give tert-butyl (R)-(1-(2-methyl-4-(4,4,5,5-tetramethyl-1,3,2-dioxaborolan-2-yl)phenyl)ethyl)carbamate as a yellow oil (4.0 g, yield: 87%). ¹H NMR: (400 MHz, CD₃OD) δ: 7.53 (d, J=7.6 Hz, 1H), 7.50 (s, 1H), 7.30 (d, J=7.6 Hz, 1H), 3.65 (s, 1H), 2.37 (s, 3H), 1.41 (s, 9H), 1.33 (s, 12H), 1.25-1.22 (m, 3H).

7. Synthesis of tert-butyl (R)-(1-(4-(2-(cyclopropanecarboxamido)pyridin-4-yl)-2-methylphenyl)ethyl)carbamate

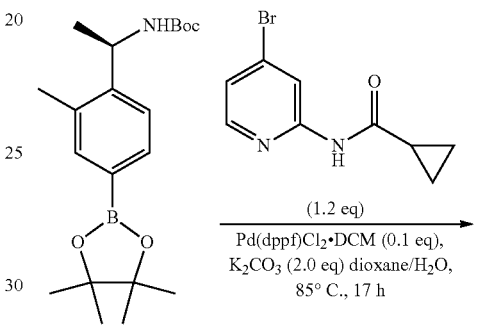

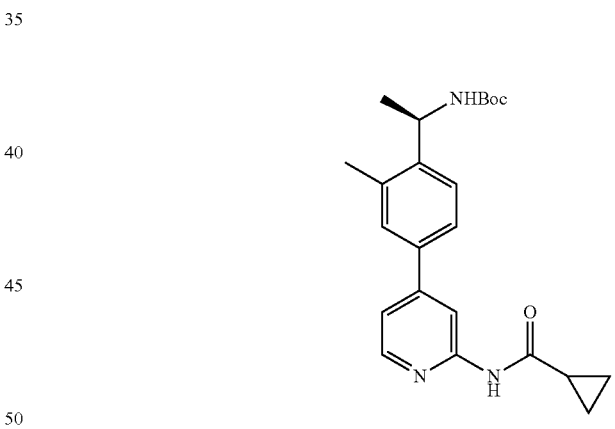

To a solution of tert-butyl (R)-(1-(2-methyl-4-(4,4,5,5-tetramethyl-1,3,2-dioxaborolan-2-yl)phenyl)ethyl)carbamate (300 mg, 0.83 mmol) in 1,4-dioxane (6 mL) and H₂O (2 mL) were added N-(4-bromopyridin-2-yl)cyclopropanecarboxamide (240 mg, 1.0 mmol), Pd(dppf)Cl₂·DCM (68 mg, 0.08 mmol) and K₂CO₃ (230 mg, 1.66 mmol). The mixture was heated to 85° C. under N₂ and stirred at that temperature for 17 h. The reaction mixture was cooled to rt and concentrated in vacuo. The crude material was purified by silica-gel column chromatography (petroleum ether/EtOAc, 1:1) to give tert-butyl (R)-(1-(4-(2-(cyclopropanecarboxamido)pyridin-4-yl)-2-methylphenyl)ethyl)carbamate as a yellow amorphous solid (250 mg, yield: 76%). ESI-MS (M+H)⁺: 396.2.

8. Synthesis of (R)—N-(4-(4-(1-aminoethyl)-3-methylphenyl)pyridin-2-yl)cyclopropanecarboxamide Hydrochloride

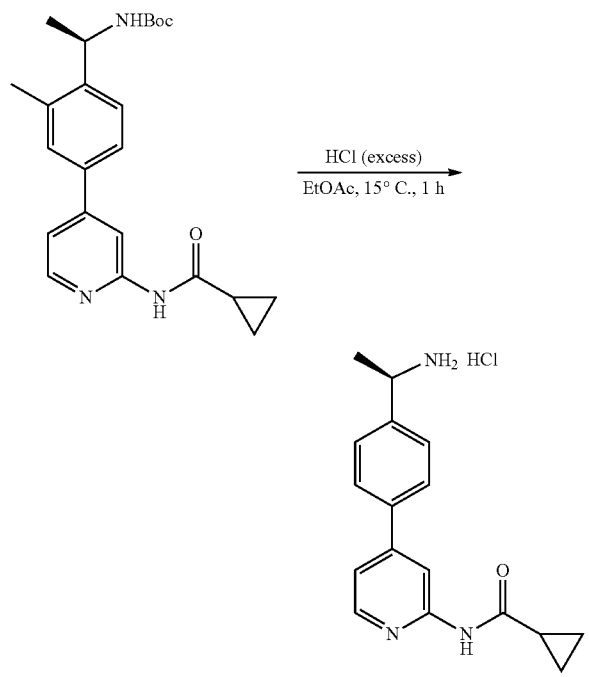

To a mixture of tert-butyl (R)-(1-(4-(2-(cyclopropanecarboxamido)pyridin-4-yl)-2-methylphenyl)ethyl)carbamate (250 mg, 0.63 mmol) in EtOAc (2 mL) at 15° C. was added an HCl/EtOAc solution (4 M, 6 mL). The mixture was stirred at 15° C. for 1 h and filtered. The filter cake was dried in vacuo to give (R)—N-(4-(4-(1-aminoethyl)-3-methylphenyl)pyridin-2-yl)cyclopropanecarboxamide hydrochloride as a yellow solid (200 mg, yield: 96%), which was carried forward without further purification. ESI-MS (M+H)$^+$: 296.0.

9. Synthesis of (R)-5-(tert-butyl)-N-(1-(4-(2-(cyclopropanecarboxamido)pyridin-4-yl)-2-methylphenyl)ethyl)-1,2,4-oxadiazole-3-carboxamide (Compound 19)

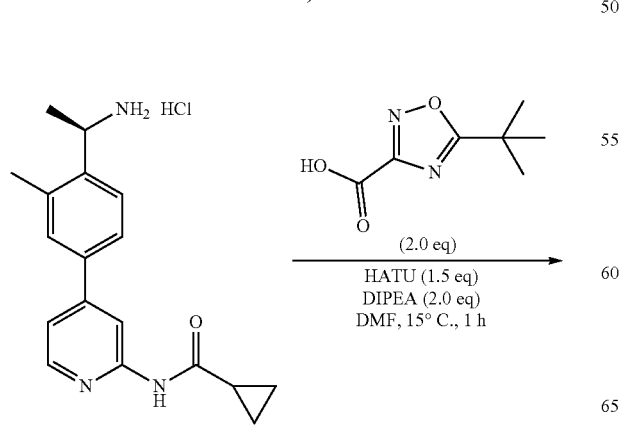

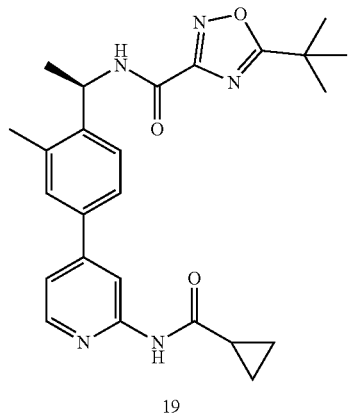

To a mixture of (R)—N-(4-(4-(1-aminoethyl)-3-methylphenyl)pyridin-2-yl)cyclopropanecarboxamide hydrochloride (100 mg, 0.30 mmol) in DMF (5 mL) at 15° C. was added 5-(tert-butyl)-1,2,4-oxadiazole-3-carboxylic acid (102 mg, 0.60 mmol), DIPEA (78 mg, 0.60 mmol) and HATU (172 mg, 0.45 mmol). The mixture was stirred at 15° C. for 1 h, filtered, and concentrated in vacuo. The crude material was purified by prep-HPLC (CH$_3$CN/H$_2$O with 0.05% HCl/H$_2$O as mobile phase) to give (R)-5-(tert-butyl)-N-(1-(4-(2-(cyclopropanecarboxamido)pyridin-4-yl)-2-methylphenyl)ethyl)-1,2,4-oxadiazole-3-carboxamide as a white solid (108 mg, yield: 80%). ESI-MS (M+H)$^+$: 448.2. $^1$H NMR (400 MHz, CD$_3$OD) δ: 8.31 (d, J=6.8 Hz, 1H), 7.83 (dd, J$_1$=6.4 Hz, J$_2$=1.6 Hz, 1H), 7.72-7.70 (m, 3H), 7.64 (d, J=8.0 Hz, 1H), 5.47 (dd, J$_1$=14.0 Hz, J$_2$=6.8 Hz, 1H), 2.57 (s, 3H), 1.98-1.92 (m, 1H), 1.58 (d, J=6.8 Hz, 3H), 1.47 (s, 9H), 1.19-1.15 (m, 2H), 1.13-1.09 (m, 2H).

Example 20: 5-(tert-butyl)-N-(4-(2-(cyclopropanecarboxamido)-5-fluoropyridin-4-yl)-2-methylbenzyl)-1,2,4-oxadiazole-3-carboxamide (Compound 20)

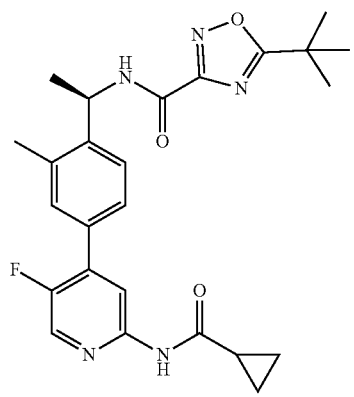

1. Synthesis of tert-butyl (R)-(1-(4-(2-chloro-5-fluoropyridin-4-yl)-2-methylphenyl)ethyl)carbamate

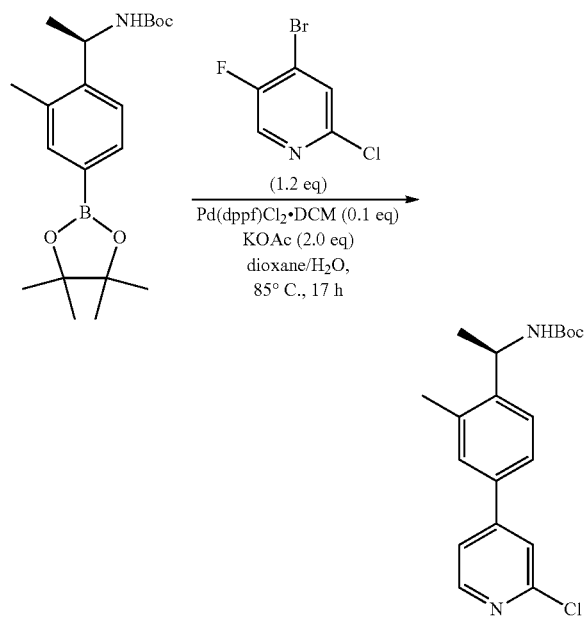

To a solution of tert-butyl (R)-(1-(2-methyl-4-(4,4,5,5-tetramethyl-1,3,2-dioxaborolan-2-yl)phenyl)ethyl)carbamate (500 mg, 1.38 mmol) in 1,4-dioxane/H$_2$O (v/v=3/1, 12 mL) were added 2-chloro-5-fluoro-4-iodopyridine (427 mg, 1.66 mmol) and KOAc (272 mg, 2.77 mmol). Then Pd(dppf)Cl$_2$·DCM (113 mg, 0.14 mmol) was added under N$_2$ atmosphere and the reaction mixture was heated to 85° C. The mixture was stirred at that temperature for 17 h under N$_2$, then was concentrated in vacuo. The crude material was purified by silica-gel column chromatography (petroleum ether/EtOAc, 5:1) to give tert-butyl (R)-(1-(4-(2-chloro-5-fluoropyridin-4-yl)-2-methylphenyl)ethyl)carbamate as a yellow amorphous solid (400 mg, yield: 80%). ESI-MS (M+H)$^+$: 365.0. $^1$H NMR (400 MHz, CD$_3$OD) δ: 8.31 (d, J=2.0 Hz, 1H), 7.59 (d, J=6.0 Hz, 1H), 7.47 (s, 2H), 7.43 (s, 1H), 4.95-4.93 (m, 1H), 2.45 (s, 3H), 1.42 (s, 9H), 1.36 (d, J=6.8 Hz, 3H).

2. Synthesis of tert-butyl (R)-(1-(4-(2-(cyclopropanecarboxamido)-5-fluoropyridin-4-yl)-2-methylphenyl)ethyl)carbamate

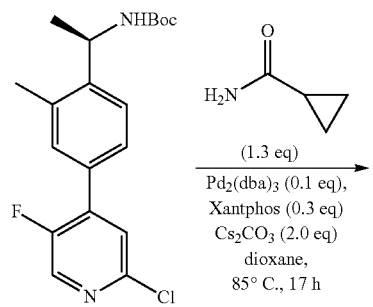

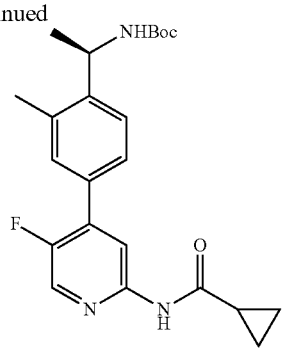

To a solution of tert-butyl (R)-(1-(4-(2-chloro-5-fluoropyridin-4-yl)-2-methylphenyl)ethyl)carbamate (400 mg, 1.1 mmol) in 1,4-dioxane (10 mL) were added cyclopropanecarboxamide (121 mg, 1.4 mmol) and Cs$_2$CO$_3$ (714 mg, 2.2 mmol). Then Pd$_2$(dba)$_3$ (101 mg, 0.11 mmol) and Xantphos (191 mg, 0.33 mmol) were added under an N$_2$ atmosphere. The reaction mixture was heated to 85° C. and stirred at that temperature under N$_2$ for 17 h. The reaction mixture was cooled to rt and concentrated under vacuum. The crude material was purified by silica-gel column chromatography (petroleum ether/EtOAc, grading from 10:1 to 3:1) to give tert-butyl (R)-(1-(4-(2-(cyclopropanecarboxamido)-5-fluoropyridin-4-yl)-2-methylphenyl)ethyl)carbamate as a yellow amorphous solid (220 mg, yield: 48%). ESI-MS (M+H)$^+$: 414.1.

3. Synthesis of (R)—N-(4-(4-(1-aminoethyl)-3-methylphenyl)-5-fluoropyridin-2-yl)cyclopropanecarboxamide Hydrochloride

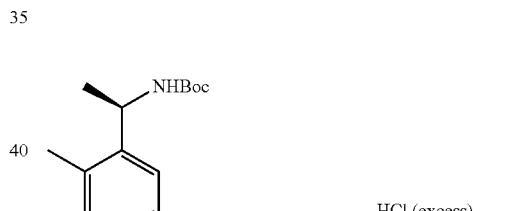

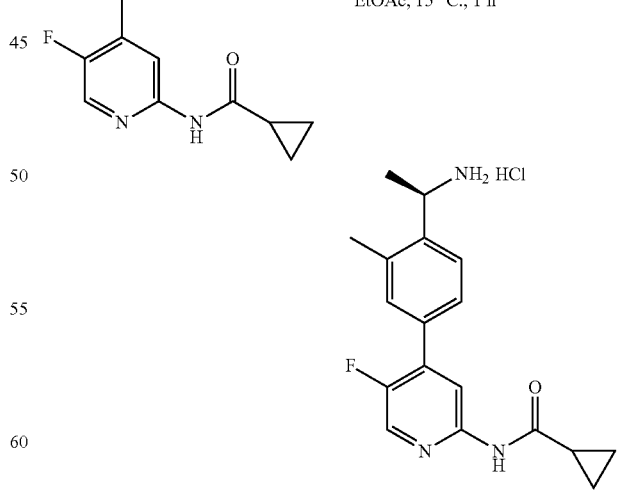

To a solution of tert-butyl (R)-(1-(4-(2-(cyclopropanecarboxamido)-5-fluoropyridin-4-yl)-2-methylphenyl)ethyl)carbamate (220 mg, 0.53 mmol) in EtOAc (2 mL) at 15° C. was added a solution of HC/EtOAc (1.25 M, 8 mL), and the resulting mixture was stirred at 15° C. for 1 h. The mixture was filtered and the filter cake was dried in vacuo to give (R)—N-(4-(4-(1-aminoethyl)-3-methylphenyl)-5-fluoropyridin-2-yl)cyclopropanecarboxamide hydrochloride as a yellow solid (150 mg, yield: 81%), which was carried forward without further purification. ESI-MS (M+H)$^+$: 314.0.

4. Synthesis of (R)-5-(tert-butyl)-N-(1-(4-(2-(cyclopropanecarboxamido)-5-fluoropyridin-4-yl)-2-methylphenyl)ethyl)-1,2,4-oxadiazole-3-carboxamide (Compound 20)

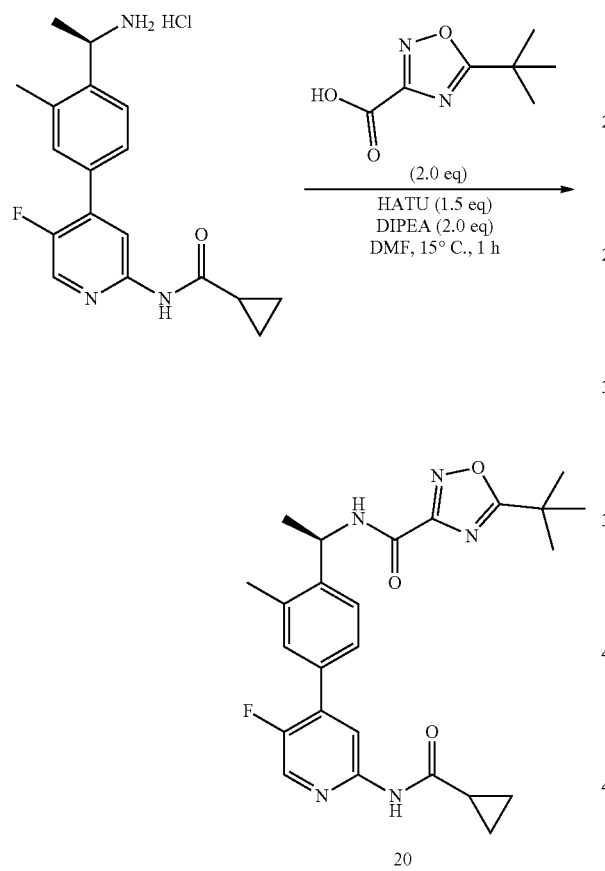

20

To a solution of (R)—N-(4-(4-(1-aminoethyl)-3-methylphenyl)-5-fluoropyridin-2-yl)cyclopropanecarboxamide hydrochloride (100 mg, 0.29 mmol) in DMF (5 mL) at 15° C. were added DIPEA (75 mg, 0.58 mmol), 5-(tert-butyl)-1,2,4-oxadiazole-3-carboxylic acid (97 mg, 0.57 mmol) and HATU (165 mg, 0.43 mmol). The mixture was stirred at 15° C. for 1 h, filtered, and the filtrate was purified by prep-HPLC (CH$_3$CN/H$_2$O with 0.05% HCl/H$_2$O as mobile phase) to give (R)-5-(tert-butyl)-N-(1-(4-(2-(cyclopropanecarboxamido)-5-fluoropyridin-4-yl)-2-methylphenyl)ethyl)-1,2,4-oxadiazole-3-carboxamide as a white solid (75 mg, yield: 56%). ESI-MS (M+Na)$^+$: 488.2. $^1$H NMR (400 MHz, CD$_3$OD) δ: 8.25 (s, 1H), 8.12 (d, J=5.6 Hz, 1H), 7.56 (d, J=8.0 Hz, 1H), 7.50-7.47 (m, 2H), 5.47 (dd, J$_1$=13.6 Hz, J$_2$=6.8 Hz, 1H), 2.51 (s, 3H), 1.88-1.87 (m, 1H), 1.58 (d, J=6.8 Hz, 3H), 1.47 (s, 9H), 1.02-0.99 (m, 2H), 0.95-0.90 (m, 2H).

Example 21: (R)-5-(tert-butyl)-N-(1-(2-chloro-4-(2-(cyclopropanecarboxamido)pyridin-4-yl)phenyl)ethyl)-1,2,4-oxadiazole-3-carboxamide (Compound 21)

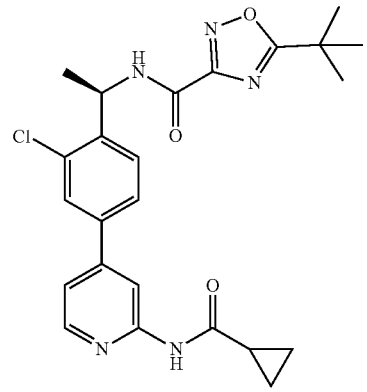

21

1. Synthesis of 4-bromo-2-chloro-N-methoxy-N-methylbenzamide

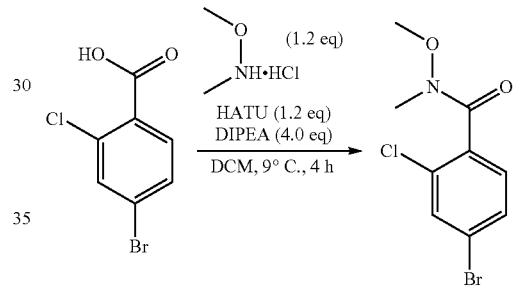

To a solution of 4-bromo-2-chlorobenzoic acid (8 g, 34 mmol) and N,O-dimethylhydroxylamine hydrochloride (4 g, 41 mmol) in DCM (200 mL) at 9° C. were added HATU (15.5 g, 41 mmol) and DIPEA (17.6 g, 136 mmol). The reaction mixture was stirred at 9° C. for 4 h and then was concentrated in vacuo. The crude was purified by silica-gel column chromatography (petroleum ether/EtOAc, grading from 7:1 to 2:1) to give 4-bromo-2-chloro-N-methoxy-N-methylbenzamide as a light brown oil (5.6 g, yield: 60%). $^1$H NMR: (400 MHz, CDCl$_3$) δ: 7.59 (d, J=2.0 Hz, 1H), 7.45 (d, J=8.0 Hz, 1H), 7.21 (d, J=8.0 Hz, 1H), 3.46 (s, 3H), 3.37 (s, 3H).

2. Synthesis of 1-(4-bromo-2-chlorophenyl)ethan-1-one

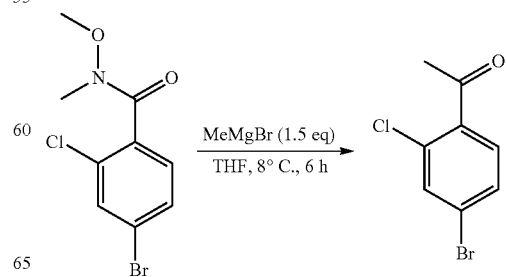

To a solution of 4-bromo-2-chloro-N-methoxy-N-methylbenzamide (5.6 g, 20 mmol, 1 eq.) in THF (80 mL) was added MeMgBr (3 M, 10 mL, 30 mmol, 1.5 eq.) at 8° C. The reaction mixture was stirred at 8° C. for 6 h and then was concentrated in vacuo. The residue was dissolved in EtOAc (100 mL) and was poured into saturated aqueous NH$_4$Cl solution (200 mL). The layers were separated and the aqueous layer was extracted with EtOAc (100 mL). The combined organic extracts were dried (Na$_2$SO$_4$), filtered, and concentrated in vacuo to give 1-(4-bromo-2-chlorophenyl)ethan-1-one as a light brown solid (4 g, yield: 86%), which was carried forward without further purification. $^1$H NMR: (400 MHz, CDCl$_3$) δ: 7.60 (s, 1H), 7.48-7.43 (m, 2H), 2.63 (s, 3H).

3. Synthesis of (S,E)-N-(1-(4-bromo-2-chlorophenyl)ethylidene)-2-methylpropane-2-sulfinamide

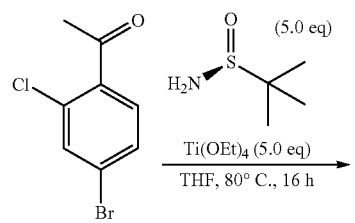

To a solution of 1-(4-bromo-2-chlorophenyl)ethan-1-one (4 g, 17.1 mmol) and (S)-2-methylpropane-2-sulfinamide (10.3 g, 85.5 mmol) in THF (100 mL) was added Ti(IV)(OEt)$_4$ (19.5 g, 85.5 mmol) at 9° C. The reaction mixture was heated to 80° C. and stirred at that temperature for 16 h. The reaction mixture was concentrated in vacuo and the residue was dissolved in EtOAc (120 mL). The organic phase was poured into saturated aqueous NH$_4$Cl solution (250 mL), the layers were separated, and the aqueous phase was extracted with EtOAc (120 mL). The combined organic extracts were dried (Na$_2$SO$_4$), filtered, and concentrated in vacuo. The crude material was purified by silica-gel column chromatography (petroleum ether/EtOAc, grading from 8:1 to 3:1) to give (S,E)-N-(1-(4-bromo-2-chlorophenyl)ethylidene)-2-methylpropane-2-sulfinamide as an orange oil (3.7 g, yield: 65%). $^1$H NMR (400 MHz, CDCl$_3$) δ: 7.58-7.55 (m, 1H), 7.44 (d, J=8.0 Hz, 1H), 7.22 (d, J=8.0 Hz, 1H), 2.70 (s, 3H), 1.29 (s, 9H).

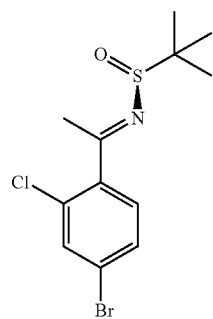

4. Synthesis of (S)—N—((R)-1-(4-bromo-2-chlorophenyl)ethyl)-2-methylpropane-2-sulfinamide

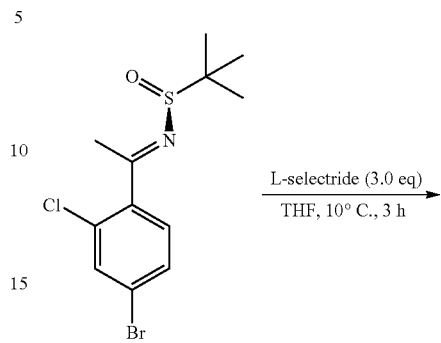

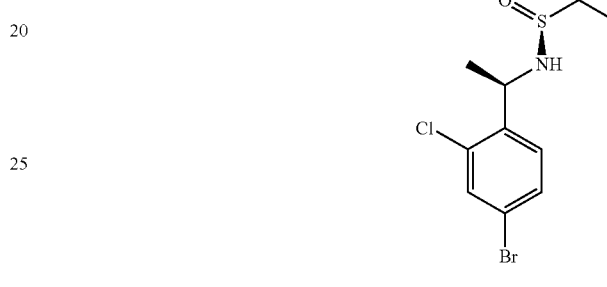

To a solution of (S,E)-N-(1-(4-bromo-2-chlorophenyl)ethylidene)-2-methylpropane-2-sulfinamide (2 g, 6 mmol) in THF (100 mL) at 10° C. under N$_2$ was added dropwise a solution of L-selectride (1 M, 18 mL, 18 mmol). The reaction mixture was stirred at 10° C. under N$_2$ for 3 h and then was concentrated in vacuo. The residue was dissolved in EtOAc (100 mL) and was poured into a saturated aqueous NH$_4$Cl solution (300 mL). The layers were separated and the aqueous phase was extracted with EtOAc (100 mL×2). The combined organic extracts were dried (Na$_2$SO$_4$), filtered, and concentrated in vacuo. The crude material was purified by silica-gel column chromatography (petroleum ether/EtOAc, grading from 6:1 to 1:2) to give (S)—N—((R)-1-(4-bromo-2-chlorophenyl)ethyl)-2-methylpropane-2-sulfinamide as a light brown solid (1.3 g, yield:64%). $^1$H NMR (400 MHz, CDCl$_3$) δ: 7.52-7.38 (m, 2H), 7.32-7.30 (m, 1H), 4.99 (q, J=6.4 Hz, 1H), 3.34 (s, 1H), 1.52 (d, J=6.4 Hz, 3H), 1.20 (s, 9H).

5. Synthesis of (R)-1-(4-bromo-2-chlorophenyl)ethan-1-amine Hydrochloride

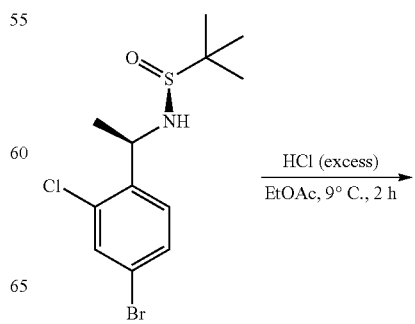

-continued

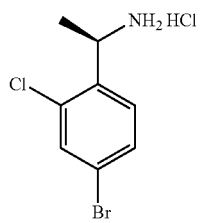

To a solution of (S)—N—((R)-1-(4-bromo-2-chlorophenyl)ethyl)-2-methylpropane-2-sulfinamide (2.02 g, 5.98 mmol) in EtOAc (5 mL) at 9° C. was added a solution of HC/EtOAc (2 M, 50 mL). The reaction mixture was stirred at 9° C. for 2 h. The resulting suspension was filtered and the filter cake was dried in vacuo to give (R)-1-(4-bromo-2-chlorophenyl)ethan-1-amine hydrochloride as a light gray solid (1.6 g, yield: 99%), which was carried forward without further purification. $^1$H NMR (400 MHz, DMSO-$d_6$) δ: 8.83 (br s, 3H), 7.81 (d, J=2.0 Hz, 1H), 7.75-7.70 (m, 2H), 4.60 (q, J=6.4 Hz, 1H), 1.47 (d, J=6.4 Hz, 3H).

6. Synthesis of tert-butyl (R)-(1-(4-bromo-2-chlorophenyl)ethyl)carbamate

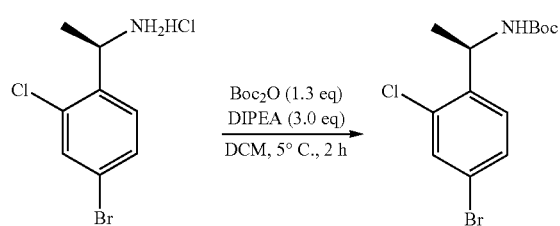

To a solution of (R)-1-(4-bromo-2-chlorophenyl)ethan-1-amine hydrochloride (1.6 g, 5.92 mmol) and DIPEA (2.3 g, 17.8 mmol) in DCM (80 mL) at 5° C. was added Boc$_2$O (1.7 g, 7.70 mmol). The reaction mixture was stirred at 5° C. for 2 h. The reaction mixture was concentrated in vacuo and the crude material was purified by silica-gel column chromatography (petroleum ether/EtOAc, grading from 15:1 to 5:1) to give tert-butyl (R)-(1-(4-bromo-2-chlorophenyl)ethyl) carbamate as a light gray solid (1.8 g, yield: 91%). $^1$H NMR: (400 MHz, CDCl$_3$) δ: 7.50 (d, J=2.0 Hz, 1H), 7.39-7.36 (m, 1H), 7.21 (d, J=8.0 Hz, 1H), 5.05-4.94 (m, 2H), 1.45-1.36 (m, 12H).

7. Synthesis of tert-butyl (R)-(1-(2-chloro-4-(4,4,5,5-tetramethyl-1,3,2-dioxaborolan-2-yl)phenyl)ethyl)carbamate

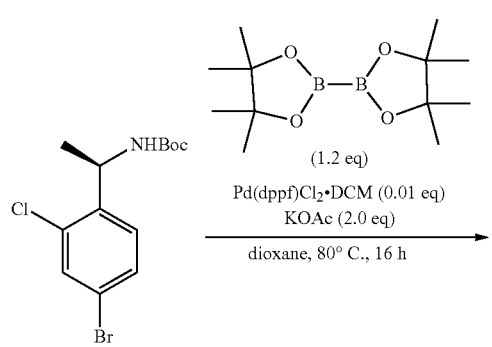

-continued

To a solution of tert-butyl (R)-(1-(4-bromo-2-chlorophenyl)ethyl)carbamate (1.8 g, 5.38 mmol) in 1,4-dioxane (80 mL) under N$_2$ were added bis(pinacolato)diboron (1.77 g, 6.99 mmol), Pd(dppf)Cl$_2$·DCM (351 mg, 0.43 mmol) and KOAc (1.06 g, 10.8 mmol). The mixture was heated to 80° C. under N$_2$ and stirred at that temperature for 16 h, cooled to rt, and concentrated in vacuo. The crude material was purified by silica-gel column chromatography (petroleum ether/EtOAc, grading from 12:1 to 3:1) to give tert-butyl (R)-(1-(2-chloro-4-(4,4,5,5-tetramethyl-1,3,2-dioxaborolan-2-yl)phenyl)ethyl)carbamate as a white solid (1.5 g, yield: 73%) as a pale white solid. ESI-MS (M-t-Bu)$^+$: 326.0.

8. Synthesis of tert-butyl (R)-(1-(2-chloro-4-(2-(cyclopropanecarboxamido)pyridin-4-yl)phenyl)ethyl)carbamate

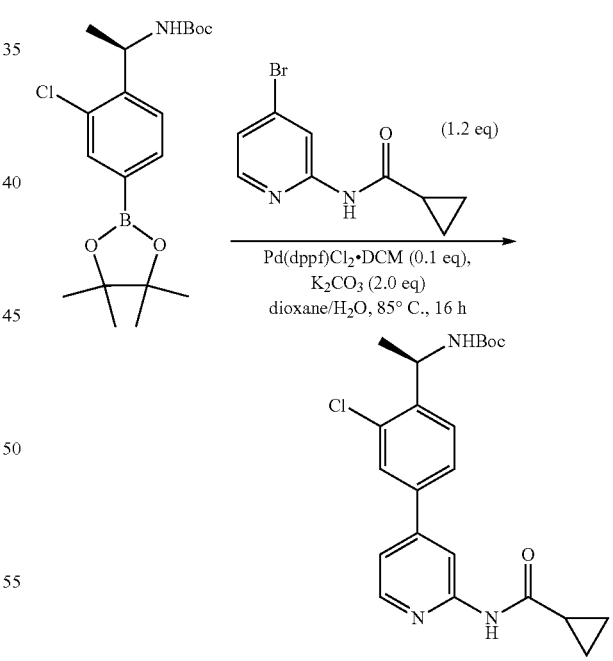

To a solution of tert-butyl (R)-(1-(2-chloro-4-(4,4,5,5-tetramethyl-1,3,2-dioxaborolan-2-yl)phenyl)ethyl)carbamate (200 mg, 0.52 mmol) in 1,4-dioxane (15 mL) and H$_2$O (3 mL) were added N-(4-bromopyridin-2-yl)cyclopropanecarboxamide (152 mg, 0.63 mmol), Pd(dppf)Cl$_2$·DCM (21 mg, 0.03 mmol) and K$_2$CO$_3$ (145 mg, 1.05 mmol). The mixture was heated to 85° C. under N$_2$ and stirred at that temperature for 16 h. The reaction mixture was cooled to rt and concentrated in vacuo. The crude material was purified by silica-gel column chromatography (petroleum ether/EtOAc, grading from 10:1 to 1:1) to give tert-butyl (R)-(1-(2-chloro-4-(2-(cyclopropanecarboxamido)pyridin-4-yl)phenyl)ethyl)carbamate as a white solid (180 mg, yield: 83%). ESI-MS (M+H)$^+$: 416.1.

9. Synthesis of (R)—N-(4-(4-(1-aminoethyl)-3-chlorophenyl)pyridin-2-yl)cyclopropanecarboxamide Hydrochloride

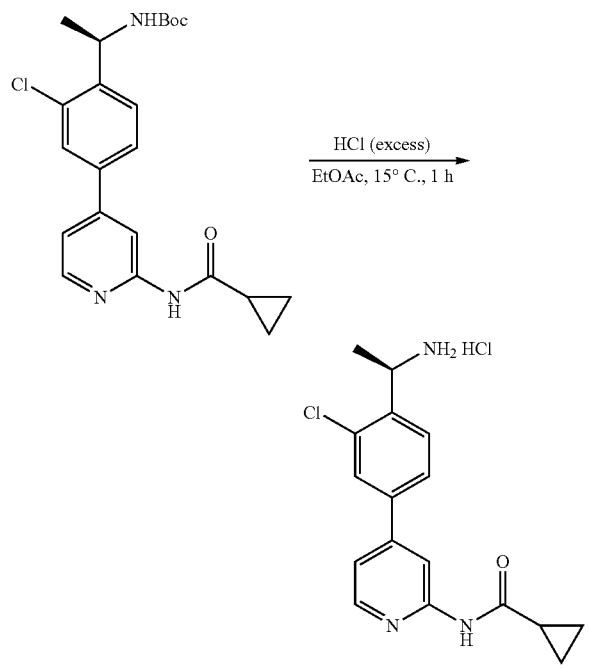

To a solution of tert-butyl (R)-(1-(2-chloro-4-(2-(cyclopropanecarboxamido)pyridin-4-yl)phenyl)ethyl)carbamate (180 mg, 0.43 mmol) in DCM (10 mL) at 20° C. was added an HCl/EtOAc solution (4 M, 10 mL). The mixture was stirred at 20° C. for 2 h and was concentrated in vacuo to give crude (R)—N-(4-(4-(1-aminoethyl)-3-chlorophenyl)pyridin-2-yl)cyclopropanecarboxamide hydrochloride as a yellow solid (130 mg, crude), which was carried forward without further purification. ESI-MS (M+H)$^+$: 316.1.

10. Synthesis of (R)-5-(tert-butyl)-N-(1-(2-chloro-4-(2-(cyclopropanecarboxamido)pyridin-4-yl)phenyl)ethyl)-1,2,4-oxadiazole-3-carboxamide (Compound 21)

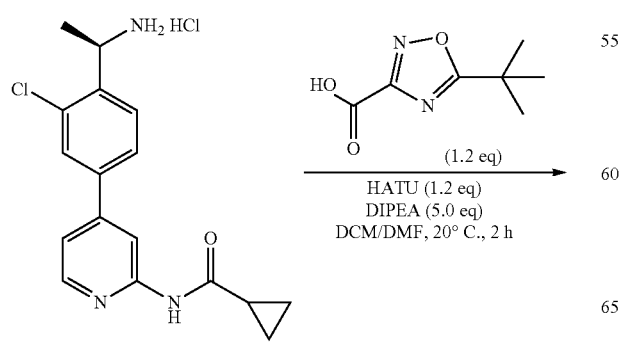

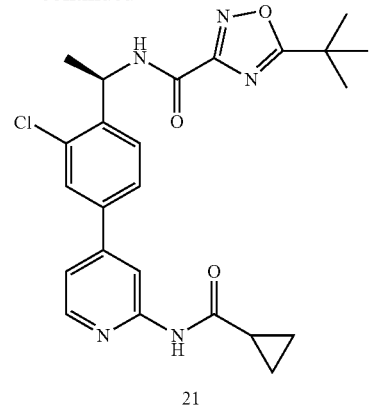

21

To a solution of (R)—N-(4-(4-(1-aminoethyl)-3-chlorophenyl)pyridin-2-yl)cyclopropanecarboxamide hydrochloride (130 mg, 0.41 mmol) in a DCM/DMF mixture (v/v=25/1, 52 mL) at 20° C. were added 5-(tert-butyl)-1,2,4-oxadiazole-3-carboxylic acid (84 mg, 0.49 mmol), HATU (187 mg, 0.49 mmol), and DIPEA (266 mg, 2.1 mmol). The reaction mixture was stirred at 20° C. for 2 h, poured into H$_2$O (100 mL), and extracted with DCM (50 mL×2). The combined organic extracts were concentrated in vacuo to give crude material. The crude material was purified by prep-HPLC (CH$_3$CN/H$_2$O with 0.05% HCl/H$_2$O as mobile phase) to give (R)-5-(tert-butyl)-N-(1-(2-chloro-4-(2-(cyclopropanecarboxamido)pyridin-4-yl)phenyl)ethyl)-1,2,4-oxadiazole-3-carboxamide as a white solid (87 mg, yield: 45%, ee: 99.5%). ESI-MS (M+Na)$^+$: 490.1. $^1$H NMR (400 mHz, CD$_3$OD) δ: 8.35 (d, J=6.4 Hz, 1H), 7.90 (d, J=1.6 Hz, 1H), 7.85 (s, 1H), 7.79-7.75 (m, 1H), 7.73-7.67 (m, 2H), 5.61 (q, J=7.2 Hz, 1H), 1.96-1.89 (m, 1H), 1.60 (d, J=7.2 Hz, 3H), 1.48 (s, 9H), 1.16-1.10 (m, 2H), 1.08-1.03 (m, 2H).

Example 22: (R)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide (Compound 22)

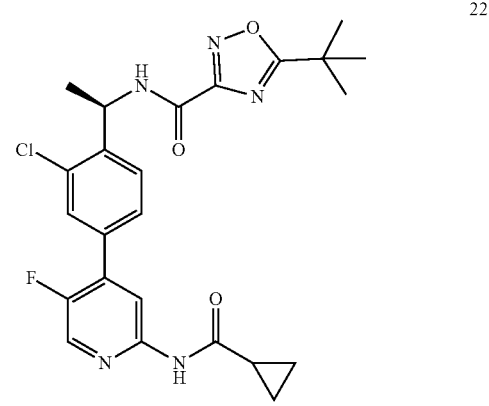 [SMILES: C[C@@H](NC(=O)c1noc(C(C)(C)C)n1)c1ccc(-c2cc(NC(=O)C3CC3)ncc2F)cc1Cl]

22

1. Synthesis of tert-butyl (R)-(1-(2-chloro-4-(2-chloro-5-fluoropyridin-4-yl)phenyl)ethyl)carbamate

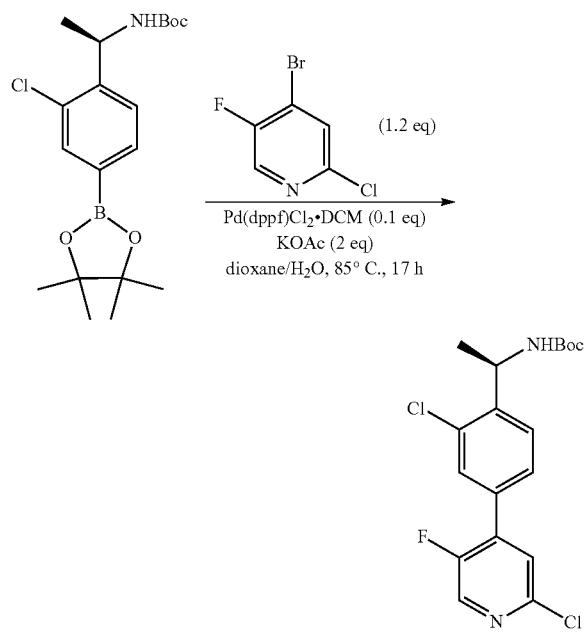

To a solution of tert-butyl (R)-(1-(2-chloro-4-(4,4,5,5-tetramethyl-1,3,2-dioxaborolan-2-yl)phenyl)ethyl)carbamate (400 mg, 1.05 mmol) in 1,4-dioxane/H$_2$O (v/v=10/1, 22 mL) were added 2-chloro-5-fluoro-4-iodopyridine (324 mg, 1.26 mmol) and KOAc (206 mg, 2.10 mmol). Then Pd(dppf)Cl$_2$·DCM (43 mg, 0.05 mmol) was added under N$_2$ atmosphere and the reaction mixture was heated to 85° C. The mixture was stirred at that temperature for 5 h under N$_2$, then was concentrated in vacuo. The crude material was purified by silica-gel column chromatography (petroleum ether/EtOAc, grading from 20:1 to 10:1) to give tert-butyl (R)-(1-(2-chloro-4-(2-chloro-5-fluoropyridin-4-yl)phenyl)ethyl)carbamate as a colorless oil (250 mg, yield: 62%). ESI-MS (M+H)$^+$: 385.0.

2. Synthesis of tert-butyl (R)-(1-(2-chloro-4-(2-(cyclopropanecarboxamido)-5-fluoropyridin-4-yl)phenyl)ethyl)carbamate

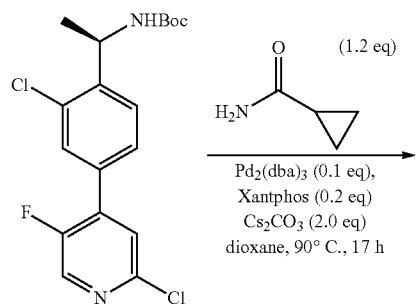

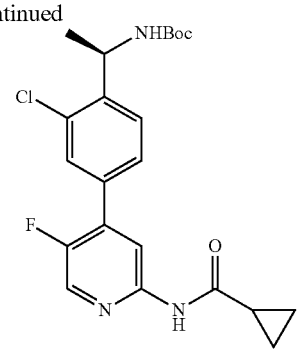

To a solution of tert-butyl (R)-(1-(2-chloro-4-(2-chloro-5-fluoropyridin-4-yl)phenyl)ethyl)carbamate (250 mg, 0.65 mmol) in 1,4-dioxane (20 mL) were added cyclopropanecarboxamide (66 mg, 0.78 mmol) and Cs$_2$CO$_3$ (423 mg, 1.3 mmol). Then Pd$_2$(dba)$_3$ (60 mg, 0.07 mmol) and Xantphos (75 mg, 0.13 mmol) were added under an N$_2$ atmosphere. The reaction mixture was heated to 90° C. and stirred at that temperature under N$_2$ for 17 h. The reaction mixture was cooled to rt and concentrated under vacuum. The crude material was purified by silica-gel column chromatography (petroleum ether/EtOAc, grading from 10:1 to 1:1) to give tert-butyl (R)-(1-(2-chloro-4-(2-(cyclopropanecarboxamido)-5-fluoropyridin-4-yl)phenyl)ethyl)carbamate as a yellow solid (130 mg, yield: 46%). ESI-MS (M+H)$^+$: 434.0.

3. Synthesis of (R)—N-(4-(4-(1-aminoethyl)-3-chlorophenyl)-5-fluoropyridin-2-yl)cyclopropanecarboxamide Hydrochloride

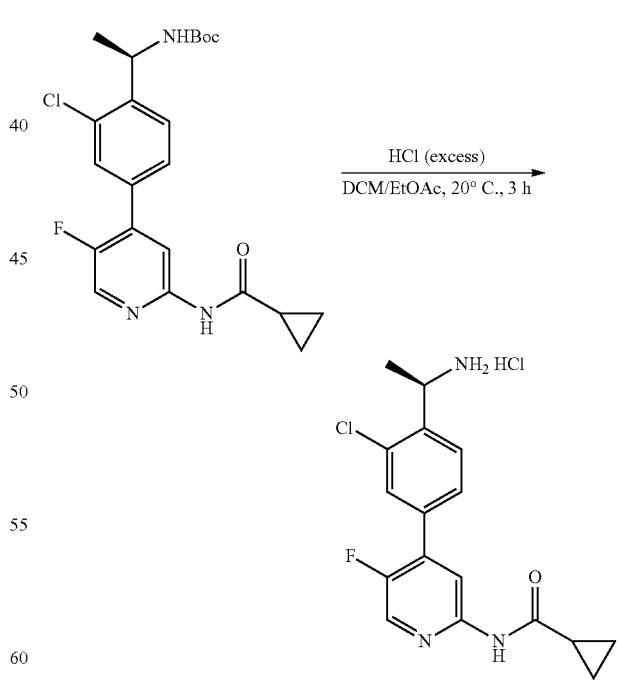

To a solution of tert-butyl (R)-(1-(2-chloro-4-(2-(cyclopropanecarboxamido)-5-fluoropyridin-4-yl)phenyl)ethyl)carbamate (130 mg, 0.30 mmol) in DCM (10 mL) at 20° C. was added a solution of HCl/EtOAc (1.25 M, 10 mL), and the resulting mixture was stirred at 20° C. for 3 h. The reaction mixture was concentrated in vacuo to give crude (R)—N-(4-(4-(1-aminoethyl)-3-chlorophenyl)-5-fluoropyridin-2-yl)cyclopropanecarboxamide hydrochloride as a yellow solid (100 mg, crude), which was carried forward without further purification. ESI-MS (M+H)+: 333.9.

4. Synthesis of (R)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide (Compound 22)

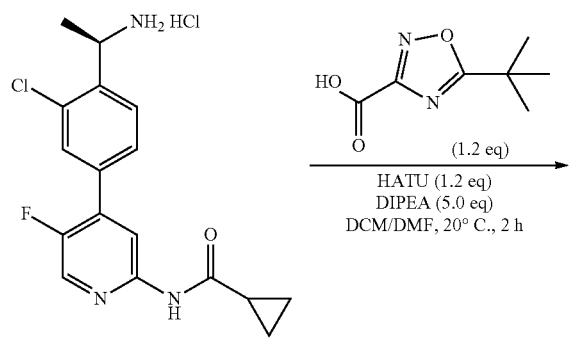

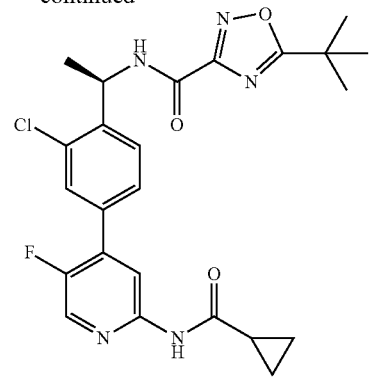

22

To a solution of (R)—N-(4-(4-(1-aminoethyl)-3-chlorophenyl)-5-fluoropyridin-2-yl)cyclopropanecarboxamide hydrochloride (100 mg, 0.30 mmol) in a DCM/DMF mixture (v/v=25/1, 52 mL) at 20° C. were added DIPEA (194 mg, 1.5 mmol), 5-(tert-butyl)-1,2,4-oxadiazole-3-carboxylic acid (62 mg, 0.36 mmol) and HATU (137 mg, 0.36 mmol). The mixture was stirred at 20° C. for 2 h, poured into H$_2$O (100 mL), and extracted with DCM (50 mL×2). The combined organic extracts were concentrated in vacuo and the crude material was purified by prep-HPLC (CH$_3$CN/H$_2$O with 0.05% HCl/H$_2$O as mobile phase) to give (R)-5-(tert-butyl)-N-(1-(2-chloro-4-(2-(cyclopropanecarboxamido)-5-fluoropyridin-4-yl)phenyl)ethyl)-1,2,4-oxadiazole-3-carboxamide as a white solid (48 mg, yield: 33%, ee: 98.9%). ESI-MS (M+H)+: 486.1. $^1$H NMR: (400 MHz, CD$_3$OD) δ: 8.33 (d, J=2.8 Hz, 1H), 8.01 (d, J=6.0 Hz, 1H), 7.75 (s, 1H), 7.69-7.61 (m, 2H), 5.61 (q, J=7.2 Hz, 1H), 1.93-1.84 (m, 1H), 1.61 (d, J=7.2 Hz, 3H), 1.48 (s, 9H), 1.07-1.03 (m, 2H), 1.00-0.95 (m, 2H).

Examples 23-107

The following compounds were prepared according to procedures similar to those described in Examples 1-22.

| Compd No. | Structure | Chemical Name | MS |
|---|---|---|---|
| 23 | 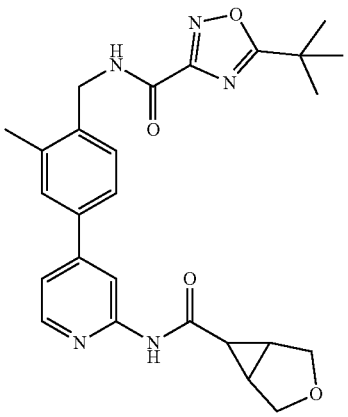 [SMILES: Cc1cc(-c2ccnc(NC(=O)C3C4COCC43)c2)ccc1CNC(=O)c1noc(C(C)(C)C)n1] | N-(4-(2-(3-oxobicyclo[3.1.0]hexane-6-carboxamido)pyridin-4-yl)-2-methylbenzyl)-5-(tert-butyl)-1,2,4-oxadiazole-3-carboxamide | ESI-MS (M + H)+: 476.1; Calculated MW: 475.54 |

| Compd No. | Structure | Chemical Name | MS |
|---|---|---|---|
| 24 | 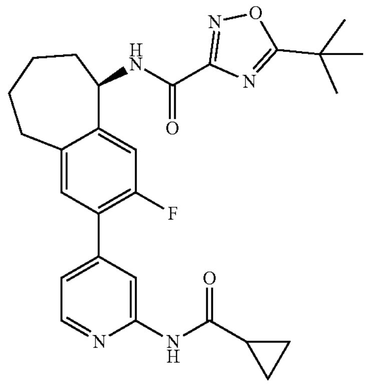 [SMILES: CC(C)(C)c1nc(C(=O)N[C@@H]2CCCCc3cc(-c4ccnc(NC(=O)C5CC5)c4)c(F)cc32)no1] | (R)-5-(tert-butyl)-N-(2-(2-(cyclopropanecarboxamido)pyridin-4-yl)-3-fluoro-6,7,8,9-tetrahydro-5H-benzo[7]annulen-5-yl)-1,2,4-oxadiazole-3-carboxamide | ESI-MS (M + H)⁺: 492; Calculated MW: 491.557 |
| 25 | 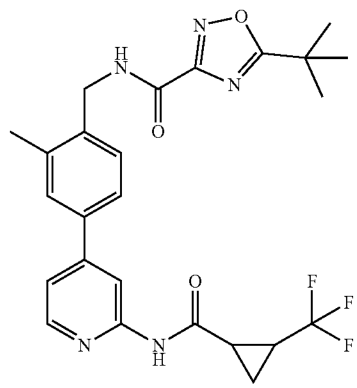 [SMILES: Cc1cc(-c2ccnc(NC(=O)C3CC3C(F)(F)F)c2)ccc1CNC(=O)c1noc(C(C)(C)C)n1] | 5-(tert-butyl)-N-(2-methyl-4-(2-(2-(trifluoromethyl)cyclopropane-1-carboxamido)pyridin-4-yl)benzyl)-1,2,4-oxadiazole-3-carboxamide | ESI-MS (M + H)⁺: 502.1; Calculated MW: 501.501 |
| 26 | 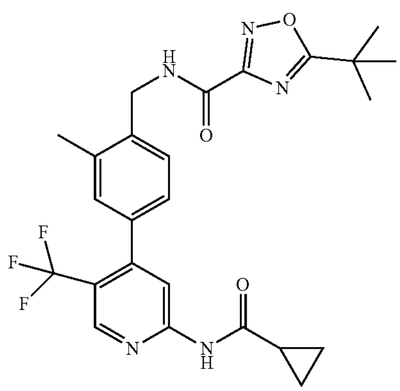 [SMILES: Cc1cc(-c2cc(NC(=O)C3CC3)ncc2C(F)(F)F)ccc1CNC(=O)c1noc(C(C)(C)C)n1] | 5-(tert-butyl)-N-(4-(2-(cyclopropanecarboxamido)-5-(trifluoromethyl)pyridin-4-yl)-2-methylbenzyl)-1,2,4-oxadiazole-3-carboxamide | ESI-MS (M + H)⁺: 502.1; Calculated MW: 501.501 |
| 27 | 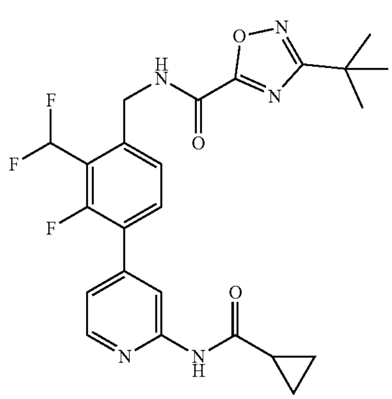 [SMILES: CC(C)(C)c1noc(C(=O)NCc2ccc(-c3ccnc(NC(=O)C4CC4)c3)c(F)c2C(F)F)n1] | 3-(tert-butyl)-N-(4-(2-(cyclopropanecarboxamido)pyridin-4-yl)-2-(difluoromethyl)-3-fluorobenzyl)-1,2,4-oxadiazole-5-carboxamide | ESI-MS (M + H)⁺: 488.1; Calculated MW: 487.474 |

| Compd No. | Structure | Chemical Name | MS |
|---|---|---|---|
| 28 | 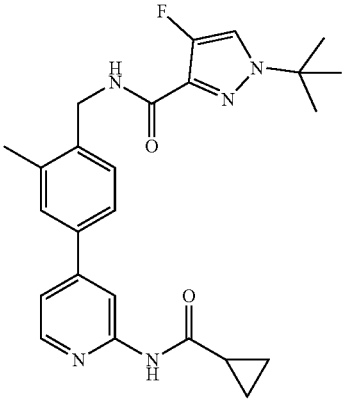 [SMILES: Cc1cc(-c2ccnc(NC(=O)C3CC3)c2)ccc1CNC(=O)c1nn(C(C)(C)C)cc1F] | 1-(tert-butyl)-N-(4-(2-(cyclopropanecarboxamido)pyridin-4-yl)-2-methylbenzyl)-4-fluoro-1H-pyrazole-3-carboxamide | ESI-MS (M + H)$^+$: 450.3; Calculated MW: 449.521 |
| 29 | 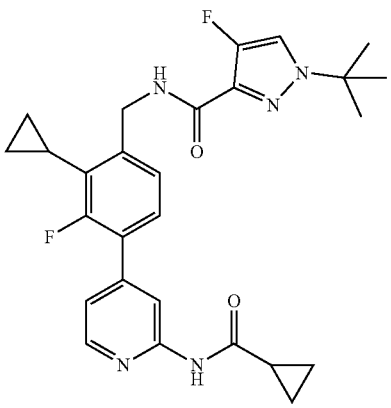 [SMILES: CC(C)(C)n1cc(F)c(C(=O)NCc2ccc(-c3ccnc(NC(=O)C4CC4)c3)c(F)c2C2CC2)n1] | 1-(tert-butyl)-N-(4-(2-(cyclopropanecarboxamido)pyridin-4-yl)-2-cyclopropyl-3-fluorobenzyl)-4-fluoro-1H-pyrazole-3-carboxamide | ESI-MS (M + H)$^+$: 494.3; Calculated MW: 493.548 |
| 30 | 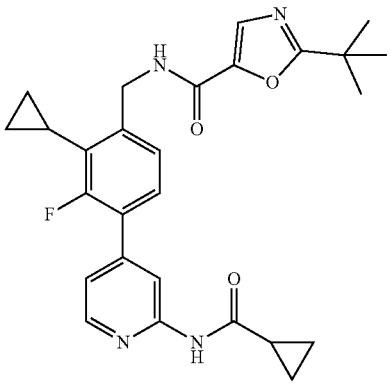 [SMILES: CC(C)(C)c1ncc(C(=O)NCc2ccc(-c3ccnc(NC(=O)C4CC4)c3)c(F)c2C2CC2)o1] | 2-(tert-butyl)-N-(4-(2-(cyclopropanecarboxamido)pyridin-4-yl)-2-cyclopropyl-3-fluorobenzyl)oxazole-5-carboxamide | ESI-MS (M + H)$^+$: 477.3; Calculated MW: 476.543 |

-continued

| Compd No. | Structure | Chemical Name | MS |
|---|---|---|---|
| 31 | 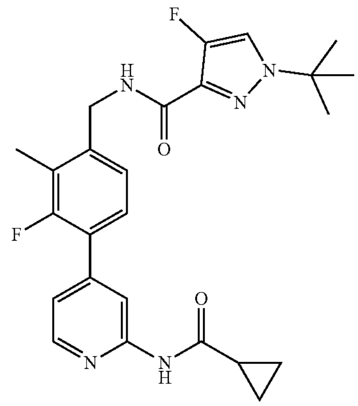 [SMILES: Cc1c(CNC(=O)c2nn(C(C)(C)C)cc2F)ccc(-c2ccnc(NC(=O)C3CC3)c2)c1F] | 1-(tert-butyl)-N-(4-(2-(cyclopropanecarboxamido)pyridin-4-yl)-3-fluoro-2-methylbenzyl)-4-fluoro-1H-pyrazole-3-carboxamide | ESI-MS (M + H)$^+$: 468.3; Calculated MW: 467.511 |
| 32 | 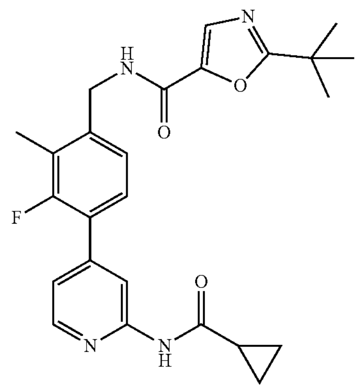 [SMILES: Cc1c(CNC(=O)c2cnc(C(C)(C)C)o2)ccc(-c2ccnc(NC(=O)C3CC3)c2)c1F] | 2-(tert-butyl)-N-(4-(2-(cyclopropanecarboxamido)pyridin-4-yl)-3-fluoro-2-methylbenzyl)oxazole-5-carboxamide | ESI-MS (M + H)$^+$: 451.3; Calculated MW: 450.505 |
| 33 | 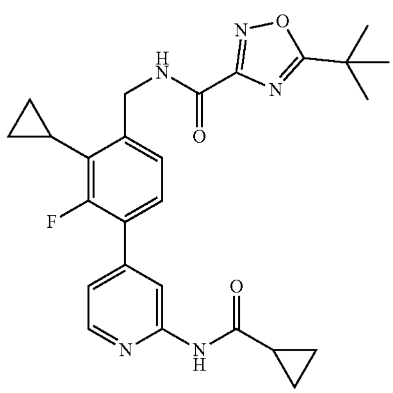 [SMILES: CC(C)(C)c1nc(C(=O)NCc2ccc(-c3ccnc(NC(=O)C4CC4)c3)c(F)c2C2CC2)no1] | 5-(tert-butyl)-N-(4-(2-(cyclopropanecarboxamido)pyridin-4-yl)-2-cyclopropyl-3-fluorobenzyl)-1,2,4-oxadiazole-3-carboxamide | ESI-MS (M + H)$^+$: 478.3; Calculated MW: 477.531 |
| 34 | 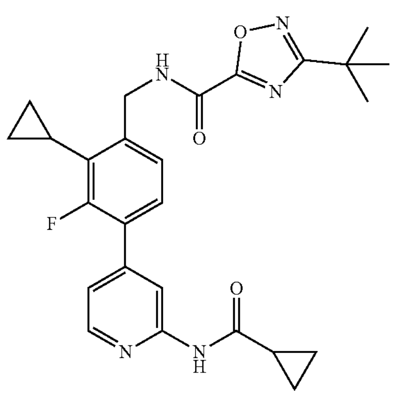 [SMILES: CC(C)(C)c1noc(C(=O)NCc2ccc(-c3ccnc(NC(=O)C4CC4)c3)c(F)c2C2CC2)n1] | 3-(tert-butyl)-N-(4-(2-(cyclopropanecarboxamido)pyridin-4-yl)-2-cyclopropyl-3-fluorobenzyl)-1,2,4-oxadiazole-5-carboxamide | ESI-MS (M + H)$^+$: 478.3; Calculated MW: 477.531 |

| Compd No. | Structure | Chemical Name | MS |
|---|---|---|---|
| 35 | 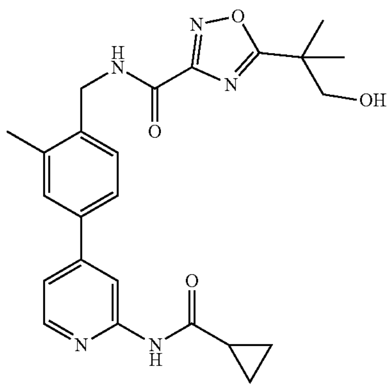 [SMILES: Cc1cc(-c2ccnc(NC(=O)C3CC3)c2)ccc1CNC(=O)c1noc(C(C)(C)CO)n1] | N-(4-(2-(cyclopropanecarboxamido)pyridin-4-yl)-2-methylbenzyl)-5-(1-hydroxy-2-methylpropan-2-yl)-1,2,4-oxadiazole-3-carboxamide | ESI-MS (M + H)+: 450.1; Calculated MW: 449.502 |
| 36 | 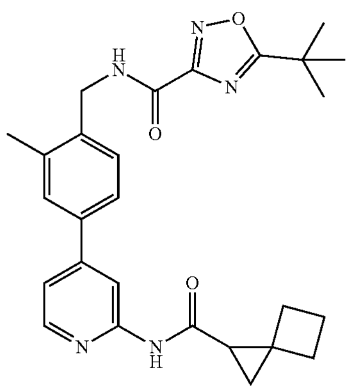 [SMILES: Cc1cc(-c2ccnc(NC(=O)C3CC34CCC4)c2)ccc1CNC(=O)c1noc(C(C)(C)C)n1] | 5-(tert-butyl)-N-(2-methyl-4-(2-spiro[2.3]hexane-1-carboxamido)pyridin-4-yl)benzyl)-1,2,4-oxadiazole-3-carboxamide | ESI-MS (M + H)+: 474.1; Calculated WW: 473.567 |
| 37 | 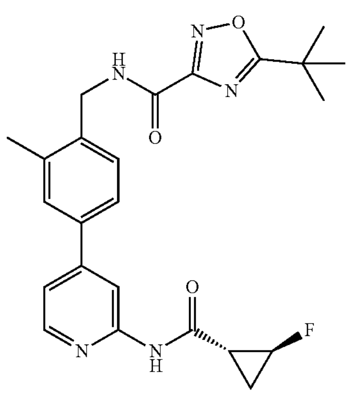 [SMILES: Cc1cc(-c2ccnc(NC(=O)[C@H]3C[C@@H]3F)c2)ccc1CNC(=O)c1noc(C(C)(C)C)n1] | 5-(tert-butyl)-N-(4-(2-((1R,2S)-2-fluorocyclopropane-1-carboxamido)pyridin-4-yl)-2-methylbenzyl)-1,2,4-oxadiazole-3-carboxamide | ESI-MS (M + H)+: 452.1; Calculated MW: 451.493 |
| 38 | 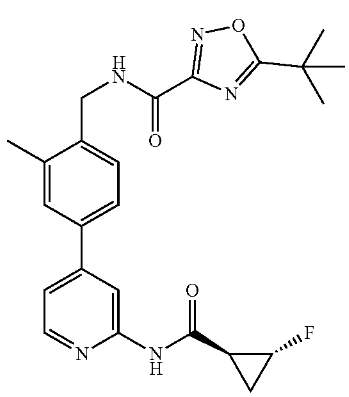 [SMILES: Cc1cc(-c2ccnc(NC(=O)[C@@H]3C[C@H]3F)c2)ccc1CNC(=O)c1noc(C(C)(C)C)n1] | 5-(tert-butyl)-N-(4-(2-((1S,2R)-2-fluorocyclopropane-1-carboxamido)pyridin-4-yl)-2-methylbenzyl)-1,2,4-oxadiazole-3-carboxamide | ESI-MS (M + H)+: 452.1; Calculated MW: 451.493 |

-continued

| Compd No. | Structure | Chemical Name | MS |
|---|---|---|---|
| 39 | 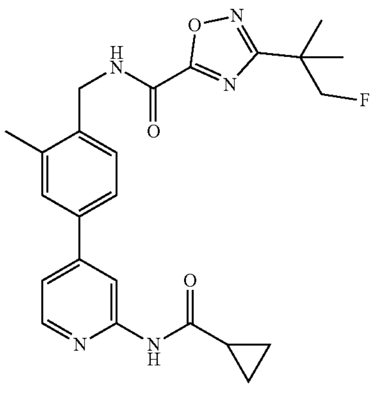 [SMILES: Cc1cc(-c2ccnc(NC(=O)C3CC3)c2)ccc1CNC(=O)c1nc(C(C)(C)CF)no1] | N-(4-(2-(cyclopropanecarboxamido)pyridin-4-yl)-2-methylbenzyl)-3-(1-fluoro-2-methylpropan-2-yl)-1,2,4-oxadiazole-5-carboxamide | ESI-MS (M + H)⁺: 452.1; Calculated MW: 451.493 |
| 40 | 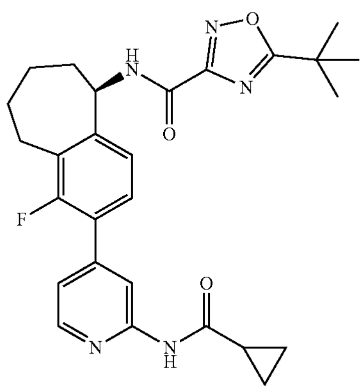 [SMILES: CC(C)(C)c1nc(C(=O)N[C@@H]2CCCCc3c2ccc(-c2ccnc(NC(=O)C4CC4)c2)c3F)no1] | (R)-5-(tert-butyl)-N-(2-(2-(cyclopropanecarboxamido)pyridin-4-yl)-1-fluoro-6,7,8,9-tetrahydro-5H-benzo[7]annulen-5-yl)-1,2,4-oxadiazole-3-carboxamide | ESI-MS (M + H)⁺: 492.1; Calculated MW: 491.557 |
| 41 | 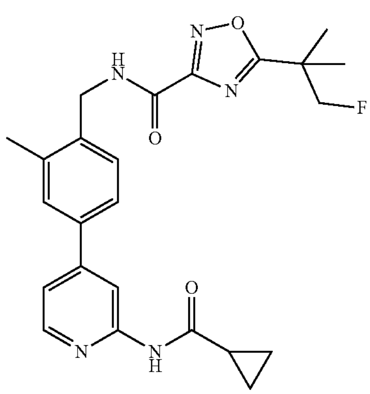 [SMILES: Cc1cc(-c2ccnc(NC(=O)C3CC3)c2)ccc1CNC(=O)c1noc(C(C)(C)CF)n1] | N-(4-(2-(cyclopropanecarboxamido)pyridin-4-yl)-2-methylbenzyl)-5-(1-fluoro-2-methylpropan-2-yl)-1,2,4-oxadiazole-3-carboxamide | ESI-MS (M + H)⁺: 452.1; Calculated MW: 451.493 |
| 42 | 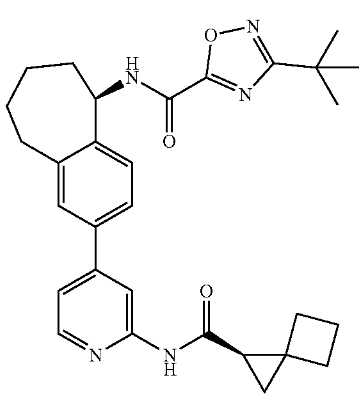 [SMILES: CC(C)(C)c1noc(C(=O)N[C@@H]2CCCCc3cc(-c4ccnc(NC(=O)[C@@H]5CC56CCC6)c4)ccc32)n1] | 3-(tert-butyl)-N-((R)-2-(2-((R)-spiro[2.3]hexane-1-carboxamido)pyridin-4-yl)-6,7,8,9-tetrahydro-5H-benzo[7]annulen-5-yl)-1,2,4-oxadiazole-5-carboxamide | ESI-MS (M + H)⁺: 514.3; Calculated MW: 513.631 |

-continued

| Compd No. | Structure | Chemical Name | MS |
|---|---|---|---|
| 43 | 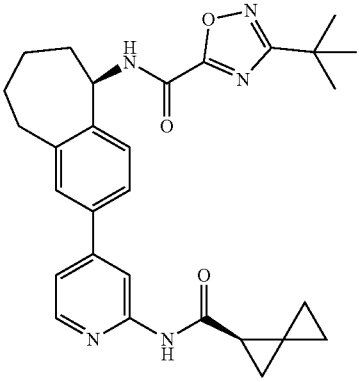 [SMILES: CC(C)(C)c1noc(C(=O)N[C@@H]2CCCCc3cc(-c4ccnc(NC(=O)[C@@H]5CC56CC6)c4)ccc32)n1] | 3-(tert-butyl)-N-((R)-2-(2-((R)-spiro[2.2]pentane-1-carboxamido)pyridin-4-yl)-6,7,8,9-tetrahydro-5H-benzo[7]annulen-6-yl)-1,2,4-oxadiazole-5-carboxamide | ESI-MS (M + H)+: 500.2; Calculated MW: 499.604 |
| 44 | 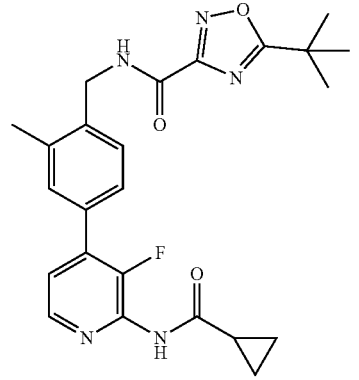 [SMILES: Cc1cc(-c2ccnc(NC(=O)C3CC3)c2F)ccc1CNC(=O)c1noc(C(C)(C)C)n1] | 5-(tert-butyl)-N-(4-(2-(cyclopropanecarboxamido)-3-fluoropyridin-4-yl)-2-methylbenzyl)-1,2,4-oxadiazole-3-carboxamide | ESI-MS (M + H)+: 452.1; Calculated MW: 451.493 |
| 45 | 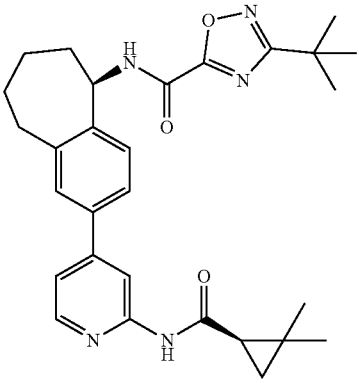 [SMILES: CC(C)(C)c1noc(C(=O)N[C@@H]2CCCCc3cc(-c4ccnc(NC(=O)[C@@H]5CC5(C)C)c4)ccc32)n1] | 3-(tert-butyl)-N-((R)-2-(2-((R)-2,2-dimethylcyclopropane-1-carboxamido)pyridin-4-yl)-6,7,8,9-tetrahydro-5H-benzo[7]annulen-5-yl)-1,2,4-oxadiazole-5-carboxamide | ESI-MS (M + H)+: 502.2; Calculated MW: 501.62 |
| 46 | 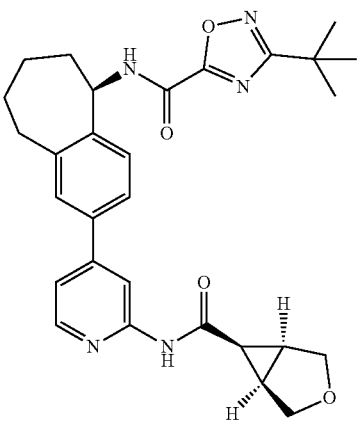 [SMILES: CC(C)(C)c1noc(C(=O)N[C@@H]2CCCCc3cc(-c4ccnc(NC(=O)[C@@H]5[C@@H]6COC[C@@H]65)c4)ccc32)n1] | N-((R)-2-(2-(((1R,5S,6s)-3-oxabicyclo[3.1.0]hexane-6-carboxamido)pyridin-4-yl)-6,7,8,9-tetrahydro-5H-benzo[7]annulen-5-yl)-3-(tert-butyl)-1,2,4-oxadiazole-5-carboxamide | ESI-MS (M + H)+: 516.2; Calculated MW: 515.603 |

| Compd No. | Structure | Chemical Name | MS |
|---|---|---|---|
| 47 | 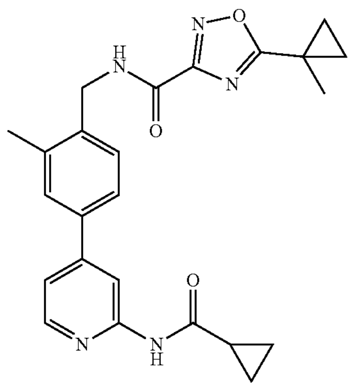 [SMILES: Cc1cc(-c2ccnc(NC(=O)C3CC3)c2)ccc1CNC(=O)c1noc(C2(C)CC2)n1] | N-(4-(2-(cyclopropanecarboxamido)pyridin-4-yl)-2-methylbenzyl)-5-(1-methylcyclopropyl)-1,2,4-oxadiazole-3-carboxamide | ESI-MS (M + H)⁺: 432.1; Calculated MW: 431.487 |
| 48 | 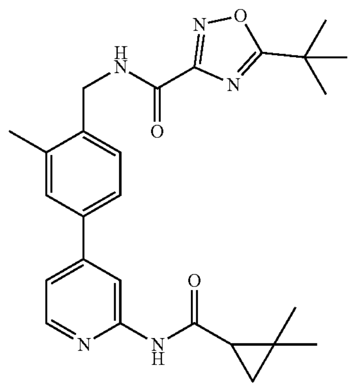 [SMILES: Cc1cc(-c2ccnc(NC(=O)C3CC3(C)C)c2)ccc1CNC(=O)c1noc(C(C)(C)C)n1] | 5-(tert-butyl)-N-(4-(2-(2,2-dimethylcyclopropane-1-carboxamido)pyridin-4-yl)-2-methylbenzyl)-1,2,4-oxadiazole-3-carboxamide | ESI-MS (M + H)⁺: 462.2; Calculated MW: 461.556 |
| 49 | 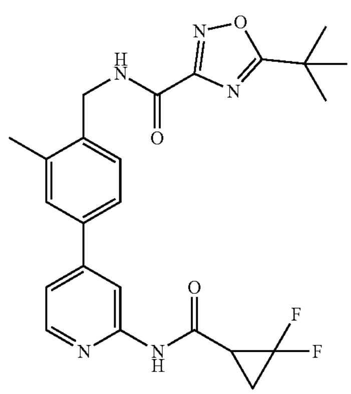 [SMILES: Cc1cc(-c2ccnc(NC(=O)C3CC3(F)F)c2)ccc1CNC(=O)c1noc(C(C)(C)C)n1] | 5-(tert-butyl)-N-(4-(2-(2,2-difluorocyclopropane-1-carboxamido)pyridin-4-yl)-2-methylbenzyl)-1,2,4-oxadiazole-3-carboxamide | ESI-MS (M + H)⁺: 470.2; Calculated MW: 469.484 |
| 50 | 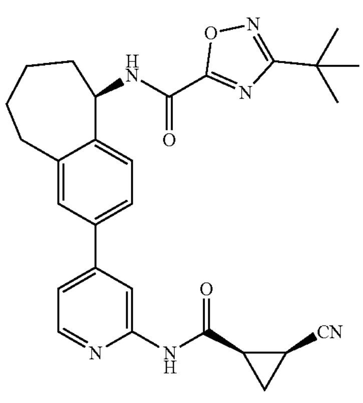 [SMILES: CC(C)(C)c1noc(C(=O)N[C@@H]2CCCCc3cc(-c4ccnc(NC(=O)[C@@H]5C[C@@H]5C#N)c4)ccc32)n1] | 3-(tert-butyl)-N-((R)-2-(2-((1R,2S)-2-cyanocyclopropane-1-carboxamido)pyridin-4-yl)-6,7,8,9-tetrahydro-5H-benzo[7]annulen-5-yl)-1,2,4-oxadiazole-5-carboxamide | ESI-MS (M + H)⁺: 499.2; Calculated MW: 498.576 |

| Compd No. | Structure | Chemical Name | MS |
|---|---|---|---|
| 51 | 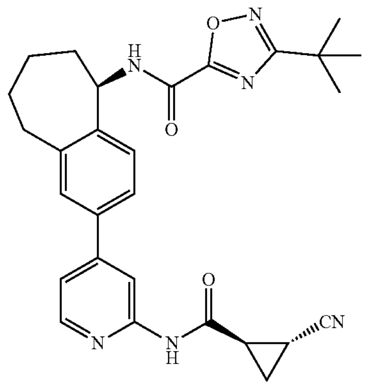 [SMILES: CC(C)(C)c1noc(C(=O)N[C@@H]2CCCCc3cc(-c4ccnc(NC(=O)[C@@H]5C[C@H]5C#N)c4)ccc32)n1] | 3-(tert-butyl)-N-((R)-2-(2-((1R,2R)-2-cyanocyclopropane-1-carboxamido)pyridin-4-yl)-6,7,8,9-tetrahydro-5H-benzo[7]annulen-5-yl)-1,2,4-oxadiazole-5-carboxamide | ESI-MS (M + H)⁺: 499.3; Calculated MW: 498.576 |
| 52 | 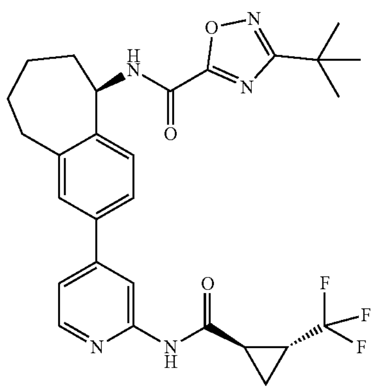 [SMILES: CC(C)(C)c1noc(C(=O)N[C@@H]2CCCCc3cc(-c4ccnc(NC(=O)[C@@H]5C[C@H]5C(F)(F)F)c4)ccc32)n1] | 3-(tert-butyl)-N-((R)-2-(2-((1R,2R)-2-(trifluoromethyl)cyclopropane-1-carboxamido)pyridin-4-yl)-6,7,8,9-tetrahydro-5H-benzo[7]annulen-5-yl)-1,2,4-oxadiazole-5-carboxamide | ESI-MS (M + H)⁺: 542.2; Calculated MW: 541.565 |
| 53 | 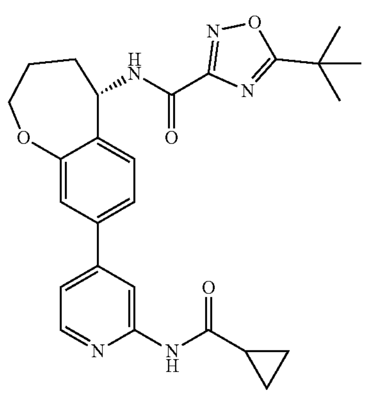 [SMILES: CC(C)(C)c1nc(C(=O)N[C@H]2CCCOc3cc(-c4ccnc(NC(=O)C5CC5)c4)ccc32)no1] | (S)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide | ESI-MS (M + H)⁺: 476.3; Calculated MW: 475.54 |
| 54 | 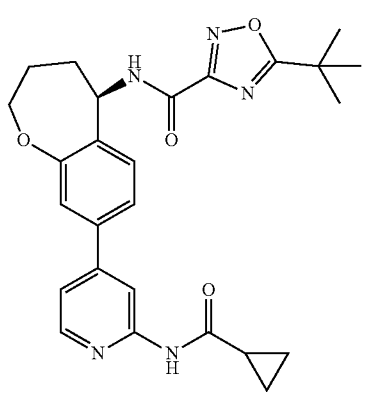 [SMILES: CC(C)(C)c1nc(C(=O)N[C@@H]2CCCOc3cc(-c4ccnc(NC(=O)C5CC5)c4)ccc32)no1] | (R)-5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide | ESI-MS (M + H)⁺: 476.3; Calculated MW: 475.54 |

-continued

| Compd No. | Structure | Chemical Name | MS |
|---|---|---|---|
| 55 | 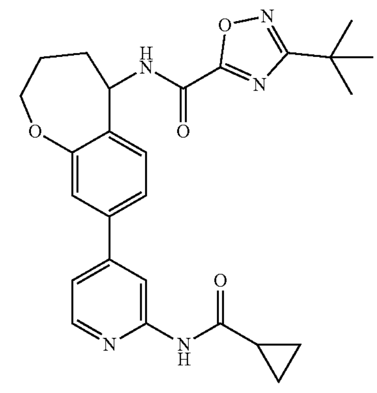 [SMILES: CC(C)(C)c1noc(C(=O)NC2CCCOc3cc(-c4ccnc(NC(=O)C5CC5)c4)ccc32)n1] | 3-(tert-butyl)-N-(8-(2-(cyclopropanecarboxamido)pyridin-4-yl)-2,3,4,5-tetrahydrobenzo[b]oxepin-5-yl)-1,2,4-oxadiazole-5-carboxamide | ESI-MS (M + H)+: 476.2; Calculated MW: 475.54 |
| 56 | 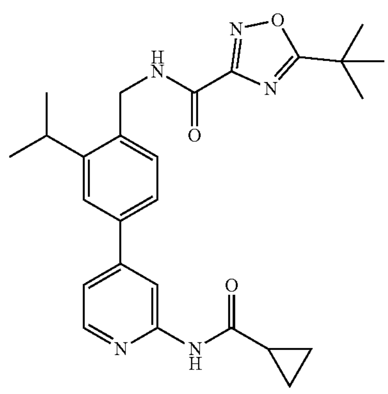 [SMILES: CC(C)c1cc(-c2ccnc(NC(=O)C3CC3)c2)ccc1CNC(=O)c1noc(C(C)(C)C)n1] | 5-(tert-butyl)-N-(4-(2-(cyclopropanecarboxamido)pyridin-4-yl)-2-isopropylbenzyl)-1,2,4-oxadiazole-3-carboxamide | ESI-MS (M + H)+: 462.1; Calculated MW: 461.556 |
| 57 | 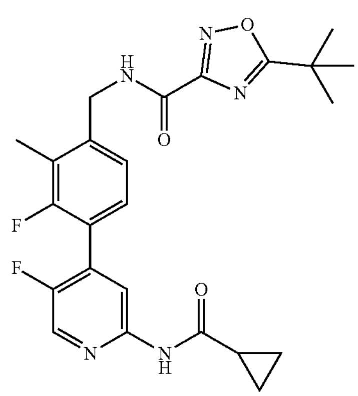 [SMILES: Cc1c(CNC(=O)c2noc(C(C)(C)C)n2)ccc(-c2cc(NC(=O)C3CC3)ncc2F)c1F] | 5-(tert-butyl)-N-(4-(2-(cyclopropanecarboxamido)-5-fluoropyridin-4-yl)-3-fluoro-2-methylbenzyl)-1,2,4-oxadiazole-3-carboxamide | ESI-MS (M + H)+: 470.2; Calculated MS: 469.484 |
| 58 | 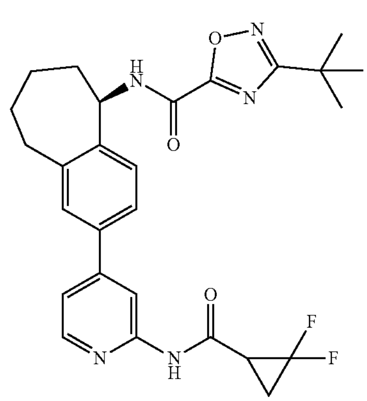 [SMILES: CC(C)(C)c1noc(C(=O)N[C@@H]2CCCCc3cc(-c4ccnc(NC(=O)C5CC5(F)F)c4)ccc32)n1] | 3-(tert-butyl)-N-((5R)-2-(2-(2,2-difluorocyclopropane-1-carboxamido)pyridin-4-yl)-6,7,8,9-tetrahydro-5H-benzo[7]annulen-5-yl)-1,2,4-oxadiazole-5-carboxamide | ESI-MS (M + H)+: 510.2; Calculated MW: 509.548 |

-continued

| Compd No. | Structure | Chemical Name | MS |
|---|---|---|---|
| 59 | 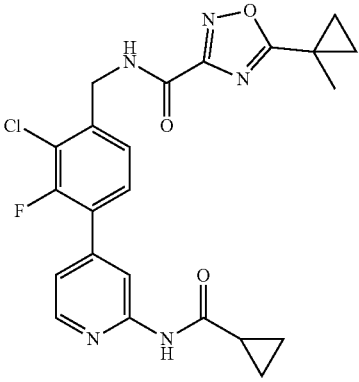 [SMILES: CC1(c2nc(C(=O)NCc3ccc(-c4ccnc(NC(=O)C5CC5)c4)c(F)c3Cl)no2)CC1] | N-(2-chloro-4-(2-(cyclopropanecarboxamido)pyridin-4-yl)-3-fluorobenzyl)-5-(1-methylcyclopropyl)-1,2,4-oxadiazole-3-carboxamide | ESI-MS (M + H)+: 470.1; Calculated MW: 469.896 |
| 60 | 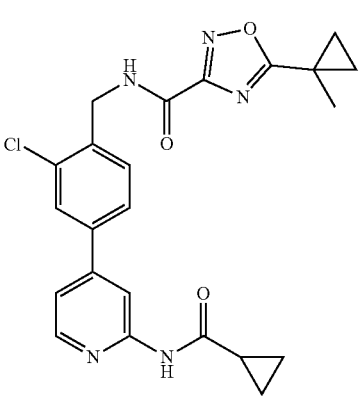 [SMILES: CC1(c2nc(C(=O)NCc3ccc(-c4ccnc(NC(=O)C5CC5)c4)cc3Cl)no2)CC1] | N-(2-chloro-4-(2-(cyclopropanecarboxamido)pyridin-4-yl)benzyl)-5-(1-methylcyclopropyl)-1,2,4-oxadiazole-3-carboxamide | ESI-MS (M + H)+: 452.1; Calculated MW: 451.905 |
| 61 | 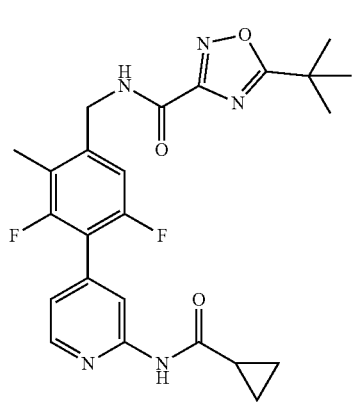 [SMILES: Cc1c(CNC(=O)c2noc(C(C)(C)C)n2)cc(F)c(-c2ccnc(NC(=O)C3CC3)c2)c1F] | 5-(tert-butyl)-N-(4-(2-(cyclopropanecarboxamido)pyridin-4-yl)-3,5-difluoro-2-methylbenzyl)-1,2,4-oxadiazole-3-carboxamide | ESI-MS (M + H)+: 470.2; Calculated MW: 469.484 |
| 62 | 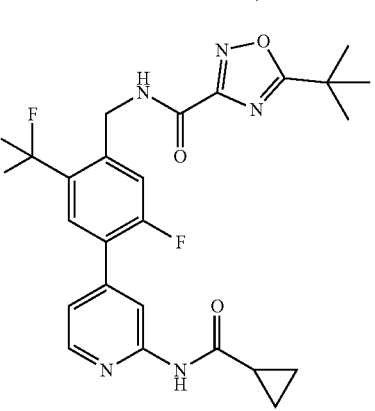 | 5-(tert-butyl)-N-(4-(2-(cyclopropanecarboxamido)pyridin-4-yl)-5-fluoro-2-(trifluoromethyl)benzyl)-1,2,4-oxadiazole-3-carboxamide | ESI-MS (M + H)+: 560.2; Calculated MW: 505.465 |

| Compd No. | Structure | Chemical Name | MS |
|---|---|---|---|
| 63 | 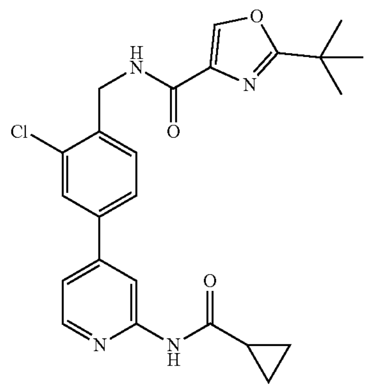 [SMILES: CC(C)(C)c1nc(C(=O)NCc2ccc(-c3ccnc(NC(=O)C4CC4)c3)cc2Cl)co1] | 2-(tert-butyl)-N-(2-chloro-4-(2-(cyclopropanecarboxamido)pyridin-4-yl)benzyl)oxazole-4-carboxamide | ESI-MS (M + H)⁺: 453.2; Calculated MW: 452.933 |
| 64 | 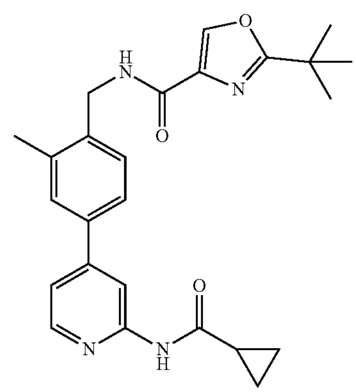 [SMILES: Cc1cc(-c2ccnc(NC(=O)C3CC3)c2)ccc1CNC(=O)c1coc(C(C)(C)C)n1] | 2-(tert-butyl)-N-(4-(2-(cyclopropanecarboxamido)pyridin-4-yl)-2-methylbenzyl)oxazole-4-carboxamide | ESI-MS (M + H)⁺: 433.2; Calculated MW: 432.515 |
| 65 | 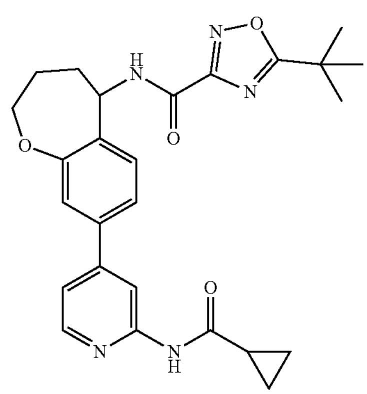 [SMILES: CC(C)(C)c1nc(C(=O)NC2CCCOc3cc(-c4ccnc(NC(=O)C5CC5)c4)ccc32)no1] | 5-(tert-butyl)-N-(8-(2-(cyclopropanecarboxamido)pyridin-4-yl)-2,3,4,5-tetrahydrobenzo[b]oxepin-5-yl)-1,2,4-oxadiazole-3-carboxamide | ESI-MS (M + H)⁺: 476.3; Calculated MW: 475.54 |
| 66 | 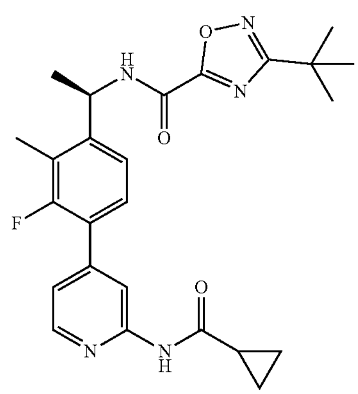 [SMILES: Cc1c([C@@H](C)NC(=O)c2nc(C(C)(C)C)no2)ccc(-c2ccnc(NC(=O)C3CC3)c2)c1F] | (R)-3-(tert-butyl)-N-(1-(4-(2-(cyclopropanecarboxamido)pyridin-4-yl)-3-fluoro-2-methylphenyl)ethyl)-1,2,4-oxadiazole-5-carboxamide | ESI-MS (M + H)⁺: 466.2; Calculated MW: 465.52 |

-continued

| Compd No. | Structure | Chemical Name | MS |
|---|---|---|---|
| 67 | 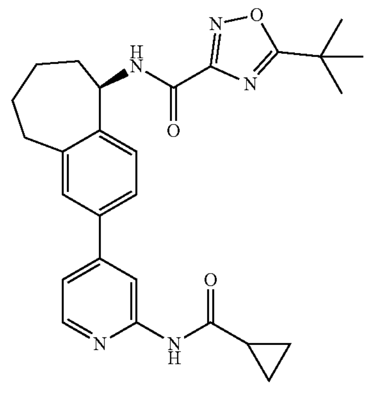 [SMILES: CC(C)(C)c1nc(C(=O)N[C@@H]2CCCCc3cc(-c4ccnc(NC(=O)C5CC5)c4)ccc32)no1] | (R)-5-(tert-butyl)-N-(2-(2-(cyclopropanecarboxamido)pyridin-4-yl)-6,7,8,9-tetrahydro-5H-benzo[7]annulen-5-yl)-1,2,4-oxadiazole-3-carboxamide | ESI-MS (M + H)⁺: 474.2; Calculated MW: 473.567 |
| 68 | 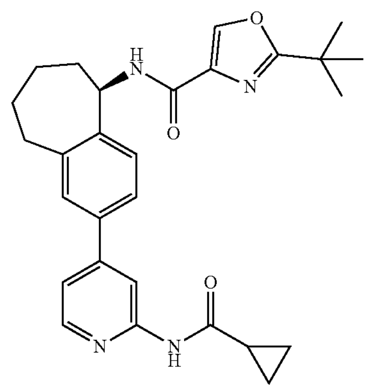 [SMILES: CC(C)(C)c1nc(C(=O)N[C@@H]2CCCCc3cc(-c4ccnc(NC(=O)C5CC5)c4)ccc32)co1] | (R)-2-(tert-butyl)-N-(2-(2-(cyclopropanecarboxamido)pyridin-4-yl)-6,7,8,9-tetrahydro-5H-benzo[7]annulen-5-yl)oxazole-4-carboxamide | ESI-MS (M + H)⁺: 473.2; Calculated MW: 472.579 |
| 69 | 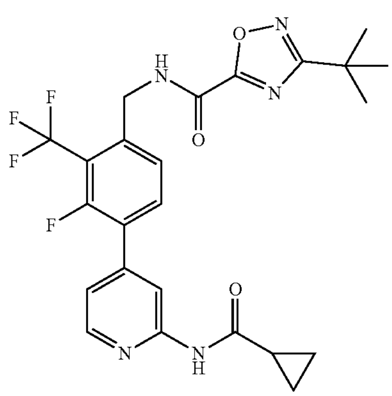 [SMILES: CC(C)(C)c1noc(C(=O)NCc2ccc(-c3ccnc(NC(=O)C4CC4)c3)c(F)c2C(F)(F)F)n1] | 3-(tert-butyl)-N-(4-(2-(cyclopropanecarboxamido)pyridin-4-yl)-3-fluoro-2-(trifluoromethyl)benzyl)-1,2,4-oxadiazole-5-carboxamide | ESI-MS (M + H)⁺: 506.2; Calculated MW: 505.465 |
| 70 | 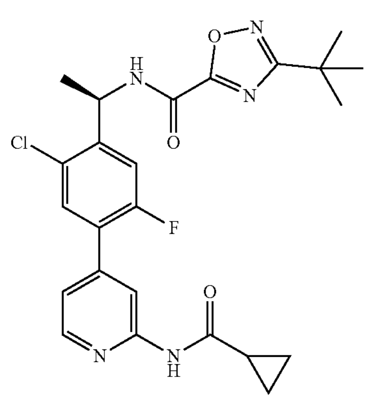 [SMILES: C[C@@H](NC(=O)c1nc(C(C)(C)C)no1)c1cc(F)c(-c2ccnc(NC(=O)C3CC3)c2)cc1Cl] | (R)-3-(tert-butyl)-N-(1-(2-chloro-4-(2-(cyclopropanecarboxamido)pyridin-4-yl)-5-fluorophenyl)ethyl)-1,2,4-oxadiazole-5-carboxamide | ESI-MS (M + H)⁺: 486.3; Calculated MW: 485.938 |

-continued

| Compd No. | Structure | Chemical Name | MS |
|---|---|---|---|
| 71 | 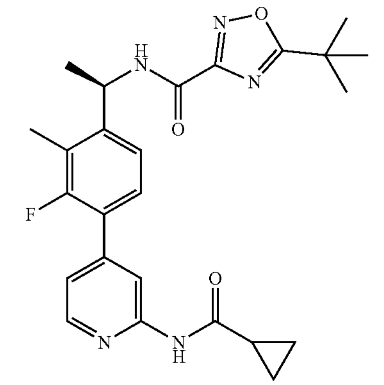 [SMILES: Cc1c([C@@H](C)NC(=O)c2noc(C(C)(C)C)n2)ccc(-c2ccnc(NC(=O)C3CC3)c2)c1F] | (R)-5-(tert-butyl)-N-(1-(4-(2-(cyclopropanecarboxamido)pyridin-4-yl)-3-fluoro-2-methyphenyl)ethyl)-1,2,4-oxadiazole-3-carboxamide | ESI-MS (M + H)$^+$: 466.2; Calculated MW: 465.52 |
| 72 | 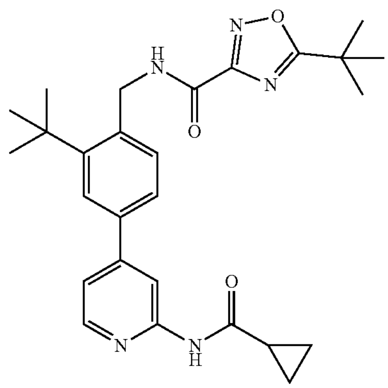 [SMILES: CC(C)(C)c1nc(C(=O)NCc2ccc(-c3ccnc(NC(=O)C4CC4)c3)cc2C(C)(C)C)no1] | 5-(tert-butyl)-N-(2-tert-butyl)-4-(2-(cyclopropanecarboxamido)pyridin-4-yl)benzyl)-1,2,4-oxadiazole-3-carboxamide | ESI-MS (M + H)$^+$: 476.2; Calculated MW: 475.583 |
| 73 | 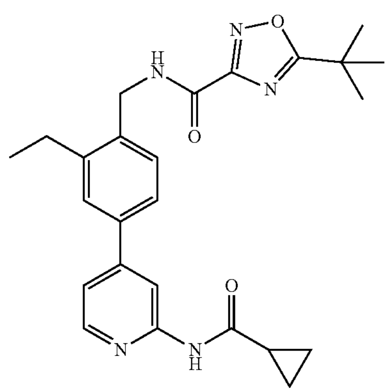 [SMILES: CCc1cc(-c2ccnc(NC(=O)C3CC3)c2)ccc1CNC(=O)c1noc(C(C)(C)C)n1] | 5-(tert-butyl)-N-(4-(2-(cyclopropanecarboxamido)pyridin-4-yl)-2-ethylbenzyl)-1,2,4-oxadiazole-3-carboxamide | ESI-MS (M + H)$^+$: 448.2; Calculated MW: 447.529 |
| 74 | 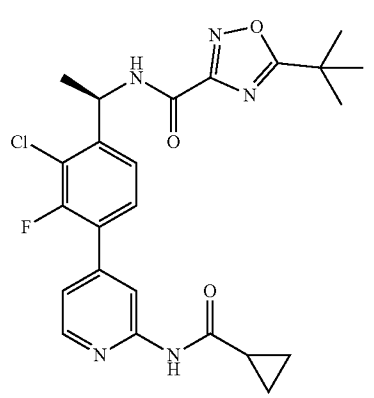 [SMILES: C[C@@H](NC(=O)c1noc(C(C)(C)C)n1)c1ccc(-c2ccnc(NC(=O)C3CC3)c2)c(F)c1Cl] | (R)-5-(tert-butyl)-N-(1-(2-chloro-4-(2-(cyclopropanecarboxamido)pyridin-4-yl)-3-fluorophenyl)ethyl)-1,2,4-oxadiazole-3-carboxamide | ESI-MS (M + H)$^+$: 486.1; Calculated MW: 485.938 |

| Compd No. | Structure | Chemical Name | MS |
|---|---|---|---|
| 75 | 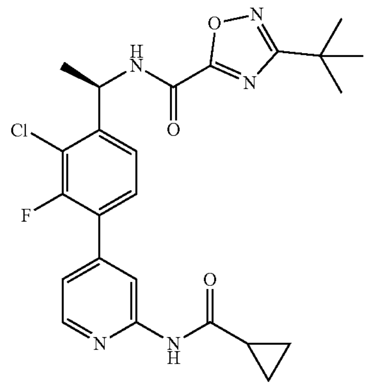 [SMILES: C[C@@H](NC(=O)c1nc(C(C)(C)C)no1)c1ccc(-c2ccnc(NC(=O)C3CC3)c2)c(F)c1Cl] | (R)-3-(tert-butyl)-N-(1-(2-chloro-4-(2-(cyclopropanecarboxamido)pyridin-4-yl)-3-fluorophenyl)ethyl)-1,2,4-oxadiazole-5-carboxamide | ESI-MS (M + H)⁺: 486.2; Calculated MW: 485.938 |
| 76 | 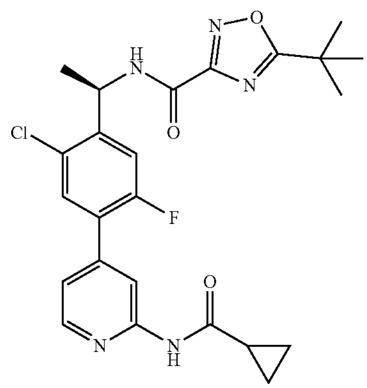 [SMILES: C[C@@H](NC(=O)c1noc(C(C)(C)C)n1)c1cc(F)c(-c2ccnc(NC(=O)C3CC3)c2)cc1Cl] | (R)-5-(tert-butyl)-N-(1-(2-chloro-4-(2-(cyclopropanecarboxamido)pyridin-4-yl)-5-fluorophenyl)ethyl)-1,2,4-oxadiazole-3-carboxamide | ESI-MS (M + H)⁺: 486.1; Calculated MW: 485.938 |
| 77 | 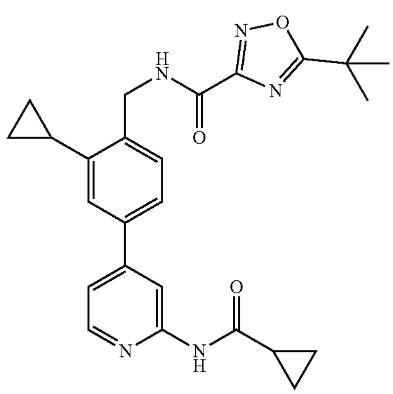 [SMILES: CC(C)(C)c1nc(C(=O)NCc2ccc(-c3ccnc(NC(=O)C4CC4)c3)cc2C2CC2)no1] | 5-(tert-butyl)-N-(4-(2-(cyclopropanecarboxamido)pyridin-4-yl)-2-cyclopropylbenzyl)-1,2,4-oxadiazole-3-carboxamide | ESI-MS (M + H)⁺: 460.2; Calculated MW: 459.54 |
| 78 | 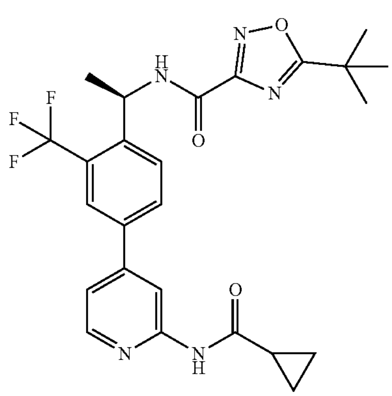 [SMILES: C[C@@H](NC(=O)c1noc(C(C)(C)C)n1)c1ccc(-c2ccnc(NC(=O)C3CC3)c2)cc1C(F)(F)F] | (R)-5-(tert-butyl)-N-(1-(4-(2-(cyclopropanecarboxamido)pyridin-4-yl)-2-(trifluoromethyl)phenyl)ethyl)-1,2,4-oxadiazole-3-carboxamide | ESI-MS (M + H)⁺: 502.1; Calculated MW: 501.501 |

| Compd No. | Structure | Chemical Name | MS |
|---|---|---|---|
| 79 | 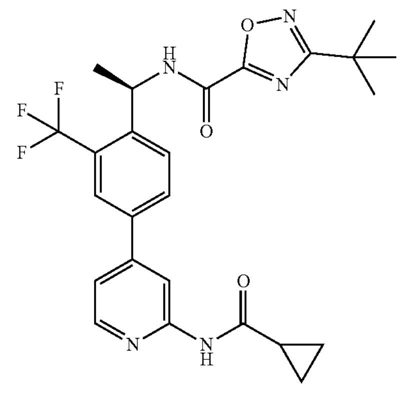 [SMILES: C[C@@H](NC(=O)c1nc(C(C)(C)C)no1)c1ccc(-c2ccnc(NC(=O)C3CC3)c2)cc1C(F)(F)F] | (R)-3-(tert-butyl)-N-(1-(4-(2-(cyclopropanecarboxamido)pyridin-4-yl)-2-(trifluoromethyl)phenyl)ethyl)-1,2,4-oxadiazole-5-carboxamide | ESI-MS (M + H)+: 502.2; Calculated MW: 501.501 |
| 80 | 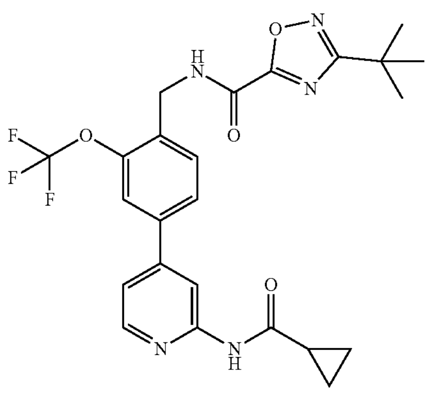 [SMILES: CC(C)(C)c1noc(C(=O)NCc2ccc(-c3ccnc(NC(=O)C4CC4)c3)cc2OC(F)(F)F)n1] | 3-(tert-butyl)-N-(4-(2-(cyclopropanecarboxamido)pyridin-4-yl)-2-(trifluoromethoxy)benzyl)-1,2,4-oxadiazole-5-carboxamide | ESI-MS (M + H)+: 504.2; Calculated MW: 503.474 |
| 81 | 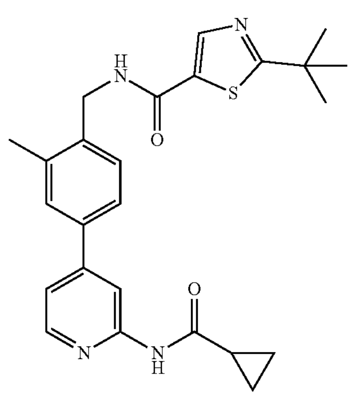 [SMILES: Cc1cc(-c2ccnc(NC(=O)C3CC3)c2)ccc1CNC(=O)c1cnc(C(C)(C)C)s1] | 2-(tert-butyl)-N-(4-(2-(cyclopropanecarboxamido)pyridin-4-yl)-2-methylbenzyl)thiazole-5-carboxamide | ESI-MS (M + H)+: 449.2; Calculated MW: 448.58 |
| 82 | 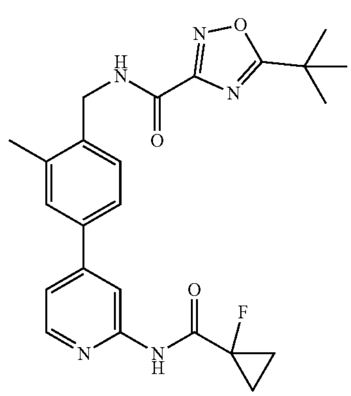 [SMILES: Cc1cc(-c2ccnc(NC(=O)C3(F)CC3)c2)ccc1CNC(=O)c1noc(C(C)(C)C)n1] | 5-(tert-butyl)-N-(4-(2-(1-fluorocyclopropane-1-carboxamido)pyridin-4-yl)-2-methylbenzyl)-1,2,4-oxadiazole-3-carboxamide | ESI-MS (M + H)+: 452.2; Calculated MW: 451.493 |

| Compd No. | Structure | Chemical Name | MS |
|---|---|---|---|
| 83 | 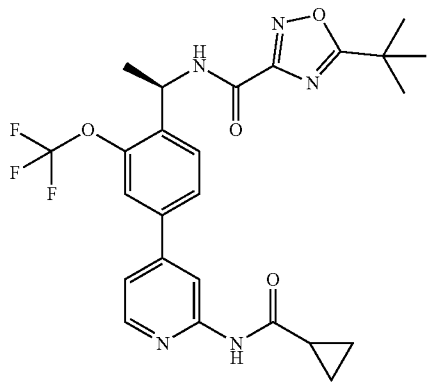 [SMILES: C[C@@H](NC(=O)c1noc(C(C)(C)C)n1)c1ccc(-c2ccnc(NC(=O)C3CC3)c2)cc1OC(F)(F)F] | (R)-5-(tert-butyl)-N-(1-(4-(2-(cyclopropanecarboxamido)pyridin-4-yl)-2-(trifluoromethoxy)phenyl)ethyl)-1,2,4-oxadiazole-3-carboxamide | ESI-MS (M + H)+: 518.1; Calculated MW: 517.5 |
| 84 | 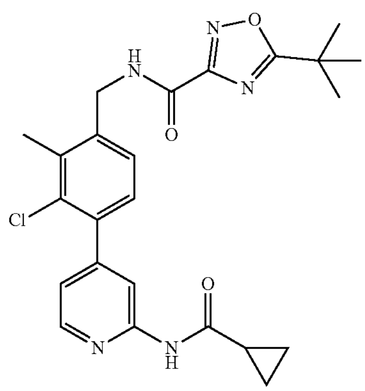 [SMILES: Cc1c(CNC(=O)c2noc(C(C)(C)C)n2)ccc(-c2ccnc(NC(=O)C3CC3)c2)c1Cl] | 5-(tert-butyl)-N-(3-chloro-4-(2-(cyclopropanecarboxamido)pyridin-4-yl)-2-methylbenzyl)-1,2,4-oxadiazole-3-carboxamide | ESI-MS (M + H)+: 468.1; Calculated MW: 467.948 |
| 85 | 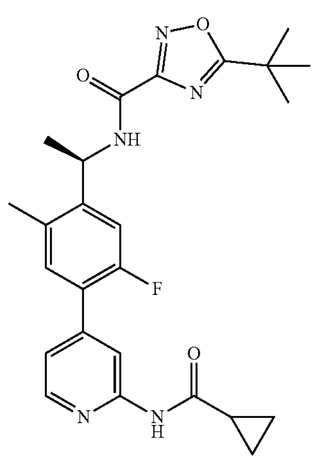 [SMILES: Cc1cc(-c2ccnc(NC(=O)C3CC3)c2)c(F)cc1[C@@H](C)NC(=O)c1noc(C(C)(C)C)n1] | (R)-5-(tert-butyl)-N-(1-(4-(2-(cyclopropanecarboxamido)pyridin-4-yl)-5-fluoro-2-methylphenyl)ethyl)-1,2,4-oxadiazole-3-carboxamide | ESI-MS (M + H)+: 466.2; Calculated MW: 465.52 |

-continued

| Compd No. | Structure | Chemical Name | MS |
|---|---|---|---|
| 86 | 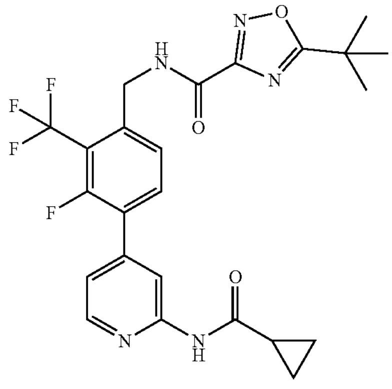 [SMILES: CC(C)(C)c1nc(C(=O)NCc2ccc(-c3ccnc(NC(=O)C4CC4)c3)c(F)c2C(F)(F)F)no1] | 5-(tert-butyl)-N-(4-(2-(cyclopropanecarboxamido)pyridin-4-yl)-3-fluoro-2-(trifluoromethyl)benzyl)-1,2,4-oxadiazole-3-carboxamide | ESI-MS (M + H)+: 506.1; Calculated MW: 505.465 |
| 87 | 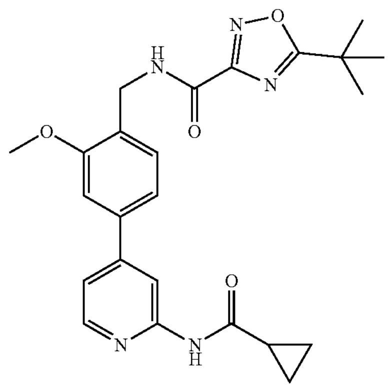 | 5-(tert-butyl)-N-(4-(2-(cyclopropanecarboxamido)pyridin-4-yl)-2-methoxybenzyl)-1,2,4-oxadiazole-3-carboxamide | ESI-MS (M + H)+: 450.1; Calculated MW: 449.502 |
| 88 | 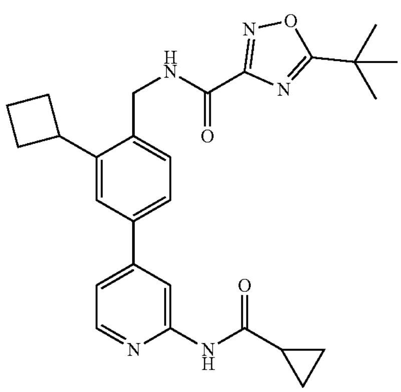 [SMILES: CC(C)(C)c1nc(C(=O)NCc2ccc(-c3ccnc(NC(=O)C4CC4)c3)cc2C2CCC2)no1] | 5-(tert-butyl)-N-(2-cyclobutyl-4-(2-(cyclopropanecarboxamido)pyridin-4-yl)benzyl)-1,2,4-oxadiazole-3-carboxamide | ESI-MS (M + H)+: 474.2; Calculated MW: 473.567 |
| 89 | 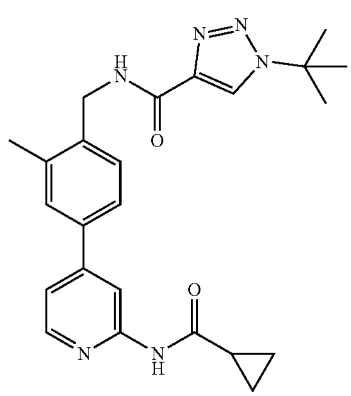 | 1-(tert-butyl)-N-(4-(2-(cyclopropanecarboxamido)pyridin-4-yl)-2-methylbenzyl)-1H-1,2,3-triazole-4-carboxamide | ESI-MS (M + H)+: 433.2; Calculated MW: 432.518 |

| Compd No. | Structure | Chemical Name | MS |
|---|---|---|---|
| 90 | 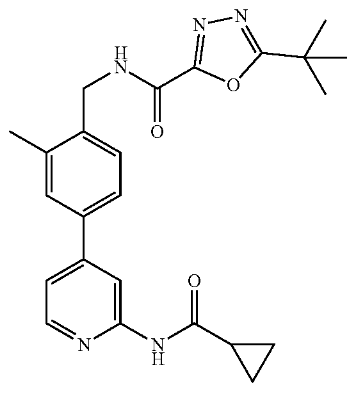 [SMILES: Cc1cc(-c2ccnc(NC(=O)C3CC3)c2)ccc1CNC(=O)c1nnc(C(C)(C)C)o1] | 5-(tert-butyl)-N-(4-(2-(cyclopropanecarboxamido)pyridin-4-yl)-2-methylbenzyl)-1,3,4-oxadiazole-2-carboxamide | ESI-MS (M + H)+: 434.1; Calculated MW: 433.503 |
| 91 | 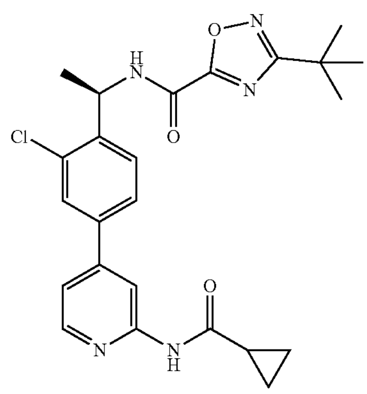 [SMILES: C[C@@H](NC(=O)c1nc(C(C)(C)C)no1)c1ccc(-c2ccnc(NC(=O)C3CC3)c2)cc1Cl] | (R)-3-(tert-butyl)-N-(1-(2-chloro-4-(2-(cyclopropanecarboxamido)pyridin-4-yl)phenyl)ethyl)-1,2,4-oxadiazole-5-carboxamide | ESI-MS (M + H)+: 468.2; Calculated MW: 467.948 |
| 92 | 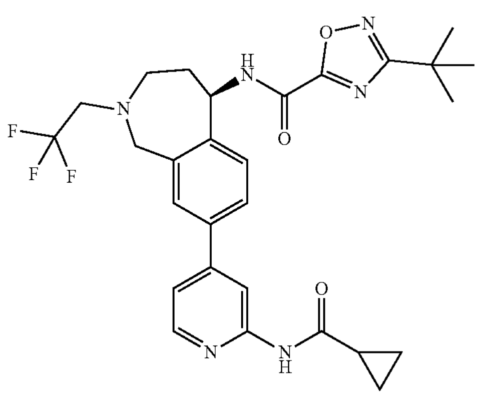 [SMILES: CC(C)(C)c1noc(C(=O)N[C@@H]2CCN(CC(F)(F)F)Cc3cc(-c4ccnc(NC(=O)C5CC5)c4)ccc32)n1] | (R)-3-(tert-butyl)-N-(8-(2-(cyclopropanecarboxamido)pyridin-4-yl)-2-(2,2,2-trifluoroethyl)-2,3,4,5-tetrahydro-1H-benzo[c]azepin-5-yl)-1,2,4-oxadiazole-5-carboxamide | ESI-MS (M + H)+: 557.3; Calculated MW: 556.579 |
| 93 | 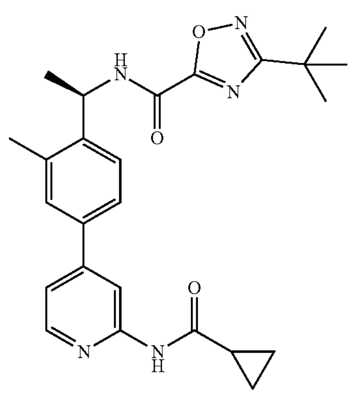 [SMILES: Cc1cc(-c2ccnc(NC(=O)C3CC3)c2)ccc1[C@@H](C)NC(=O)c1nc(C(C)(C)C)no1] | (R)-3-(tert-butyl)-N-(1-(4-(2-(cyclopropanecarboxamido)pyridin-4-yl)-2-methylphenyl)ethyl)-1,2,4-oxadiazole-5-carboxamide | ESI-MS (M + H)+: 448.2; Calculated MW: 447.529 |

-continued

| Compd No. | Structure | Chemical Name | MS |
|---|---|---|---|
| 94 | 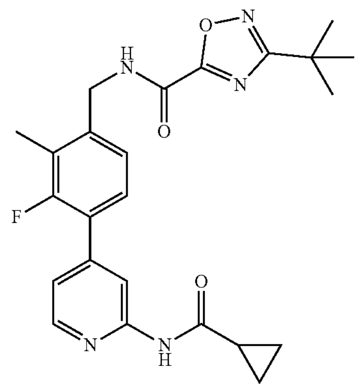 [SMILES: Cc1c(CNC(=O)c2nc(C(C)(C)C)no2)ccc(-c2ccnc(NC(=O)C3CC3)c2)c1F] | 3-(tert-butyl)-N-(4-(2-(cyclopropanecarboxamido)pyridin-4-yl)-3-fluoro-2-methylbenzyl)-1,2,4-oxadiazole-5-carboxamide | ESI-MS (M + H)⁺: 452.2; Calculated MW: 451.493 |
| 95 | 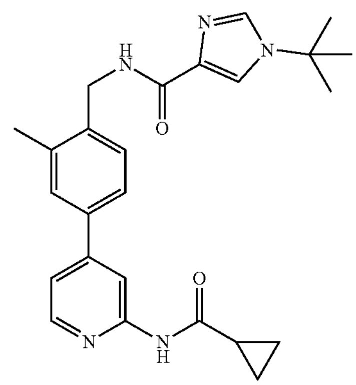 [SMILES: Cc1cc(-c2ccnc(NC(=O)C3CC3)c2)ccc1CNC(=O)c1cn(C(C)(C)C)cn1] | 1-(tert-butyl)-N-(4-(2-(cyclopropanecarboxamido)pyridin-4-yl)-2-methylbenzyl)-1H-imidazole-4-carboxamide | ESI-MS (M + H)⁺: 432.2; Calculated MW: 431.53 |
| 96 | 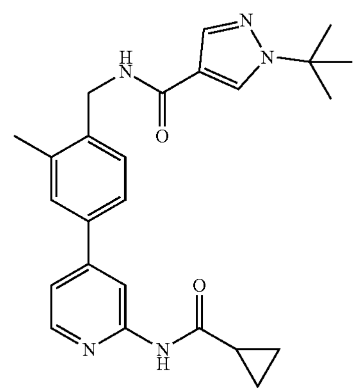 [SMILES: Cc1cc(-c2ccnc(NC(=O)C3CC3)c2)ccc1CNC(=O)c1cnn(C(C)(C)C)c1] | 1-(tert-butyl)-N-(4-(2-(cyclopropanecarboxamido)pyridin-4-yl)-2-methylbenzyl)-1H-pyrazole-4-carboxamide | ESI-MS (M + H)⁺: 432.1; Calculated MW: 431.53 |
| 97 | 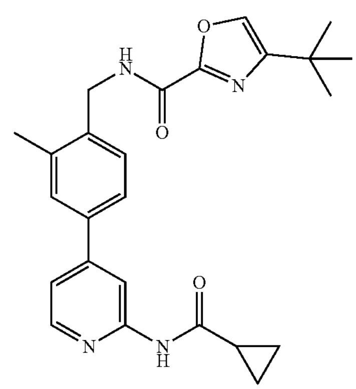 [SMILES: Cc1cc(-c2ccnc(NC(=O)C3CC3)c2)ccc1CNC(=O)c1nc(C(C)(C)C)co1] | 4-(tert-butyl)-N-(4-(2-(cyclopropanecarboxamido)pyridin-4-yl)-2-methylbenzyl)oxazole-2-carboxamide | ESI-MS (M + H)⁺: 433.1; Calculated MW: 432.515 |

-continued

| Compd No. | Structure | Chemical Name | MS |
|---|---|---|---|
| 98 | 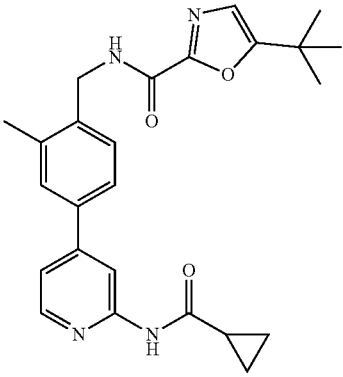 [SMILES: Cc1cc(-c2ccnc(NC(=O)C3CC3)c2)ccc1CNC(=O)c1ncc(C(C)(C)C)o1] | 5-(tert-butyl)-N-(4-(2-(cyclopropanecarboxamido)pyridin-4-yl)-2-methylbenzyl)oxazole-2-carboxamide | ESI-MS (M + H)$^+$: 433.1; Calculated MW: 432.515 |
| 99 | 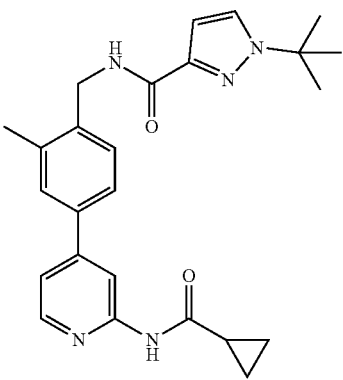 [SMILES: Cc1cc(-c2ccnc(NC(=O)C3CC3)c2)ccc1CNC(=O)c1ccn(C(C)(C)C)n1] | 1-(tert-butyl)-N-(4-(2-(cyclopropanecarboxamido)pyridin-4-yl)-2-methylbenzyl)-1H-pyrazole-3-carboxamide | ESI-MS (M + H)$^+$: 432.1; Calculated MW: 431.53 |
| 100 | 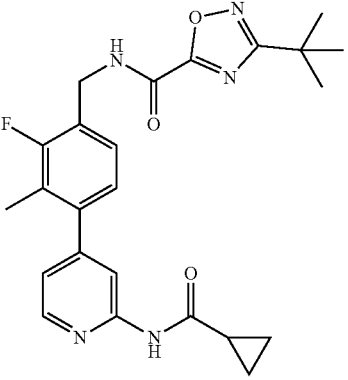 [SMILES: Cc1c(-c2ccnc(NC(=O)C3CC3)c2)ccc(CNC(=O)c2nc(C(C)(C)C)no2)c1F] | 3-(tert-butyl)-N-(4-(2-(cyclopropanecarboxamido)pyridin-4-yl)-2-fluoro-3-methylbenzyl)-1,2,4-oxadiazole-5-carboxamide | ESI-MS (M + H)$^+$: 452.2; Calculated MW: 451.493 |
| 101 | 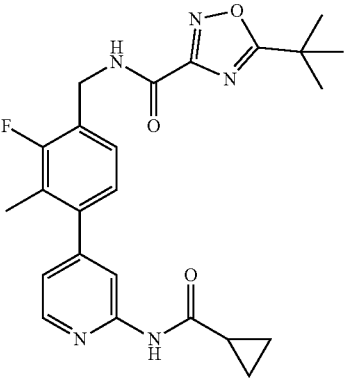 [SMILES: Cc1c(-c2ccnc(NC(=O)C3CC3)c2)ccc(CNC(=O)c2noc(C(C)(C)C)n2)c1F] | 5-(tert-butyl)-N-(4-(2-(cyclopropanecarboxamido)pyridin-4-yl)-2-fluoro-3-methylbenzyl)-1,2,4-oxadiazole-3-carboxamide | ESI-MS (M + H)$^+$: 452.2; Calculated MW: 451.493 |

| Compd No. | Structure | Chemical Name | MS |
|---|---|---|---|
| 102 | 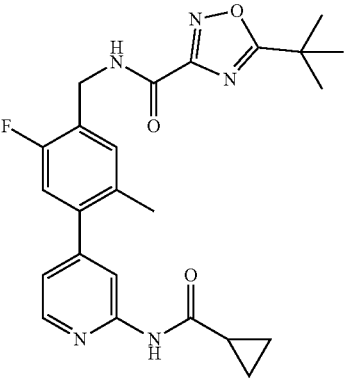 [SMILES: Cc1cc(CNC(=O)c2noc(C(C)(C)C)n2)c(F)cc1-c1ccnc(NC(=O)C2CC2)c1] | 5-(tert-butyl)-N-(4-(2-(cyclopropanecarboxamido) pyridin-4-yl)-2-fluoro-5-methylbenzyl)-1,2,4-oxadiazole-3-carboxamide | ESI-MS (M + H)$^+$: 452.2; Calculated MW: 451.493 |
| 103 | 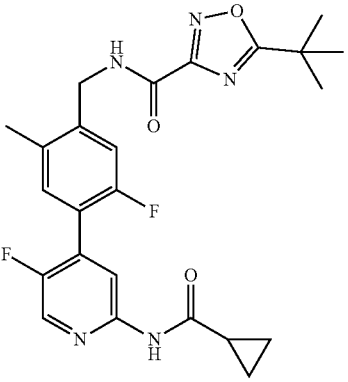 [SMILES: Cc1cc(-c2cc(NC(=O)C3CC3)ncc2F)c(F)cc1CNC(=O)c1noc(C(C)(C)C)n1] | 5-(tert-butyl)-N-(4-(2-(cyclopropanecarboxamido)-5-fluoropyridin-4-yl)-5-fluoro-2-methylbenzyl)-1,2,4-oxadiazole-3-carboxamide | ESI-MS (M + H)$^+$: 470.2; Calculated MW: 469.484 |
| 104 | 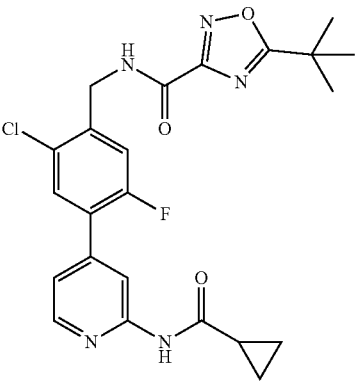 [SMILES: CC(C)(C)c1nc(C(=O)NCc2cc(F)c(-c3ccnc(NC(=O)C4CC4)c3)cc2Cl)no1] | 5-(tert-butyl)-N-(2-chloro-4-(2-(cyclopropanecarboxamido) pyridin-4-yl)-5-fluorobenzyl)-1,2,4-oxadiazole-3-carboxamide | ESI-MS (M + H)$^+$: 472.0; Calculated MW: 471.912 |
| 105 | 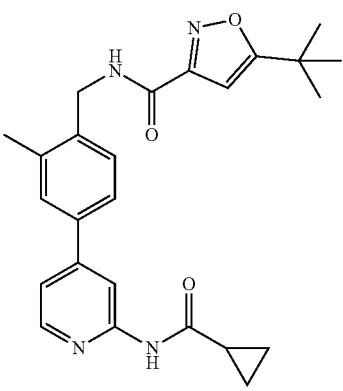 [SMILES: Cc1cc(-c2ccnc(NC(=O)C3CC3)c2)ccc1CNC(=O)c1cc(C(C)(C)C)on1] | 5-(tert-butyl)-N-(4-(2-(cyclopropanecarboxamido) pyridin-4-yl)-2-methylbenzyl)isoxazole-3-carboxamide | ESI-MS (M + H)$^+$: 433.0; Calculated MW: 432.515 |

-continued

| Compd No. | Structure | Chemical Name | MS |
|---|---|---|---|
| 106 | 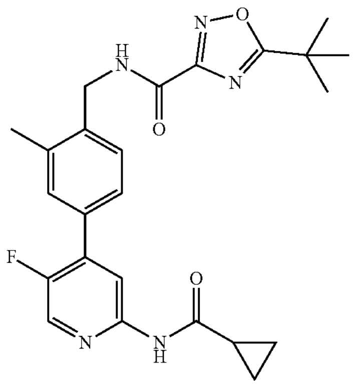 [SMILES: Cc1cc(-c2cc(NC(=O)C3CC3)ncc2F)ccc1CNC(=O)c1noc(C(C)(C)C)n1] | 5-(tert-butyl)-N-(4-(2-(cyclopropanecarboxamido)-5-fluoropyridin-4-yl)-2-methylbenzyl)-1,2,4-oxadiazole-3-carboxamide | ESI-MS (M + H)+: 452.0; Calculated MW: 451.493 |
| 107 | 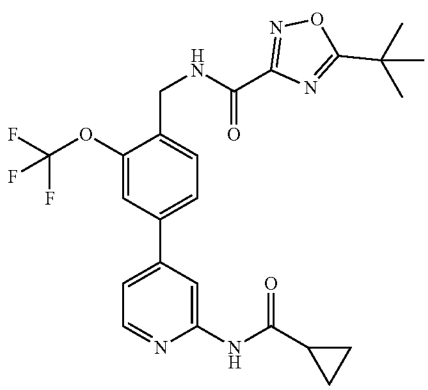 [SMILES: CC(C)(C)c1nc(C(=O)NCc2ccc(-c3ccnc(NC(=O)C4CC4)c3)cc2OC(F)(F)F)no1] | 5-(tert-butyl)-N-(4-(2-(cyclopropanecarboxamido)pyridin-4-yl)-2-(trifluoromethoxy)benzyl)-1,2,4-oxadiazole-3-carboxamide | ESI-MS (M + H)+: 504.0; Calculated MW: 503.474 |

Example 108: In Vitro BTK Kinase Assay: BTK-POLYGAT-LS ASSAY

The purpose of the BTK in vitro assay is to determine compound potency against BTK through the measurement of $IC_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 μL aliquot of a ATP/peptide master mix (final concentration; ATP 10 μM, polyGAT 100 nM) in kinase buffer (10 mM Tris-HCl pH 7.5, 10 mM $MgCl_2$, 200 μM $Na_3PO_4$, 5 mM DTT, 0.01% Triton X-100, and 0.2 mg/ml casein) is added to each well. Next, 1 pL of a 4-fold, 40× compound titration in 100% DMSO solvent is added, followed by adding 15 μL of BTK enzyme mix in 1× kinase buffer (with a final concentration of 0.25 nM). The assay is incubated for 30 minutes before being stopped with 28 pL of a 50 mM EDTA solution. Aliquots (5 μL) of the kinase reaction are transferred to a low volume white 384 well plate (Coming 3674), and 5 pL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. $IC_{50}$ values are calculated using a four parameter fit with 100% enzyme activity determined from the DMSO control and 0% activity from the EDTA control.

Table 1 shows the activity of selected compounds of this invention in the in vitro Btk kinase assay, wherein each compound number corresponds to the compound numbering set forth in Examples 1-107 herein. "†" represents an $IC_{50}$ of equal to or less than 1000 nM and greater than 10 nM; "††" represents an $IC_{50}$ of equal to or less than 10 nM and greater than 1 nM; and "†††" represents an $IC_{50}$ of equal to or less than 1 nM.

TABLE 1

| $IC_{50}$ (nM) | Compound No. |
|---|---|
| ††† | 1, 2, 3, 4, 5, 6, 7, 8, 9, 10, 11, 12, 13, 14, 15, 16, 17, 18, 19, 20, 21, 22, 24, 27, 28, 31, 32, 33, 34, 37, 38, 39, 40, 41, 42, 43, 46, 47, 49, 50, 51, 52, 54, 55, 57, 58, 59, 60, 61, 62, 63, 64, 65, 66, 67, 68, 69, 70, 71, 73, 74, 75, 76, 77, 78, 79, 80, 84, 85, 86, 87, 88, 91, 92, 93, 94, 96, 97, 100, 101, 103, 104, 105, 106, 107 |
| †† | 23, 25, 26, 29, 30, 35, 36, 44, 45, 48, 56, 72, 81, 82, 83, 89, 90, 98, 99 |
| † | 53, 95, 102 |

Example 109: In Vitro PD Assay in Human Whole Blood

Human heparinized venous blood was purchased from Bioreclamation, Inc. or SeraCare Life Sciences and shipped overnight. Whole blood was aliquoted into 96-well plate and "spiked" with serial dilutions of test compound in DMSO or with DMSO without drug. The final concentration of DMSO in all wells was 0.1%. The plate was incubated at 37° C. for 30 min. Lysis buffer containing protease and phosphatase inhibitors was added to the drug-containing samples and one of the DMSO-only samples (+PPi, high control), while lysis buffer containing protease inhibitors was added to the other DMSO-only samples (−PPi, low control). All of the lysed whole blood samples were subjected to the total BTK capture and phosphotyrosine detection method described in US20160311802, incorporated herein by reference. ECL values were graphed in Prism and a best-fit curve with restrictions on the maximum and minimum defined by the +PPi high and −PPi low controls was used to estimate the test compound concentration that results in 50% inhibition of ECL signal by interpolation.

Table 2 shows the activity of selected compounds of this invention in the pBTK assay, wherein each compound number corresponds to the compound numbering set forth in Examples 1-107 described herein. "†" represents an $IC_{50}$ of equal to or less than 10,000 nM but greater than 500 nM, "††" represents an $IC_{50}$ of equal to or less than 500 nM but greater than 100 nM; and "†††" represents an $IC_{50}$ of equal to or less than 100 nM. * represents an $IC_{50}$ value of greater than 10,000 nM.

TABLE 2

| $IC_{50}$ (nM) | Compound No. |
|---|---|
| ††† | 1, 2, 3, 5, 6, 9, 10, 11, 13, 14, 15, 17, 18, 19, 20, 21, 40, 67, 94, 107 |
| †† | 7, 8, 12, 16, 22, 39, 51, 54, 65, 66, 69, 77, 78, 79, 84, 89, 90, 91, 92, 93, 96, 97, 103, 104, |
| † | 29, 31, 32, 33, 34, 35, 37, 38, 40, 41, 42, 43, 44, 46, 47, 49, 52, 55, 57, 58, 59, 60, 61, 62, 64, 66, 68, 70, 71, 73, 76, 80, 81, 82, 83, 98, 99, 100, 101, 102, 105, 106, |
| * | 26, 30, 36, 45, 48, 53, 56, 63, 72 |

What is claimed is:

1. A compound represented by the following formula:

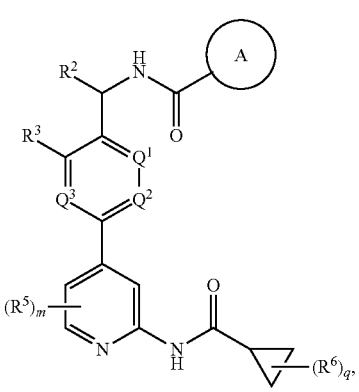

(I)

or a pharmaceutically acceptable salt, wherein:

Ring A is selected from aryl and 5- to 6-membered heteroaryl, wherein said aryl and 5- to 6-membered heteroaryl are optionally substituted with one or more $R^1$;

m is an integer selected from 0, 1, 2, and 3;

q is an integer selected from 0, 1, and 2;

$Q^1$, $Q^2$, and $Q^3$ are each selected from C—$R^4$ and N, wherein at most one of $Q^1$, $Q^2$, and $Q^3$ is N;

$R^1$ in each occurrence is independently selected from $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{1a}$, —C(O)$_2R^{1a}$, —C(O)N($R^{1a}$)$_2$, —N($R^{1a}$)$_2$, —N($R^{1a}$)C(O)$R^{1a}$, —N($R^{1a}$)C(O)$_2R^{1a}$, —N($R^{1a}$)C(O)N($R^{1a}$)$_2$, —N($R^{1a}$)S(O)$_2R^{1a}$, —O$R^{1a}$, —OC(O)$R^{1a}$, —OC(O)N($R^{1a}$)$_2$, —S$R^{1a}$, —S(O)$R^{1a}$, —S(O)$_2R^{1a}$, —S(O)N($R^{1a}$)$_2$, and —S(O)$_2$N($R^{1a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^{1a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{10}$;

$R^2$ is selected from H and $C_{1-6}$alkyl;

$R^3$ is selected from $C_{1-6}$alkyl, $C_{2-6}$alkenyl, $C_{2-6}$alkynyl, 4- to 6-membered monocyclic carbocyclyl, and 4- to 6-membered monocyclic heterocyclyl, halo, —CN, —C(O)$R^{3a}$, —C(O)$_2R^{3a}$, —C(O)N($R^{3a}$)$_2$, —N($R^{3a}$)$_2$, —N($R^{3a}$)C(O)$R^{3a}$, —N($R^{3a}$)C(O)$_2R^{3a}$, —N($R^{3a}$)C(O)N($R^{3a}$)$_2$, —N($R^{3a}$)S(O)$_2R^{3a}$, —O$R^{3a}$, —OC(O)$R^{3a}$, —OC(O)N($R^{3a}$)$_2$, —S$R^{3a}$, —S(O)$R^{3a}$, —S(O)$_2R^{3a}$, —S(O)N($R^{3a}$)$_2$, and —S(O)$_2$N($R^{3a}$)$_2$ wherein said $C_{1-6}$alkyl, $C_{2-6}$alkenyl, $_{2-6}$alkynyl, 4- to 6-membered monocyclic carbocyclyl, and 4- to 6-membered monocyclic heterocyclyl are optionally substituted with one or more $R^{30}$;

$R^{3a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{30}$;

or $R^2$ and $R^3$, together with their intervening atoms, form a seven-membered carbocyclic or heterocyclic ring, wherein said seven-membered carbocyclic or heterocyclic ring is optionally substituted with one or more $R^{20}$;

$R^4$ in each occurrence is independently selected from H, $C_{1-6}$alkyl, $C_{2-6}$alkenyl, $C_{2-6}$alkynyl, 4- to 6-membered monocyclic carbocyclyl, 4- to 6-membered monocyclic heterocyclyl, halo, —CN, —C(O)$R^{4a}$, —C(O)$_2R^{4a}$, —C(O)N($R^{4a}$)$_2$, —N($R^{4a}$)$_2$, —N($R^{4a}$)C(O)$R^{4a}$, —N($R^{4a}$)C(O)$_2R^{4a}$, —N($R^{4a}$)C(O)N($R^{4a}$)$_2$, —N($R^{4a}$)S(O)$_2R^{4a}$, —O$R^{4a}$, —OC(O)$R^{4a}$, —OC(O)N($R^{4a}$)$_2$, —S$R^{4a}$, —S(O)$R^{4a}$, —S(O)$_2R^{4a}$, —S(O)N($R^{4a}$)$_2$, and —S(O)$_2$N($R^{4a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^{4a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{40}$;

$R^5$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{5a}$, —C(O)$_2R^{5a}$, —C(O)N($R^{5a}$)$_2$, —N($R^{5a}$)$_2$, —N($R^{5a}$)C(O)$R^{5a}$, —N($R^{5a}$)C(O)$_2R^{5a}$, —N($R^{5a}$)C(O)N($R^{5a}$)$_2$, —N($R^{5a}$)S(O)$_2R^{5a}$, —O$R^{5a}$, —OC(O)$R^{5a}$, —OC(O)N($R^{5a}$)$_2$, —S$R^{5a}$, —S(O)$R^{5a}$, —S(O)$_2R^{5a}$, —S(O)N($R^{5a}$)$_2$, and —S(O)$_2$N($R^{5a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$;

$R^{5a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{50}$;

$R^6$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{6a}$, —C(O)$_2R^{6a}$, —C(O)N($R^{6a}$)$_2$, —N($R^{6a}$)$_2$, —N($R^{6a}$)C(O)$R^{6a}$, —N($R^{6a}$)C(O)$_2R^{6a}$, —N($R^{6a}$)C(O)N($R^{6a}$)$_2$, —N($R^{6a}$)S(O)$_2R^{6a}$, —O$R^{6a}$, —OC(O)$R^{6a}$, —OC(O)N($R^{6a}$)$_2$, —S$R^{6a}$, —S(O)$R^{6a}$, —S(O)$_2R^{6a}$, —S(O)N($R^{6a}$)$_2$, and —S(O)$_2$N($R^{6a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{60}$;

or two $R^6$ substituents, together with their intervening atoms, form a 3- to five-membered carbocyclic or a 3- to five-membered heterocyclic ring, wherein said 3- to five-membered carbocyclic and 3- to five-membered heterocyclic ring are optionally substituted with one or more $R^{60}$;

$R^{6a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{60}$;

$R^{10}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{10a}$, —C(O)$_2R^{10a}$, —C(O)N($R^{10a}$)$_2$, —N($R^{10a}$)$_2$, —N($R^{10a}$)C(O)$R^{10a}$, —N($R^{10a}$)C(O)$_2R^{10a}$, —N($R^{10a}$)C(O)N($R^{10a}$)$_2$, —N($R^{10a}$)S(O)$_2R^{10a}$, —O$R^{10a}$, —OC(O)$R^{10a}$, —OC(O)N($R^{10a}$)$_2$, —S$R^{10a}$, —S(O)$R^{10a}$, —S(O)$_2R^{10a}$, —S(O)N($R^{10a}$)$_2$, and —S(O)$_2$N($R^{10a}$)$_2$;

$R^{10a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{20}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{20a}$, —C(O)$_2R^{20a}$, —C(O)N($R^{20a}$)$_2$, —N($R^{20a}$)$_2$, —N($R^{20a}$)C(O)$R^{20a}$, —N($R^{20a}$)C(O)$_2R^{20a}$, —N($R^{20a}$)C(O)N($R^{20a}$)$_2$, —N($R^{20a}$)S(O)$_2R^{20a}$, —O$R^{20a}$, —OC(O)$R^{20a}$, —OC(O)N($R^{20a}$)$_2$, —S$R^{20a}$, —S(O)$R^{20a}$, S(O)$_2R^{20a}$, —S(O)N($R^{20a}$)$_2$, and —S(O)$_2$N($R^{20a}$)$_2$, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally substituted with one or more $R^{25}$;

$R^{20a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl, wherein said $C_{1-6}$alkyl, $C_{2-6}$alkenyl, $C_{2-6}$alkynyl, 4- to 6-membered monocyclic carbocyclyl, and 4- to 6-membered monocyclic heterocyclyl in each occurrence are optionally and independently substituted with one or more $R^{25}$;

$R^{25}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{25a}$, —C(O)$_2R^{25a}$, —C(O)N($R^{25a}$)$_2$, —N($R^{25a}$)$_2$, —N($R^{25a}$)C(O)$R^{25a}$, —N($R^{25a}$)C(O)$_2R^{25a}$, —N($R^{25a}$)C(O)N($R^{25a}$)$_2$, —N($R^{25a}$)S(O)$_2R^{25a}$, —O$R^{25a}$, —OC(O)$R^{25a}$, —OC(O)N($R^{25a}$)$_2$, —S$R^{25a}$, —S(O)$R^{25a}$, —S(O)$_2R^{25a}$, —S(O)N($R^{25a}$)$_2$, and —S(O)$_2$N($R^{25a}$)$_2$;

$R^{25a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{30}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{30a}$, —C(O)$_2R^{30a}$, —C(O)N($R^{30a}$)$_2$, —N($R^{30a}$)$_2$, —N($R^{30a}$)C(O)$R^{30a}$, —N($R^{30a}$)C(O)$_2R^{30a}$, —N($R^{30a}$)C(O)N($R^{30a}$)$_2$, —N($R^{30a}$)S(O)$_2R^{30a}$, —O$R^{30a}$, —OC(O)$R^{30a}$, —OC(O)N($R^{30a}$)$_2$, —S$R^{30a}$, —S(O)$R^{30a}$, —S(O)$_2R^{30a}$, —S(O)N($R^{30a}$)$_2$, and —S(O)$_2$N($R^{30a}$)$_2$;

$R^{30a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{40}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{40a}$, —C(O)$_2R^{40a}$, —C(O)N($R^{40a}$)$_2$, —N($R^{40a}$)$_2$, —N($R^{40a}$)C(O)$R^{40a}$, —N($R^{40a}$)C(O)$_2R^{40a}$, —N($R^{40a}$)C(O)N($R^{40a}$)$_2$, —N($R^{40a}$)S(O)$_2R^{40a}$, —O$R^{40a}$, —OC(O)$R^{40a}$, —OC(O)N($R^{40a}$)$_2$, —S$R^{40a}$, —S(O)$R^{40a}$, —S(O)$_2R^{40a}$, —S(O)N($R^{40a}$)$_2$, and —S(O)$_2$N($R^{40a}$)$_2$;

$R^{40a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{50}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{50a}$, —C(O)$_2R^{50a}$, —C(O)N($R^{50a}$)$_2$, —N($R^{50a}$)$_2$, —N($R^{50a}$)C(O)$R^{50a}$, —N($R^{50a}$)C(O)$_2R^{50a}$, —N($R^{50a}$)C(O)N($R^{50a}$)$_2$, —N($R^{50a}$)S(O)$_2R^{50a}$, —O$R^{50a}$, —OC(O)$R^{50a}$, —OC(O)N($R^{50a}$)$_2$, —S$R^{50a}$, —S(O)$R^{50a}$, —S(O)$_2R^{50a}$, —S(O)N($R^{50a}$)$_2$, and —S(O)$_2$N($R^{50a}$)$_2$;

$R^{50a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl;

$R^{60}$ in each occurrence is independently selected from $C_{1-6}$alkyl, $C_{2-6}$alkenyl, $C_{2-6}$alkynyl, 4-to 6-membered monocyclic carbocyclyl, 4- to 6-membered monocyclic heterocyclyl, halo, —CN, —C(O)$R^{60a}$, —C(O)$_2R^{60a}$, —C(O)N($R^{60a}$)$_2$, —N($R^{60a}$)$_2$, —N($R^{60a}$)C(O)$R^{60a}$, —N($R^{60a}$)C(O)$_2R^{60a}$, —N($R^{60a}$)C(O)N($R^{60a}$)$_2$, —N($R^{60a}$)S(O)$_2R^{60a}$, —O$R^{60a}$, —OC(O)$R^{60a}$, —OC(O)N($R^{60a}$)$_2$, —S$R^{60a}$, —S(O)$R^{60a}$, —S(O)$_2R^{60a}$, —S(O)N($R^{60a}$)$_2$, and —S(O)$_2$N($R^{60a}$)$_2$; and $R^{60a}$ in each occurrence is independently selected from H, $C_{1-6}$alkyl, $C_{2-6}$alkenyl, $C_{2-6}$alkynyl, 4- to 6-membered monocyclic carbocyclyl, and 4- to 6-membered monocyclic heterocyclyl.

2. The compound of claim 1, wherein the compound is represented by the following formula:

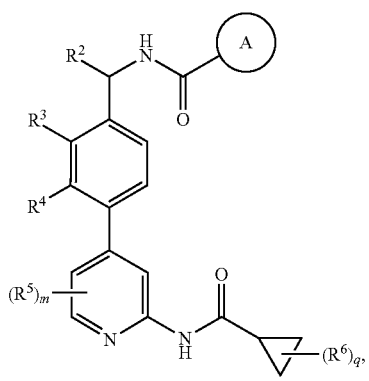

(II)

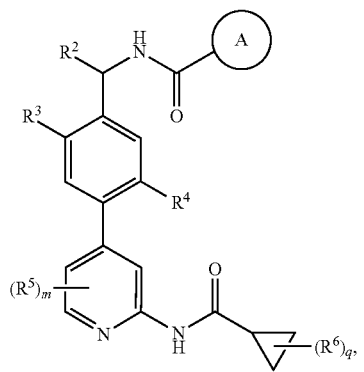

(III)

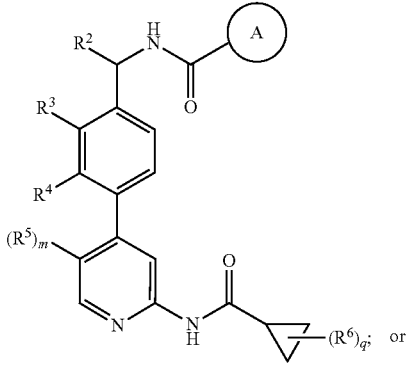

(IV)

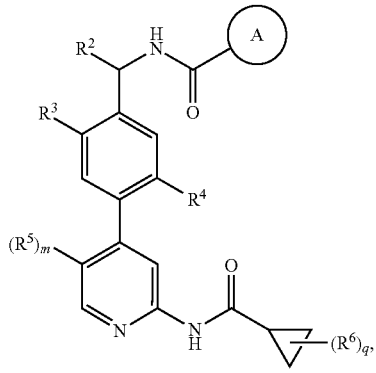

(V)

or a pharmaceutically acceptable salt thereof, wherein m is 0 or 1.

3. The compound of claim 2, wherein $R^3$ is $C_{1-6}$ alkyl, $C_{3-5}$cycloalkyl, halo, or —O$R^{3a}$, wherein said $C_{1-6}$alkyl or $C_{3-5}$cycloalkyl is optionally substituted with one to three $R^{30}$ independently selected from $C_{1-3}$alkyl and halo; and $R^{3a}$ is $C_{1-6}$ alkyl optionally substituted with one to three halo.

4. The compound of claim 2, wherein $R^2$ is H or methyl.

5. The compound of claim 2, wherein $R^2$ and $R^3$, together with their intervening atoms, form a seven-membered carbocyclic or heterocyclic ring, wherein said seven-membered heterocyclic ring has one heteroatom selected from N and O; and said seven-membered carbocyclic or heterocyclic ring is optionally substituted with one or two $R^{20}$.

6. The compound of claim 5, wherein the compound is represented by the following formula:

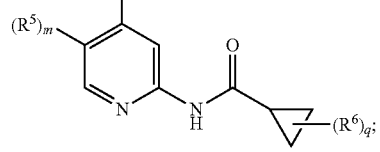

(VIa)

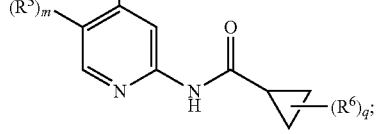

(VIa')

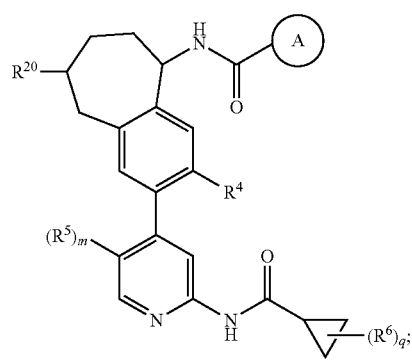
(VIb)
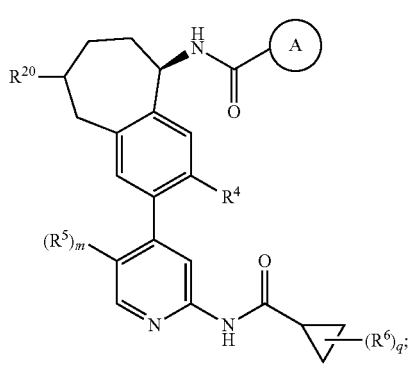
(VIb')
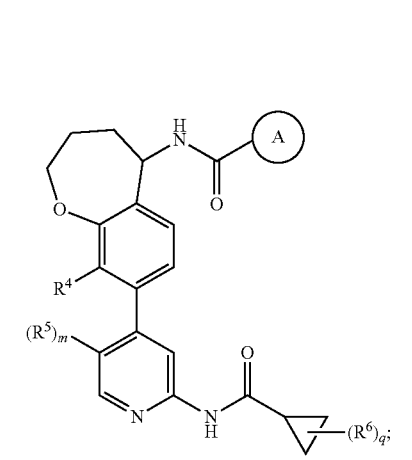
(VIIa)
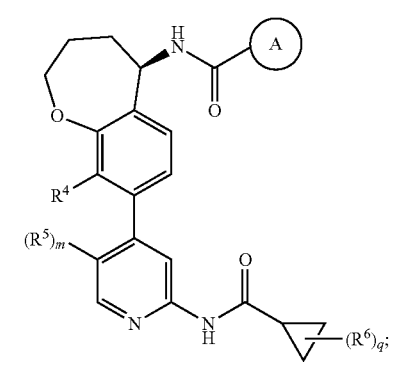
(VIIa')
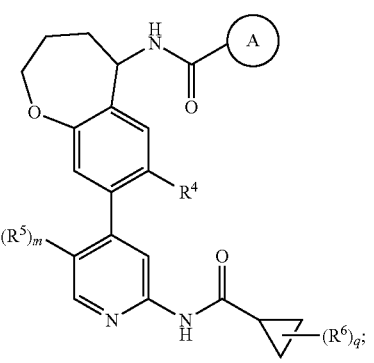
(VIIb)
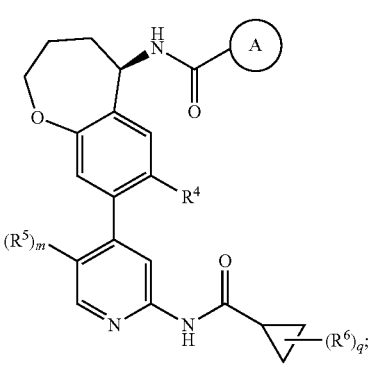
(VIIb')
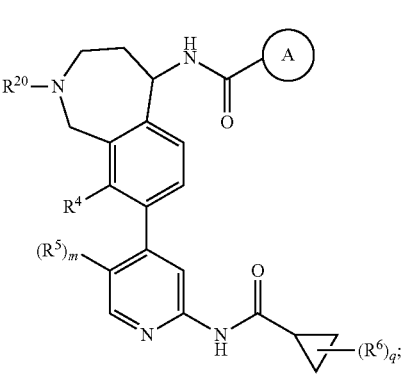
(VIIIa)
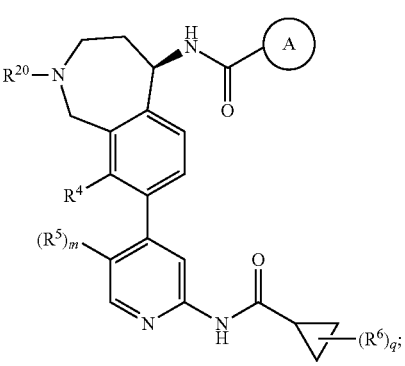
(VIIIa')

-continued

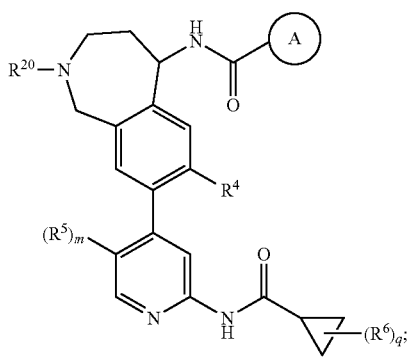
(VIIIb)

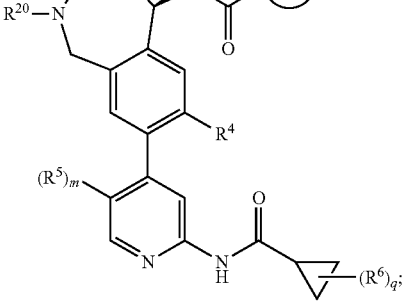
(VIIIb')

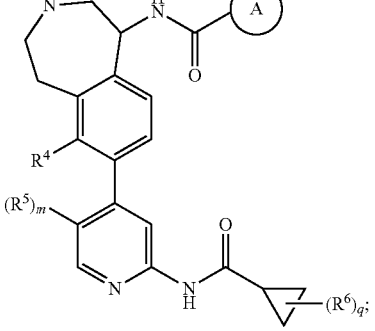
(IXa)

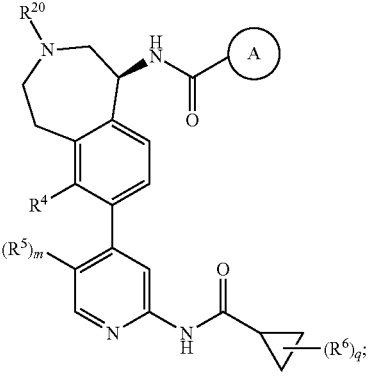
(IXa')

-continued

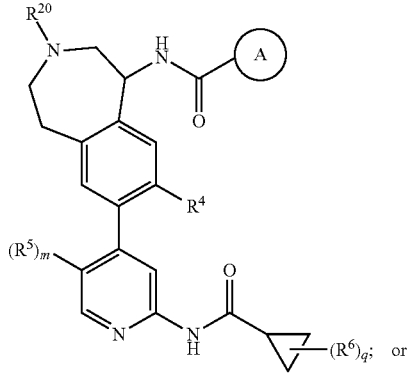
(IXb)

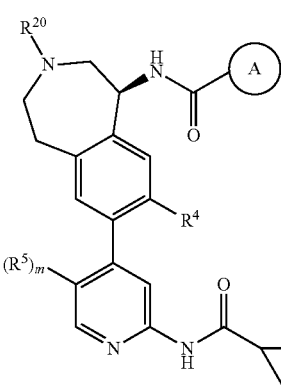
(IXb'); or or a pharmaceutically acceptable salt thereof, wherein:

$R^{20}$ is selected from H, $C_{1-6}$alkyl, $C_{3-6}$cycloalkyl, saturated 4- to 6-membered monocyclic heterocyclyl, —C(O)$R^{20a}$, —C(O)$_2R^{20a}$, and —S(O)$_2R^{20a}$, wherein said $C_{1-6}$alkyl, $C_{3-6}$cycloalkyl, and saturated 4- to 6-membered monocyclic heterocyclyl are optionally substituted with one to three $R^{25}$;

$R^{20a}$ in each occurrence is independently selected from H, $C_{1-6}$alkyl, $C_{4-6}$cycloalkyl, and saturated 4- to 6-membered monocyclic heterocyclyl, wherein said $C_{1-6}$alkyl, $C_{4-6}$cycloalkyl, and saturated 4- to 6-membered monocyclic heterocyclyl in each occurrence are optionally and independently substituted with one or more $R^{25}$;

$R^{25}$ in each occurrence is independently selected from $C_{1-6}$alkyl, $C_{3-6}$cycloalkyl, saturated 4-to 6-membered monocyclic heterocyclyl, halo, —CN, —N($R^{25a}$)$_2$, and —O$R^{25a}$, and $R^{25a}$ in each occurrence is independently H or $C_{1-6}$alkyl.

7. The compound of claim 6, wherein Ring A is a 5-membered N-containing heteroaryl having 1 or 2 additional heteroatoms independently selected from O, N and S, wherein ring A is optionally substituted with one or two independently selected $R^1$.

8. The compound of claim 6, wherein Ring A is represented by the following formula:

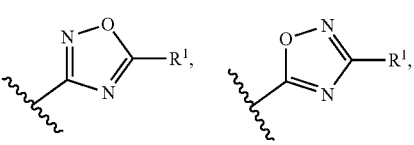

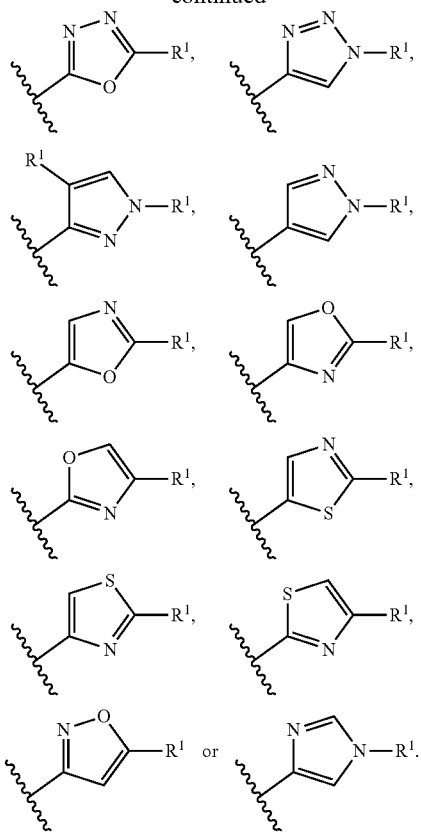

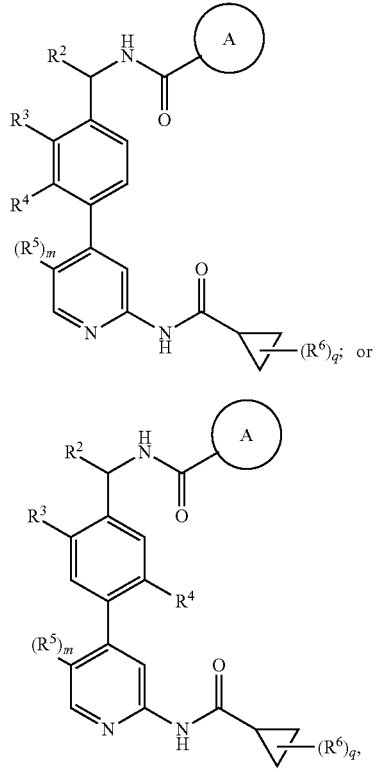

9. The compound of claim 6, wherein $R^1$ in each occurrence is independently halo, $C_{1-6}$alkyl or $C_{3-5}$cycloalkyl; wherein said $C_{1-6}$alkyl and $C_{3-5}$cycloalkyl are optionally substituted with one to three independently selected $R^{10}$; and $R^{10}$ in each occurrence is independently selected from halo, —OH, and $C_{1-6}$alkyl.

10. The compound of claim 6, wherein $R^4$ is H halo or $C_{1-3}$alkyl.

11. The compound of claim 6, wherein m is 0 or m is 1, and $R^5$ is halo or $C_{1-3}$alkyl optionally substituted with one to three fluoro.

12. The compound of claim 6, wherein q is 0.

13. The compound of claim 6, wherein $R^6$ in each occurrence is independently selected from halo, —CN, and $C_{1-6}$alkyl optionally substituted with one to three halo.

14. The compound of claim 6, wherein q is 2; and two $R^6$ substituents, together with their intervening atoms, form a three- to five-membered cycloalkyl or a four- to five-membered saturated heterocyclic ring.

15. The compound of claim 14, wherein two $R^6$ substituents, together with their intervening atoms, form cyclopropyl, cyclobutyl, cyclopentyl, azetidinyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, or oxathiolanyl.

16. The compound of claim 1, wherein the compound is represented by the following formula:

or a pharmaceutically acceptable salt thereof, wherein:
Ring A is oxadiazole optionally substituted with one or two independently selected $R^1$;
$R^1$ in each occurrence is independently halo or $C_{1-6}$alkyl;
$R^2$ is H or $C_{1-3}$alkyl;
$R^3$ is halo or $C_{1-3}$alkyl;
or $R^2$ and $R^3$, together with their intervening atoms, form a seven-membered carbocyclic or heterocyclic ring, wherein said seven-membered heterocyclic ring has one heteroatom selected from N and O; and said seven-membered carbocyclic or heterocyclic ring is optionally substituted with one $R^{20}$
$R^{20}$ is $C_{1-6}$alkyl optionally substituted with one to three fluoro;
$R^4$ is H or halo;
$R^5$ is halo;
$R^6$ is halo or $C_{1-3}$alkyl;
m is 0 or 1; and
q is 0 or 1.

17. The compound of claim 16, wherein Ring A is represented by the following formula:

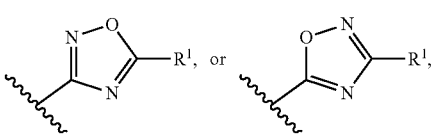

wherein $R^1$ is —C(CH$_3$)$_3$;
q is 0; or q is 1, and $R^6$ is —F or —CH$_3$;
m is 0; or m is 1, and $R^5$ —F or —Cl;
$R^2$ is H or —CH$_3$ $R^3$ is —Cl, —CH$_3$ or —CF$_3$;

$R^4$ is H or —F.

18. The compound of claim 16, wherein the compound is represented by the following formula:

(VIc)

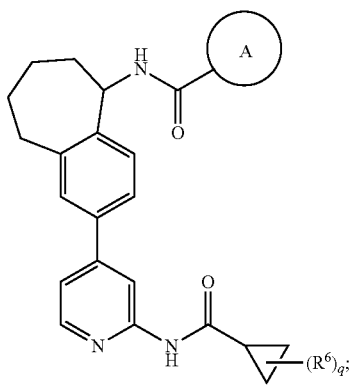

(VIc')

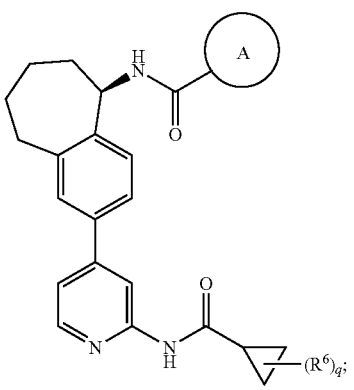

(VIIIc)

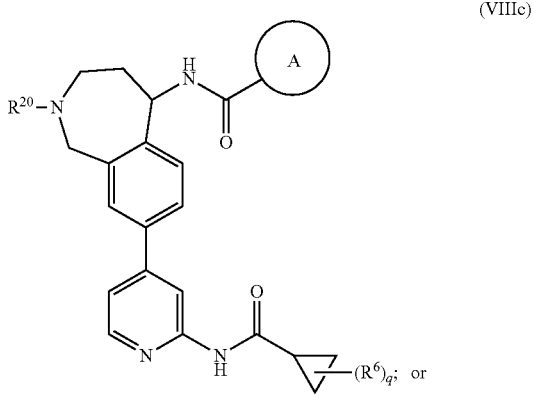

(VIIIc')

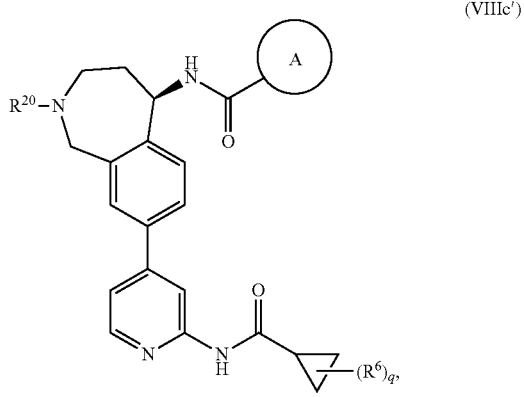

or a pharmaceutically acceptable salt thereof, wherein $R^{20}$ is —CH$_2$CF$_3$.

19. A pharmaceutical composition comprising a compound of claim 1, or a pharmaceutically acceptable salt thereof, and a pharmaceutically acceptable excipient.

20. A method of treating a disorder responsive to inhibition of Bruton's tyrosine kinase in a subject comprising administering to the subject an effective amount of a compound of claim 1, or a pharmaceutically acceptable salt thereof.

21. The method of claim 20, wherein the disorder is an autoimmune disorder or multiple sclerosis.

* * * * *